US008304546B2

(12) United States Patent
Otsubo et al.

(10) Patent No.: US 8,304,546 B2
(45) Date of Patent: Nov. 6, 2012

(54) QUINOLONE COMPOUND AND PHARMACEUTICAL COMPOSITION

(75) Inventors: Kenji Otsubo, Osaka (JP); Takahito Yamauchi, Osaka (JP); Yuji Ochi, Osaka (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/668,164

(22) PCT Filed: Dec. 4, 2009

(86) PCT No.: PCT/JP2009/070719
§ 371 (c)(1),
(2), (4) Date: Apr. 7, 2010

(87) PCT Pub. No.: WO2010/064735
PCT Pub. Date: Jun. 10, 2010

(65) Prior Publication Data
US 2011/0269705 A1  Nov. 3, 2011

(30) Foreign Application Priority Data
Dec. 5, 2008  (JP) ................................. 2008-310739

(51) Int. Cl.
*C07D 215/38* (2006.01)
(52) U.S. Cl. .................................................... 546/159
(58) Field of Classification Search .................. 546/159; 514/312
See application file for complete search history.

(56) References Cited

U.S. PATENT DOCUMENTS

| 6,297,257 | B1 | 10/2001 | Napoletano et al. |
| 6,645,983 | B1 | 11/2003 | Joseph et al. |
| 2010/0130546 | A1* | 5/2010 | Otsubo et al. ................. 514/312 |
| 2011/0269705 | A1 | 11/2011 | Otsubo et al. |

FOREIGN PATENT DOCUMENTS

| EP | 0163888 A1 | 12/1985 |
| EP | 0498723 A1 | 8/1992 |
| EP | 1 886 996 A1 | 2/2008 |
| KR | 2005-104957 A | 11/2005 |
| WO | 98/17662 A1 | 4/1998 |
| WO | 98/48790 A1 | 11/1998 |
| WO | 99/32449 A2 | 7/1999 |
| WO | 00/42026 A1 | 7/2000 |
| WO | 00/62765 A2 | 10/2000 |
| WO | 01/12607 A2 | 2/2001 |
| WO | 01/17986 A1 | 3/2001 |
| WO | 02/22074 A2 | 3/2002 |
| WO | 02/26713 A1 | 4/2002 |
| WO | 02/30407 A1 | 4/2002 |
| WO | 02/074307 A1 | 9/2002 |
| WO | 03/035635 A1 | 5/2003 |
| WO | 2004/007461 A1 | 1/2004 |
| WO | 2004/016255 A1 | 2/2004 |
| WO | 2004/087160 A1 | 10/2004 |
| WO | 2004/091485 A2 | 10/2004 |
| WO | 2005/032559 A1 | 4/2005 |
| WO | 2005/034960 A1 | 4/2005 |
| WO | 2005/049008 A1 | 6/2005 |
| WO | 2006/045096 A2 | 4/2006 |
| WO | 2006/096780 A2 | 9/2006 |
| WO | 2008/150029 A1 | 12/2008 |
| WO | 2009/053799 A1 | 4/2009 |

OTHER PUBLICATIONS

Kazutoshi Nakano, et al. "Mitochondria and Cell Death", Journal of Clinical and Experimental Medicine, vol. 225, No. 6, May 10, 2008, pp. 501-507, English abstract.
Zhu-Ping Xiao, et al. "Synthesis, Antiproliferative Activity, and Structure-Activity Relationships of 3-Aryl-1 H-quinolin-4-ones", ChemMedChem vol. 3, No. 7, 2008, 1077-1082.
International Search Report on PCT International Application No. PCT/JP2009/070383 mailed Jan. 12, 2010.
Office Action for U.S. Appl. No. 12/599,003 dated Jan. 31, 2012.
Gary Fiskum et al., "Mitochondrial Mechanisms of Neural Cell Death and Neuroprotective Interventions in Parkinson's Disease", Annals New York Academy of Sciences, 2003, pp. 111-119, vol. 991.
Sunitha Bollimuntha et al., "TRPC1-Mediated Inhibition of 1-Methyl-4-Phenylpyridinium Ion Neurotoxicity in Human SH-SY5Y Neuroblastoma Cells", The Journal of Biologcal Chemistry, Jan. 21, 2005, pp. 2132-2140, vol. 280, No. 3, The American Society for Biochemistry and Molecular Biology, Inc.

(Continued)

*Primary Examiner* — D M Seaman
(74) *Attorney, Agent, or Firm* — Sughrue Mion, PLLC

(57) ABSTRACT

The present invention provides a quinolone compound that inhibits the chronic progression of Parkinson's disease or protects dopamine neurons from disease etiology, thereby suppressing the progression of neurological dysfunction, so as to prolong the period of time until L-dopa is administered while also improving neuronal function; the quinolone compound of the invention is represented by Formula (1):

(1)

wherein:
$R_1$ represents hydrogen or the like;
$R_2$ represents hydrogen or the like;
$R_3$ represents substituted or unsubstituted phenyl or the like;
$R_4$ represents halogen or the like;
$R_5$ represents hydrogen or the like;
$R_6$ represents hydrogen or the like; and
$R_7$ represents hydrogen or the like.

17 Claims, No Drawings

OTHER PUBLICATIONS

Tiesong Shang et al., "Death-Associated Protein Kinase as a Sensor of Mitochondrial Membrane Potential", The Journal of Biological Chemistry, Oct. 14, 2005, pp. 34644-34653, vol. 280, No. 41, The American Society for Biochemistry and Molecular Biology, Inc.

Masami Nakai et al., "1-Methyl-4-Phenylpyridinium ($MPP^+$) Decreases Mitochondrial Oxidation-Reduction (REDOX) Activity and Membrane Potential ($\delta_{\psi m}$) in Rat Striatum", Experimental Neurology, 2003, pp. 103-110, vol. 179, Elsevier Science.

Piu Chan et al., "Rapid ATP Loss Caused by 1-Methyl-4-Pheyl-1,2,3,6-Tetrahydropyridine in Mouse Brain", Journal of Neurochemistry, 1991, pp. 348-351, vol. 57, No. 1, Raven Press, Ltd., New York.

Atsushi Mori et al., "Neural Mechanisms Underlying Motor Dysfunction as Detected by the Tail Suspension Test in MPTP-Treated C57BL/6 Mice", Neuroscience Research, 2005, pp. 265-274, vol. 51.

Jin-Ichi Koizumi et al., "Experimental Studies of Ischemic Brain Edema", Jpn. J. Stroke, 1986, pp. 1-8, vol. 8, No. 1, English Abstract.

Hisashi Kitagawa et al., "Intracerebral Adenosine Infusion Improves Neuroogical Outcome After Transient Focal Ischemia in Rats", Neurological Research, Apr. 2002, pp. 317-323, vol. 24, Forefront Publishing Corp.

Office Action for U.S. Appl. No. 12/559,003 dated Jan. 31, 2012.

Guo Hua Jin, et al., Synthesis of azaisoflavones and their inhibitory activities of NO production in activated microglia, Bioorganic & Medicinal Chemistry Letters, Jul. 15, 2008, pp. 4092-4094, vol. 18, No. 14, Pergamon, Elsevier Science, GB.

Wang, Xiaoli, et al., The Study on $^1$H NMR of 5(7)-Chloro-6-Fluro-3-Phenyl-4-(1H)-Quinolinone Derivatives, Chinese Journal of Magnetic Resonance, Dec. 6, 1998, pp. 543-546, vol. 15, No. 6, School of Pharmacy, West China University of Medical Sciences, Chendu 610041, English-language Abstract.

Diana Alonso, et al., Marine compounds for the therapeutic treatment of neurological disorders, Expert Opinion on Therapeutic Patents, Oct. 2005, pp. 1377-1386, vol. 15, No. 10, GB, Ashley Publications Ltd.

International Search Report corresponding to Application No. PCT/JP2009/070719, dated Mar. 30, 2010.

* cited by examiner

QUINOLONE COMPOUND AND PHARMACEUTICAL COMPOSITION

TECHNICAL FIELD

The present invention relates to quinolone compounds and pharmaceutical compositions.

BACKGROUND ART

Parkinson's disease is a chronic, progressive neurodegenerative disease that generally develops after middle age. Initial symptoms include unilateral resting tremor, akinesia and rigidity. The tremors, akinesia, and rigidity are called the three major signs of Parkinson's disease, and each of them is caused by the selective death of dopaminergic neurons projected from the substantia nigra to the striatum. The etiology of the disease is still unknown; however, accumulated evidence suggests that an impaired energy-generating system accompanied by abnormal mitochondrial function of nigrostriatal dopaminergic neurons triggers the neurodegenerative disorder of the disease. The mitochondrial dysfunction has been assumed to subsequently cause oxidative stress and failure of calcium homeostasis, thereby resulting in neurodegeneration (Non-Patent Document 1).

Treatments of Parkinson's disease are roughly classified into medical management (medication) and surgical management (stereotaxic operation). Of these, medication is an established therapy and regarded as a basic treatment. In the medication, a symptomatic therapeutic agent is used to compensate for the nigrostriatal dopaminergic neuronal function denatured by Parkinson's disease. L-dopa exhibits the most remarkable therapeutic effects. It is said that no agent exceeds the effectiveness of L-dopa. Currently, L-dopa is used together with a dopa decarboxylase inhibitor to prevent the metabolism thereof in the periphery, and the desired clinical effects have been obtained.

However, L-dopa treatment has drawbacks in that, after several years of usage, there is a recurrence of movement disorders such as dyskinesia, and the sustainability and stability of the drug's effects are lost, resulting in fluctuations within each day. Moreover, side effects including digestive problems such as nausea and vomiting brought on by excessive release of dopamine, circulatory organ problems such as orthostatic hypotension, tachycardia and arrhythmia, and neurological manifestations such as hallucination, delusion and distraction have been a cause for concern.

Thus, in order to decrease the L-dopa preparation dosage and thereby reduce the side effects, multidrug therapies, in which dopamine receptor agonists, dopamine metabolism enzyme inhibitors, dopamine releasers, central anticholinergic agents and the like are used in combination, are employed. While such therapeutic advances remarkably improve prognoses, there is still no fundamental cure for Parkinson's disease and other neurodegenerative diseases. Medication must be taken for the rest of the patient's life, and the aforementioned drawbacks, i.e., decreased efficacy during long-term administration, side effects, and uncontrollable disease progression, can result from L-dopa monotherapy. In addition, it is difficult to expect dramatic effects, even with the employment of multidrug therapies.

Alzheimer's disease is a progressive neurodegenerative disease that affects various cognitive functions, primarily causing impairment of memory. Pathologically, Alzheimer's disease is characterized by the degeneration of synapses or neurons in the hippocampus and cerebral cortex, and the accumulation of two types of abnormal fibrils, i.e., senile plaques and changes in neurofibrils. Although the disease etiology is not completely understood, amyloid β protein (Aβ), which is derived from amyloid precursor protein (APP) by various mechanisms, is known to play an important role. Currently, cholinesterase inhibitors (tacrine, Aricept, rivastigmine, and galantamine) are used in the treatment of Alzheimer's disease for ameliorating symptoms, because acetylcholinergic nervous system in the brain is involved in cognitive function, and marked deficits in the acetylcholinergic system are observed in Alzheimer's disease. N-methyl-D-aspartate glutamate receptor antagonists (memantine) are also in practical use because hyperexcitability of the mechanism of glutamate neurotransmission is associated with neural degeneration or impairment. Neither monotherapy nor combination therapy using these drugs, however, has produced sufficient therapeutic effects, nor are they capable of halting the progression of the disease. Furthermore, gastrointestinal symptoms such as nausea and diarrhea are observed as side effects of cholinesterase.

With respect to ischemic neurodegenerative disorders induced by cerebral infarctions, such as atherothrombotic cerebral infarction, lacunar infarction, cardiogenic cerebral embolism, etc., the usage of very early thrombolytic therapy using tissue plasminogen activator (tPA) is rapidly increasing. This therapy, however, has many problems including a window as short as within three hours after the onset of disease, hemorrhagic complications, etc. In Japan, a free radical scavenger, edaravone, is used for a brain protection therapy. Although edaravone can be used concomitantly with tPA, sufficient clinical results have not been obtained.

Accordingly, there exists a strong need for a pharmaceutical agent having a novel mechanism of action, or a neuroprotectant for preventing neural degeneration or impairment from its etiologies such as abnormal mitochondrial function, etc.

CITATION LIST

Non Patent Literature

NPL 1: Ann. N.Y. Acad. Sci. 991: 111-119 (2003)

SUMMARY OF INVENTION

Technical Problem

An object of the present invention is to provide a novel compound that inhibits the chronic progression of Parkinson's disease or protects dopamine neurons from the disease itself, thereby suppressing the progression of neurological dysfunction, so as to prolong the period of time until L-dopa is administered while also improving neuronal function.

Another object of the invention is to provide an agent that is useful in treating diseases that induce cell death, and more specifically, to provide an agent having efficacy for treating Alzheimer's disease, or improving dysfunction or neurologic deficits induced by cerebral apoplexy.

Solution to Problem

The present inventors conducted extensive research to accomplish the aforementioned object. Consequently, they succeeded in producing a compound represented by Formula (1) shown below, which protects and improves mitochondrial function, and/or protects neurons and repairs neuronal function. The present invention has been accomplished based on the above findings.

The invention provides a quinolone compound, a process for producing the same, and a pharmaceutical composition as set forth in the following Items 1 to 23.

Item 1. A quinolone compound represented by Formula (1):

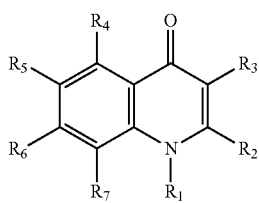

(1)

or a salt thereof,
wherein $R_1$ represents:
(1) hydrogen,
(2) lower alkyl,
(3) halogen-substituted lower alkyl,
(4) lower alkenyl,
(5) lower alkanoyl,
(6) halogen-substituted lower alkanoyl,
(7) hydroxy lower alkyl,
(8) protected hydroxy lower alkyl,
(9) hydroxy lower alkanoyl,
(10) protected hydroxy lower alkanoyl,
(11) lower alkylthio lower alkyl,
(12) amino lower alkylthio lower alkyl optionally having one or more lower alkyl groups,
(13) hydroxy lower alkylthio lower alkyl,
(14) carboxy lower alkylthio lower alkyl,
(15) lower alkoxycarbonyl lower alkylthio lower alkyl,
(16) amino lower alkylthiocarbonyl lower alkyl optionally having one or more lower alkyl groups,
(17) hydroxy lower alkylsulfonyl lower alkyl,
(18) carboxy lower alkylsulfonyl lower alkyl,
(19) lower alkoxycarbonyl lower alkylsulfonyl lower alkyl,
(20) lower alkanoyl lower alkylsulfonyl lower alkyl,
(21) piperazinyl lower alkylsulfonyl lower alkyl optionally having one or more lower alkyl groups on the piperazine ring,
(22) piperazinylcarbonyl lower alkylsulfonyl lower alkyl optionally having one or more lower alkyl groups on the piperazine ring,
(23) lower alkanoyl lower alkyl,
(24) carboxy lower alkyl,
(25) lower alkoxycarbonyl lower alkyl,
(26) piperazinyl lower alkoxycarbonyl lower alkyl optionally having one or more lower alkyl groups on the piperazine ring,
(27) morpholinyl lower alkyl,
(28) oxazepanyl lower alkyl,
(29) amino lower alkyl optionally having one or more lower alkyl groups,
(30) piperazyl lower alkyl optionally having, on the piperazine ring, one or more substituents selected from the group consisting of lower alkyl, lower alkoxy lower alkyl, and pyridyl,
(31) piperidyl lower alkyl optionally having one or more morpholinyl groups,
(32) azetidyl lower alkyl optionally having one or more hydroxy groups on the azetidine ring,
(33) isoindolinyl lower alkyl optionally having one or more oxo groups,
(34) amino lower alkanoyloxy lower alkyl optionally having one or more substituents selected from the group consisting of lower alkyl and lower alkoxycarbonyl,
(35) carbamoyl lower alkyl optionally having one or more substituents selected from lower alkyl; morpholinyl lower alkyl; piperidyl optionally having one or more substituents selected from the group consisting of lower alkyl and lower alkoxycarbonyl; and piperazinyl lower alkyl optionally having one or more lower alkyl groups,
(36) phosphonooxy lower alkyl optionally having one or more hydroxy-protecting groups,
(37) phosphonooxy lower alkanoyloxy lower alkyl optionally having one or more hydroxy-protecting groups,
(38) benzoyloxy lower alkyl optionally having, on the benzene ring, one or more substituents selected from the group consisting of hydroxy, protected hydroxy, and phosphonooxy optionally having one or more hydroxyl-protecting groups,
(39) tetrahydropyranyl optionally having one or more substituents selected from the group consisting of hydroxy, hydroxy lower alkyl and carboxyl, or
(40) lower alkanoylamino lower alkyl optionally having, on the lower alkanoyl group, one or more substituents selected from the group consisting of halogen; hydroxy; amino; lower alkoxycarbonylamino; piperazinyl optionally having one or more lower alkoxy lower alkyl groups; imidazolyl; and morpholinylpiperidyl;
$R_2$ represents:
(1) hydrogen,
(2) lower alkyl,
(3) lower alkanoyl,
(4) hydroxy lower alkyl,
(5) carboxy,
(6) lower alkoxycarbonyl,
(7) carbamoyl optionally having one or more substituents selected from the group consisting of lower alkyl; halogen-substituted lower alkyl; hydroxy lower alkyl; piperazinyl lower alkyl optionally having one or more lower alkyl groups; and morpholinyl lower alkyl,
(8) carbamoyl lower alkyl optionally having one or more lower alkyl groups,
(9) morpholinyl lower alkyl,
(10) piperazinyl lower alkyl optionally having one or more substituents selected from the group consisting of lower alkyl and pyridyl optionally having one or more lower alkyl groups,
(11) diazepanyl lower alkyl,
(12) amino lower alkyl optionally having one or more substituents selected from the group consisting of lower alkyl, halogen-substituted lower alkyl, hydroxy lower alkyl, and morpholinyl lower alkyl,
(13) lower alkoxycarbonyl lower alkyl, or
(14) carboxy lower alkyl;
$R_3$ represents phenyl, thienyl, furyl, pyrazolyl, or pyrimidinyl, wherein:
the aromatic or heterocyclic ring represented by $R_3$ may be substituted with one or more substituents selected from the group consisting of the following substituents (1) to (14):
(1) lower alkyl,
(2) lower alkoxy,
(3) lower alkanoyl,
(4) halogen,
(5) hydroxy,
(6) hydroxy lower alkyl,
(7) hydroxy lower alkoxy,
(8) protected hydroxy lower alkoxy,
(9) carboxy lower alkoxy,
(10) lower alkoxycarbonyl lower alkoxy,
(11) pyrrolidinylcarbonyl,

(12) carbamoyl lower alkoxy optionally having one or more lower alkyl groups,
(13) carbamoyl optionally having one or more morpholinyl lower alkyl groups, and
(14) morpholinylpiperidylcarbonyl;

$R_4$ represents halogen, lower alkyl, or lower alkoxy;
$R_5$ represents hydrogen or halogen;
$R_4$ and $R_5$ may be linked to form a group represented by any of the following formulae:

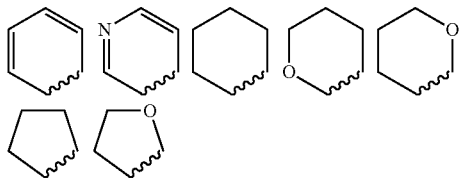

or a group represented by the following formula:

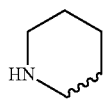

the group optionally having one or more substituents selected from the group consisting of lower alkyl and oxo groups;

$R_6$ represents hydrogen or lower alkoxy;
$R_7$ represents any of the following groups (1) to (11):
(1) hydrogen,
(2) lower alkoxy,
(3) hydroxy lower alkoxy,
(4) protected hydroxy lower alkoxy,
(5) lower alkoxy lower alkoxy,
(6) carbamoyl lower alkoxy optionally having one or more substituents selected from the group consisting of lower alkyl and morpholinyl lower alkyl,
(7) amino optionally having one or two substituents selected from the group consisting of lower alkyl and cyclo $C_3$-$C_8$ alkyl,
(8) cyclo $C_3$-$C_8$ alkyloxy,
(9) carboxy lower alkoxy,
(10) lower alkoxycarbonyl lower alkoxy, and
(11) pyrrolidinyl; and $R_6$ and $R_7$ may be linked to form a group represented by any of the following formulae:

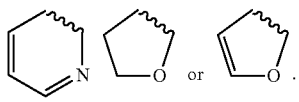

Item 2. A quinolone compound of General Formula (1) or a salt thereof according to Item 1, wherein:

$R_4$ and $R_5$ may be linked to form a group represented by any of the following formulae:

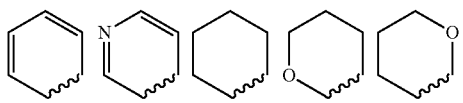

or a group represented by the following formula:

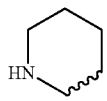

the group optionally having one or two substituents selected from the group consisting of lower alkyl or oxo groups.

Item 3. A quinolone compound of General Formula (1) or a salt thereof according to Item 2, wherein:
$R_1$ represents:
(1) hydrogen,
(2) lower alkyl,
(3) halogen-substituted lower alkyl,
(4) lower alkenyl,
(5) lower alkanoyl,
(6) halogen-substituted lower alkanoyl,
(7) hydroxy lower alkyl,
(8) phenyl lower alkoxy lower alkyl,
(9) hydroxy lower alkanoyl,
(10) phenyl lower alkoxy lower alkanoyl,
(11) lower alkylthio lower alkyl,
(12) amino lower alkylthio lower alkyl optionally having, on the amino group, two lower alkyl groups,
(13) hydroxy lower alkylthio lower alkyl,
(14) carboxy lower alkylthio lower alkyl,
(15) lower alkoxycarbonyl lower alkylthio lower alkyl,
(16) amino lower alkylthiocarbonyl lower alkyl optionally having, on the amino group, two lower alkyl groups,
(17) hydroxy lower alkylsulfonyl lower alkyl,
(18) carboxy lower alkylsulfonyl lower alkyl,
(19) lower alkoxycarbonyl lower alkylsulfonyl lower alkyl,
(20) lower alkanoyl lower alkylsulfonyl lower alkyl,
(21) piperazinyl lower alkylsulfonyl lower alkyl optionally having one lower alkyl group on the piperazine ring,
(22) piperazinylcarbonyl lower alkylsulfonyl lower alkyl optionally having one lower alkyl group on the piperazine ring,
(23) lower alkanoyl lower alkyl,
(24) carboxy lower alkyl,
(25) lower alkoxycarbonyl lower alkyl,
(26) piperazinyl lower alkoxycarbonyl lower alkyl optionally having one lower alkyl group on the piperazine ring,
(27) morpholinyl lower alkyl,
(28) oxazepanyl lower alkyl,
(29) amino lower alkyl optionally having one lower alkyl group on the amino group,
(30) piperazyl lower alkyl optionally having, on the piperazine ring, one substituent selected from the group consisting of lower alkyl, lower alkoxy lower alkyl, and pyridyl,
(31) piperidyl lower alkyl optionally having one morpholinyl group on the piperidine ring,
(32) azetidyl lower alkyl optionally having one hydroxy group on the azetidine ring,
(33) isoindolinyl lower alkyl optionally having two oxo groups on the isoindoline ring,

(34) amino lower alkanoyloxy lower alkyl optionally having, on the amino group, one or two substituents selected from the group consisting of lower alkyl and lower alkoxycarbonyl,
(35) carbamoyl lower alkyl optionally having, on the carbamoyl group, one substituent selected from lower alkyl; morpholinyl lower alkyl; piperidyl optionally having one substituent selected from the group consisting of lower alkyl and lower alkoxycarbonyl; and piperazinyl lower alkyl optionally having one lower alkyl group,
(36) phosphonooxy lower alkyl optionally having one or two lower alkyl groups on the phosphonooxy group,
(37) phosphonooxy lower alkanoyloxy lower alkyl optionally having one or two lower alkyl groups on the phosphonooxy group,
(38) benzoyloxy lower alkyl optionally having, on the benzene ring, one substituent selected from the group consisting of hydroxy, benzyloxy, and phosphonooxy optionally having one or two lower alkyl groups,
(39) tetrahydropyranyl optionally having three hydroxy groups and one hydroxy lower alkyl group, or
(40) lower alkanoylamino lower alkyl optionally having, on the lower alkanoyl group, one or two substituents selected from the group consisting of halogen; hydroxy; amino; lower alkoxycarbonylamino; piperazinyl optionally having one lower alkoxy lower alkyl group; imidazolyl; and morpholinylpiperidyl;

$R_2$ represents:
(1) hydrogen,
(2) lower alkyl,
(3) lower alkanoyl,
(4) hydroxy lower alkyl,
(5) carboxy,
(6) lower alkoxycarbonyl,
(7) carbamoyl optionally having one or two substituents selected from the group consisting of lower alkyl; halogen-substituted lower alkyl; hydroxy lower alkyl; piperazinyl lower alkyl optionally having one lower alkyl group on the piperazine ring; and morpholinyl lower alkyl,
(8) carbamoyl lower alkyl optionally having one lower alkyl group on the carbamoyl group,
(9) morpholinyl lower alkyl,
(10) piperazinyl lower alkyl optionally having, on the piperazine ring, one substituent selected from the group consisting of lower alkyl and pyridyl optionally having one lower alkyl group,
(11) diazepanyl lower alkyl, or
(12) amino lower alkyl optionally having, on the amino group, one or two substituents selected from the group consisting of lower alkyl, halogen-substituted lower alkyl, hydroxy lower alkyl, and morpholinyl lower alkyl;

$R_3$ represents phenyl, thienyl, furyl, pyrazolyl, or pyrimidinyl, wherein:
the aromatic or heterocyclic ring represented by $R_3$ may be substituted with one or two substituents selected from the group consisting of the following substituents (1) to (14):
(1) lower alkyl,
(2) lower alkoxy,
(3) lower alkanoyl,
(4) halogen,
(5) hydroxy,
(6) hydroxy lower alkyl,
(7) hydroxy lower alkoxy,
(8) tetrahydropyranyloxy lower alkoxy,
(9) carboxy lower alkoxy,
(10) lower alkoxycarbonyl lower alkoxy,
(11) pyrrolidinylcarbonyl,
(12) carbamoyl lower alkoxy optionally having one lower alkyl group on the carbamoyl group,
(13) carbamoyl optionally having one morpholinyl lower alkyl group, and
(14) morpholinylpiperidylcarbonyl;

$R_6$ represents hydrogen or lower alkoxy; and
$R_7$ represents any of the following groups (1) to (11):
(1) hydrogen,
(2) lower alkoxy,
(3) hydroxy lower alkoxy,
(4) benzyloxy lower alkoxy,
(5) lower alkoxy lower alkoxy,
(6) carbamoyl lower alkoxy optionally having, on the carbamoyl group, one substituent selected from the group consisting of lower alkyl and morpholinyl lower alkyl,
(7) amino optionally having two substituents selected from the group consisting of lower alkyl and cyclo $C_3$-$C_8$ alkyl,
(8) cyclo $C_3$-$C_8$ alkyloxy,
(9) carboxy lower alkoxy,
(10) lower alkoxycarbonyl lower alkoxy, and
(11) pyrrolidinyl.

Item 4. A quinolone compound of General Formula (1) or a salt thereof according to Item 3, wherein $R_1$ represents:
(1) hydrogen,
(2) lower alkyl,
(3) halogen-substituted lower alkyl,
(24) carboxy lower alkyl,
(25) lower alkoxycarbonyl lower alkyl,
(27) morpholinyl lower alkyl,
(28) oxazepanyl lower alkyl,
(30) piperazyl lower alkyl optionally having, on the piperazine ring, one lower alkoxy lower alkyl,
(31) piperidyl lower alkyl,
(35) carbamoyl lower alkyl optionally having one morpholinyl lower alkyl, or
(36) phosphonooxy lower alkyl optionally having one or two lower alkyl groups $R_2$ represents:
(1) hydrogen, or
(2) lower alkyl, $R_3$ represents phenyl, thienyl, or furyl, wherein:
the aromatic or heterocyclic ring represented by $R_3$ may be substituted with one lower alkoxy group, $R_6$ represents hydrogen; and
$R_7$ represents lower alkoxy.

Item 5. A quinolone compound of General Formula (1) or a salt thereof according to Item 1, wherein
$R_6$ and $R_7$ may be linked to form a group represented by any of the following formulae:

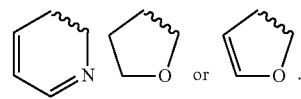

Item 6. A quinolone compound of General Formula (1) or a salt thereof according to Item 5, wherein
$R_1$ represents:
(1) hydrogen,
(2) lower alkyl, or
(36) phosphonooxy lower alkyl optionally having one or two lower alkyl groups;
$R_2$ represents hydrogen,
$R_3$ represents phenyl wherein the aromatic or heterocyclic ring represented by $R_3$ may be substituted with one lower alkoxy group;

R₄ represents lower alkyl, or lower alkoxy; and
R₅ represents hydrogen.

Item 7. A quinolone compound of General Formula (1) or a salt thereof according to Item 1, wherein
R₁ represents:
(3) halogen-substituted lower alkyl,
(4) lower alkenyl,
(5) lower alkanoyl,
(6) halogen-substituted lower alkanoyl,
(7) hydroxy lower alkyl,
(8) phenyl lower alkoxy lower alkyl,
(9) hydroxy lower alkanoyl,
(10) phenyl lower alkoxy lower alkanoyl,
(11) lower alkylthio lower alkyl,
(12) amino lower alkylthio lower alkyl optionally having one or two lower alkyl groups,
(13) hydroxy lower alkylthio lower alkyl,
(14) carboxy lower alkylthio lower alkyl,
(15) lower alkoxycarbonyl lower alkylthio lower alkyl,
(16) amino lower alkylthiocarbonyl lower alkyl optionally having one or two lower alkyl groups,
(17) hydroxy lower alkylsulfonyl lower alkyl,
(18) carboxy lower alkylsulfonyl lower alkyl,
(19) lower alkoxycarbonyl lower alkylsulfonyl lower alkyl,
(20) lower alkanoyl lower alkylsulfonyl lower alkyl,
(21) piperazinyl lower alkylsulfonyl lower alkyl optionally having one lower alkyl group on the piperazine ring,
(22) piperazinylcarbonyl lower alkylsulfonyl lower alkyl optionally having one lower alkyl group on the piperazine ring,
(23) lower alkanoyl lower alkyl,
(24) carboxy lower alkyl,
(25) lower alkoxycarbonyl lower alkyl,
(26) piperazinyl lower alkoxycarbonyl lower alkyl optionally having one lower alkyl group on the piperazine ring,
(27) morpholinyl lower alkyl,
(28) oxazepanyl lower alkyl,
(29) amino lower alkyl optionally having one or two lower alkyl groups,
(30) piperazyl lower alkyl optionally having, on the piperazine ring, one substituent selected from the group consisting of lower alkyl, lower alkoxy lower alkyl, and pyridyl,
(31) piperidyl lower alkyl optionally having one morpholinyl group,
(32) azetidyl lower alkyl optionally having one hydroxy group on the azetidine ring,
(33) isoindolinyl lower alkyl optionally having one or two oxo groups,
(34) amino lower alkanoyloxy lower alkyl optionally having one or two substituents selected from the group consisting of lower alkyl and lower alkoxycarbonyl,
(35) carbamoyl lower alkyl optionally having one or two substituents selected from lower alkyl; morpholinyl lower alkyl; piperidyl optionally having one substituent selected from the group consisting of lower alkyl and lower alkoxycarbonyl; and piperazinyl lower alkyl optionally having one lower alkyl group,
(36) phosphonooxy lower alkyl optionally having one or two lower alkyl groups on the phosphonooxy group,
(37) phosphonooxy lower alkanoyloxy lower alkyl optionally having one or two lower alkyl groups on the phosphonooxy group,
(38) benzoyloxy lower alkyl optionally having, on the benzene ring, one substituent selected from the group consisting of hydroxy, benzyloxy, and phosphonooxy optionally having one or two lower alkyl groups,
(39) tetrahydropyranyl optionally having one to four substituents selected from the group consisting of hydroxy, hydroxy lower alkyl and carboxyl, or
(40) lower alkanoylamino lower alkyl optionally having, on the lower alkanoyl group, one or two substituents selected from the group consisting of halogen; hydroxy; amino; lower alkoxycarbonylamino; piperazinyl optionally having one lower alkoxy lower alkyl group; imidazolyl; and morpholinylpiperidyl;

R₂ represents:
(1) hydrogen,
(2) lower alkyl,
(3) lower alkanoyl,
(4) hydroxy lower alkyl,
(5) carboxy,
(6) lower alkoxycarbonyl,
(7) carbamoyl optionally having one or two substituents selected from the group consisting of lower alkyl; halogen-substituted lower alkyl; hydroxy lower alkyl; piperazinyl lower alkyl optionally having one lower alkyl group on the piperazine ring; and morpholinyl lower alkyl,
(8) carbamoyl lower alkyl optionally having one lower alkyl group on the carbamoyl group,
(9) morpholinyl lower alkyl,
(10) piperazinyl lower alkyl optionally having, on the piperazine ring, one substituent selected from the group consisting of lower alkyl and pyridyl optionally having one lower alkyl group,
(11) diazepanyl lower alkyl, or
(12) amino lower alkyl optionally having, on the amino group, one or two substituents selected from the group consisting of lower alkyl, halogen-substituted lower alkyl, hydroxy lower alkyl, and morpholinyl lower alkyl;

R₃ represents phenyl, thienyl, furyl, pyrazolyl, or pyrimidinyl, wherein:
the aromatic or heterocyclic ring represented by R₃ may be substituted with one or two substituents selected from the group consisting of the following substituents (1) to (14):
(1) lower alkyl,
(2) lower alkoxy,
(3) lower alkanoyl,
(4) halogen,
(5) hydroxy,
(6) hydroxy lower alkyl,
(7) hydroxy lower alkoxy,
(8) tetrahydropyranyloxy lower alkoxy,
(9) carboxy lower alkoxy,
(10) lower alkoxycarbonyl lower alkoxy,
(11) pyrrolidinylcarbonyl,
(12) carbamoyl lower alkoxy optionally having one or two lower alkyl groups,
(13) carbamoyl optionally having one morpholinyl lower alkyl group, and
(14) morpholinylpiperidylcarbonyl;

R₄ represents halogen, lower alkyl, or lower alkoxy;
R₅ represents hydrogen or halogen;
R₆ represents hydrogen or lower alkoxy; and
R₇ represents any of the following groups (1) to (11):
(1) hydrogen,
(2) lower alkoxy,
(3) hydroxy lower alkoxy,
(4) benzyloxy lower alkoxy,
(5) lower alkoxy lower alkoxy,
(6) carbamoyl lower alkoxy optionally having one substituent selected from the group consisting of lower alkyl and morpholinyl lower alkyl, (7) amino optionally having one or two substituents selected from the group consisting of lower alkyl and cyclo $C_3$-$C_8$ alkyl,
(8) cyclo $C_3$-$C_8$ alkyloxy,
(9) carboxy lower alkoxy,
(10) lower alkoxycarbonyl lower alkoxy, and
(11) pyrrolidinyl.

Item 8. A quinolone compound of General Formula (1) or a salt thereof according to Item 7, wherein
$R_1$ represents:
(3) halogen-substituted lower alkyl,
(4) lower alkenyl,
(5) lower alkanoyl,
(6) halogen-substituted lower alkanoyl,
(8) benzyloxy lower alkyl,
(10) benzyloxy lower alkanoyl,
(11) lower alkylthio lower alkyl,
(12) amino lower alkylthio lower alkyl optionally having one or two lower alkyl groups,
(13) hydroxy lower alkylthio lower alkyl,
(14) carboxy lower alkylthio lower alkyl,
(15) lower alkoxycarbonyl lower alkylthio lower alkyl,
(16) amino lower alkylthiocarbonyl lower alkyl optionally having one or two lower alkyl groups,
(17) hydroxy lower alkylsulfonyl lower alkyl,
(18) carboxy lower alkylsulfonyl lower alkyl,
(19) lower alkoxycarbonyl lower alkylsulfonyl lower alkyl,
(20) lower alkanoyl lower alkylsulfonyl lower alkyl,
(21) piperazinyl lower alkylsulfonyl lower alkyl optionally having one lower alkyl group on the piperazine ring,
(22) piperazinylcarbonyl lower alkylsulfonyl lower alkyl optionally having one lower alkyl group on the piperazine ring,
(24) carboxy lower alkyl,
(25) lower alkoxycarbonyl lower alkyl,
(26) piperazinyl lower alkoxycarbonyl lower alkyl optionally having one lower alkyl group on the piperazine ring,
(27) morpholinyl lower alkyl,
(29) amino lower alkyl optionally having one or two lower alkyl groups,
(30) piperazyl lower alkyl optionally having, on the piperazine ring, one substituent selected from the group consisting of lower alkyl, lower alkoxy lower alkyl, and pyridyl,
(31) piperidyl lower alkyl optionally having one morpholinyl group,
(32) azetidyl lower alkyl optionally having one hydroxy group on the azetidine ring,
(33) isoindolinyl lower alkyl optionally having one or two oxo groups,
(34) amino lower alkanoyloxy lower alkyl optionally having one or two substituents selected from the group consisting of lower alkyl and lower alkoxycarbonyl,
(35) carbamoyl lower alkyl optionally having one or two substituents selected from lower alkyl; morpholinyl lower alkyl; piperidyl optionally having one substituent selected from the group consisting of lower alkyl and lower alkoxycarbonyl; and piperazinyl lower alkyl optionally having one lower alkyl group,
(36) phosphonooxy lower alkyl optionally having one or two lower alkyl groups on the phosphonooxy group,
(37) phosphonooxy lower alkanoyloxy lower alkyl optionally having one or two lower alkyl groups on the phosphonooxy group,
(38) benzoyloxy lower alkyl optionally having, on the benzene ring, one substituent selected from the group consisting of hydroxy, benzyloxy, and phosphonooxy optionally having one or two lower alkyl groups,
(39) tetrahydropyranyl optionally having one or four substituents selected from the group consisting of hydroxy, hydroxy lower alkyl and carboxyl, or
(40) lower alkanoylamino lower alkyl optionally having, on the lower alkanoyl group, one or two substituents selected from the group consisting of halogen; hydroxy; amino; lower alkoxycarbonylamino; piperazinyl optionally having one lower alkoxy lower alkyl group; imidazolyl; and morpholinylpiperidyl;
$R_2$ represents hydrogen;
$R_3$ represents phenyl, pyrazolyl, or pyrimidinyl, wherein:
the aromatic or heterocyclic ring represented by $R_3$ may be substituted with one or two substituents selected from the group consisting of the following substituents (1), (2), (4), (5), (7), (8), (10), (11), and (12):
(1) lower alkyl,
(2) lower alkoxy,
(4) halogen,
(5) hydroxy,
(7) hydroxy lower alkoxy,
(8) tetrahydropyranyloxy lower alkoxy,
(10) lower alkoxycarbonyl lower alkoxy,
(11) pyrrolidinylcarbonyl, and
(12) carbamoyl lower alkoxy;
$R_4$ represents halogen;
$R_5$ represents hydrogen or halogen;
$R_6$ represents hydrogen; and
$R_7$ represents any of the following groups (2), (7), (8) and (11):
(2) lower alkoxy,
(7) amino optionally having one or two substituents selected from the group consisting of lower alkyl and cyclo $C_3$-$C_8$ alkyl,
(8) cyclo $C_3$-$C_8$ alkyloxy, and
(11) pyrrolidinyl.

Item 9. A quinolone compound of General Formula (1) or a salt thereof according to Item 1, wherein
$R_1$ represents:
(1) hydrogen, or
(2) lower alkyl;
$R_2$ represents:
(3) lower alkanoyl,
(4) hydroxy lower alkyl,
(5) carboxy,
(6) lower alkoxycarbonyl,
(7) carbamoyl optionally having one or two substituents selected from the group consisting of lower alkyl; halogen-substituted lower alkyl; hydroxy lower alkyl; piperazinyl lower alkyl optionally having one lower alkyl group; and morpholinyl lower alkyl,
(8) carbamoyl lower alkyl optionally having one lower alkyl group,
(9) morpholinyl lower alkyl,
(10) piperazinyl lower alkyl optionally having one substituent selected from the group consisting of lower alkyl and pyridyl optionally having one lower alkyl group,
(11) diazepanyl lower alkyl,
(12) amino lower alkyl optionally having one or two substituents selected from the group consisting of lower alkyl, halogen-substituted lower alkyl, hydroxy lower alkyl, and morpholinyl lower alkyl,
(13) lower alkoxycarbonyl lower alkyl, or
(14) carboxy lower alkyl;

$R_3$ represents phenyl, thienyl, furyl, pyrazolyl, or pyrimidinyl, wherein:
the aromatic or heterocyclic ring represented by $R_3$ may be substituted with one substituent selected from the group consisting of the following substituents (1) to (14):
(1) lower alkyl,
(2) lower alkoxy,
(3) lower alkanoyl,
(4) halogen,
(5) hydroxy,
(6) hydroxy lower alkyl,
(7) hydroxy lower alkoxy,
(8) protected hydroxy lower alkoxy,
(9) carboxy lower alkoxy,
(10) lower alkoxycarbonyl lower alkoxy,
(11) pyrrolidinylcarbonyl,
(12) carbamoyl lower alkoxy optionally having one lower alkyl group,
(13) carbamoyl optionally having one morpholinyl lower alkyl group, and
(14) morpholinylpiperidylcarbonyl;
$R_4$ represents halogen, lower alkyl, or lower alkoxy;
$R_5$ represents hydrogen or halogen;
$R_6$ represents hydrogen or lower alkoxy; and
$R_7$ represents any of the following groups (1) to (11):
(1) hydrogen,
(2) lower alkoxy,
(3) hydroxy lower alkoxy,
(4) benzyloxy lower alkoxy,
(5) lower alkoxy lower alkoxy,
(6) carbamoyl lower alkoxy optionally having one substituent selected from the group consisting of lower alkyl and morpholinyl lower alkyl,
(7) amino optionally having one or two substituents selected from the group consisting of lower alkyl and cyclo $C_3$-$C_8$ alkyl,
(8) cyclo $C_3$-$C_8$ alkyloxy,
(9) carboxy lower alkoxy,
(10) lower alkoxycarbonyl lower alkoxy, and
(11) pyrrolidinyl.

Item 10. A quinolone compound of General Formula (1) or a salt thereof according to Item 9, wherein
$R_1$ represents hydrogen;
$R_2$ represents:
(3) lower alkanoyl,
(4) hydroxy lower alkyl,
(5) carboxy,
(6) lower alkoxycarbonyl,
(7) carbamoyl optionally having one or two substituents selected from the group consisting of lower alkyl; halogen-substituted lower alkyl; hydroxy lower alkyl; piperazinyl lower alkyl optionally having one lower alkyl group; and morpholinyl lower alkyl,
(8) carbamoyl lower alkyl optionally having one lower alkyl group,
(9) morpholinyl lower alkyl,
(10) piperazinyl lower alkyl optionally having one substituent selected from the group consisting of lower alkyl and pyridyl optionally having one lower alkyl group,
(11) diazepanyl lower alkyl,
(12) amino lower alkyl optionally having one or two substituents selected from the group consisting of lower alkyl, halogen-substituted lower alkyl, hydroxy lower alkyl, and morpholinyl lower alkyl, or
(14) carboxy lower alkyl;
$R_3$ represents phenyl, wherein:
the phenyl represented by $R_3$ is substituted with one lower alkoxy group,
$R_4$ represents halogen;
$R_5$ represents hydrogen;
$R_6$ represents hydrogen; and
$R_7$ represents lower alkoxy.

Item 11. A quinolone compound of General Formula (1) or a salt thereof according to Item 1, wherein
$R_1$ represents:
(1) hydrogen, or
(2) lower alkyl;
$R_2$ represents hydrogen;
$R_3$ represents phenyl, thienyl, furyl, pyrazolyl, or pyrimidinyl, wherein:
the aromatic or heterocyclic ring represented by $R_3$ may be substituted with one substituent selected from the group consisting of the following substituents (7), (8), (9), (10), (12), (13) and (14):
(7) hydroxy lower alkoxy,
(8) benzyloxy lower alkoxy,
(9) carboxy lower alkoxy,
(10) lower alkoxycarbonyl lower alkoxy,
(12) carbamoyl lower alkoxy optionally having one lower alkyl group,
(13) carbamoyl optionally having one morpholinyl lower alkyl group, and
(14) morpholinylpiperidylcarbonyl;
$R_4$ represents halogen, lower alkyl, or lower alkoxy;
$R_5$ represents hydrogen or halogen;
$R_6$ represents hydrogen or lower alkoxy; and
$R_7$ represents any of the following groups (1) to (11):
(1) hydrogen,
(2) lower alkoxy,
(3) hydroxy lower alkoxy,
(4) benzyloxy lower alkoxy,
(5) lower alkoxy lower alkoxy,
(6) carbamoyl lower alkoxy optionally having one substituent selected from the group consisting of lower alkyl and morpholinyl lower alkyl,
(7) amino optionally having one or two substituents selected from the group consisting of lower alkyl and cyclo $C_3$-$C_8$ alkyl,
(8) cyclo $C_3$-$C_8$ alkyloxy,
(9) carboxy lower alkoxy,
(10) lower alkoxycarbonyl lower alkoxy, and
(11) pyrrolidinyl.

Item 12. A quinolone compound of General Formula (1) or a salt thereof according to Item 11, wherein
$R_1$ represents hydrogen;
$R_3$ represents phenyl, wherein:
the phenyl represented by $R_3$ may be substituted with one substituent selected from the group consisting of the following substituents (7) to (14):
(7) hydroxy lower alkoxy,
(8) benzyloxy lower alkoxy,
(9) carboxy lower alkoxy,
(10) lower alkoxycarbonyl lower alkoxy,
(11) pyrrolidinylcarbonyl,
(12) carbamoyl lower alkoxy optionally having one lower alkyl group,
(13) carbamoyl optionally having one morpholinyl lower alkyl group, and
(14) morpholinylpiperidylcarbonyl;
$R_4$ represents halogen;
$R_5$ represents hydrogen;

$R_6$ represents hydrogen; and
$R_7$ represents any of the following groups (2) and (11):
(2) lower alkoxy; and
(11) pyrrolidinyl.

Item 13. A quinolone compound of General Formula (1) or a salt thereof according to Item 1, wherein
$R_1$ represents:
(1) hydrogen or
(2) lower alkyl;
$R_2$ represents hydrogen;
$R_3$ represents phenyl, wherein:
the phenyl represented by $R_3$ is substituted with one lower alkoxy,
$R_4$ represents halogen, lower alkyl, or lower alkoxy;
$R_5$ represents hydrogen or halogen;
$R_6$ represents hydrogen or lower alkoxy; and
$R_7$ represents any of the following groups (4), (6), (9) and (10):
(4) benzyloxy lower alkoxy,
(6) carbamoyl lower alkoxy optionally having one substituent selected from the group consisting of lower alkyl and morpholinyl lower alkyl,
(9) carboxy lower alkoxy, and
(10) lower alkoxycarbonyl lower alkoxy.

Item 14. A quinolone compound of General Formula (1) or a salt thereof according to Item 13, wherein
$R_1$ represents hydrogen;
$R_3$ represents phenyl, wherein:
the phenyl represented by $R_3$ may be substituted with one lower alkoxy,
$R_4$ represents halogen;
$R_5$ represents hydrogen;
$R_6$ represents hydrogen; and
$R_7$ represents any of the following groups (4), (6), (9), (10) and (11):
(4) benzyloxy lower alkoxy,
(6) carbamoyl lower alkoxy optionally having one substituent selected from the group consisting of lower alkyl and morpholinyl lower alkyl,
(9) carboxy lower alkoxy,
(10) lower alkoxycarbonyl lower alkoxy, and
(11) pyrrolidinyl.

Item 15. A pharmaceutical composition comprising a quinolone compound of General Formula (1) of any one of Items 1 to 14 or a salt thereof as an active ingredient; and a pharmaceutically acceptable carrier.

Item 16. A prophylactic and/or therapeutic agent for neurodegenerative diseases, diseases induced by neurological dysfunction, or diseases induced by deterioration of mitochondrial function, the agent comprising as an active ingredient a quinolone compound of General Formula (1) of any one of Items 1 to 14 or a salt thereof.

Item 17. A prophylactic and/or therapeutic agent according to Item 16, wherein the neurodegenerative disease is selected from the group consisting of Parkinson's disease, Parkinson's syndrome, juvenile parkinsonism, striatonigral degeneration, progressive supranuclear palsy, pure akinesia, Alzheimer's disease, Pick's disease, prion disease, corticobasal degeneration, diffuse Lewy body disease, Huntington's disease, chorea-acanthocytosis, benign hereditary chorea, paroxysmal choreoathetosis, essential tremor, essential myoclonus, Gilles de la Tourette's syndrome, Rett's syndrome, degenerative ballism, dystonia musculorum deformance, athetosis, spasmodic torticollis, Meige syndrome, cerebral palsy, Wilson's disease, Segawa's disease, Hallervorden-Spatz syndrome, neuroaxonal dystrophy, pallidal atrophy, spino-cerebellar degeneration, cerebral cortical atrophy, Holmes-type cerebellar atrophy, olivopontocerebellar atrophy, hereditary olivopontocerebellar atrophy, Joseph disease, dentatorubro-pallidoluysian atrophy, Gerstmann-Straussler-Scheinker disease, Friedreich's Ataxia, Roussy-Levy syndrome, May-White syndrome, congenital cerebellar ataxia, hereditary episodic ataxia, ataxia telangiectasia, amyotrophic lateral sclerosis, progressive bulbar palsy, spinal progressive muscular atrophy, spinobulbar muscular atrophy, Werdnig-Hoffmann disease, Kugelberg-Welander disease, hereditary spastic paraparesis, syringomyelia, syringobulbia, Arnold-Chiari malformation, Stiffman syndrome, Klippel-Feil syndrome, Fazio-Londe syndrome, lower myelopathy, Dandy-Walker syndrome, spina bifida, Sjogren-Larsson syndrome, radiation myelopathy, age-related macular degeneration, and cerebral apoplexy selected from the group consisting of cerebral infarction and cerebral hemorrhage and/or associated dysfunction or neurologic deficits.

Item 18. A prophylactic and/or therapeutic agent according to Item 16, wherein the disease induced by neurological dysfunction is selected from the group consisting of spinal cord injury, chemotherapy-induced neuropathy, diabetic neuropathy, radiation damage, and a demyelinating disease selected from the group consisting of multiple sclerosis, acute disseminated encephalomyelitis, transverse myelitis, progressive multifocal leucoencephalopathy, subacute sclerosing panencephalitis, chronic inflammatory demyelinating polyneuropathy and Guillain-Barre syndrome.

Item 19. A prophylactic and/or therapeutic agent according to Item 16, wherein the disease induced by deterioration of mitochondrial function is selected from the group consisting of Pearson's syndrome, diabetes, deafness, malignant migraine, Leber's disease, MELAS, MERRF, MERRF/MELAS overlap syndrome, NARP, pure myopathy, mitochondrial cardiomyopathy, myopathy, dementia, gastrointestinal ataxia, acquired sideroblastic anemia, aminoglycoside-induced hearing loss, complex III deficiency due to inherited variants of cytochrome b, multiple symmetrical lipomatosis, ataxia, myoclonus, retinopathy, MNGIE, ANT1 disease, Twinkle disease, POLG disease, recurrent myoglobinuria, SANDO, ARCO, complex I deficiency, complex II deficiency, optic nerve atrophy, fatal infantile complex IV deficiency, mitochondrial DNA deficiency, mitochondrial DNA deficiency syndrome, Leigh's encephalomyelopathy, chronic-progressive-external-ophthalmoplegia syndrome (CPEO), Kearns-Sayre syndrome, encephalopathy, lactacidemia, myoglobinuria, drug-induced mitochondrial diseases, schizophrenia, major depression disorder, bipolar I disorder, bipolar II disorder, mixed episode, dysthymic disorders, atypical depression, seasonal affective disorders, postpartum depression, minor depression, recurrent brief depressive disorder, intractable depression/chronic depression, double depression, and acute renal failure.

Item 20. A prophylactic and/or therapeutic agent comprising as an active ingredient the compound of any one of Items 1 to 14 or a salt thereof, the prophylactic and/or therapeutic agent being used for treating or preventing ischemic heart diseases and/or associated dysfunction, cardiac failure, myocardosis, aortic dissection, immunodeficiency, autoimmune diseases, pancreatic insufficiency, diabetes, atheroembolic renal disease, polycytic kidney, medullary cystic disease, renal cortical necrosis, malignant nephrosclerosis, renal failure, hepatic encephalopathy, liver failure, chronic obstructive pulmonary disease, pulmonary embolism, bronchiectasis, silicosis, black lung, idiopathic pulmonary fibrosis, Stevens-Johnson syndrome, toxic epidermal necrolysis, muscular dystrophy, clostridial muscle necrosis, and femoral condyle necrosis.

Item 21. Use of a quinolone compound of General Formula (1) of any one of Item 1 to 20 or a salt thereof as a drug.

Item 22. A method for treating or preventing neurodegenerative diseases, diseases induced by neurological dysfunction, or diseases induced by deterioration of mitochondrial function, comprising administering a quinolone compound of General Formula (1) of Item 1 or a salt thereof to a human or an animal.

Item 23. A process for producing a quinolone compound represented by Formula (1b):

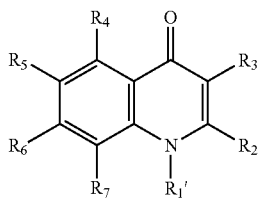

wherein $R_2$, $R_3$, $R_4$, $R_5$, $R_6$, and $R_7$ are as defined in Item 1, and $R_1'$ is a group represented by $R_1$ as defined in Item 1 other than hydrogen, or a salt thereof; the process comprising reacting a compound represented by the formula:

wherein $X_2$ represents a group that undergoes the same substitution reaction as that of a halogen or a halogen atom, with a compound represented by the formula:

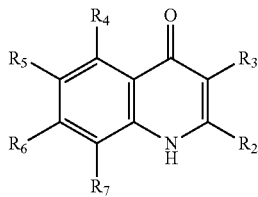

wherein $R_2$, $R_3$, $R_4$, $R_5$, $R_6$ and $R_7$ are as defined in Item 1.

A further embodiment of the quinolone compound represented by Formula (1) is as follows:

Formula (1):

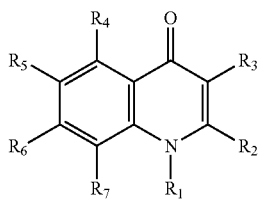

wherein $R_1$ represents:
(1) hydrogen,
(2) lower alkyl,
(3) halogen-substituted lower alkyl,
(4) lower alkenyl,
(5) lower alkanoyl,
(6) halogen-substituted lower alkanoyl,
(7) hydroxy lower alkyl,
(8) phenyl lower alkoxy lower alkyl,
(9) hydroxy lower alkanoyl,
(10) phenyl lower alkoxy lower alkanoyl,
(11) lower alkylthio lower alkyl,
(12) amino lower alkylthio lower alkyl optionally having, on the amino group, one or two, and preferably two, lower alkyl groups;
(13) hydroxy lower alkylthio lower alkyl,
(14) carboxy lower alkylthio lower alkyl,
(15) lower alkoxycarbonyl lower alkylthio lower alkyl,
(16) amino lower alkylthiocarbonyl lower alkyl optionally having, on the amino group, one or two, and preferably two, lower alkyl groups,
(17) hydroxy lower alkylsulfonyl lower alkyl,
(18) carboxy lower alkylsulfonyl lower alkyl,
(19) lower alkoxycarbonyl lower alkylsulfonyl lower alkyl,
(20) lower alkanoyl lower alkylsulfonyl lower alkyl,
(21) piperazinyl lower alkylsulfonyl lower alkyl optionally having one lower alkyl group on the piperazine ring,
(22) piperazinylcarbonyl lower alkylsulfonyl lower alkyl optionally having one lower alkyl group on the piperazine ring,
(23) lower alkanoyl lower alkyl,
(24) carboxy lower alkyl,
(25) lower alkoxycarbonyl lower alkyl,
(26) piperazinyl lower alkoxycarbonyl lower alkyl optionally having one lower alkyl group on the piperazine ring,
(27) morpholinyl lower alkyl,
(28) oxazepanyl lower alkyl,
(29) amino lower alkyl optionally having one lower alkyl group on the amino group,
(30) piperazyl lower alkyl optionally having, on the piperazine ring, one substituent selected from the group consisting of lower alkyl, lower alkoxy lower alkyl, and pyridyl,
(31) piperidyl lower alkyl optionally having one morpholinyl group on the piperidine ring,
(32) azetidyl lower alkyl optionally having one hydroxy group on the azetidine ring,
(33) isoindolinyl lower alkyl optionally having two oxo groups on the isoindoline ring,
(34) amino lower alkanoyloxy lower alkyl optionally having, on the amino group, one or two substituents selected from the group consisting of lower alkyl and lower alkoxycarbonyl,
(35) carbamoyl lower alkyl optionally having, on the carbamoyl group, one or two substituents selected from lower alkyl; morpholinyl lower alkyl; piperidyl optionally having one substituent selected from the group consisting of lower alkyl and lower alkoxycarbonyl; and piperazinyl lower alkyl optionally having one lower alkyl group,
(36) phosphonooxy lower alkyl optionally having one or two lower alkyl groups on the phosphonooxy group,
(37) phosphonooxy lower alkanoyloxy lower alkyl optionally having one or two lower alkyl groups on the phosphonooxy group,
(38) benzoyloxy lower alkyl optionally having, on the benzene ring, one substituent selected from the group consisting of hydroxy, protected hydroxy, and phosphonooxy optionally having one or two lower alkyl groups,
(39) tetrahydropyranyl optionally having one to four, and preferably four, substituents selected from the group consisting of hydroxy, hydroxy lower alkyl and carboxyl; and, more preferably, tetrahydropyranyl having three hydroxy groups and one hydroxy lower alkyl group, or
(40) lower alkanoylamino lower alkyl optionally having, on the lower alkanoyl group, one or two substituents selected from the group consisting of halogen; hydroxy; amino; lower alkoxycarbonylamino; piperazinyl optionally having one lower alkoxy lower alkyl group; imidazolyl; and morpholinylpiperidyl;

$R_2$ represents:
(1) hydrogen,
(2) lower alkyl,
(3) lower alkanoyl,
(4) hydroxy lower alkyl,
(5) carboxy;
(6) lower alkoxycarbonyl,
(7) carbamoyl optionally having one or two substituents selected from the group consisting of lower alkyl; halogen-substituted lower alkyl; hydroxy lower alkyl; piperazinyl lower alkyl optionally having one lower alkyl group on the piperazine ring; and morpholinyl lower alkyl,
(8) carbamoyl lower alkyl optionally having one lower alkyl group on the carbamoyl group,
(9) morpholinyl lower alkyl,
(10) piperazinyl lower alkyl optionally having, on the piperazine ring, one substituent selected from the group consisting of lower alkyl and pyridyl optionally having one lower alkyl group,
(11) diazepanyl lower alkyl, or
(12) amino lower alkyl optionally having, on the amino group, one or two substituents selected from the group consisting of lower alkyl, halogen-substituted lower alkyl, hydroxy lower alkyl, and morpholinyl lower alkyl;

$R_3$ represents phenyl, thienyl, furyl, pyrazolyl, or pyrimidinyl, wherein:

the aromatic or heterocyclic ring represented by $R_3$ may be substituted with one or two substituents selected from the group consisting of the following substituents (1) to (14):
(1) lower alkyl,
(2) lower alkoxy,
(3) lower alkanoyl,
(4) halogen,
(5) hydroxy,
(6) hydroxy lower alkyl,
(7) hydroxy lower alkoxy,
(8) protected hydroxy lower alkoxy,
(9) carboxy lower alkoxy,
(10) lower alkoxycarbonyl lower alkoxy,
(11) pyrrolidinylcarbonyl,
(12) carbamoyl lower alkoxy optionally having one lower alkyl group on the carbamoyl group,
(13) carbamoyl optionally having one morpholinyl lower alkyl group, and
(14) morpholinylpiperidylcarbonyl;

$R_4$ represents halogen, lower alkyl, or lower alkoxy;
$R_5$ represents hydrogen or halogen;
$R_4$ and $R_5$ may be linked to form a group represented by any of the following formulae:

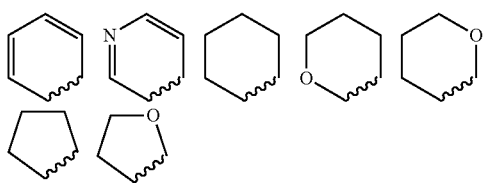

or a group represented by the following formula:

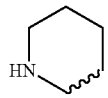

the group optionally having one or two substituents selected from the group consisting of lower alkyl or oxo;
$R_6$ represents hydrogen or lower alkoxy;
$R_7$ represents any of the following groups (1) to (11):
(1) hydrogen,
(2) lower alkoxy,
(3) hydroxy lower alkoxy,
(4) protected hydroxy lower alkoxy,
(5) lower alkoxy lower alkoxy,
(6) carbamoyl lower alkoxy optionally having, on the carbamoyl group, one substituent selected from the group consisting of lower alkyl and morpholinyl lower alkyl,
(7) amino optionally having two substituents selected from the group consisting of lower alkyl and cyclo $C_3$-$C_8$ alkyl,
(8) cyclo $C_3$-$C_8$ alkyloxy,
(9) carboxy lower alkoxy,
(10) lower alkoxycarbonyl lower alkoxy, and
(11) pyrrolidinyl; and $R_6$ and $R_7$ may be linked to form a group represented by any of the following formulae:

Preferred embodiments of various definitions used herein and included in the scope of the invention are described next.

The term "lower" refers to a group having 1 to 6 carbons (preferably 1 to 4 carbons) unless otherwise specified.

Examples of lower alkyl groups include straight or branched $C_{1-6}$ (preferably $C_{1-4}$) alkyl groups such as methyl, ethyl, n-propyl, isopropyl, n-butyl, isobutyl, tert-butyl, sec-butyl, n-pentyl, 1-ethylpropyl, isopentyl, neopentyl, n-hexyl, 1,2,2-trimethylpropyl, 3,3-dimethylbutyl, 2-ethylbutyl, isohexyl, 3-methylpentyl, etc.

Examples of lower alkenyl groups include straight or branched $C_{2-6}$ alkenyl groups with 1-3 double bonds, including both trans and cis forms. Examples thereof include vinyl, 1-propenyl, 2-propenyl, 1-methyl-1-propenyl, 2-methyl-1-propenyl, 2-methyl-2-propenyl, 2-propenyl, 2-butenyl, 1-butenyl, 3-butenyl, 2-pentenyl, 1-pentenyl, 3-pentenyl, 4-pentenyl, 1,3-butadienyl, 1,3-pentadienyl, 2-penten-4-yl, 2-hexenyl, 1-hexenyl, 5-hexenyl, 3-hexenyl, 4-hexenyl, 3,3-dimethyl-1-propenyl, 2-ethyl-1-propenyl, 1,3,5-hexatrienyl, 1,3-hexadienyl, 1,4-hexadienyl, etc.

Examples of $C_3$-$C_8$ cycloalkyl groups include cyclopropyl, cyclobutyl, cyclopentyl, cyclohexyl, cycloheptyl, cyclooctyl, etc.

The $C_3$-$C_8$ cycloalkyl moieties of the $C_3$-$C_8$ cycloalkyloxy groups are as described above.

Examples of $C_3$-$C_8$ cycloalkyl lower alkyl groups include the lower alkyl groups having one to three (preferably one) $C_3$-$C_8$ cycloalkyl group(s) described above.

Examples of lower alkoxy groups include straight or branched $C_{1-6}$ (preferably $C_{1-4}$) alkoxy groups such as methoxy, ethoxy, n-propoxy, isopropoxy, n-butoxy, isobutoxy, tert-butoxy, sec-butoxy, n-pentyloxy, isopentyloxy, neopentyloxy, n-hexyloxy, isohexyloxy, 3-methylpentyloxy, etc.

Examples of lower alkoxy lower alkyl groups include the lower alkyl groups having one to three (preferably one) lower alkoxy group(s) described above.

Examples of halogen atoms include fluorine, chlorine, bromine, and iodine.

Examples of halogen-substituted lower alkyl groups include the lower alkyl groups having one to seven halogen atom(s), preferably one to three halogen atom(s). Examples thereof include fluoromethyl, difluoromethyl, trifluoromethyl, chloromethyl, dichloromethyl, trichloromethyl, bromomethyl, dibromomethyl, dichlorofluoromethyl, 2,2-difluoroethyl, 2,2,2-trifluoroethyl, pentafluoroethyl, 2-fluoroethyl, 2-bromoethyl, 2-chloroethyl, 3-bromopropyl, 3-chloropropyl, 3,3,3-trifluoropropyl, heptafluoropropyl, 2,2,3,3,3-pentafluoropropyl, heptafluoroisopropyl, 3-chloropropyl, 2-chloropropyl, 3-bromopropyl, 4,4,4-trifluorobutyl, 4,4,4,3,3-pentafluorobutyl, 4-chlorobutyl, 4-bromobutyl, 2-chlorobutyl, 5,5,5-trifluoropentyl, 5-chloropentyl, 6,6,6-trifluorohexyl, 6-chlorohexyl, perfluorohexyl, etc.

Examples of halogen-substituted lower alkoxy groups include the lower alkoxy groups having one to seven halogen atom(s), preferably one to three halogen atom(s). Examples thereof include fluoromethoxy, difluoromethoxy, trifluoromethoxy, chloromethoxy, dichloromethoxy, trichloromethoxy, bromomethoxy, dibromomethoxy, dichlorofluoromethoxy, 2,2,2-trifluoroethoxy, pentafluoroethoxy, 2-chloroethoxy, 3,3,3-trifluoropropoxy, heptafluoropropoxy, heptafluoroisopropoxy, 3-chloropropoxy, 2-chloropropoxy, 3-bromopropoxy, 4,4,4-trifluorobutoxy, 4,4,4,3,3-pentafluorobutoxy, 4-chlorobutoxy, 4-bromobutoxy, 2-chlorobutoxy, 5,5,5-trifluoropentoxy, 5-chloropentoxy, 6,6,6-trifluorohexyloxy, 6-chlorohexyloxy, etc.

Examples of lower alkylthio groups include alkylthio groups wherein the alkyl moiety is the lower alkyl group mentioned above.

Examples of lower alkanoyl groups include straight or branched $C_{1-6}$ (preferably $C_{1-4}$) alkanoyl groups such as formyl, acetyl, propionyl, butyryl, isobutyryl, pentanoyl, tert-butylcarbonyl, hexanoyl, etc.

Examples of halogen-substituted lower alkanoyl groups include the lower alkanoyl groups having one to seven halogen atom(s), preferably one to three halogen atom(s). Examples thereof include fluoroacetyl, difluoroacetyl, trifluoroacetyl, chloroacetyl, dichloroacetyl, bromoacetyl, dibromoacetyl, 2,2-difluoroethyl, 2,2,2-trifluoropropionyl, pentafluoropropionyl, 3-chlorobutanoyl, 3,3,3-trichlorobutanoyl, 4-chlorobutanoyl, etc.

Examples of protected hydroxy groups include the lower alkyl groups described above, the lower alkanoyl groups described above, phenyl (lower) alkyl groups (such as benzyl, 4-methoxybenzyl, trityl, etc.), tetrahydropyranyl groups, etc.

Examples of hydroxy lower alkyl groups include the lower alkyl groups having one to three (preferably one) hydroxy group(s).

Examples of protected hydroxy lower alkyl groups include the lower alkyl groups having one to three (preferably one) protected hydroxy group(s) described above.

Examples of amino lower alkanoyl groups include the lower alkanoyl groups having one to three (preferably one) amino group(s).

Examples of hydroxy lower alkanoyl groups include the lower alkanoyl groups having one to three (preferably one) hydroxy group(s).

Examples of protected hydroxy lower alkanoyl groups include the lower alkanoyl groups having one to three (preferably one) protected hydroxy group(s) described above.

Examples of phosphonooxy lower alkanoyl groups include the lower alkanoyl groups having one to three (preferably one) protected phosphonooxy group(s).

The phosphonooxy lower alkanoyl moieties of the phosphonooxy lower alkanoyloxy groups are as described above.

Examples of phosphonooxy lower alkanoyloxy lower alkyl groups include the lower alkyl groups having one to three (preferably one) phosphonooxy lower alkanoyloxy group(s) described above.

Examples of amino lower alkyl groups include the lower alkyl groups having one to three (preferably one) amino group(s).

Examples of carboxy lower alkyl groups include the lower alkyl groups having one to three (preferably one) carboxy group(s).

Examples of carbamoyl lower alkyl groups include the lower alkyl groups having one to three (preferably one) carbamoyl group(s).

Examples of lower alkanoyl lower alkyl groups include the lower alkyl groups having one to three (preferably one) lower alkanoyl group(s).

Examples of lower alkoxy lower alkyl groups include the lower alkyl groups having one to three (preferably one) lower alkoxy group(s).

Examples of phosphonooxy lower alkyl groups include the lower alkyl groups having one to three (preferably one) phosphonooxy group(s).

Examples of lower alkylthio lower alkyl groups include the lower alkyl groups having one to three (preferably one) lower alkylthio group(s) described above.

The lower alkanoyl moieties of the lower alkanoyl amino groups are as described above.

Examples of lower alkanoyl amino lower alkyl groups include the lower alkyl groups having one to three (preferably one) lower alkanoyl amino group(s) described above.

The amino lower alkyl moieties of the amino lower alkylthio groups are as described above.

Examples of amino lower alkylthio lower alkyl groups include the lower alkyl groups having one to three (preferably one) amino lower alkylthio group(s) described above.

The hydroxy lower alkyl moieties of the hydroxy lower alkylthio groups are as described above.

Examples of hydroxy lower alkylthio lower alkyl groups include the lower alkyl groups having one to three (preferably one) hydroxy lower alkylthio group(s) described above.

The carboxy lower alkyl moieties of the carboxy lower alkylthio groups are as described above.

Examples of carboxy lower alkylthio lower alkyl groups include the lower alkyl groups having one to three (preferably one) carboxy lower alkylthio group(s) described above.

The lower alkoxy moieties of the lower alkoxy carbonyl groups are as described above.

The lower alkoxy carbonyl moieties of the lower alkoxy carbonyl amino groups are as described above.

Examples of lower alkoxy carbonyl lower alkyl groups include the lower alkyl groups having one to three (preferably one) lower alkoxy carbonyl group(s) described above.

The lower alkoxy carbonyl lower alkyl moieties of the lower alkoxy carbonyl lower alkylthio groups are as described above.

Examples of lower alkoxy carbonyl lower alkylthio lower alkyl groups include the lower alkyl groups having one to three (preferably one) lower alkoxy carbonyl lower alkylthio group(s) described above.

The lower alkyl moieties of the lower alkylthio carbonyl groups are as described above.

The amino lower alkanoyl moieties of the amino lower alkanoyloxy groups are as described above.

Examples of amino lower alkanoyloxy lower alkyl groups include the lower alkyl groups having one to three (preferably one) amino lower alkanoyloxy group(s).

Examples of amino lower alkylthio carbonyl groups include the lower alkylthio carbonyl groups having one to three (preferably one) amino group(s).

Examples of amino lower alkylthio carbonyl lower alkyl groups include the lower alkyl groups having one to three (preferably one) amino lower alkylthio carbonyl group(s) described above.

Examples of benzoyloxy lower alkyl groups include the lower alkyl groups having one to three (preferably one) benzoyloxy group(s).

The hydroxy lower alkyl moieties of the hydroxy lower alkylsulfonyl groups are as described above.

Examples of hydroxy lower alkylsulfonyl lower alkyl groups include the lower alkyl groups having one to three (preferably one) hydroxy lower alkylsulfonyl group(s) described above.

The carboxy lower alkyl moieties of the carboxy lower alkylsulfonyl groups are as described above.

Examples of carboxy lower alkylsulfonyl lower alkyl groups include the lower alkyl groups having one to three (preferably one) carboxy lower alkylsulfonyl group(s) described above.

The lower alkoxy carbonyl lower alkyl moieties of the lower alkoxy carbonyl lower alkylsulfonyl groups are as described above.

Examples of lower alkoxy carbonyl lower alkylsulfonyl lower alkyl groups include the lower alkyl groups having one to three (preferably one) lower alkoxy carbonyl lower alkylsulfonyl group(s) described above.

The lower alkanoyl lower alkyl moieties of the lower alkanoyl lower alkylsulfonyl groups are as described above.

Examples of lower alkanoyl lower alkylsulfonyl lower alkyl groups include the lower alkyl groups having one to three (preferably one) lower alkanoyl lower alkylsulfonyl group(s) described above.

Examples of hydroxy lower alkoxy groups include the lower alkoxy groups having one to three (preferably one) hydroxy group(s).

Examples of protected hydroxy lower alkoxy groups include the lower alkoxy groups having one to three (preferably one) protected hydroxy group(s) described above.

Examples of carboxy lower alkoxy groups include the lower alkoxy groups having one to three (preferably one) carboxy group(s).

Examples of lower alkoxy carbonyl lower alkoxy groups include the lower alkoxy groups having one to three (preferably one) lower alkoxy carbonyl groups described above.

Examples of carbamoyl lower alkoxy groups include the lower alkoxy groups having one to three (preferably one) carbamoyl group(s).

Examples of lower alkoxy lower alkoxy groups include the lower alkoxy groups having one to three (preferably one) lower alkoxy group(s) described above.

Examples of piperazinyl lower alkyl groups include the lower alkyl groups having one to three (preferably one) piperazinyl group(s).

Examples of piperazinyl lower alkylsulfonyl lower alkyl groups include the lower alkyl groups having one to three (preferably one) piperazinyl lower alkylsulfonyl group(s) wherein the piperazinyl lower alkyl moieties are as described above.

Examples of piperazinyl carbonyl lower alkylsulfonyl groups include the lower alkylsulfonyl groups having one to three (preferably one) piperazinyl carbonyl group(s).

Examples of piperazinyl carbonyl lower alkylsulfonyl lower alkyl groups include the lower alkyl groups having one to three (preferably one) piperazinyl carbonyl lower alkylsulfonyl group(s) described above.

Examples of piperazinyl lower alkoxy carbonyl groups include the lower alkoxy carbonyl groups having one to three (preferably one) piperazinyl group(s).

Examples of piperazinyl lower alkoxy carbonyl lower alkyl groups include the lower alkyl groups having one to three (preferably one) piperazinyl lower alkoxy carbonyl group(s).

Examples of morpholinyl lower alkyl groups include the lower alkyl groups having one to three (preferably one) morpholinyl group(s).

Examples of oxazepanyl lower alkyl groups include the lower alkyl groups having one to three (preferably one) oxazepanyl group(s).

Examples of piperidyl lower alkyl groups include the lower alkyl groups having one to three (preferably one) piperidyl group(s).

Examples of azetidyl lower alkyl groups include the lower alkyl groups having one to three (preferably one) azetidyl group(s).

Examples of isoindolyl lower alkyl groups include the lower alkyl groups having one to three (preferably one) isoindolyl group(s).

Examples of diazepanyl lower alkyl groups include the lower alkyl groups having one to three (preferably one) diazepanyl group(s).

The process of producing the compound of the invention is described below in detail.

The quinolone compound represented by General Formula (1) (hereinafter also referred to as Compound (1)) can be produced by various methods; for example, by a method according to the following Reaction Scheme 1 or 2.

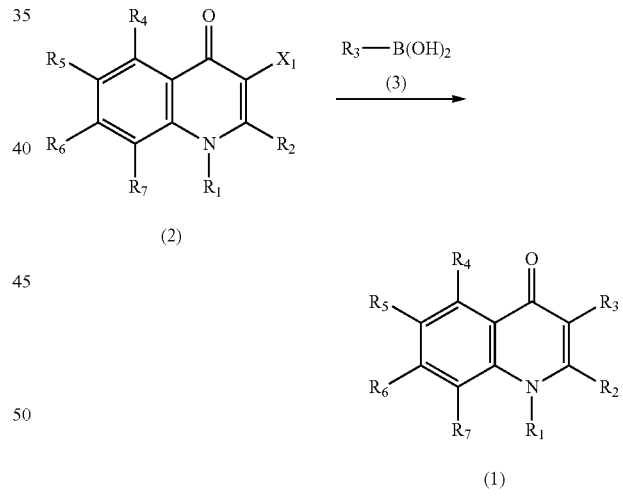

wherein $R_1$, $R_2$, $R_3$, $R_4$, $R_5$, $R_6$, and $R_7$ are as defined above, and $X_1$ represents a halogen atom.

Examples of halogen atoms represented by $X_1$ include fluorine, chlorine, bromine, and iodine.

Preferable leaving groups in the reaction include halogens. Among these, iodine is particularly preferable.

Compound (1) can be produced by the reaction of the compound represented by General Formula (2) with the compound represented by General Formula (3) in an inert solvent or without using any solvents, in the presence or absence of a basic compound, in the presence of a palladium catalyst.

Examples of inert solvents include water; ethers such as dioxane, tetrahydrofuran, diethyl ether, 1,2-dimethoxyethane, diethylene glycol dimethyl ether, and ethylene glycol dimethyl ether; aromatic hydrocarbons such as benzene, toluene, and xylene; lower alcohols such as methanol, ethanol, and isopropanol; ketones such as acetone and methyl ethyl ketone; and polar solvents such as N,N-dimethylformamide (DMF), dimethyl sulfoxide (DMSO), hexamethylphosphoric triamide, and acetonitrile. These inert solvents can be used singly or in combinations of two or more.

Palladium compounds used in the reaction are not particularly limited, but include, for example, tetravalent palladium catalysts such as sodium hexachloropalladiumate(IV) tetrahydrate and potassium hexachloropalladiumate(IV); divalent palladium catalysts such as palladium(II) chloride, palladium(II) bromide, palladium(II) acetate, palladium(II) acetylacetonato, dichlorobis(benzonitrile)palladium(II), dichlorobis(acetonitrile)palladium(II), dichlorobis(triphenylphosphine)palladium(II), dichlorotetraamminepalladium(II), dichloro(cycloocta-1,5-diene)palladium(II), palladium(II) trifluoroacetate, and 1,1'-bis(diphenylphosphino)ferrocene dichloropalladium(II)-dichloromethane complex; zerovalent palladium catalysts such as tris(dibenzylideneacetone)2 palladium(0), tris(dibenzylideneacetone)2 palladium (0) chloroform complex, and tetrakis(triphenylphosphine)palladium(0), etc. These palladium compounds are used singly or in combinations of two or more.

In the reaction, the amount of the palladium catalyst is not particularly limited, but is typically in the range from 0.000001 to 20 moles in terms of palladium relative to 1 mol of the compound of General Formula (2). The amount of the palladium catalyst is preferably in the range from 0.0001 to 5 moles in terms of palladium relative to 1 mol of the compound of General Formula (2).

This reaction advantageously proceeds in the presence of a suitable ligand. Examples of ligands of the palladium catalyst include 2,2'-bis(diphenylphosphino)-1,1'-binaphthyl(BINAP), tri-o-tolylphosphine, bis(diphenylphosphino)ferrocene, triphenylphosphine, tri-t-butylphosphine, and 9,9-dimethyl-4,5-bis(diphenylphosphino)xanthene (XANTPHOS). These ligands are used singly or in combinations of two or more.

The proportion of the palladium catalyst and ligand is not particularly limited. The amount of the ligand is about 0.1 to about 100 moles, preferably about 0.5 to about 15 moles, per mole of the palladium catalyst.

Various known inorganic and organic bases can be used as basic compounds.

Inorganic bases include, for example, alkali metal hydroxides such as sodium hydroxide, potassium hydroxide, cesium hydroxide, and lithium hydroxide; alkali metal carbonates such as sodium carbonate, potassium carbonate, cesium carbonate, and lithium carbonate; alkali metal hydrogencarbonates such as lithium hydrogencarbonate, sodium hydrogencarbonate, and potassium hydrogencarbonate; alkali metals such as sodium and potassium; phosphates such as sodium phosphate and potassium phosphate; amides such as sodium amide; and alkali metal hydrides such as sodium hydride and potassium hydride.

Organic bases include, for example, alkali metal lower alkoxides such as sodium methoxide, sodium ethoxide, sodium t-butoxide, potassium methoxide, potassium ethoxide, and potassium t-butoxide, and amines such as triethylamine, tripropylamine, pyridine, quinoline, piperidine, imidazole, N-ethyldiisopropylamine, dimethylaminopyridine, trimethylamine, dimethylaniline, N-methylmorpholine, 1,5-diazabicyclo[4.3.0]non-5-ene (DBN), 1,8-diazabicyclo[5.4.0]undec-7-ene (DBU), 1,4-diazabicyclo[2.2.2]octane (DABCO), etc.

Such basic compounds can be used singly or in combinations of two or more. More preferable basic compounds used in the reaction include alkali metal carbonates such as sodium carbonate, potassium carbonate, cesium carbonate, and lithium carbonate.

A basic compound is usually used in an amount of 0.5 to 10 moles, preferably 0.5 to 6 moles, per mole of the compound of General Formula (2).

In the above Reaction Scheme 1, the compound of General Formula (3) is usually used in an amount of at least about 1 mole, preferably about 1 to about 5 moles, per mole of the compound of General Formula (2).

The reaction can be conducted under normal pressure, under inert gas atmospheres including nitrogen, argon, etc., or under increased pressure.

The reaction proceeds usually at room temperature to 200° C., and preferably at room temperature to 150° C., and is usually completed in about 1 to about 30 hours. The reaction is also achieved by heating at 100 to 200° C. for 5 minutes to 1 hour using a microwave reactor.

The compound represented by General Formula (3), which is used as a starting material in Reaction Scheme 1 is an easily available known compound. The compound represented by General Formula (2) includes a novel compound, and the compound is produced in accordance with Reaction Scheme 6 shown below.

Reaction Scheme 2

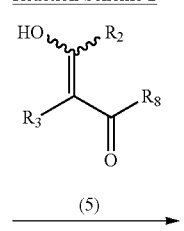

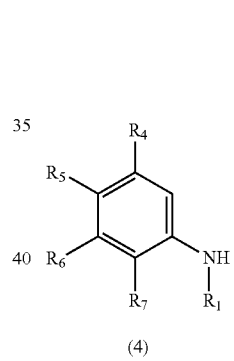

(4)

(5)

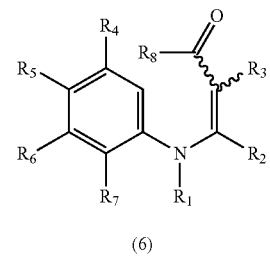

(6)

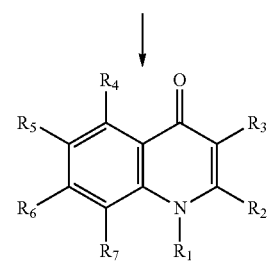

(1)

wherein $R_1$, $R_2$, $R_3$, $R_4$, $R_5$, $R_6$, and $R_7$ are as defined above, and $R_8$ represents a lower alkoxy group.

The lower alkoxy group represented by $R_8$ in General Formula (5) has the same definition as described above.

The compound represented by General Formulae (4) is reacted with the compound represented by General Formula (5) in an inert solvent or without using any solvents, in the presence or absence of an acid catalyst, thereby giving an intermediate compound represented by General Formula (6). Then, the resulting compound is cyclized to produce the compound represented by General Formula (1).

Examples of inert solvents include water; ethers such as dioxane, tetrahydrofuran, diethyl ether, 1,2-dimethoxyethane, diethylene glycol dimethyl ether, and ethylene glycol dimethyl ether; aromatic hydrocarbons such as benzene, toluene, and xylene; lower alcohols such as methanol, ethanol, and isopropanol; and polar solvents such as N,N-dimethylformamide (DMF), dimethyl sulfoxide (DMSO), hexamethylphosphoric triamide, and acetonitrile. These inert solvents can be used singly or in combinations of two or more.

Various kinds of known acid catalysts can be used, including toluenesulfonic acid, methanesulfonic acid, xylene sulfonic acid, sulfuric acid, glacial acetic acid, boron trifluoride, acidic ion exchangers, etc. These acid catalysts can be used singly or in combinations of two or more.

Among such acids, acidic ion exchangers are preferably used. Examples of acidic ion exchangers include polymeric cation exchangers available from the market such as Lewatit S100, Zeo-karb 225, Dowex 50, Amberlite IR120, or Amberlyst 15 and like styrene sulfonic acid polymers; Lewatit PN, Zeo-karb 215 or 315, and like polysulfonic acid condensates; Lewatit CNO, Duolite CS100, and like m-phenolic carboxylic acid resins; or Permutit C, Zeo-karb 226 or Amberlite IRC 50, and like polyacrylates. Of these, Amberlyst 15 is particularly preferred.

An acid catalyst is usually used in an amount of 0.0001 to 100 moles, preferably 0.5 to 6 moles, per mole of the compound of General Formula (4).

In Reaction Scheme 2, the compound of General Formula (5) is usually used in an amount of at least about 1 mole, preferably about 1 to about 5 moles, per mole of the compound of General Formula (4).

The reaction can be conducted under normal pressure, under inert gas atmospheres including nitrogen, argon, etc., or under increased pressure.

The reaction proceeds usually at room temperature to 200° C., and preferably at room temperature to 150° C. During the reaction, azeotropic removal of water is conducted until the reaction water generation is completed. The reaction is usually finished in about 1 to about 30 hours.

The process of producing the compound of General Formula (1) via a cyclization reaction of the intermediate compound represented by General Formula (6) can be carried out by heating the compound in a solvent such as diphenyl ether, or by heating the compound in the absence of a solvent. The reaction is conducted at 150 to 300° C. for 5 minutes to 2 hours.

The compound represented by General Formula (4), used as a starting material in Reaction Scheme 2 described above is a known compound or can be produced easily using a known compound. The compound represented by General Formula (5) includes a novel compound, and the compound is manufactured in accordance with, for example, the methods shown in Reaction Scheme 4 and Reaction Scheme 5 described below.

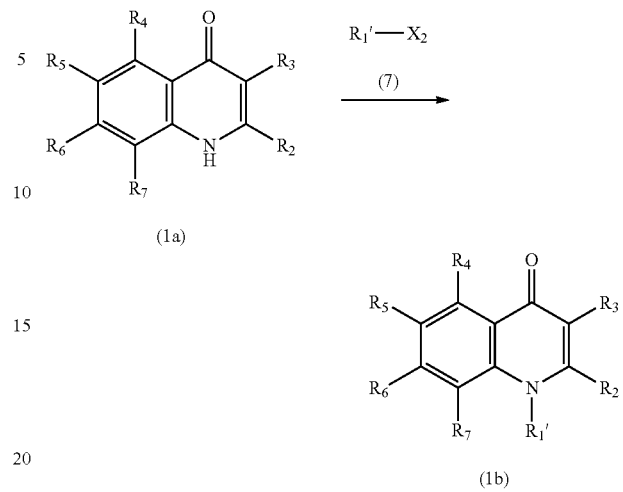

Reaction Scheme 3 wherein $R_2$, $R_3$, $R_4$, $R_5$, $R_6$, and $R_7$ are as defined above, and $R_1'$ is a group represented by $R_1$ other than hydrogen, and $X_2$ represents a group that undergoes the same substitution reaction as that of a halogen or a halogen atom.

Halogens represented by $X_2$ in General Formula (7) include the halogen atom described above. Groups that undergo the same substitution reaction as that of the halogen atoms represented by $X_2$ include lower alkane sulfonyloxy groups, aryl sulfonyloxy groups, aralkyl sulfonyloxy groups, etc.

Examples of lower alkane sulfonyloxy groups include straight or branched $C_{1-6}$ alkane sulfonyloxy groups, such as methane sulfonyloxy, ethane sulfonyloxy, n-propane sulfonyloxy, isopropane sulfonyloxy, n-butane sulfonyloxy, tert-butane sulfonyloxy, n-pentane sulfonyloxy, and n-hexane sulfonyloxy.

Examples of aryl sulfonyloxy groups include naphthyl sulfonyloxy and phenyl sulfonyloxy optionally substituted on a phenyl ring with one to three substituent(s) selected from the group consisting of straight or branched $C_{1-6}$ alkyl groups, straight or branched $C_{1-6}$ alkoxy groups, nitro groups, and halogen atoms as a substituent(s). Examples of phenyl sulfonyloxy groups optionally substituted with the above substituent(s) include phenyl sulfonyloxy, 4-methylphenyl sulfonyloxy, 2-methylphenyl sulfonyloxy, 4-nitrophenyl sulfonyloxy, 4-methoxyphenyl sulfonyloxy, 2-nitrophenyl sulfonyloxy, 3-chlorophenyl sulfonyloxy, etc. Examples of naphthyl sulfonyloxy groups include α-naphthyl sulfonyloxy, β-naphthyl sulfonyloxy, etc.

Examples of aralkyl sulfonyloxy groups include phenyl-substituted straight or branched $C_{1-6}$ alkane sulfonyloxy groups that may have, on the phenyl ring, one to three substituent(s) selected from the group consisting of straight or branched $C_{1-6}$ alkyl groups, straight or branched $C_{1-6}$ alkoxy groups, a nitro group and halogen atoms as a substituent(s); and naphtyl-substituted straight or branched $C_{1-6}$ alkane sulfonyloxy groups. Examples of alkane sulfonyloxy groups substituted with the above-mentioned phenyl group(s) include benzyl sulfonyloxy, 2-phenylethyl sulfonyloxy, 4-phenylbutyl sulfonyloxy, 4-methylbenzyl sulfonyloxy, 2-methylbenzyl sulfonyloxy, 4-nitrobenzyl sulfonyloxy, 4-methoxybenzyl sulfonyloxy, 3-chlorobenzyl sulfonyloxy, etc. Examples of alkane sulfonyloxy groups substituted with the above-mentioned naphthyl group(s) include α-naphthylmethyl sulfonyloxy, β-naphthylmethyl sulfonyloxy, etc.

The compound represented by General Formula (1b) can be produced by the reaction of the compound represented by General Formula (1a) with the compound represented by General Formula (7) in an inert solvent or without using any solvents, in the presence or absence of a basic compound.

Examples of inert solvents include water; ethers such as dioxane, tetrahydrofuran, diethyl ether, 1,2-dimethoxyethane, diethylene glycol dimethyl ether, and ethylene glycol dimethyl ether; aromatic hydrocarbons such as benzene, toluene, and xylene; lower alcohols such as methanol, ethanol, and isopropanol; ketones such as acetone and methyl ethyl ketone; and polar solvents such as N,N-dimethylformamide (DMF), dimethyl sulfoxide (DMSO), hexamethylphosphoric triamide, and acetonitrile. These inert solvents can be used singly or in combinations of two or more.

As a basic compound, various known inorganic bases and organic bases can be used.

Inorganic bases include, for example, alkali metal hydroxides such as sodium hydroxide, potassium hydroxide, cesium hydroxide, and lithium hydroxide; alkali metal carbonates such as sodium carbonate, potassium carbonate, cesium carbonate, and lithium carbonate; alkali metal hydrogen carbonates such as lithium hydrogen carbonate, sodium hydrogen carbonate, and potassium hydrogen carbonate; alkali metals such as sodium and potassium; amides such as sodium amide; and alkali metal hydrides such as sodium hydride and potassium hydride.

Organic bases include, for example, alkali metal lower alkoxides such as sodium methoxide, sodium ethoxide, sodium t-butoxide, potassium methoxide, potassium ethoxide, and potassium t-butoxide; and amines such as triethylamine, tripropylamine, pyridine, quinoline, piperidine, imidazole, N-ethyl diisopropylamine, dimethylaminopyridine, trimethylamine, dimethylaniline, N-methylmorpholine, 1,5-diazabicyclo[4.3.0]non-5-ene (DBN), 1,8-diazabicyclo[5.4.0]undec-7-ene (DBU), 1,4-diazabicyclo[2.2.2]octane (DABCO), etc.

Such basic compounds can be used singly or in combinations of two or more. More preferable basic compounds used in the reaction include inorganic bases such as sodium hydride and potassium hydride.

A basic compound is usually used in an amount of 0.5 to 10 moles, preferably 0.5 to 6 moles, per mole of the compound of General Formula (1a).

In Reaction Scheme 1, the compound of General Formula (7) is usually used in an amount of at least about 1 mole, preferably 1 to about 5 moles, per mole of the compound of General Formula (1a).

The reaction can be conducted under normal pressure, under inert gas atmospheres including nitrogen, argon, etc., or under increased pressure.

The reaction proceeds usually at 0° C. to 200° C., and preferably at room temperature to 150° C., and is usually completed in about 1 to about 30 hours.

The compound represented by General Formula (7), which is used as a starting material in Reaction Scheme 3 is an easily available known compound.

Compound (5) and Compound (2), which are the starting materials of the compound of the invention, include novel compounds, and can be produced by various methods; for example, by methods according to the following Reaction Schemes 4 to 6.

Reaction Scheme 4

(8) → (9) → (5)

wherein $R_2$, $R_3$, and $R_8$ are as defined above, and $R_9$ represents a lower alkoxy group.

The lower alkoxy group represented by $R_9$ in General Formula (9) has the same definition as described above.

The compound represented by General Formula (5) can be produced by the reaction of the compound represented by General Formula (8) with the compound represented by General Formula (9) in an inert solvent or without using any solvents, in the presence or absence of a basic compound.

Examples of inert solvents include water; ethers such as dioxane, tetrahydrofuran, diethyl ether, 1,2-dimethoxyethane, diethylene glycol dimethyl ether, and ethylene glycol dimethyl ether; aromatic hydrocarbons such as benzene, toluene, and xylene; lower alcohols such as methanol, ethanol, and isopropanol; ketones such as acetone and methyl ethyl ketone; and polar solvents such as N,N-dimethylformamide (DMF), dimethyl sulfoxide (DMSO), hexamethylphosphoric triamide, and acetonitrile. These inert solvents can be used singly or in combinations of two or more.

As a basic compound, various known inorganic bases and organic bases can be used.

Inorganic bases include, for example, alkali metal hydroxides such as sodium hydroxide, potassium hydroxide, cesium hydroxide, and lithium hydroxide; alkali metal carbonates such as sodium carbonate, potassium carbonate, cesium carbonate, and lithium carbonate; alkali metal hydrogencarbonates such as lithium hydrogencarbonate, sodium hydrogencarbonate, and potassium hydrogencarbonate; alkali metals such as sodium and potassium; amides such as sodium amide; and alkali metal hydrides such as sodium hydride and potassium hydride.

Organic bases include, for example, alkali metal lower alkoxides such as sodium methoxide, sodium ethoxide, sodium t-butoxide, potassium methoxide, potassium ethoxide, and potassium t-butoxide; and amines such as triethylamine, tripropylamine, pyridine, quinoline, piperidine, imidazole, N-ethyldiisopropylamine, dimethylaminopyridine, trimethylamine, dimethylaniline, N-methylmorpholine, 1,5-diazabicyclo[4.3.0]non-5-ene (DBN), 1,8-diazabicyclo[5.4.0]undec-7-ene (DBU), 1,4-diazabicyclo[2.2.2]octane (DABCO), etc.

These basic compounds are used singly or in combinations of two or more. More preferable examples of basic compounds used in the reaction include inorganic bases such as sodium hydroxide, potassium hydroxide, etc.

A basic compound is usually used in an amount of about 1 to about 10 moles, preferably about 1 to about 6 moles, per mole of the compound of General Formula (8).

In Reaction Scheme 4, the compound of General Formula (9) is usually used in an amount of at least about 1 mole, preferably about 1 to about 5 moles, per mole of the compound of General Formula (8).

The reaction can be conducted under normal pressure, under inert gas atmospheres including nitrogen, argon, etc., or under increased pressure.

The reaction proceeds usually at room temperature to 200° C., and preferably at room temperature to 150° C., and is usually completed in about 1 to about 30 hours.

The compounds represented by General Formulae (8) and (9), which are used as starting materials in Reaction Scheme 4, are easily available known compounds.

Reaction Scheme 5

(8') → (9') → (5)

wherein $R_2$, $R_3$, and $R_8$ are as defined above, and $X_3$ represents a halogen atom.

The halogen atom represented by $X_3$ in General Formula (9') has the same definition as described above.

The compound represented by General Formula (5) can be produced by the reaction of the compound represented by General Formula (8') with the compound represented by General Formula (9') in an inert solvent or without using any solvents, in the presence of a basic compound such as cesium carbonate and a copper catalyst such as copper iodide.

Preferable examples of inert solvents include polar solvents such as N,N-dimethylformamide (DMF), dimethyl sulfoxide (DMSO), hexamethylphosphoric triamide, and acetonitrile. These inert solvents can be used singly or in combinations of two or more.

The reaction may be conducted in the presence of amino acids such as L-proline.

The reaction can be conducted under normal pressure, under inert gas atmospheres including nitrogen, argon, etc., or under increased pressure.

The reaction proceeds usually at room temperature to 200° C., and preferably at room temperature to 150° C., and is usually completed in about 1 to about 30 hours.

The compounds represented by General Formulae (8') and (9') used as starting materials in Reaction Scheme 5 described above are known compounds, or can be produced easily using known compounds.

ethane, diethylene glycol dimethyl ether, and ethylene glycol dimethyl ether; halogenated hydrocarbons such as methylene chloride, chloroform, 1,2-dichloroethane, and carbon tetrachloride; aromatic hydrocarbons such as benzene, toluene, and xylene; lower alcohols such as methanol, ethanol, and isopropanol; and polar solvents such as N,N-dimethylformamide (DMF), dimethyl sulfoxide (DMSO), hexamethylphosphoric triamide, and acetonitrile. The compound represented by General Formula (11) can be used as a solvent in place of the solvents mentioned above. These inert solvents can be used singly or in combinations of two or more.

In Reaction Scheme 6, the compound of General Formula (10) is usually used in an amount of at least 1 mole, preferably about 1 to about 5 moles, per mole of the compound of General Formula (4).

The compound represented by General Formula (11) is used in an amount exceeding that of the compound of General Formula (10).

The reaction can be conducted under normal pressure, under inert gas atmospheres including nitrogen, argon, etc., or under increased pressure.

The reaction proceeds usually at room temperature to 200° C., and preferably at room temperature to 150° C., and is usually completed in about 1 to about 30 hours.

Reaction Scheme 6

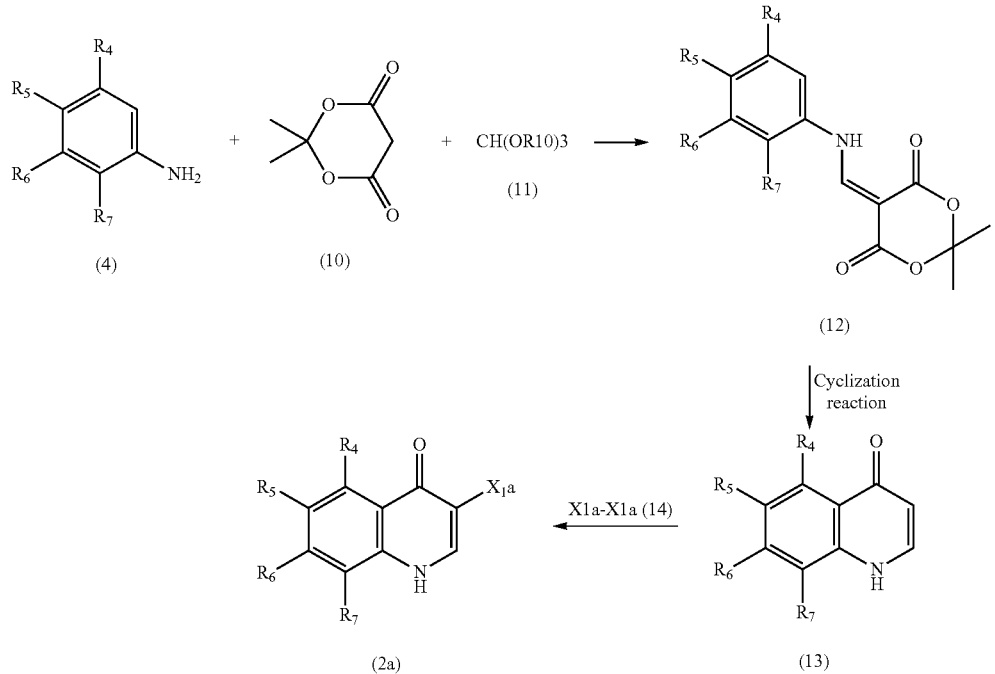

wherein $R_4$, $R_5$, $R_6$, and $R_7$ are as defined above, and $X_{1a}$ represents a halogen atom. $R_{10}$ represents a lower alkyl group.

The lower alkyl group represented by $R_{10}$ and a halogen atom represented by $X_{1a}$ have the same definitions as described above.

The compound represented by General Formula (12) can be produced by the condensation reaction of the compounds represented by General Formulae (4), (10), and (11) in an inert solvent or without using any solvents.

Examples of inert solvents include water; ethers such as dioxane, tetrahydrofuran, diethyl ether, 1,2-dimethoxy- The compound represented by General Formula (13) can be produced by the cyclization reaction of the compound represented by General Formula (12) in an inert solvent or without using any solvents.

Examples of inert solvents include ethers such as diphenyl ether.

The reaction can be conducted under normal pressure, under inert gas atmospheres including nitrogen, argon, etc., or under increased pressure.

The reaction proceeds usually at room temperature to 300° C., and preferably at 150 to 300° C., and is usually completed in about 1 to about 30 hours.

The compound represented by General Formula (2a) can be produced by the reaction of the compound represented by General Formula (13) with the compound represented by General Formula (14) in an inert solvent or without using any solvents, in the presence or absence of a basic compound.

Examples of inert solvents include water; ethers such as dioxane, tetrahydrofuran, diethyl ether, 1,2-dimethoxyethane, diethyleneglycol dimethyl ether, and ethylene glycol dimethyl ether; aromatic hydrocarbons such as benzene, toluene, and xylene; lower alcohols such as methanol, ethanol, and isopropanol; ketones such as acetone and methyl ethyl ketone; polar solvents such as N,N-dimethylformamide (DMF), dimethyl sulfoxide (DMSO), hexamethylphosphoric triamide, and acetonitrile. These inert solvents can be used singly or in combinations of two or more.

As a basic compound, various known inorganic bases and organic bases can be used.

Inorganic bases include, for example, alkali metal hydroxides such as sodium hydroxide, potassium hydroxide, cesium hydroxide, and lithium hydroxide; alkali metal carbonates such as sodium carbonate, potassium carbonate, cesium carbonate, and lithium carbonate; alkali metal hydrogencarbonates such as lithium hydrogencarbonate, sodium hydrogencarbonate, and potassium hydrogencarbonate; alkali metals such as sodium and potassium; amides such as sodium amide; and alkali metal hydrides such as sodium hydride and potassium hydride.

Organic bases include, for example, alkali metal alkoxides such as sodium methoxide, sodium ethoxide, sodium t-butoxide, potassium methoxide, potassium ethoxide, and potassium t-butoxide; and amines such as triethylamine, tripropylamine, pyridine, quinoline, piperidine, imidazole, N-ethyldiisopropylamine, dimethylaminopyridine, trimethylamine, dimethylaniline, N-methylmorpholine, 1,5-diazabicyclo[4.3.0]non-5-ene (DBN), 1,8-diazabicyclo[5.4.0]undec-7-ene (DBU), 1,4-diazabicyclo[2.2.2]octane (DABCO), etc.

Such basic compounds can be used singly or in combinations of two or more. More preferable basic compounds used in the reaction include alkali metal carbonates such as sodium carbonate, potassium carbonate, cesium carbonate, and lithium carbonate, etc.

A basic compound is usually used in an amount of 0.5 to 10 moles, preferably 0.5 to 6 moles, per mole of the compound of General Formula (13).

In Reaction Scheme 6, the compound of General Formula (14) is usually used in an amount of at least 0.5 moles, preferably about 0.5 to about 5 moles, per mole of the compound of General Formula (13).

The reaction can be conducted under normal pressure, under inert gas atmospheres including nitrogen, argon, etc., or under increased pressure.

The reaction proceeds usually at room temperature to 200° C., and preferably at room temperature to 150° C., and is usually completed in about 1 to about 30 hours.

The compounds represented by General Formulae (10), (11) and (14), which are used as starting materials in Reaction Scheme 6, are easily available known compounds.

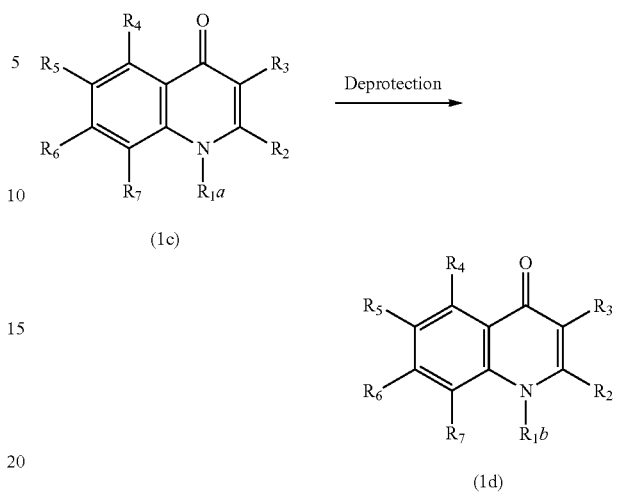

Reaction Scheme 7 wherein $R_2$, $R_3$, $R_4$, $R_5$, $R_6$, and $R_7$ are as defined above; $R_1a$ represents a phosphonooxy lower alkyl group having one or more hydroxy-protecting groups, a phosphonooxy lower alkanoyloxy lower alkyl group having one or more hydroxy-protecting groups, or a benzoyloxy lower alkyl group having one or more phosphonooxy groups substituted with one or more hydroxy-protecting groups on the benzene ring; and $R_1b$ represents a phosphonooxy lower alkyl group, a phosphonooxy lower alkanoyloxy lower alkyl group, or a benzoyloxy lower alkyl group having one or more phosphonooxy groups on the benzene ring.

Compound (1d) can be produced by the deprotection of the hydroxy-protecting group from Compound (1c) in an inert solvent or without using any solvents.

Examples of inert solvents include water; ethers such as dioxane, tetrahydrofuran, diethyl ether, 1,2-dimethoxyethane, diethylene glycol dimethyl ether, and ethylene glycol dimethyl ether; halogenated hydrocarbons such as methylene chloride, chloroform, 1,2-dichloroethane, and carbon tetrachloride; aromatic hydrocarbons such as benzene, toluene, and xylene; lower alcohols such as methanol, ethanol, and isopropanol; and polar solvents such as N,N-dimethylformamide (DMF), dimethyl sulfoxide (DMSO), hexamethylphosphoric triamide, and acetonitrile. The compound represented by General Formula (1c) may also be used as a solvent instead of the above solvents. These inert solvents can be used singly or in combinations of two or more.

This reaction is carried out by a conventional method such as hydrolysis or reduction.

Hydrolysis is carried out preferably in the presence of bases or acids including a Lewis acid.

Suitable examples of bases include inorganic bases such as alkali metal hydroxides (e.g., sodium hydroxide, potassium hydroxide), alkali earth metal hydroxides (e.g., magnesium hydroxide, calcium hydroxide), alkali metal carbonates (e.g., sodium carbonate, potassium carbonate), alkali earth metal carbonates (e.g., magnesium carbonate, calcium carbonate), alkali metal hydrogencarbonates (e.g., sodium hydrogencarbonate, potassium hydrogencarbonate); and organic bases such as trialkyl amines (e.g., trimethylamine, triethylamine), picoline, 1,5-diazabicyclo[4.3.0]non-5-en, and 1,4-diazabicyclo[2.2.2]octane, and 1,8-diazabicyclo[5.4.0]undeca-7-en.

Examples of suitable acids include organic acids (e.g., formic acid, acetic acid, propionic acid, trichloroacetic acid, trifluoroacetic acid) and inorganic acids (e.g., hydrochloric acid, hydrobromic acid, sulfuric acid). Deprotection using Lewis acids such as trihaloacetic acids (e.g., trichloroacetic acid, trifluoroacetic acid) is carried out preferably in the presence of a cation scavenger (e.g., anisole, phenol). In the reaction, a liquid base or acid can also be used as a solvent.

The reaction temperature is not limited, and the reaction is usually carried out under cooling or warming.

Reduction methods applicable to the elimination reaction include chemical reduction and catalytic reduction.

Suitable reducing agents for use in chemical reduction are a combination of a metal (e.g., tin, zinc, iron) or metallic compound (e.g., chromium chloride, chromium acetate) and an organic or inorganic acid (e.g. formic acid, acetic acid, propionic acid, trifluoroacetic acid, p-toluenesulfonic acid, hydrochloric acid, hydrobromic acid).

Suitable catalysts for use in catalytic reduction are conventional ones such as platinum catalysts (e.g. platinum plate, spongy platinum, platinum black, colloidal platinum, platinum oxide, platinum wire), palladium catalysts (e.g. spongy palladium, palladium black, palladium oxide, palladium-carbon, colloidal palladium, palladium-barium sulfate, palladium-barium carbonate), nickel catalysts (e.g. reduced nickel, nickel oxide, Raney nickel), cobalt catalysts (e.g. reduced cobalt, Raney cobalt), iron catalysts (e.g. reduced iron, Raney iron), copper catalysts (e.g. reduced copper, Raney copper, Ullman copper), and the like.

The reaction is usually carried out in a conventional solvent which does not adversely influence the reaction, such as water; an alcohol such as methanol, ethanol, trifluoroethanol, or ethyleneglycol; an ether such as acetone, diethylether, dioxane, or tetrahydrofuran; a halogenated hydrocarbon such as chloroform, methylene chloride, or ethylene chloride; an ester such as methyl acetate or ethyl acetate; acetonitrile; N,N-dimethylformamide; pyridine; any other organic solvent; or a mixture of these solvents. The reaction usually proceeds at room temperature to 200° C., and preferably at room temperature to 150° C., and is usually completed in about 1 to about 30 hours.

Further, the conditions for the deprotection reaction of the hydroxy-protecting group are not limited to the reaction conditions described above. For example, reactions described by T. W. Green and P. G. M. Wuts (Protective Groups in Organic Synthesis, 4th edition) and John Wiley & Sons (New York, 1991, P. 309) can also be applied to the reaction process.

The raw material compounds used in each of the reaction schemes described above may include suitable salts, and the objective compounds obtained via each of the reactions may form suitable salts. These preferable salts include the following preferable salts of Compound (1).

Suitable salts of Compound (1) are pharmacologically allowable salts including, for example, salts of inorganic bases such as metal salts including alkali metal salts (e.g., sodium salts, potassium salts, etc.) and alkaline earth metal salts (e.g., calcium salts, magnesium salts, etc.), ammonium salts, alkali metal carbonates (e.g., lithium carbonate, potassium carbonate, sodium carbonate, cesium carbonate, etc.), alkali metal hydrogencarbonates (e.g., lithium hydrogencarbonate, sodium hydrogencarbonate, potassium hydrogencarbonate, etc.), and alkali metal hydroxides (e.g., lithium hydroxide, sodium hydroxide, potassium hydroxide, cesium hydroxide, etc.); salts of organic bases such as tri(lower) alkylamine (e.g., trimethylamine, triethylamine, N-ethyldiisopropylamine, etc.), pyridine, quinoline, piperidine, imidazole, picoline, dimethylaminopyridine, dimethylaniline, N-(lower)alkyl-morpholine (e.g., N-methylmorpholine, etc.), 1,5-diazabicyclo[4.3.0]non-5-ene (DBN), 1,8-diazabicyclo[5.4.0]undec-7-ene (DBU), 1,4-diazabicyclo[2.2.2]octane (DABCO), and trishydroxymethyl amino methane; inorganic acid salts such as hydrochloride, hydrobromide, hydroiodide, sulfate, nitrate, and phosphate; and organic acid salts such as formate, acetate, propionate, oxalate, malonate, succinate, fumarate, maleate, lactate, malate, citrate, tartrate, carbonate, picrate, methanesulfonate, ethanesulfonate, p-toluenesulfonate, and glutamate.

In addition, compounds in a form in which a solvate (for example, hydrate, ethanolate, etc.) was added to the starting materials and the objective compound shown in each of the reaction schemes are also included in each of the general formulae. Hydrate can be mentioned as a preferable solvate.

Each of the objective compounds obtained according to the above reaction schemes can be isolated and purified from the reaction mixture by, for example, cooling the reaction mixture first, performing an isolation procedure such as filtration, concentration, extraction, etc., to separate a crude reaction product, and then subjecting the crude reaction product to a usual purification procedure such as column chromatography, recrystallization, etc.

The compound represented by General Formula (1) according to the present invention naturally includes geometrical isomers, stereoisomers, optical isomers, and like isomers.

The following points should be noted regarding the compound of General Formula (1) shown above. Specifically, when $R_1$ of General Formula (1) represents a hydrogen atom, the compound includes a tautomer of the quinolone ring. That is, in the quinolone compound of General Formula (1), when $R_1$ represents a hydrogen atom (1'),

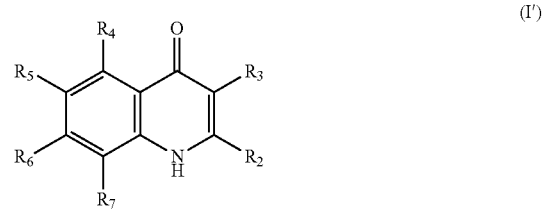

(1')

wherein $R_2$, $R_3$, $R_4$, $R_5$, $R_6$, and $R_7$ are as defined above, the compound of the tautomer can be represented by Formula (1"),

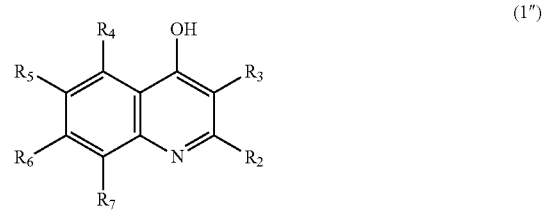

(1")

wherein $R_2$, $R_3$, $R_4$, $R_5$, $R_6$, and $R_7$ are as defined above. That is, both of the compounds represented by Formulae (1') and (1") are in the tautomeric equilibrium state represented by the following balance formula.

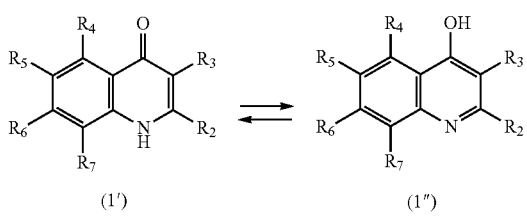

wherein $R_2$, $R_3$, $R_4$, $R_5$, $R_6$, and $R_7$ are as defined above.

Such tautomerism between a 4-quinolone compound and a 4-hydroxyquinoline compound is technically known, and it is obvious for a person skilled in the art that both of the above-described tautomers are balanced and mutually exchangeable.

Therefore, the compound represented by General Formula (1) of the present invention naturally includes the tautomers as mentioned above.

In the specification, the constitutional formula of a 4-quinolone compound is suitably used as a constitutional formula of the objective or starting material including compounds of such tautomers.

The present invention also includes isotopically labeled compounds that are identical to the compounds represented by Formula (1), except that one or more atoms are replaced by one or more atoms having specific atomic mass or mass numbers. Examples of isotopes that can be incorporated into the compounds of the present invention include hydrogen, carbon, nitrogen, oxygen, sulfur, fluorine, and chlorine, such as $^2$H, $^3$H, $^{13}$C, $^{14}$C, $^{15}$N, $^{18}$O, $^{17}$O, $^{18}$F, and $^{36}$Cl. Certain isotopically labeled compounds of the present invention, which include the above-described isotopes and/or other isotopes of other atoms, for example, those into which radioisotopes such as $^3$H and $^{14}$C are incorporated, are useful in drug and/or substrate tissue distribution assay. Tritiated (i.e., $^3$H), and carbon-14 (i.e., $^{14}$C) isotopes are particularly preferred for their ease of preparation and detectability. Further, substitution with heavier isotopes such as deuterium (i.e., $^2$H) can afford certain therapeutic advantages resulting from greater metabolic stability, for example, an increased in vivo half-life or reduced dosage requirements. The isotopically labeled compounds of the present invention can generally be prepared by substituting a readily available, isotopically labeled reagent for a non-isotopically labeled reagent according to the method disclosed in the schemes above and/or in the Examples below.

The compound of General Formula (1) and the salt thereof are used in the form of general pharmaceutical preparations. The preparations are obtained using typically employed diluents or excipients such as fillers, extenders, binders, wetting agents, disintegrators, surfactants, lubricants, etc. The form of such pharmaceutical preparations can be selected according to the purpose of the therapy. Typical examples include tablets, pills, powders, solutions, suspensions, emulsions, granules, capsules, suppositories, injections (solutions, suspensions, etc.), and the like.

To form tablets, any of various carriers conventionally known in this field can be used. Examples thereof include lactose, white sugar, sodium chloride, glucose, urea, starch, calcium carbonate, kaolin, crystalline cellulose, silicic acid, and other excipients; water, ethanol, propanol, simple syrup, glucose solutions, starch solutions, gelatin solutions, carboxymethylcellulose, shellac, methylcellulose, potassium phosphate, polyvinylpyrrolidone and other binders; dry starch, sodium alginate, agar powder, laminarin powder, sodium hydrogen carbonate, calcium carbonate, fatty acid esters of polyoxyethylene sorbitan, sodium lauryl sulfate, stearic acid monoglycerides, starch, lactose and other disintegrators; white sugar, stearin, cacao butter, hydrogenated oils and other disintegration inhibitors; quaternary ammonium bases, sodium lauryl sulfate and other absorption promoters; glycerol, starch and other wetting agents; starch, lactose, kaolin, bentonite, colloidal silicic acid and other adsorbents; purified talc, stearates, boric acid powder, polyethylene glycol and other lubricants; etc. Further, such tablets may be coated with typical coating materials as required, to prepare, for example, sugar-coated tablets, gelatin-coated tablets, enteric-coated tablets, film-coated tablets, double- or multi-layered tablets, etc.

To form pills, any of various carriers conventionally known in this field can be used. Examples thereof include glucose, lactose, starch, cacao butter, hydrogenated vegetable oils, kaolin, talc and other excipients; gum arabic powder, tragacanth powder, gelatin, ethanol and other binders; laminarin, agar and other disintegrators; etc.

To form suppositories, any of various carriers conventionally known in this field can be used. Examples thereof include polyethylene glycol, cacao butter, higher alcohols, esters of higher alcohols, gelatin, semi synthetic glycerides, etc.

Capsules can be prepared by mixing the active principal compound with the above-mentioned carriers to enclose the former in a hard gelatin capsule, soft gelatin capsule or the like.

To form an injection, a solution, emulsion or suspension is sterilized and preferably made isotonic to blood. Any of the diluents widely used for such forms in this field can be employed to form the injection. Examples of such diluents include water, ethyl alcohol, macrogol, propylene glycol, ethoxylated isostearyl alcohol, polyoxylated isostearyl alcohol, fatty acid esters of polyoxyethylene sorbitan, etc.

In this case, the pharmaceutical preparation may contain sodium chloride, glucose or glycerol in an amount sufficient to prepare an isotonic solution, and may contain typical solubilizers, buffers, analgesic agents, etc. Further, if necessary, the pharmaceutical preparation may contain coloring agents, preservatives, flavors, sweetening agents, etc., and/or other medicines.

The amount of the compound represented by the General Formula (1) and the salt thereof included in the pharmaceutical preparation of the present invention is not limited, and can be suitably selected from a wide range. The proportion is generally about 0.1 to about 70 wt. %, preferably about 0.1 to about 30 wt. % of the pharmaceutical preparation.

The route of administration of the pharmaceutical preparation of the present invention is not particularly limited, and the preparation is administered by a route suitable to the form of the preparation, patient's age, sex and other conditions, and severity of the disease. For example, tablets, pills, solutions, suspensions, emulsions, granules and capsules are administered orally. Injections are intravenously administered singly or as mixed with typical injection transfusions such as glucose solutions, amino acid solutions or the like, or singly administered intramuscularly, intracutaneously, subcutaneously or intraperitoneally, as required. Suppositories are administered intrarectally.

The dosage of the pharmaceutical preparation of the invention is suitably selected according to the method of use, patient's age, sex and other conditions, and severity of the disease. The amount of active principal compound is usually about 0.1 to about 10 mg/kg body weight/day. Further, it is desirable that the pharmaceutical preparation in each unit of the administration form contains the active principal compound in an amount of about 1 to about 200 mg.

The use of the compound of the present invention in combination with L-dopa preparations, dopamine receptor agonists, dopamine metabolism enzyme inhibitors, dopamine release-rate-promoting preparations, central anticholinergic agents, and the like can achieve effects such as dosage reduction, improvement of side effects, increased therapeutic efficacy, etc., which were not attained by known therapies.

Advantageous Effect of Invention

The compounds of the invention protect and improve mitochondrial function, and/or protect neurons and repair neuronal function, and hence are effective in the treatment or prevention of neurodegenerative diseases, diseases induced by neurological dysfunction, and diseases induced by deterioration of mitochondrial function.

Examples of neurodegenerative diseases include Parkinson's disease, Parkinson's syndrome, juvenile parkinsonism, striatonigral degeneration, progressive supranuclear palsy, pure akinesia, Alzheimer's disease, Pick's disease, prion disease, corticobasal degeneration, diffuse Lewy body disease, Huntington's disease, chorea-acanthocytosis, benign hereditary chorea, paroxysmal choreoathetosis, essential tremor, essential myoclonus, Gilles de la Tourette's syndrome, Rett's syndrome, degenerative ballism, dystonia musculorum deformance, athetosis, spasmodic torticollis, Meige syndrome, cerebral palsy, Wilson's disease, Segawa's disease, Hallervorden-Spatz syndrome, neuroaxonal dystrophy, pallidal atrophy, spino-cerebellar degeneration, cerebral cortical atrophy, Holmes-type cerebellar atrophy, olivopontocerebellar atrophy, hereditary olivopontocerebellar atrophy, Joseph disease, dentatorubropallidoluysian atrophy, Gerstmann-Straussler-Scheinker disease, Friedreich's Ataxia, Roussy-Levy syndrome, May-White syndrome, congenital cerebellar ataxia, hereditary episodic ataxia, ataxia telangiectasia, amyotrophic lateral sclerosis, progressive bulbar palsy, spinal progressive muscular atrophy, spinobulbar muscular atrophy, Werdnig-Hoffmann disease, Kugelberg-Welander disease, hereditary spastic paraparesis, syringomyelia, syringobulbia, Arnold-Chiari malformation, Stiffman syndrome, Klippel-Feil syndrome, Fazio-Londe syndrome, lower myelopathy, Dandy-Walker syndrome, spina bifida, Sjogren-Larsson syndrome, radiation myelopathy, age-related macular degeneration, and cerebral apoplexy (e.g., cerebral infarction and cerebral hemorrhage) and/or dysfunction or neurologic deficits associated with cerebral apoplexy.

Examples of diseases induced by neurological dysfunction include spinal cord injury, chemotherapy-induced neuropathy, diabetic neuropathy, radiation damage, and demyelinating diseases (e.g., multiple sclerosis, acute disseminated encephalomyelitis, transverse myelitis, progressive multifocal leucoencephalopathy, subacute sclerosing panencephalitis, chronic inflammatory demyelinating polyneuropathy and Guillain-Barre syndrome).

Examples of diseases induced by deterioration of mitochondrial function include Pearson's syndrome, diabetes, deafness, malignant migraine, Leber's disease, MELAS, MERRF, MERRF/MELAS overlap syndrome, NARP, pure myopathy, mitochondrial cardiomyopathy, myopathy, dementia, gastrointestinal ataxia, acquired sideroblastic anemia, aminoglycoside-induced hearing loss, complex III deficiency due to inherited variants of cytochrome b, multiple symmetrical lipomatosis, ataxia, myoclonus, retinopathy, MNGIE, ANTI disease, Twinkle disease, POLG disease, recurrent myoglobinuria, SANDO, ARCO, complex I deficiency, complex II deficiency, optic nerve atrophy, fatal infantile complex IV deficiency, mitochondrial DNA deficiency, mitochondrial DNA deficiency syndrome, Leigh's encephalomyelopathy, chronic-progressive-external-ophthalmoplegia syndrome (CPEO), Kearns-Sayre syndrome, encephalopathy, lactacidemia, myoglobinuria, drug-induced mitochondrial diseases, schizophrenia, major depression disorder, bipolar I disorder, bipolar II disorder, mixed episode, dysthymic disorders, atypical depression, seasonal affective disorders, postpartum depression, minor depression, recurrent brief depressive disorder, intractable depression/chronic depression, double depression and acute renal failure.

Furthermore, the compound of the invention is effective in the prevention or treatment of diseases such as ischemic heart diseases (e.g., myocardial infarction and/or associated dysfunction, arrhythmia, angina pectoris, occlusion after PTCA, etc.) and/or associated dysfunction, cardiac failure, myocardosis, aortic dissection, immunodeficiency, autoimmune diseases, pancreatic insufficiency, diabetes, atheroembolic renal disease, polycytic kidney disease, medullary cystic disease, renal cortical necrosis, malignant nephrosclerosis, renal failure, hepatic encephalopathy, liver failure, chronic obstructive pulmonary disease, pulmonary embolism, bronchiectasis, silicosis, black lung, idiopathic pulmonary fibrosis, Stevens-Johnson syndrome, toxic epidermal necrolysis, muscular dystrophy, clostridial muscle necrosis, and femoral condyle necrosis.

The compound of the invention can achieve effects heretofore unattained by known therapies, such as reduced dose, reduced side effects, and potentiated therapeutic effects, when it is administered in combination with L-dopa preparations, dopamine receptor agonists, dopamine metabolism enzyme inhibitors, dopamine release-rate-promoting preparations, central anticholinergic agents, cholinesterase inhibitors, N-methyl-D-aspartate glutamate receptor antagonists, or other agents used in thrombolytic therapy, cerebral edema therapy, brain protection therapy, antithrombotic therapy, and blood plasma dilution therapy.

Some of Compounds (1) of the invention or salts thereof exhibit remarkably high solubility in, for example, water.

Particularly Compound (1d) or a salt thereof exhibits remarkably high solubility in, for example, water.

DESCRIPTION OF EMBODIMENTS

Hereinafter, the present invention is described in more detail with reference to Reference Examples, Examples and Pharmacological Test Examples.

Reference Example 1

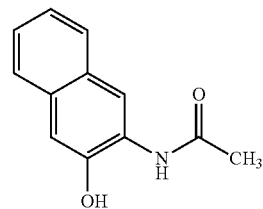

Production of
N-(3-hydroxynaphthalen-2-yl)acetamide

An acetone solution (60 ml) of 3-amino-2-naphthol (5.0 g, 31.4 mmol) was added to an aqueous solution (20 ml) of sodium carbonate (4.77 g, 34.5 mmol). The mixture was cooled in an ice-water bath, and then acetyl chloride (2.27 ml, 32.0 mmol) was added to the mixture dropwise over 5 minutes. The resulting mixture was stirred at 0° C. for 4 hours and then allowed to stand at room temperature overnight. 2N Hydrochloric acid was added to the reaction mixture to adjust its pH to 3. The generated insoluble matter was separated, washed with water, and then dried, giving a white powder of N-(3-hydroxynaphthalen-2-yl)acetamide (4.9 g, yield: 78%).

Reference Example 2

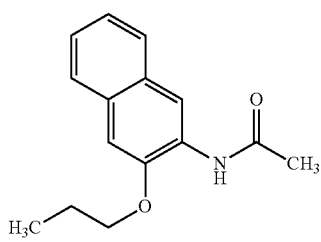

Production of N-(3-propoxynaphthalen-2-yl)acetamide

N-(3-Hydroxynaphthalen-2-yl)acetamide (4.87 g, 24.2 mmol) was suspended in acetonitrile (50 ml). A 1-iodopropane (4.52 g, 26.6 mmol) acetonitrile solution (40 ml) and potassium carbonate (4.35 g, 31.5 mmol) were added thereto, and the resulting mixture was stirred for 3 hours while heating under reflux. The mixture was then cooled to room temperature and concentrated to dryness under reduced pressure. Water was added to the residue, followed by extraction using dichloromethane. The thus-obtained organic layer was concentrated to dryness under reduced pressure, and the residue was then purified using silica gel column chromatography (dichloromethane:ethyl acetate=20:1). The purified product was concentrated to dryness under reduced pressure, giving a white powder of N-(3-propoxynaphthalen-2-yl)acetamide (5.64 g, yield: 96%).

Reference Example 3

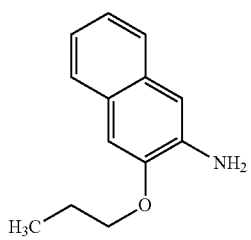

Production of 3-propoxynaphthalen-2-ylamine

N-(3-Propoxynaphthalen-2-yl)acetamide (2.5 g, 10.2 mmol) was dissolved in ethanol (10 ml). Concentrated hydrochloric acid (5.2 ml) was added thereto, and the resulting mixture was stirred for 4 hours while heating under reflux. The reaction mixture was cooled to room temperature, and a 5N aqueous sodium hydroxide solution (12.5 ml) was added thereto to adjust its pH to 11, followed by extraction using dichloromethane. The thus-obtained organic layer was concentrated to dryness under reduced pressure, and the residue was then purified using silica gel column chromatography (dichloromethane). The purified product was concentrated to dryness under reduced pressure, giving a white powder of 3-propoxynaphthalen-2-ylamine (2.05 g, yield: 100%).

Reference Example 4

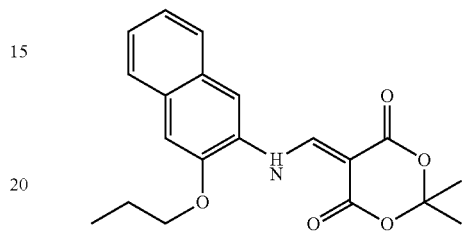

Production of 2,2-dimethyl-5-[(3-propoxynaphthalen-2-ylamino)methylene][1,3]dioxane-4,6-dione Meldrum's acid (2.59 g, 17.9 mmol) was added to methyl orthoformate (16 ml), and the mixture was stirred for 2 hours while heating under reflux. 3-Propoxynaphthalen-2-ylamine (2.5 g, 12.4 mmol) was added thereto, and the resulting mixture was stirred for 4 hours while heating under reflux. The reaction mixture was cooled to room temperature and then concentrated to dryness under reduced pressure to recrystallize the residue from methanol, giving a pale brown powder of 2,2-dimethyl-5-[(3-propoxynaphthalen-2-ylamino) methylene][1,3]dioxane-4,6-dione (4.19 g, yield: 95%).

Reference Example 5

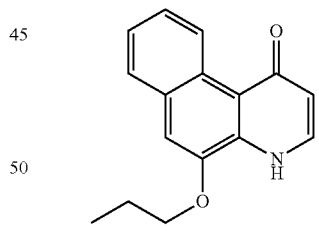

Production of 5-propoxy-4H-benzo[f]quinolin-1-one 2,2-Dimethyl-5-[(3-propoxynaphthalen-2-ylamino) methylene][1,3]dioxane-4,6-dione (4.19 g, 11.7 mmol) was added to diphenyl ether (15 ml), and the mixture was heated with a mantle heater and then maintained under reflux for 2 hours. The mixture was cooled to room temperature and purified using silica gel column chromatography (dichloromethane: methanol=70:1→9:1). The purified product was concentrated to dryness under reduced pressure, giving a dark brown powder of 5-propoxy-4H-benzo[f]quinolin-1-one (3.15 g, yield: 61%).

Reference Example 6

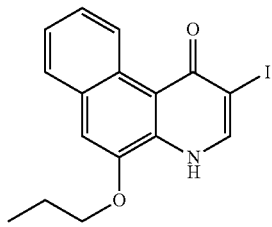

Production of
2-iodo-5-propoxy-4H-benzo[f]quinolin-1-one

5-Propoxy-4H-benzo[f]quinolin-1-one (2.66 g, 10.5 mmol) was suspended in DMF (20 ml). Potassium carbonate (1.63 g, 11.8 mmol) and iodine (2.95 g, 11.6 mmol) were added to the suspension, followed by stirring at room temperature for 3 hours. The reaction mixture was poured into an aqueous sodium thiosulfate solution (9.14 g, 100 ml), followed by stirring for 5 minutes. Ethyl acetate was added to the reaction mixture and stirred. Subsequently, insoluble matter was collected by filtration, and the filtrate was then separated. The thus-obtained organic layer was washed with an aqueous saturated sodium chloride solution, and then concentrated to dryness under reduced pressure. The residue was added to the collected insoluble matter, followed by purification using silica gel column chromatography (dichloromethane:methanol=50:1→20:1). The purified product was concentrated to dryness under reduced pressure, giving a pale brown powder of 2-iodo-5-propoxy-4H-benzo[f]quinolin-1-one (3.48 g, yield: 87%).

Reference Example 7

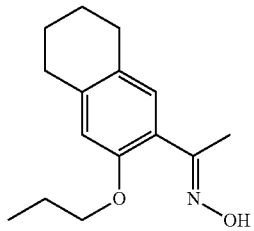

Production of 1-(3-propoxy-5,6,7,8-tetrahydronaphthalen-2-yl)ethanone oxime 1-(3-Propoxy-5,6,7,8-tetrahydronaphthalen-2-yl)ethanone (8.88 g, 38.2 mmol) was dissolved in a mixed solvent of chloroform (20 ml) and methanol (80 ml). Hydroxylamine hydrochloride (4.05 g, 58.2 mmol) and pyridine (9.46 ml, 117 mmol) were added to the solution and stirred for 16 hours while heating under reflux. The reaction mixture was cooled to room temperature, and then concentrated to dryness under reduced pressure. 2N hydrochloric acid (30 ml) and water were added to the residue, followed by extraction using dichloromethane. The thus-obtained organic layer was concentrated to dryness under reduced pressure, and the residue was then purified using silica gel column chromatography (n-hexane:ethyl acetate=5:1). The purified product was concentrated to dryness under reduced pressure, giving a pale yellow powder of 1-(3-propoxy-5,6,7,8-tetrahydronaphthalen-2-yl)ethanone oxime (8.87 g, yield: 94%).

Reference Example 8

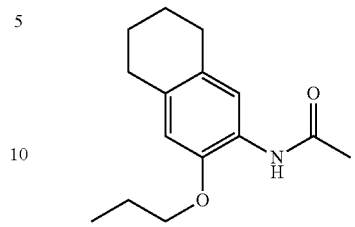

Production of N-(3-propoxy-5,6,7,8-tetrahydronaphthalen-2-yl)acetamide

Indium chloride (1.19 g, 5.39 mmol) was added to an acetonitrile solution (150 ml) of 1-(3-propoxy-5,6,7,8-tetrahydronaphthalen-2-yl)ethanone oxime (8.87 g, 35.8 mmol) and the mixture was stirred for 3 hours while heating under reflux. The reaction mixture was cooled to room temperature, and then concentrated to dryness under reduced pressure. Water was added to the residue, followed by extraction using dichloromethane. The thus-obtained organic layer was concentrated to dryness under reduced pressure, and the residue was then purified using silica gel column chromatography (n-hexane:ethyl acetate=3:1). The purified product was concentrated to dryness under reduced pressure, giving a white powder of N-(3-propoxy-5,6,7,8-tetrahydronaphthalen-2-yl)acetamide (8.65 g, yield: 98%).

Reference Example 9

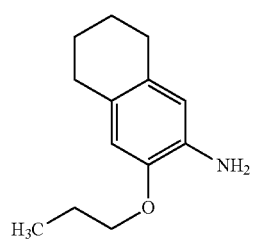

Production of
3-propoxy-5,6,7,8-tetrahydronaphthalen-2-ylamine

3-Propoxy-5,6,7,8-tetrahydronaphthalen-2-ylamine was produced in the same manner as in Reference Example 3.

Reference Example 10

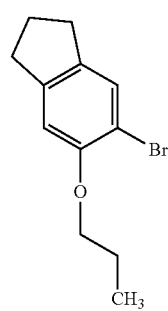

Production of 5-bromo-6-propoxyindan

5-Bromo-6-propoxyindan was produced in the same manner as in Reference Example 2.

Reference Example 11

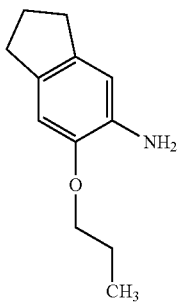

Production of 6-propoxy-indan-5-ylamine

To a 5-bromo-6-propoxyindan (8.24 g, 32.2 mmol) toluene solution (80 ml) were added a benzophenone imine (6.40 g, 35.3 mmol) toluene solution (40 ml), tris(dibenzylideneacetone)dipalladium (742 mg, 0.8 mmol), 9,9-dimethyl-4,5-bis (diphenylphosphino)xanthene (XANTPHOS, 936 mg, 1.6 mmol), and cesium carbonate (15.72 g, 48.3 mmol). The resulting mixture was stirred at 100° C. under a nitrogen atmosphere for 47 hours, and then cooled to room temperature. Water and saturated ammonium chloride solution were added to the reaction mixture, followed by extraction using ethyl acetate. The organic layer was dried over anhydrous magnesium sulfate, and then concentrated to dryness under reduced pressure. The generated residue was dissolved in diethyl ether (130 ml). Concentrated hydrochloric acid (25 ml) was added to the solution, followed by stirring for 2 hours. A 5N aqueous sodium hydroxide solution (72 ml) was added to the reaction mixture to adjust its pH to 11, followed by concentration under reduced pressure. The residue was dissolved in dichloromethane and washed with an aqueous saturated sodium chloride solution. The thus-obtained organic layer was concentrated to dryness under reduced pressure, and the generated residue was then purified using silica gel column chromatography (dichloromethane:ethyl acetate=90: 1). The purified product was concentrated to dryness under reduced pressure, giving a pale brown oily substance of 6-propoxy-indan-5-ylamine (1.02 g, yield: 17%).

Reference Example 12

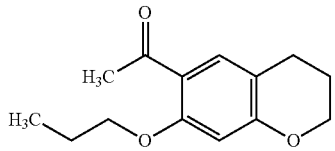

Production of 1-(7-propoxychroman-6-yl)ethanone 1-(7-Hydroxychroman-6-yl)ethanone (3.0 g, 15.6 mmol) was dissolved in DMF (20 ml). Sodium hydride (60% oil base, 686 mg, 1.1 equivalent weight) was added thereto while ice cooling, and then stirred for 10 minutes. 1-Iodopropane (2.92 g, 1.1 equivalent weight) was added to the mixture and then stirred at room temperature for 3 hours. Water was added to the reaction mixture, followed by extraction using ethyl acetate. The thus-obtained organic layer was concentrated to dryness under reduced pressure, and the residue was then purified using silica gel column chromatography (n-hexane: ethyl acetate=1:0→0:1). The purified product was concentrated to dryness under reduced pressure, giving a white powder of 1-(7-propoxychroman-6-yl)ethanone (4.2 g, yield: quantitative).

Reference Example 13

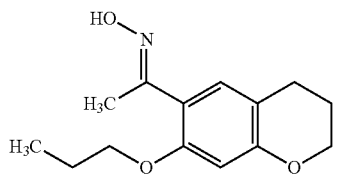

Production of 1-(7-propoxychroman-6-yl)ethanone oxime 1-(7-Propoxychroman-6-yl)ethanone oxime was produced in the same manner as in Reference Example 7.

Reference Example 14

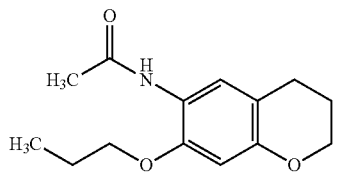

Production of N-(7-propoxychroman-6-yl)acetamide

N-(7-propoxychroman-6-yl)acetamide was produced in the same manner as in Reference Example 8.

Reference Example 15

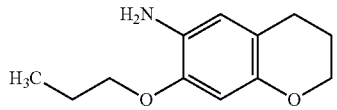

Production of 7-propoxychroman-6-ylamine

7-Propoxychroman-6-ylamine was produced in the same manner as in Reference Example 3.

Reference Example 16

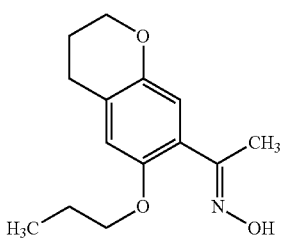

Production of 1-(6-propoxychroman-7-yl)ethanone oxime 1-(6-Propoxychroman-7-yl)ethanone oxime was produced in the same manner as in Reference Example 7.

Reference Example 17

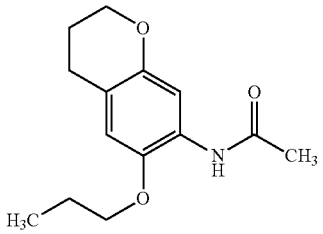

Production of N-(6-propoxychroman-7-yl)acetamide

N-(6-Propoxychroman-7-yl)acetamide was produced in the same manner as in Reference Example 8.

Reference Example 18

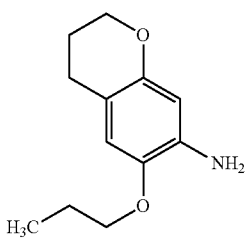

Production of 6-propoxychroman-7-ylamine

6-Propoxychroman-7-ylamine was produced in the same manner as in Reference Example 3.

Reference Example 19

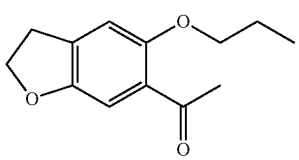

Production of 1-(5-propoxy-2,3-dihydrobenzofuran-6-yl)ethanone 1-(5-Propoxy-2,3-dihydrobenzofuran-6-yl)ethanone was produced in the same manner as in Reference Example 12.

Reference Example 20

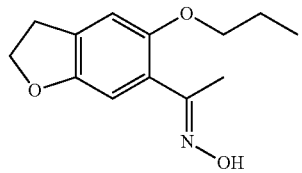

Production of 1-(5-propoxy-2,3-dihydrobenzofuran-6-yl)ethanone oxime 1-(5-Propoxy-2,3-dihydrobenzofuran-6-yl)ethanone oxime was produced in the same manner as in Reference Example 7.

Reference Example 21

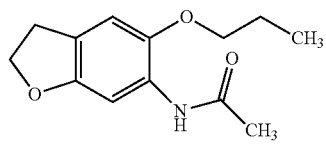

Production of N-(5-propoxy-2,3-dihydrobenzofuran-6-yl)acetamide

N-(5-Propoxy-2,3-dihydrobenzofuran-6-yl)acetamide was produced in the same manner as in Reference Example 8.

Reference Example 22

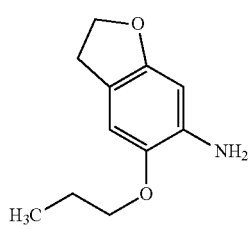

Production of 5-propoxy-2,3-dihydrobenzofuran-6-ylamine

5-Propoxy-2,3-dihydrobenzofuran-6-ylamine was produced in the same manner as in Reference Example 3.

Reference Example 23

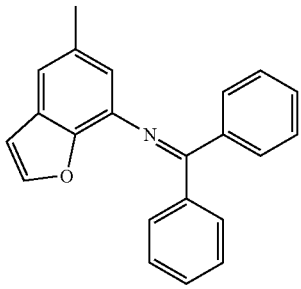

Production of
benzhydrylidene(5-methylbenzofuran-7-yl)amine

To a 7-bromo-5-methylbenzofuran (9.71 g, 46 mmol) toluene solution (100 ml) were added a benzophenone imine (10.25 g, 56 mmol) toluene solution (55 ml), tris(dibenzylideneacetone)dipalladium (1.1 g, 1 mmol), 2,2'-bis(diphenylphosphino)-1,1'-binaphthyl (BINAP, 2.1 g, 3.45 mmol), and sodium t-butoxide (3.1 g, 31 mmol). The resulting mixture was then stirred for 4 hours while heating under reflux in a nitrogen atmosphere. The reaction mixture was cooled to room temperature, and water and saturated ammonium chloride solution were added thereto, followed by extraction using ethyl acetate. The organic layer was dried over anhydrous magnesium sulfate and then concentrated to dryness under reduced pressure. The residue was purified using silica gel column chromatography (n-hexane:ethyl acetate=10:1). The solvent was removed under a reduced pressure, giving a yellow oily substance of benzhydrylidene(5-methylbenzofuran-7-yl) amine (17.9 g, yield: 81%).

Reference Example 24

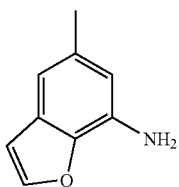

Production of 5-methylbenzofuran-7-ylamine

Benzhydrylidene(5-methylbenzofuran-7-yl)amine (17.9 g, 0.57 mmol) was dissolved in THF (150 ml). 5N Hydrochloric acid (50 ml) was added thereto, followed by stirring at room temperature for 2 hours. A 5N aqueous sodium hydroxide solution (40 ml) was added to the reaction mixture, followed by extraction using ethyl acetate. The extract was sequentially washed with an aqueous saturated sodium hydrogen solution and an aqueous saturated sodium chloride solution. The organic layer was dried over magnesium sulfate and concentrated to dryness under reduced pressure. The residue was purified using silica gel column chromatography (n-hexane:ethyl acetate=50:1→10:1). The purified product was concentrated to dryness under reduced pressure, giving a dark brown oily substance of 5-methylbenzofuran-7-ylamine (2.5 g, yield: 30%).

Reference Example 25

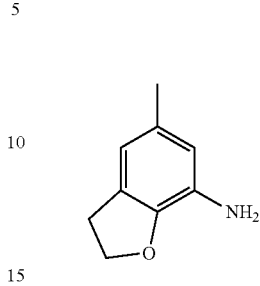

Production of
5-methyl-2,3-dihydrobenzofuran-7-ylamine

5-Methylbenzofuran-7-ylamine (1.3 g, 8.8 mmol) and 10% palladium carbon (500 mg) were added to ethanol (50 ml), followed by conduction of catalytic reduction at room temperature under ordinary pressure. The catalyst was removed by celite filtration, and the obtained filtrate was condensed under reduced pressure. The residue was dissolved in dichloromethane, dried over anhydrous magnesium sulfate, and then concentrated to dryness under reduced pressure, giving a white powder of 5-methyl-2,3-dihydrobenzofuran-7-ylamine (1.15 g, yield: 87%).

Example 1

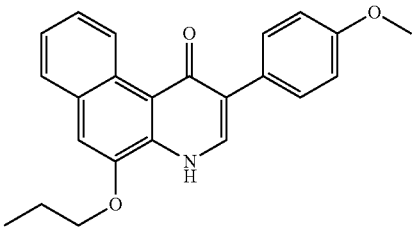

Production of 2-(4-methoxyphenyl)-5-propoxy-4H-benzo[f]quinolin-1-one

To a benzene solution (50 ml) containing 3-propoxynaphthalen-2-ylamine (2.05 g, 10.18 mmol) and ethyl α-(hydroxymethylene)-4-methoxyphenylacetate (2.29 g, 10.3 mmol) was added 350 mg of Amberlyst 15 (Sigma-Aldrich). The resulting mixture was heated under reflux for 21 hours using a Dean-Stark trap. The reaction mixture was then cooled to room temperature, filtered to remove resin, and then the filtrate was concentrated under reduced pressure. Diphenyl ether (2.2 ml) was added to the residue, and the mixture was then heated with a mantle heater and stirred for 1.5 hours under reflux. The resulting reaction mixture was cooled to room temperature, and then directly purified using silica gel column chromatography (dichloromethane:methanol=100:1→60:1). The purified product was concentrated under reduced pressure to recrystallize the residue from ethyl acetate-n-hexane, giving a pale yellow powder of 2-(4-methoxyphenyl)-5-propoxy-4H-benzo[f]quinolin-1-one (1.55 g, yield: 42%).

Melting point: 172-174° C.

$^1$H-NMR (DMSO-$d_6$) δ ppm: 1.08 (3H, t, J=7.3 Hz), 1.87-1.95 (2H, m), 3.77 (3H, s), 4.22 (2H, t, J=6.5 Hz), 6.97 (2H, d, J=8.8 Hz), 7.47-7.52 (3H, m), 7.64 (2H, d, J=8.8 Hz), 7.83-7.87 (1H, m), 7.92 (1H, s), 10.24-10.28 (1H, m), 11.60 (1H, brs).

Example 2

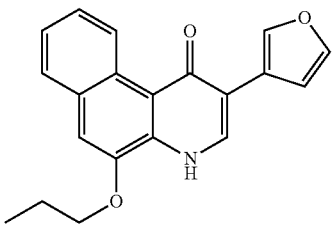

Production of
2-furan-3-yl-5-propoxy-4H-benzo[f]quinolin-1-one

3-Iodo-5-propoxy-4H-benzo[f]quinolin-1-one (1.06 g, 2.79 mmol) was suspended in dimethoxyethane (20 ml). Furan-3-boron acid (354 mg, 3.16 mmol), [1,1'-bis(diphenylphosphino)ferrocene]dichloropalladium (II)-dichloromethane complex ($PdCl_2(DPPF) \cdot CH_2Cl_2$, 123 mg, 0.11 mmol) and a 2N aqueous sodium carbonate solution (4.0 ml) were sequentially added to the suspension. The mixture was stirred at 90 to 100° C. under a nitrogen atmosphere for hours. The reaction mixture was cooled to room temperature, water was added thereto, and the resulting mixture was subjected to extraction using dichloromethane. The thus-obtained organic layer was concentrated under reduced pressure, and the residue was purified using silica gel column chromatography (dichloromethane:ethyl acetate=80:1). The purified product was concentrated under reduced pressure, the residue was washed with ethyl acetate and then dried, giving a pale brown powder of 2-furan-3-yl-5-propoxy-4H-benzo[f]quinolin-1-one (430 mg, yield: 48%).

Melting point: 252-254° C.

$^1$H-NMR (DMSO-$d_6$) δ ppm: 1.10 (3H, t, J=7.4 Hz), 1.87-1.98 (2H, m), 4.27 (2H, t, J=6.5 Hz), 7.03 (1H, s), 7.48-7.55 (2H, m), 7.57 (1H, s), 7.72 (1H, s), 7.84-7.89 (1H, m), 8.22 (1H, s), 8.71 (1H, s), 10.24-10.30 (1H, m), 11.80 (1H, brs).

Example 3

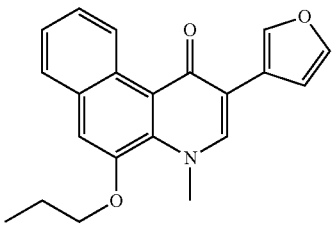

Production of 2-furan-3-yl-4-methyl-5-propoxy-4H-benzo[f]quinolin-1-one

To a DMF solution (5 ml) of 2-furan-3-yl-5-propoxy-4H-benzo[f]quinolin-1-one (300 mg, 0.94 mmol) was added sodium hydride (60% oil base, 61 mg, 1.4 mmol), and then the mixture was stirred at room temperature for 5 minutes. Methyl iodide (181 mg, 1.27 mmol) was added thereto and the resulting mixture was stirred at room temperature for 62 hours. Water and ethyl acetate were added to the reaction mixture and the resulting mixture was subjected to separation. The thus-obtained organic layer was washed with water, dried over anhydrous sodium sulfate, and then concentrated under reduced pressure. The residue was purified using silica gel column chromatography (dichloromethane:ethyl acetate=90:1→80:1). The purified product was concentrated under reduced pressure to recrystallize the residue from ethyl acetate-n-hexane, giving a pale gray powder of 2-furan-3-yl-4-methyl-5-propoxy-4H-benzo[f]quinolin-1-one (130 mg, yield: 42%).

Melting point: 165-167° C.

$^1$H-NMR (DMSO-$d_6$) δ ppm: 1.05 (3H, t, J=7.4 Hz), 1.83-1.92 (2H, m), 4.12 (2H, t, J=6.4 Hz), 4.21 (3H, s), 7.07 (1H, s), 7.45-7.51 (2H, m), 7.54 (1H, s), 7.70 (1H, s), 7.79-7.83 (1H, m), 8.36 (1H, s), 8.69 (1H, s), 10.34-10.38 (1H, m).

Example 4

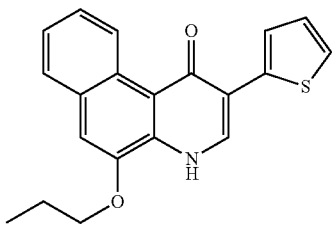

Production of 5-propoxy-2-thiophen-2-yl-4H-benzo[f]quinolin-1-one

The above compound was prepared in the same manner as in Example 1 using appropriate starting material.
Pale Brown Powder (Ethanol)
Melting point: 298-300° C.

$^1$H-NMR (DMSO-$d_6$) δ ppm: 1.10 (3H, t, J=7.4 Hz), 1.87-2.01 (2H, m), 4.27 (2H, t, J=6.5 Hz), 7.12 (1H, dd, J=3.9 Hz, 5.1 Hz), 7.47 (1H, d, J=4.7 Hz), 7.52-7.57 (2H, m), 7.59 (1H, s), 7.66 (1H, d, J=3.7 Hz), 7.87-7.91 (1H, m), 8.50 (1H, s), 10.20-10.27 (1H, m), 11.95 (1H, brs).

Example 5

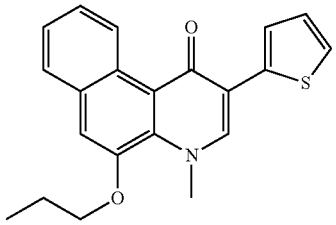

Production of 4-methyl-5-propoxy-2-thiophen-2-yl-4H-benzo[f]quinolin-1-one

The above compound was prepared in the same manner as in Example 3 using appropriate starting material.
Pale Yellow Powder (Ethyl Acetate)
Melting point: 193-195° C.

$^1$H-NMR (DMSO-$d_6$) δ ppm: 1.05 (3H, t, J=7.4 Hz), 1.84-1.92 (2H, m), 4.12 (2H, t, J=6.4 Hz), 4.23 (3H, s), 7.09-7.13 (1H, m), 7.46-7.55 (4H, m), 7.66 (1H, d, J=3.7 Hz), 7.80-7.84 (1H, m), 8.63 (1H, s), 10.32-10.36 (1H, m).

Example 6

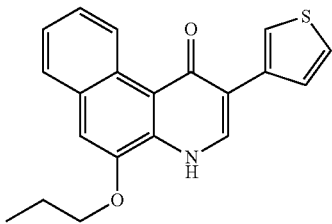

Production of 5-propoxy-2-thiophen-3-yl-4H-benzo[f]quinolin-1-one

The above compound was prepared in the same manner as in Example 1 using appropriate starting material.
Pale Brown Powder
$^1$H-NMR (DMSO-d$_6$) δ ppm: 1.10 (3H, t, J=7.3 Hz), 1.90-1.98 (2H, m), 4.27 (2H, t, J=6.5 Hz), 7.49-7.58 (4H, m), 7.63-7.66 (1H, m), 7.85-8.00 (1H, m), 8.24 (1H, s), 8.34-8.36 (1H, m), 10.23-10.29 (1H, m), 11.71 (1H, brs).

Example 7

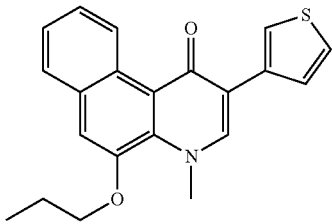

Production of 4-methyl-5-propoxy-2-thiophen-3-yl-4H-benzo[f]quinolin-1-one

The above compound was prepared in the same manner as in Example 3 using appropriate starting material.
White Powder
$^1$H-NMR (DMSO-d$_6$) δ ppm: 1.05 (3H, t, J=7.4 Hz), 1.84-1.92 (2H, m), 4.12 (2H, t, J=6.4 Hz), 4.19 (3H, s), 7.44-7.57 (4H, m), 7.70 (1H, d, J=5.1 Hz), 7.80-7.84 (1H, m), 8.38-8.40 (2H, brs), 10.30-10.34 (1H, m).

Example 8

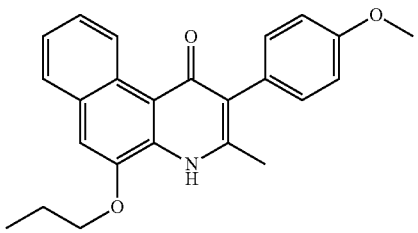

Production of 2-(4-methoxyphenyl)-3-methyl-5-propoxy-4H-benzo[f]quinolin-1-one

To a benzene solution (38 ml) containing 3-propoxynaphthalen-2-ylamine (600 mg, 2.98 mmol) and ethyl α-acetyl-4-methoxyphenylacetate (1.41 g, 5.96 mmol) was added 85 mg of Amberlyst 15 (Sigma-Aldrich). The resulting mixture was heated under reflux for 20 hours using a Dean-Stark trap. The reaction mixture was cooled to room temperature, filtered to remove resin, and then the filtrate was concentrated under reduced pressure. Diphenyl ether (2.8 ml) was added to the residue, and the mixture was then heated with a mantle heater and stirred for 70 minutes under reflux. The resulting reaction mixture was cooled to room temperature, and then directly purified using silica gel column chromatography (dichloromethane:methanol=80:1→70:1). The purified product was concentrated under reduced pressure, giving an oily substance (800 mg, yield: 72%). Ethyl acetate and n-hexane were added to the thus-obtained oily substance to crystallize and then recrystallized from ethyl acetate, giving a pale yellow powder of 2-(4-methoxyphenyl)-3-methyl-5-propoxy-4H-benzo[f]quinolin-1-one (290 mg).
Melting point: 204-206° C.
$^1$H-NMR (DMSO-d$_6$) δ ppm: 1.05 (3H, t, J=7.4 Hz), 1.90-1.98 (2H, m), 2.31 (3H, s), 3.77 (3H, s), 4.27 (2H, t, J=6.8 Hz), 6.95 (2H, d, J=8.6 Hz), 7.17 (2H, d, J=8.6 Hz), 7.39-7.50 (2H, m), 7.56 (1H, s), 7.84 (1H, dd, J=2.2 Hz, 6.5 Hz), 10.09-10.13 (1H, m), 10.79 (1H, brs).

Example 9

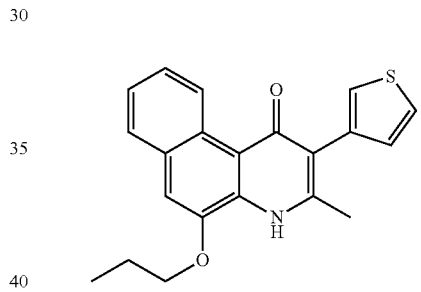

Production of 3-methyl-5-propoxy-2-thiophen-3-yl-4H-benzo[f]quinolin-1-one

The above compound was prepared in the same manner as in Example 8 using appropriate starting material.
Pale Gray Powder (Ethyl Acetate)
Melting point: 186-188° C.
$^1$H-NMR (DMSO-d$_6$) δ ppm: 1.04 (3H, t, J=7.3 Hz), 1.88-1.97 (2H, m), 2.40 (3H, s), 4.26 (2H, t, J=6.7 Hz), 7.14 (1H, d, J=4.9 Hz), 7.41-7.54 (5H, m), 7.83 (1H, d, J=6.6 Hz), 10.07-10.11 (1H, m), 10.84 (1H, brs).

Example 10

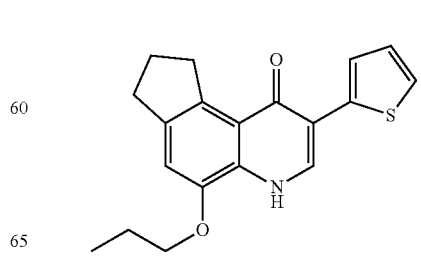

Production of 5-propoxy-8-thiophen-2-yl-1,2,3,6-tetrahydro-6-aza-cyclopenta[a]naphthalen-9-one The above compound was prepared in the same manner as in Example 1 using appropriate starting materials.
Yellow Powder $^1$H-NMR (DMSO-d$_6$) δ ppm: 1.04 (3H, t, J=7.4 Hz), 1.77-1.88 (2H, m), 1.97-2.08 (2H, m), 2.86 (2H, t, J=7.5 Hz), 3.45 (2H, t, J=7.0 Hz), 4.10 (2H, t, J=6.5 Hz), 7.05 (1H, t, J=3.8 Hz), 7.13 (1H, s), 7.36 (1H, d, J=5.1 Hz), 7.53 (1H, d, J=3.6 Hz), 8.31 (1H, s), 11.39 (1H, brs).

Example 11

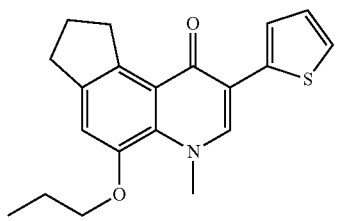

Production of 6-methyl-5-propoxy-8-thiophen-2-yl-1,2,3,6-tetrahydro-6-aza-cyclopenta[a]naphthalen-9-one The above compound was prepared in the same manner as in Example 3 using appropriate starting materials.
Orange Color Powder $^1$H-NMR (DMSO-d$_6$) δ ppm: 1.01 (3H, t, J=7.4 Hz), 1.77-1.85 (2H, m), 1.97-2.03 (2H, m), 2.84 (2H, t, J=7.6 Hz), 3.49 (2H, t, J=7.1 Hz), 4.00 (2H, t, J=6.4 Hz), 4.13 (3H, s), 7.05 (1H, t, J=3.8 Hz), 7.18 (1H, s), 7.35 (1H, d, J=4.7 Hz), 7.54 (1H, d, J=3.3 Hz), 8.48 (1H, s).

Example 12

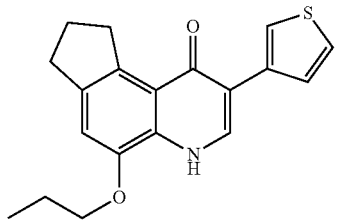

Production of 5-propoxy-8-thiophen-3-yl-1,2,3,6-tetrahydro-6-aza-cyclopenta[a]naphthalen-9-one The above compound was prepared in the same manner as in Example 1 using appropriate starting materials.
Pale Brown Powder $^1$H-NMR (DMSO-d$_6$) δ ppm: 1.03 (3H, t, J=7.4 Hz), 1.76-1.87 (2H, m), 1.95-2.07 (2H, m), 2.85 (2H, t, J=7.5 Hz), 3.30-3.55 (2H, m), 4.09 (2H, t, J=6.5 Hz), 7.11 (1H, s), 7.48-7.56 (2H, m), 8.11 (1H, d, J=6.2 Hz), 8.21-8.23 (1H, m), 11.18 (1H, d, J=5.8 Hz).

Example 13

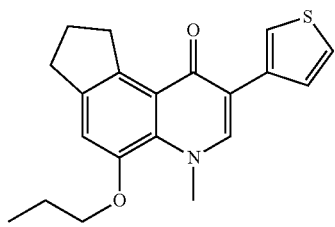

Production of 6-methyl-5-propoxy-8-thiophen-3-yl-1,2,3,6-tetrahydro-6-aza-cyclopenta[a]naphthalen-9-one The above compound was prepared in the same manner as in Example 3 using appropriate starting materials.
Pale Yellow Powder $^1$H-NMR (DMSO-d$_6$) δ ppm: 1.01 (3H, t, J=7.4 Hz), 1.76-1.85 (2H, m), 1.95-2.01 (2H, m), 2.83 (2H, t, J=7.6 Hz), 3.49 (2H, t, J=7.4 Hz), 3.99 (2H, t, J=6.5 Hz), 4.09 (3H, s), 7.15 (1H, s), 7.48-7.52 (1H, m), 7.63-7.65 (1H, m), 8.26-8.28 (2H, m).

Example 14

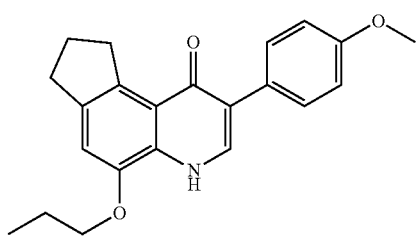

Production of 8-(4-methoxyphenyl)-5-propoxy-1,2,3,6-tetrahydro-6-aza-cyclopenta[a]naphthalen-9-one The above compound was prepared in the same manner as in Example 1 using appropriate starting materials.
Pale Brown Powder (Ethyl Acetate)
Melting point: 206-208° C.

$^1$H-NMR (DMSO-d$_6$) δ ppm: 1.02 (3H, t, J=7.4 Hz), 1.78-1.86 (2H, m), 1.96-2.02 (2H, m), 2.83 (2H, t, J=7.5 Hz), 3.40 (2H, t, J=7.3 Hz), 3.74 (3H, s), 4.07 (2H, t, J=6.4 Hz), 6.91 (2H, d, J=8.8 Hz), 7.09 (1H, s), 7.55 (2H, d, J=8.8 Hz), 7.78 (1H, d, J=5.9 Hz), 11.06 (1H, d, J=5.8 Hz).

Example 15

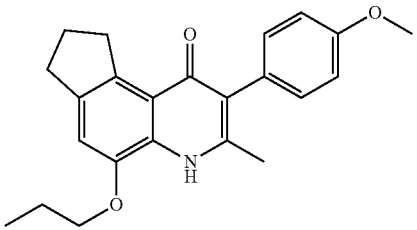

Production of 8-(4-methoxyphenyl)-7-methyl-5-propoxy-1,2,3,6-tetrahydro-6-aza-cyclopenta[a]naphthalen-9-one The above compound was prepared in the same manner as in Example 8 using appropriate starting material.
Pale Yellow Powder (Ethyl Acetate)
Melting point: 223-225° C.
$^1$H-NMR (DMSO-$d_6$) δ ppm: 0.99 (3H, t, J=7.4 Hz), 1.79-1.87 (2H, m), 1.93-1.99 (2H, m), 2.21 (3H, s), 2.82 (2H, t, J=7.4 Hz), 3.31 (2H, t, J=7.1 Hz), 3.75 (3H, s), 4.10 (2H, t, J=6.7 Hz), 6.90 (2H, d, J=8.7 Hz), 7.08 (2H, d, J=8.5 Hz), 7.10 (1H, s), 10.30 (1H, brs).

Example 16

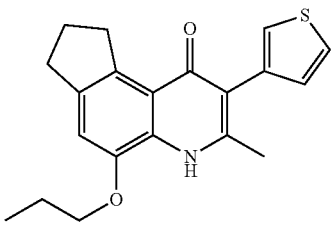

Production of 7-methyl-5-propoxy-8-thiophen-3-yl-1,2,3,6-tetrahydro-6-aza-cyclopenta[a]naphthalen-9-one The above compound was prepared in the same manner as in Example 8 using appropriate starting materials.
Pale Brown Powder (Ethyl Acetate)
Melting point: 260-262° C.
$^1$H-NMR (DMSO-$d_6$) δ ppm: 0.99 (3H, t, J=7.3 Hz), 1.79-1.87 (2H, m), 1.90-1.99 (2H, m), 2.31 (3H, s), 2.82 (2H, t, J=7.5 Hz), 3.32 (2H, t, J=7.3 Hz), 4.09 (2H, t, J=6.7 Hz), 7.04-7.10 (2H, m), 7.31-7.32 (1H, m), 7.44-7.47 (1H, m), 10.35 (1H, brs).

Example 17

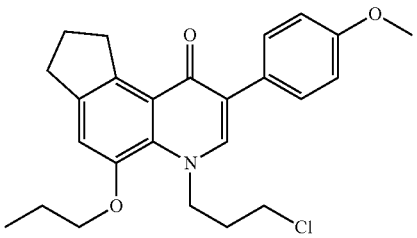

Production of 6-(3-chloropropyl)-8-(4-methoxyphenyl)-5-propoxy-1,2,3,6-tetrahydro-6-aza-cyclopenta[a]naphthalen-9-one To a DMF solution (6 ml) of 8-(4-methoxyphenyl)-5-propoxy-1,2,3,6-tetrahydro-6-aza-cyclopenta[a]naphthalen-9-one (1.26 g, 3.60 mmol) was added sodium hydride (60% oil base, 189 mg, 4.33 mmol). The mixture was stirred at room temperature for 10 minutes. To the resulting mixture was added 1-bromo-3-chloropropane (1.70 g, 10.8 mmol), followed by stirring at room temperature for 16 hours. Water and ethyl acetate were added to the reaction mixture and the resulting reaction mixture was then subjected to separation. The thus-obtained organic layer was washed with an aqueous saturated sodium chloride solution twice. After being dried over anhydrous sodium sulfate, the organic layer was concentrated under reduced pressure. The residue was purified using silica gel column chromatography (dichloromethane:ethyl acetate=20:1→12:1). The purified product was concentrated under reduced pressure, giving a yellow oily substance of 6-(3-chloropropyl)-8-(4-methoxyphenyl)-5-propoxy-1,2,3,6-tetrahydro-6-aza-cyclopenta[a]naphthalen-9-one (365 mg, yield: 92%).
$^1$H-NMR (CDCl$_3$) δ ppm: 1.07-1.13 (3H, m), 1.90-2.24 (6H, m), 2.91 (2H, t, J=7.6 Hz), 3.45 (2H, t, J=5.7 Hz), 3.67 (2H, t, J=7.5 Hz), 3.83 (3H, s), 4.04 (2H, t, J=6.7 Hz), 4.71 (2H, t, J=6.4 Hz), 6.92-7.04 (3H, m), 7.58-7.62 (3H, m).

Example 18

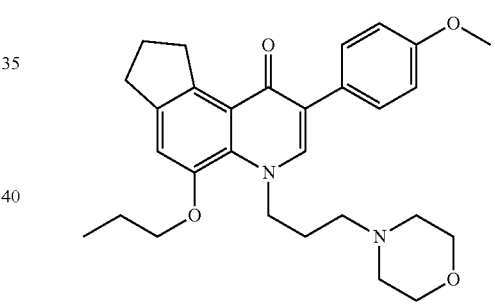

Production of 8-(4-methoxyphenyl)-6-(3-morpholin-4-ylpropyl)-5-propoxy-1,2,3,6-tetrahydro-6-aza-cyclopenta[a]naphthalen-9-one A mixture containing 6-(3-chloropropyl)-8-(4-methoxyphenyl)-5-propoxy-1,2,3,6-tetrahydro-6-aza-cyclopenta[a]naphthalen-9-one (700 mg, 1.64 mmol), morpholine (165 mg, 1.90 mmol), potassium carbonate (341 mg, 2.47 mmol), sodium iodide (295 mg, 1.97 mmol) and dimethyl formamide (3 ml) was stirred at 60° C. for 7 hours. Water and ethyl acetate were added to the reaction mixture, followed by separation. The thus-obtained organic layer was washed with an aqueous saturated sodium chloride solution twice and then concentrated under reduced pressure. The residue was purified using silica gel column chromatography (dichloromethane:methanol=70:1→50:1). The purified product was concentrated under reduced pressure to recrystallize the residue from ethyl acetate-n-hexane, giving a white powder of 8-(4-methoxyphenyl)-6-(3-morpholin-4-ylpropyl)-5-propoxy-1,2,3,6-tetrahydro-6-aza-cyclopenta[a]naphthalen-9-one (295 mg, yield: 38%).

Melting point: 135-137° C.

¹H-NMR (DMSO-d₆) δ ppm: 1.01 (3H, t, J=7.3 Hz), 1.75-1.85 (4H, m), 1.96 (2H, t, J=7.5 Hz), 2.04-2.15 (6H, m), 2.83 (2H, t, J=7.5 Hz), 3.38-3.41 (6H, m), 3.74 (3H, s), 4.02 (2H, t, J=6.5 Hz), 4.55 (2H, t, J=6.2 Hz), 6.90 (2H, d, J=8.7 Hz), 7.18 (1H, s), 7.60 (2H, d, J=8.7 Hz), 7.93 (1H, s).

Example 19

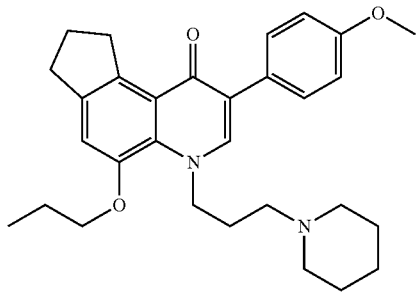

Production of 8-(4-methoxyphenyl)-6-(3-piperidin-1-ylpropyl)-5-propoxy-1,2,3,6-tetrahydro-6-aza-cyclopenta[a]naphthalen-9-one The above compound was prepared in the same manner as in Example 18 using appropriate starting material.

Pale Yellow Powder (Ethyl Acetate-n-hexane)

Melting point: 99-101° C.

¹H-NMR (DMSO-d₆) δ ppm: 1.01 (3H, t, J=7.3 Hz), 1.20-1.50 (6H, m), 1.74-1.86 (4H, m), 1.96 (2H, t, J=7.4 Hz), 2.02-2.20 (6H, m), 2.83 (2H, t, J=7.3 Hz), 3.30-3.40 (2H, m), 3.74 (3H, s), 4.02 (2H, t, J=6.4 Hz), 4.53 (2H, t, J=5.8 Hz), 6.90 (2H, d, J=8.7 Hz), 7.18 (1H, s), 7.60 (2H, d, J=8.7 Hz), 7.91 (1H, s).

Example 20

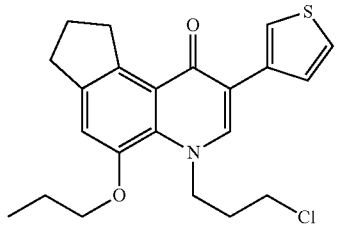

Production of 6-(3-chloropropyl)-5-propoxy-8-thiophen-3-yl-1,2,3,6-tetrahydro-6-aza-cyclopenta[a]naphthalen-9-one The above compound was prepared in the same manner as in Example 17 using appropriate starting material.

¹H-NMR (CDCl₃) δ ppm: 1.07-1.13 (3H, m), 1.88-2.25 (6H, m), 2.91 (2H, t, J=7.6 Hz), 3.45 (2H, t, J=5.8 Hz), 3.69 (2H, t, J=7.5 Hz), 4.01-4.04 (2H, m), 4.74 (2H, t, J=6.4 Hz), 7.05 (1H, s), 7.32-7.35 (1H, m), 7.43-7.47 (1H, m), 7.83 (1H, s), 8.08-8.10 (1H, m).

Example 21

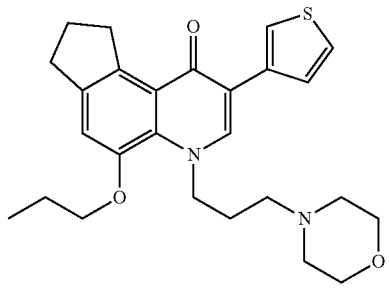

Production of 6-(3-morpholin-4-ylpropyl)-5-propoxy-8-thiophen-3-yl-1,2,3,6-tetrahydro-6-aza-cyclopenta[a]naphthalen-9-one The above compound was prepared in the same manner as in Example 18 using appropriate starting materials.

Pale Yellow Powder (Ethyl Acetate)

Melting point: 163-165° C.

¹H-NMR (DMSO-d₆) δ ppm: 1.01 (3H, t, J=7.3 Hz), 1.76-1.86 (4H, m), 1.98 (2H, t, J=7.5 Hz), 2.03-2.20 (6H, m), 2.84 (2H, t, J=7.5 Hz), 3.41-3.52 (6H, m), 4.02 (2H, t, J=6.5 Hz), 4.60 (2H, t, J=6.3 Hz), 7.18 (1H, s), 7.49-7.52 (1H, m), 7.62-7.64 (1H, m), 8.25-8.27 (1H, m), 8.30 (1H, s).

Example 22

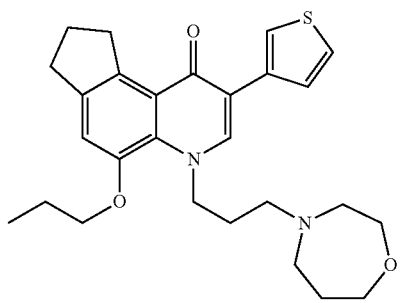

Production of 6-(3-[1,4]oxazepan-4-ylpropyl)-5-propoxy-8-thiophen-3-yl-1,2,3,6-tetrahydro-6-aza-cyclopenta[a]naphthalen-9-one The above compound was prepared in the same manner as in Example 18 using appropriate starting materials.

Pale Brown Powder (Ethyl Acetate)

Melting point: 146-148° C.

¹H-NMR (DMSO-d₆) δ ppm: 1.01 (3H, t, J=7.3 Hz), 1.60-1.64 (2H, m), 1.74-1.86 (4H, m), 1.98 (2H, t, J=7.4 Hz), 2.19 (2H, t, J=6.3 Hz), 2.40-2.45 (4H, m), 2.84 (2H, t, J=7.4 Hz), 3.51-3.59 (6H, m), 4.03 (2H, t, J=6.4 Hz), 4.60 (2H, t, J=6.0 Hz), 7.19 (1H, s), 7.48-7.51 (1H, m), 7.61 (1H, d, J=4.9 Hz), 8.23 (1H, d, J=1.8 Hz), 8.27 (1H, s).

Example 23

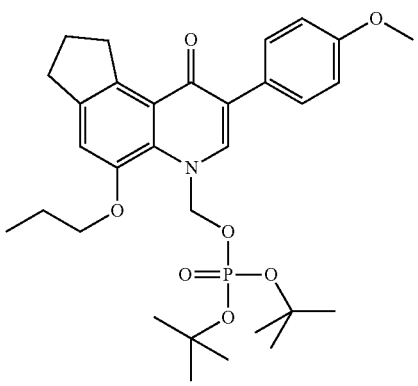

Production of di-tert-butyl 8-(4-methoxyphenyl)-9-oxo-5-propoxy-1,2,3,9-tetrahydro-6-aza-cyclopenta[a]naphthalen-6-ylmethyl phosphate To a DMF solution (10 ml) of 8-(4-methoxyphenyl)-5-propoxy-1,2,3,6-tetrahydro-6-aza-cyclopenta[a]naphthalen-9-one (400 mg, 1.15 mmol) and sodium iodide (343 mg, 2.29 mmol) was added sodium hydride (60% oil base, 74.9 mg, 1.72 mmol), and the mixture was then stirred for 10 minutes at room temperature. To the resulting mixture was added a DMF solution (20 ml) of di-tert-butyl chloromethyl phosphate (888 mg, 3.43 mmol), and the mixture was then stirred at 40° C. for 4 hours. The reaction mixture was ice-cooled, ice water was added thereto, and then the reaction mixture was subjected to extraction using ethyl acetate. The thus-obtained organic layer was washed with an aqueous saturated sodium chloride solution twice, dried over anhydrous sodium sulfate and then concentrated under reduced pressure. The residue was purified using medium pressure liquid chromatography (NH silica gel, n-hexane:ethyl acetate=100:0→0:100). The purified product was concentrated under reduced pressure, giving a white powder of di-tert-butyl 8-(4-methoxyphenyl)-9-oxo-5-propoxy-1,2,3,9-tetrahydro-6-aza-cyclopenta[a]naphthalen-6-ylmethyl phosphate (263 mg, yield: 40%).

$^1$H-NMR (CDCl$_3$) δ ppm: 1.08-1.14 (3H, t, J=7.4 Hz), 1.35 (18H, s), 1.88-2.16 (4H, m), 2.88-2.95 (2H, t, J=7.7 Hz), 3.60-3.66 (2H, t, J=7.5 Hz), 3.82 (3H, s), 4.05-4.10 (2H, t, J=6.7 Hz), 6.30-6.35 (2H, d, J=12.4 Hz), 6.90-6.97 (2H, d, J=8.8 Hz), 7.09 (1H, s), 7.57-7.63 (2H, d, J=8.8 Hz), 7.76 (1H, s).

Example 24

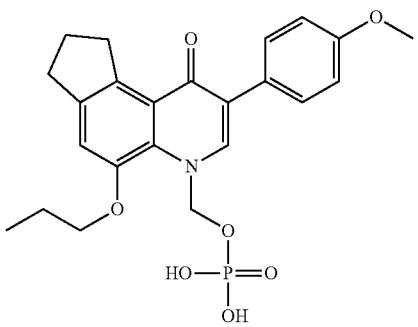

Production of [8-(4-methoxyphenyl)-9-oxo-5-propoxy-1,2,3,9-tetrahydro-6-aza-cyclopenta[a]naphthalen-6-ylmethyl]monophosphate A dichloromethane solution (4 ml) of di-tert-butyl 8-(4-methoxyphenyl)-9-oxo-5-propoxy-1,2,3,9-tetrahydro-6-aza-cyclopenta[a]naphthalen-6-ylmethyl ester (263 mg, 0.46 mmol) was ice-cooled, trifluoroacetic acid (1.2 ml) and dichloromethane (4 ml) were added thereto under a nitrogen atmosphere and the resulting mixture was stirred at 0° C. for 1 hour. This mixture was concentrated under reduced pressure. The residue was subjected to vacuum drying, giving a pale yellow powder of [8-(4-methoxyphenyl)-9-oxo-5-propoxy-1,2,3,9-tetrahydro-6-aza-cyclopenta[a]naphthalen-6-ylmethyl]monophosphate (147 mg, yield: 56%).

$^1$H-NMR (DMSO-d$_6$) δ ppm: 1.01-1.04 (3H, t, J=7.4 Hz), 1.78-1.86 (2H, m), 1.96-2.02 (2H, m), 2.83 (2H, t, J=7.5 Hz), 3.40 (2H, t, J=7.3 Hz), 3.74 (3H, s), 4.07 (2H, t, J=6.4 Hz), 6.25-6.30 (2H, d, J=10.42 Hz), 6.92-6.95 (2H, m), 7.13 (1H, s), 7.59-7.63 (2H, d, J=8.8 Hz), 7.76-7.79 (1H, d, J=5.9 Hz).

Example 25

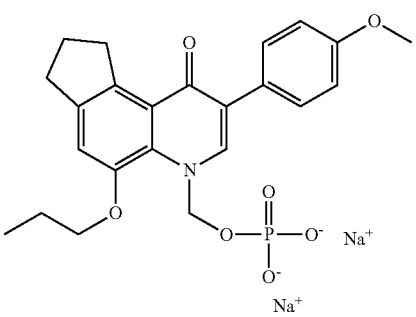

Production of [8-(4-methoxyphenyl)-9-oxo-5-propoxy-1,2,3,9-tetrahydro-6-aza-cyclopenta[a]naphthalen-6-ylmethyl]monophosphate disodium salt

[8-(4-Methoxyphenyl)-9-oxo-5-propoxy-1,2,3,9-tetrahydro-6-aza-cyclopenta[a]naphthalen-6-ylmethyl]monophosphate (147 mg, 0.32 mmol) was suspended in isopropyl alcohol (20 ml), and 1N aqueous sodium hydroxide solution (0.64 ml, 0.64 mmol) was then added thereto under a nitrogen atmosphere at 0° C. The resulting mixture was stirred for 1 hour at 0° C. The generated insoluble matter was separated and washed with acetone and dried, giving a white powder of [8-(4-methoxyphenyl)-9-oxo-5-propoxy-1,2,3,9-tetrahydro-6-aza-cyclopenta[a]naphthalen-6-ylmethyl]monophosphate disodium salt (42 mg, yield: 26%)

$^1$H-NMR (D$_2$O) δ ppm: 0.91-0.98 (3H, t, J=7.8 Hz), 1.74-1.83 (2H, m), 1.92-1.98 (2H, m), 2.75-2.81 (2H, t, J=7.6 Hz), 3.30-3.36 (2H, t, J=7.2 Hz), 3.75 (3H, s), 3.90-3.95 (2H, t, J=6.7 Hz), 5.94-5.99 (2H, d, J=9.5 Hz), 6.89-6.93 (2H, d, J=8.8 Hz), 7.15 (1H, s), 7.87-7.94 (2H, d, J=8.8 Hz), 8.58 (1H, s).

Example 26

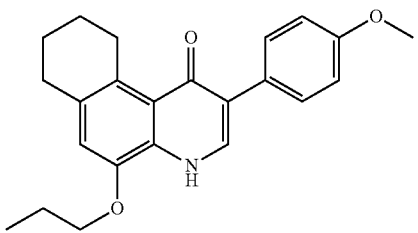

Production of 2-(4-methoxyphenyl)-5-propoxy-7,8,9,10-tetrahydro-4H-benzo[f]quinolin-1-one The above compound was prepared in the same manner as in Example 1 using appropriate starting material.
Pale Yellow Powder (Ethyl Acetate)
Melting point: 186-187° C.
$^1$H-NMR (DMSO-d$_6$) δ ppm: 1.02 (3H, t, J=7.4 Hz), 1.60-1.70 (4H, m), 1.78-1.86 (2H, m), 2.70-2.80 (2H, m), 3.30-3.40 (2H, m), 3.74 (3H, s), 4.05 (2H, t, J=6.4 Hz), 6.85 (1H, s), 6.90 (2H, d, J=8.7 Hz), 7.50 (2H, d, J=8.7 Hz), 7.72 (1H, d, J=5.1 Hz), 10.95 (1H, d, J=4.7 Hz).

Example 27

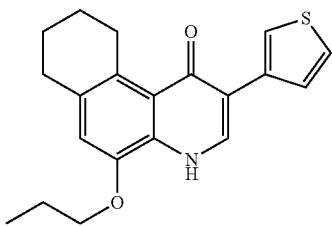

Production of 5-propoxy-2-thiophen-3-yl-7,8,9,10-tetrahydro-4H-benzo[f]quinolin-1-one The above compound was prepared in the same manner as in Example 1 using appropriate starting material.
Pale Brown Powder (Ethyl Acetate)
Melting point: 213-215° C.
$^1$H-NMR (DMSO-d$_6$) δ ppm: 1.02 (3H, t, J=7.4 Hz), 1.60-1.70 (4H, m), 1.75-1.86 (2H, m), 2.70-2.80 (2H, m), 3.30-3.40 (2H, m), 4.05 (2H, t, J=6.4 Hz), 6.85 (1H, s), 7.46-7.52 (2H, m), 8.06 (1H, s), 8.14-8.15 (1H, m), 11.10 (1H, brs).

Example 28

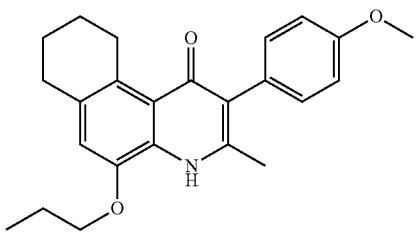

Production of 2-(4-methoxyphenyl)-3-methyl-5-propoxy-7,8,9,10-tetrahydro-4H-benzo[f]quinolin-1-one The above compound was prepared in the same manner as in Example 8 using appropriate starting material.
Pale Yellow Powder (Ethyl Acetate)
Melting point: 199-201° C.
$^1$H-NMR (DMSO-d$_6$) δ ppm: 0.98 (3H, t, J=7.3 Hz), 1.60-1.70 (4H, m), 1.78-1.87 (2H, m), 2.17 (3H, s), 2.70-2.80 (2H, m), 3.20-3.30 (2H, m), 3.74 (3H, s), 4.07 (2H, t, J=6.7 Hz), 6.84 (1H, s), 6.88 (2H, d, J=8.7 Hz), 7.06 (2H, d, J=8.5 Hz), 10.17 (1H, brs).

Example 29

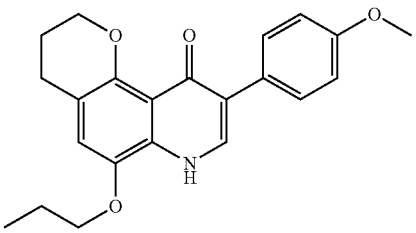

Production of 3-(4-methoxyphenyl)-10-propoxy-1,6,7,8-tetrahydro-5-oxa-1-aza-phenanthren-4-one The above compound was prepared in the same manner as in Example 1 using appropriate starting material.
Melting point: 222-223° C.
$^1$H-NMR (DMSO-d$_6$) δ ppm: 1.00-1.06 (3H, t, J=7.5 Hz), 1.74-1.95 (4H, m), 2.72-2.75 (2H, t, J=6.5 Hz), 3.75 (3H, s), 4.00-4.10 (4H, m), 6.87-6.93 (3H, m), 7.46-7.52 (2H, d, J=9.0 Hz), 7.65 (1H, s), 10.70-10.90 (1H, brs).

Example 30

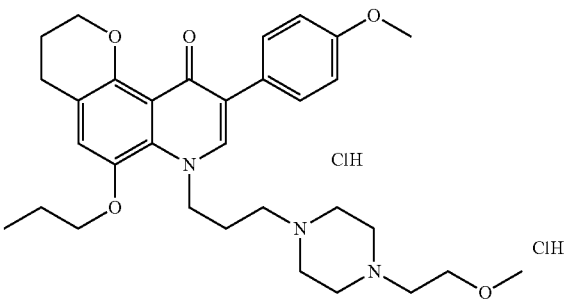

Production of 1-{3-[4-(2-methoxyethyl)piperazin-1-yl]propyl}-3-(4-methoxyphenyl)-10-propoxy-1,6,7,8-tetrahydro-5-oxa-1-aza-phenanthren-4-one dihydrochloride The above compound was prepared in the same manner as in Example 18 using appropriate starting materials.
Melting point: 145-147° C.
$^1$H-NMR (DMSO-d$_6$) δ ppm: 1.01-1.06 (3H, t, J=7.4 Hz), 1.85-2.02 (4H, m), 2.12-2.33 (2H, m), 2.84-2.89 (2H, t, J=6.3 Hz), 3.02-3.20 (2H, m), 3.28-3.80 (15H, m), 4.08-4.13 (2H, t, J=6.8 Hz), 4.28-4.31 (2H, t, J=4.6 Hz), 4.75-4.95 (2H, m), 7.00-7.03 (2H, d, J=8.9 Hz), 7.30 (1H, s), 7.63-7.66 (2H, d, J=8.9 Hz), 8.48 (1H, s).

Example 31

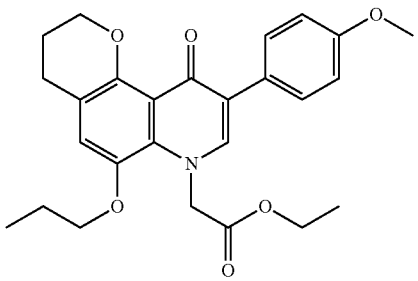

Production of ethyl[3-(4-methoxyphenyl)-4-oxo-10-propoxy-7,8-dihydro-4H,6H-5-oxa-1-aza-phenanthren-1-yl]acetate Sodium hydride (60% oil base, 80 mg, 2.0 mmol) was added to a DMF solution (10 ml) of 3-(4-methoxyphenyl)-10-propoxy-1,6,7,8-tetrahydro-5-oxa-1-aza-phenanthren-4-one (600 mg, 1.64 mmol), the resulting mixture was then stirred at room temperature for 5 minutes. Ethyl bromoacetate (330 mg, 2.0 mmol) was added thereto and the resulting mixture was stirred at room temperature for 16 hours. Water and ethyl acetate were added to the reaction mixture, followed by separation. The thus-obtained organic layer was washed with water, dried over anhydrous sodium sulfate and then concentrated under reduced pressure. The residue was purified using medium pressure liquid chromatography (NH silica gel, n-hexane:ethyl acetate=100:0→0:100). The purified product was concentrated under reduced pressure, giving a colorless oily substance ethyl[3-(4-methoxyphenyl)-4-oxo-10-propoxy-7,8-dihydro-4H,6H-5-oxa-1-aza-phenanthren-1-yl]acetate (700 mg, yield: 95%).

$^1$H-NMR (CDCl$_3$) δ ppm: 1.00-1.10 (3H, t, J=7.5 Hz), 1.25-1.28 (3H, t, J=6.0), 1.75-1.90 (2H, m), 2.02-2.43 (2H, m), 2.80-2.90 (2H, m), 3.85 (3H, s), 3.86-3.88 (2H, m), 4.10-4.13 (4H, m), 5.10 (2H, s), 6.75 (1H, s), 6.85-6.90 (2H, d, J=9.0), 7.24 (1H, s), 7.60-7.75 (2H, d, J=9.0).

Example 32

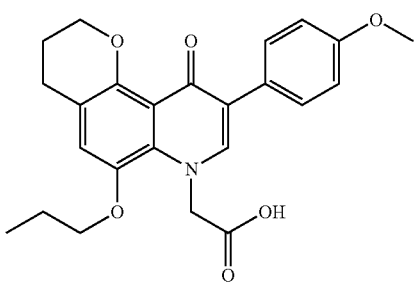

Production of [3-(4-methoxyphenyl)-4-oxo-10-propoxy-7,8-dihydro-4H,6H-5-oxa-1-aza-phenanthren-1-yl]acetic acid A 5N aqueous sodium hydroxide solution (10 ml) was added to an ethanol solution (30 ml) of ethyl[3-(4-methoxyphenyl)-4-oxo-10-propoxy-7,8-dihydro-4H,6H-5-oxa-1-aza-phenanthren-1-yl]acetate (700 mg, 1.55 mmol) and heated for 2 hours under reflux. The mixture was cooled to room temperature and concentrated under reduced pressure. While ice-cooling the concentrate, water and concentrated hydrochloric acid were added to the residue to make it acidic. Subsequently, the formed insoluble matter was separated and dried, giving a yellow powder of [3-(4-methoxyphenyl)-4-oxo-10-propoxy-7,8-dihydro-4H,6H-5-oxa-1-aza-phenanthren-1-yl]acetic acid (580 mg, yield: 88%).

$^1$H-NMR (DMSO-d$_6$) δ ppm: 0.94-1.00 (3H, t, J=7.5 Hz), 1.74-1.82 (2H, m), 1.94-1.98 (2H, m), 2.78-2.83 (2H, t, J=6.2 Hz), 3.77 (3H, s), 3.92-3.98 (2H, t, J=6.7 Hz), 4.21-4.25 (2H, t, J=4.8 Hz), 5.35 (2H, s), 6.96-7.00 (2H, d, J=8.8 Hz), 7.16 (1H, s), 7.56-7.59 (2H, d, J=8.8 Hz), 8.29 (1H, s).

Example 33

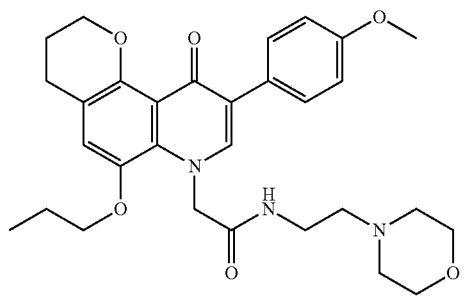

Production of 2-[3-(4-methoxyphenyl)-4-oxo-10-propoxy-7,8-dihydro-4H,6H-5-oxa-1-aza-phenanthren-1-yl]-N-(2-morpholin-4-ylethyl)acetamide 4-(2-Aminoethyl)morpholine (217 mg, 1.7 mmol) was added to a DMF solution (10 ml) of [3-(4-methoxyphenyl)-4-oxo-10-propoxy-7,8-dihydro-4H,6H-5-oxa-1-aza-phenanthren-1-yl]acetic acid (580 mg, 1.39 mmol), 2-(7-aza-1H-benzotriazol-1-yl)-1,1,3,3-tetramethyl uronium hexafluorophosphate (HATU, 790 mg, 2.1 mmol) and triethylamine (5 ml). The mixture was stirred overnight at room temperature and then concentrated under reduced pressure. Water and ethyl acetate were added to the residue, followed by separation. The thus-obtained organic layer was washed with water and concentrated under reduced pressure. The residue was purified using silica gel column chromatography (dichloromethane:methanol=10:1). The purified product was concentrated under reduced pressure, and the residue was recrystallized from ethyl acetate, giving a pale brown powder of 2-[3-(4-methoxyphenyl)-4-oxo-10-propoxy-7,8-dihydro-4H,6H-5-oxa-1-aza-phenanthren-1-yl]-N-(2-morpholin-4-ylethyl)acetamide (115 mg, yield: 16%).

Melting point: 201-203° C.

$^1$H-NMR (DMSO-d$_6$) δ ppm: 0.94-1.00 (3H, t, J=7.5 Hz), 1.71-1.77 (2H, m), 1.91-1.93 (2H, m), 2.29-2.34 (4H, m), 2.72-2.75 (2H, t, J=6.2 Hz), 3.15-3.19 (2H, m), 3.25-3.30 (2H, m), 3.33-3.54 (4H, m), 3.76 (3H, s), 3.85-3.90 (2H, t, J=6.7 Hz), 4.07-4.11 (2H, m), 5.06 (2H, s), 6.90-6.93 (3H, m), 7.54-7.58 (2H, m), 7.72 (1H, s), 7.80-7.82 (1H, m).

Example 34

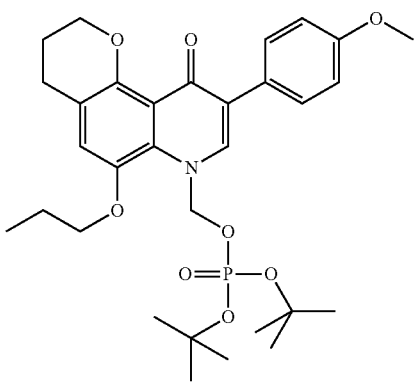

Production of di-tert-butyl 3-(4-methoxyphenyl)-4-oxo-10-propoxy-7,8-dihydro-4H,6H-5-oxa-1-aza-phenanthren-1-ylmethyl phosphate The above compound was prepared in the same manner as in Example 23 using appropriate starting material.

$^1$H-NMR (CDCl$_3$) δ ppm: 1.06-1.12 (3H, t, J=7.4 Hz), 1.36 (18H, s), 1.88-1.96 (2H, m), 2.01-2.10 (2H, m), 3.82 (3H, s), 3.98-4.03 (2H, t, J=6.7 Hz), 4.28-4.32 (2H, t, J=5.1 Hz), 6.25-6.31 (2H, d, J=12.2 Hz), 6.85-6.93 (3H, m), 7.60-7.66 (3H, m).

Example 35

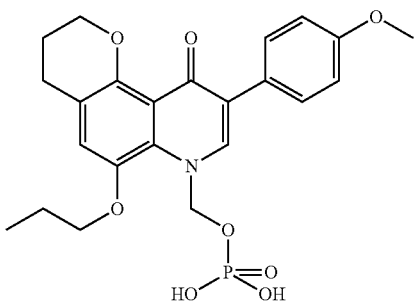

Production of [3-(4-methoxyphenyl)-4-oxo-10-propoxy-7,8-dihydro-4H,6H-5-oxa-1-aza-phenanthren-1-ylmethyl]monophosphate The above compound was prepared in the same manner as in Example 24 using appropriate starting material.

$^1$H-NMR (DMSO-d$_6$) δ ppm: 0.99-1.04 (3H, t, J=7.4 Hz), 1.74-1.95 (4H, m), 2.72-2.75 (2H, t, J=6.5 Hz), 3.75 (3H, s), 4.00-4.10 (4H, m), 6.20-6.24 (2H, d, J=10.3 Hz), 6.92-7.10 (3H, m), 7.53-7.57 (2H, m), 7.86 (1H, s).

Example 36

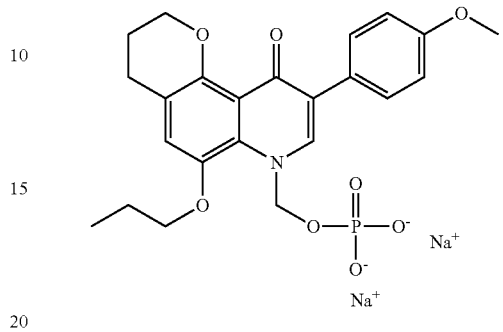

Production of [3-(4-methoxyphenyl)-4-oxo-10-propoxy-7,8-dihydro-4H,6H-5-oxa-1-aza-phenanthren-1-ylmethyl]monophosphate disodium salt The above compound was prepared in the same manner as in Example 25 using appropriate starting material.

$^1$H-NMR (D$_2$O) δ ppm: 0.91-0.97 (3H, t, J=7.4 Hz), 1.72-1.86 (2H, m), 1.90-1.94 (2H, m), 2.70-2.75 (2H, t, J=6.4 Hz), 3.74 (3H, s), 3.91-3.97 (3H, t, J=6.8 Hz), 4.11-4.15 (3H, t, J=4.8 Hz), 5.94-5.98 (2H, d, J=8.8 Hz), 6.89-6.93 (2H, d, J=8.8 Hz), 7.03 (1H, s), 7.37-7.41 (2H, d, J=8.8 Hz), 7.97 (1H, s).

Example 37

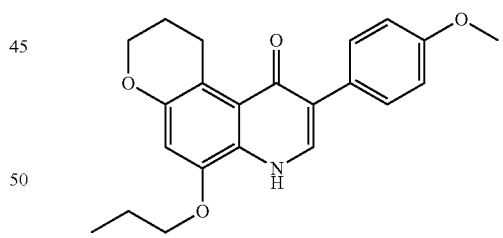

Production of 9-(4-methoxyphenyl)-6-propoxy-2,3-dihydro-1H,7H-pyrano[3,2-f]quinolin-10-one The above compound was prepared in the same manner as in Example 1 using appropriate starting material.

Melting point: 171-173° C.

$^1$H-NMR (CDCl$_3$) δ ppm: 1.03-1.10 (3H, t, J=7.5 Hz), 1.84-2.02 (4H, m), 3.52-3.58 (2H, t, J=6.5 Hz), 3.81 (3H, s), 4.02-4.07 (2H, t, J=6.6 Hz), 4.16-4.19 (2H, t, J=5.1 Hz), 6.58

(1H, s), 6.91-6.95 (2H, d, J=9.0 Hz), 7.51-7.55 (2H, d, J=9.0 Hz), 7.61-7.64 (1H, d, J=6.2 Hz), 8.86-8.88 (1H, d, J=5.45 Hz).

Example 38

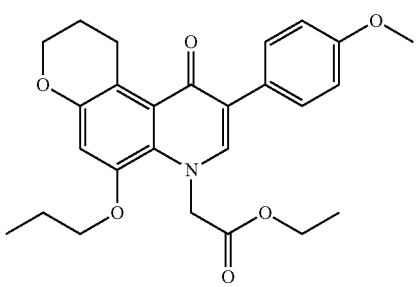

Production of ethyl[9-(4-methoxyphenyl)-10-oxo-6-propoxy-1,2,3,10-tetrahydropyrano[3,2-f]quinolin-7-yl]acetate The above compound was prepared in the same manner as in Example 31 using appropriate starting material.

$^1$H-NMR (CDCl$_3$) δ ppm: 1.01-1.07 (3H, t, J=7.5 Hz), 1.23-1.29 (3H, t, J=7.5 Hz), 1.79-1.85 (2H, m), 1.95-1.98 (2H, m), 3.49-3.54 (2H, t, J=6.5 Hz), 3.83 (3H, s), 3.91-3.96 (2H, t, 6.8 Hz), 4.11-4.27 (6H, m), 5.05 (2H, s), 6.62 (1H, s), 6.92-6.95 (2H, d, J=8.8 Hz), 7.29 (1H, s), 7.54-7.57 (2H, d, J=8.8 Hz).

Example 39

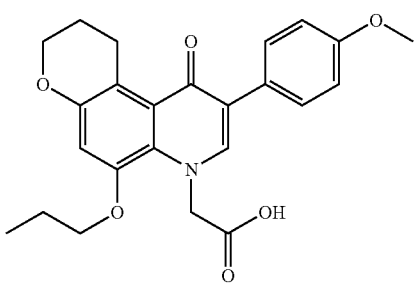

Production of [9-(4-methoxyphenyl)-10-oxo-6-propoxy-1,2,3,10-tetrahydropyrano[3,2-f]quinolin-7-yl]acetic acid The above compound was prepared in the same manner as in Example 32 using appropriate starting material.

$^1$H-NMR (DMSO-d$_6$) δ ppm: 0.94-1.00 (3H, t, J=7.5 Hz), 1.72-1.86 (4H, m), 3.11-3.33 (2H, m), 3.76 (3H, s), 3.90-3.95 (2H, t, J=6.5 Hz), 4.08-4.11 (2H, m), 5.17 (2H, s), 6.70 (1H, s), 6.90-6.95 (2H, d, J=8.8 Hz), 7.53-7.60 (2H, d, J=8.8 Hz), 8.54 (1H, s), 12.6-12.9 (1H, brs).

Example 40

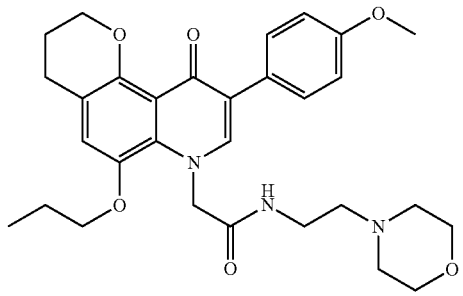

Production of 2-[9-(4-methoxyphenyl)-10-oxo-6-propoxy-1,2,3,10-tetrahydropyrano[3,2-f]quinolin-7-yl]-N-(2-morpholin-4-ylethyl)acetamide The above compound was prepared in the same manner as in Example 33 using appropriate starting material.

Melting point: 206-208° C.

$^1$H-NMR (DMSO-d$_6$) δ ppm: 0.93-0.98 (3H, t, J=7.3 Hz), 1.66-1.90 (4H, m), 3.00-3.20 (4H, m), 3.50-3.62 (2H, m), 3.76 (3H, s), 3.90-3.96 (4H, m), 4.04-4.12 (2H, m), 5.07 (2H, s), 6.70 (1H, s), 6.91-6.95 (2H, d, J=8.8 Hz), 7.56-7.59 (2H, d, J=8.8 Hz), 7.77 (1H, s), 8.10-8.25 (1H, m).

Example 41

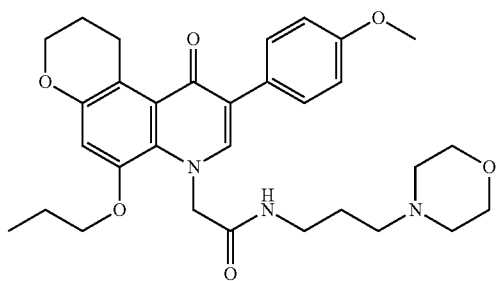

Production of 2-[9-(4-methoxyphenyl)-10-oxo-6-propoxy-1,2,3,10-tetrahydropyrano[3,2-f]quinolin-7-yl]-N-(3-morpholin-4-ylpropyl)acetamide The above compound was prepared in the same manner as in Example 33 using appropriate starting materials.

Melting point: 185-187° C.

$^1$H-NMR (DMSO-d$_6$) δ ppm: 0.94-1.00 (3H, t, J=7.4 Hz), 1.66-1.96 (6H, m), 2.90-3.21 (6H, m), 3.25-3.43 (4H, m), 3.56-3.66 (2H, t, J=11.9 Hz), 3.77 (3H, s), 3.85-4.04 (4H, m), 4.05-4.18 (2H, m), 5.09 (2H, s), 6.71 (1H, s), 6.92-6.96 (2H, d, J=8.8 Hz), 7.57-7.61 (2H, d, J=8.8 Hz), 7.79 (1H, s), 8.09-8.14 (1H, t, J=5.5 Hz).

Hz), 6.25-6.30 (2H, d, J=12.3 Hz), 6.70 (1H, s), 6.91-6.95 (2H, d, J=8.8 Hz), 7.55-7.59 (2H, d, J=8.8 Hz), 7.68 (1H, s).

Example 42

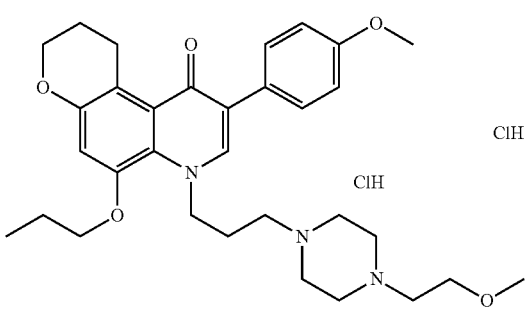

Production of 7-{3-[4-(2-methoxyethyl)piperazin-1-yl]propyl}-9-(4-methoxyphenyl)-6-propoxy-2,3-dihydro-1H,7H-pyrano[3,2-f]quinolin-10-one dihydrochloride The above compound was prepared in the same manner as in Example 18 using appropriate starting materials.

Melting point: 180-182° C.

$^1$H-NMR (DMSO-d$_6$) δ ppm: 1.00-1.05 (3H, t, J=7.4 Hz), 1.83-1.91 (4H, m), 2.00-2.20 (2H, m), 3.00-4.50 (20H, m), 4.50-4.70 (2H, m), 6.77 (1H, s), 6.90-6.95 (2H, d, J=8.8 Hz), 7.60-7.65 (2H, d, J=8.8 Hz), 7.94 (1H, s).

Example 43

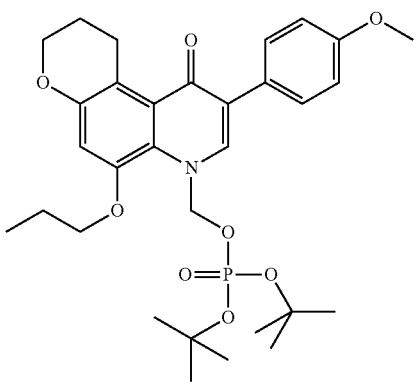

Production of di-tert-butyl 9-(4-methoxyphenyl)-10-oxo-6-propoxy-1,2,3,10-tetrahydropyrano[3,2-f]quinolin-7-ylmethyl phosphate The above compound was prepared in the same manner as in Example 23 using appropriate starting material.

$^1$H-NMR (CDCl$_3$) δ ppm: 1.07-1.13 (3H, t, J=7.4 Hz), 1.35 (18H, s), 1.89-1.98 (4H, m), 3.46-3.51 (2H, t, J=6.5 Hz), 3.82 (3H, s), 4.01-4.06 (2H, t, J=6.6 Hz), 4.16-4.21 (2H, t, J=5.0

Example 44

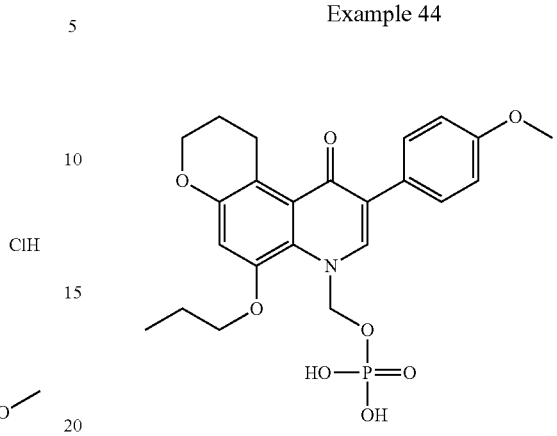

Production of [9-(4-methoxyphenyl)-10-oxo-6-propoxy-1,2,3,10-tetrahydropyrano[3,2-f]quinolin-7-ylmethyl]monophosphate The above compound was prepared in the same manner as in Example 24 using appropriate starting material.

$^1$H-NMR (DMSO-d$_6$) δ ppm: 1.03-1.10 (3H, t, J=7.5 Hz), 1.84-2.02 (4H, m), 3.52-3.58 (2H, t, J=6.5 Hz), 3.81 (3H, s), 4.02-4.07 (2H, t, J=6.6 Hz), 4.16-4.19 (2H, t, J=5.1 Hz), 6.15-6.19 (2H, d, J=10.8 Hz), 6.80 (1H, s), 6.94-6.96 (2H, d, J=9.0 Hz), 7.52-7.56 (2H, d, J=9.0 Hz), 7.69-7.72 (1H, d, J=6.2 Hz).

Example 45

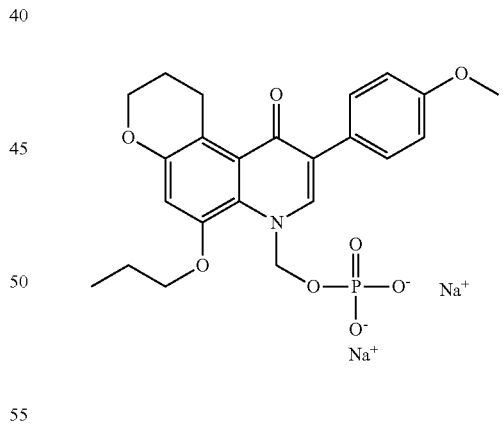

Production of [9-(4-methoxyphenyl)-10-oxo-6-propoxy-1,2,3,10-tetrahydropyrano[3,2-f]quinolin-7-ylmethyl]monophosphate disodium salt The above compound was prepared in the same manner as in Example 25 using appropriate starting material.

$^1$H-NMR (D$_2$O) δ ppm: 0.94-0.99 (2H, t, J=7.4 Hz), 1.81-1.88 (2H, m), 3.21-3.23 (2H, m), 3.78 (3H, s), 3.99-4.05 (2H, m), 4.13-4.15 (2H, m), 6.04-6.14 (2H, d, J=8.8 Hz), 6.78 (1H, s), 6.96-6.99 (2H, d, J=8.8 Hz), 7.39-7.45 (2H, m), 8.08 (1H, s).

Example 46

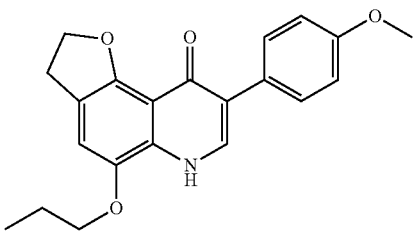

Production of 8-(4-methoxyphenyl)-5-propoxy-3,6-dihydro-2H-flo[2,3-f]quinolin-9-one The above compound was prepared in the same manner as in Example 1 using appropriate starting material.
Pale Brown Powder (Ethyl Acetate)
Melting point: 218-220° C.
$^1$H-NMR (DMSO-$d_6$) δ ppm: 1.00 (3H, t, J=7.4 Hz), 1.75-1.83 (2H, m), 3.13 (2H, t, J=8.8 Hz), 3.74 (3H, s), 4.02 (2H, t, J=6.5 Hz), 4.54 (2H, t, J=8.9 Hz), 6.91 (2H, d, J=8.7 Hz), 7.15 (1H, s), 7.51 (2H, d, J=8.7 Hz), 7.75 (1H, d, J=5.9 Hz), 10.99 (1H, d, J=5.9 Hz).

Example 47

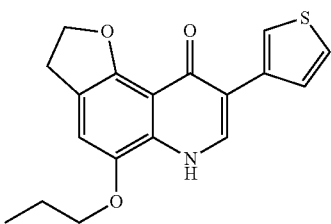

Production of 5-propoxy-8-thiophen-3-yl-3,6-dihydro-2H-flo[2,3-f]quinolin-9-one

The above compound was prepared in the same manner as in Example 1 using appropriate starting materials.
Pale Brown Powder (Ethanol)
Melting point: 275-277° C.
$^1$H-NMR (DMSO-$d_6$) δ ppm: 1.00 (3H, t, J=7.4 Hz), 1.72-1.84 (2H, m), 3.14 (2H, t, J=8.9 Hz), 4.02 (2H, t, J=6.5 Hz), 4.55 (2H, t, J=8.9 Hz), 7.15 (1H, s), 7.47-7.54 (2H, m), 8.08 (1H, d, J=6.3 Hz), 8.16-8.17 (1H, m), 11.10 (1H, d, J=6.1 Hz).

Example 48

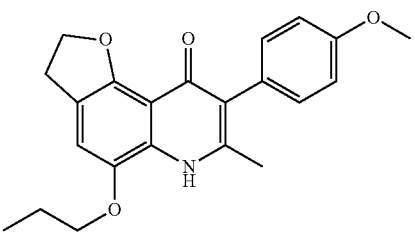

Production of 8-(4-methoxyphenyl)-7-methyl-5-propoxy-3,6-dihydro-2H-flo[2,3-f]quinolin-9-one The above compound was prepared in the same manner as in Example 8 using appropriate starting material.
Pale Brown Powder (Ethyl Acetate-n-hexane)
Melting point: 216-218° C.
$^1$H-NMR (DMSO-$d_6$) δ ppm: 0.97 (3H, t, J=7.4 Hz), 1.76-1.84 (2H, m), 2.18 (3H, s), 3.11 (2H, t, J=8.9 Hz), 3.74 (3H, s), 4.04 (2H, t, J=6.8 Hz), 4.50 (2H, t, J=8.9 Hz), 6.90 (2H, d, J=8.7 Hz), 7.06 (2H, d, J=8.6 Hz), 7.15 (1H, s), 10.19 (1H, brs).

Example 49

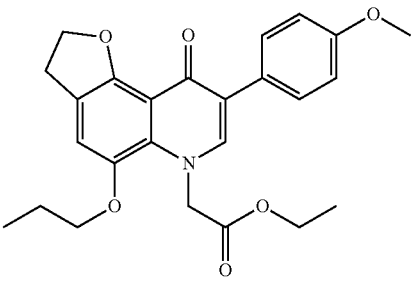

Production of ethyl[8-(4-methoxyphenyl)-9-oxo-5-propoxy-2,3-dihydro-9H-flo[2,3-f]quinolin-6-yl]acetate The above compound was prepared in the same manner as in Example 31 using appropriate starting material.
$^1$H-NMR (CDCl$_3$) δ ppm: 1.04 (3H, t, J=7.3 Hz), 1.26 (3H, t, J=7.2 Hz), 1.78-1.86 (2H, m), 3.19 (2H, t, J=8.8 Hz), 3.82 (3H, s), 3.91 (2H, t, J=6.9 Hz), 4.22 (2H, q, J=7.2 Hz), 4.75 (2H, t, J=8.9 Hz), 5.05 (2H, s), 6.90 (2H, d, J=8.8 Hz), 7.01 (1H, s), 7.31 (1H, s), 7.63 (2H, d, J=8.8 Hz).

Example 50

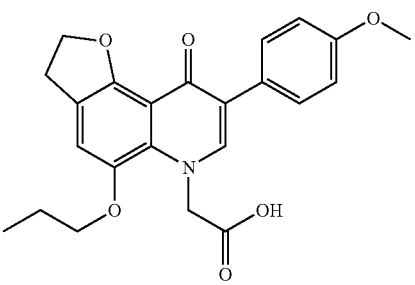

Production of [8-(4-methoxyphenyl)-9-oxo-5-propoxy-2,3-dihydro-9H-flo[2,3-f]quinolin-6-yl]acetic acid The above compound was prepared in the same manner as in Example 32 using appropriate starting material.

$^1$H-NMR (CDCl$_3$) δ ppm: 1.04 (3H, t, J=7.3 Hz), 1.26 (3H, t, J=7.2 Hz), 1.78-1.86 (2H, m), 3.19 (2H, t, J=8.8 Hz), 3.82 (3H, s), 3.91 (2H, t, J=6.9 Hz), 4.22 (2H, q, J=7.2 Hz), 4.75 (2H, t, J=8.9 Hz), 5.05 (2H, s), 6.90 (2H, d, J=8.8 Hz), 7.01 (1H, s), 7.31 (1H, s), 7.63 (2H, d, J=8.8 Hz).

Example 51

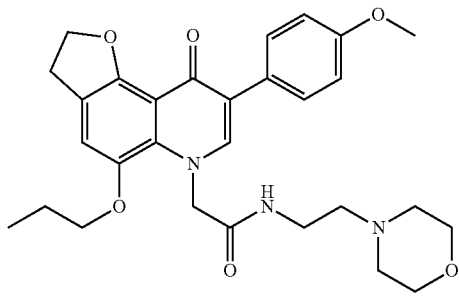

Production of 2-[8-(4-methoxyphenyl)-9-oxo-5-propoxy-2,3-dihydro-9H-flo[2,3-f]quinolin-6-yl]-N-(2-morpholin-4-ylethyl)acetamide The above compound was prepared in the same manner as in Example 33 using appropriate starting material.

$^1$H-NMR (DMSO-d$_6$) δ ppm: 0.92 (3H, t, J=7.3 Hz), 1.67-1.76 (2H, m), 2.28-2.33 (6H, m), 3.08-3.17 (4H, m), 3.47-3.51 (4H, m), 3.75 (3H, s), 3.86 (2H, t, J=6.7 Hz), 4.53 (2H, t, J=8.9 Hz), 5.06 (2H, s), 6.90 (2H, d, J=8.8 Hz), 7.19 (1H, s), 7.54 (2H, d, J=8.8 Hz), 7.74 (1H, s), 7.83 (1H, t, J=5.4 Hz).

Example 52

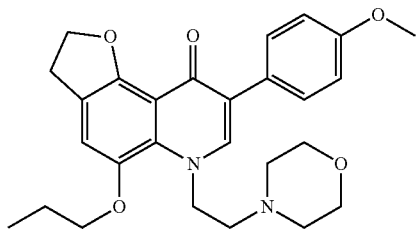

Production of 8-(4-methoxyphenyl)-6-(2-morpholin-4-ylethyl)-5-propoxy-3,6-dihydro-2H-flo[2,3-f]quinolin-9-one The above compound was prepared in the same manner as in Example 18 using appropriate starting materials.

$^1$H-NMR (DMSO-d$_6$) δ ppm: 0.99 (3H, t, J=7.3 Hz), 1.74-1.82 (2H, m), 2.30-2.33 (4H, m), 2.54 (2H, t, J=5.5 Hz), 3.14 (2H, t, J=8.8 Hz), 3.42-3.45 (4H, m), 3.74 (3H, s), 3.97 (2H, t, J=6.5 Hz), 4.50-4.61 (4H, m), 6.92 (2H, d, J=8.8 Hz), 7.25 (1H, s), 7.56 (2H, d, J=8.8 Hz), 7.81 (1H, s).

Example 53

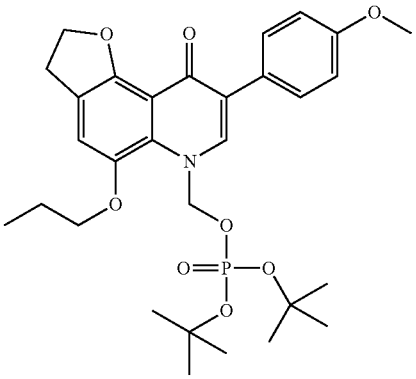

Production of di-tert-butyl 8-(4-methoxyphenyl)-9-oxo-5-propoxy-2,3-dihydro-9H-flo[2,3-f]quinolin-6-ylmethyl phosphate The above compound was prepared in the same manner as in Example 23 using appropriate starting material.

$^1$H-NMR (CDCl$_3$) δ ppm: 1.06-1.12 (3H, t, J=7.4 Hz), 1.36 (18H, s), 1.85-1.97 (2H, m), 3.19-3.26 (2H, t, J=9.0 Hz), 3.82 (3H, s), 4.00-4.05 (2H, t, J=6.7 Hz), 4.73-4.80 (2H, t, J=9.0 Hz), 6.28-6.34 (2H, d, J=12.6 Hz), 6.88-6.94 (2H, d, J=8.8 Hz), 7.11 (1H, s), 7.63-7.70 (2H, d, J=8.8 Hz), 7.74 (1H, s).

Example 54

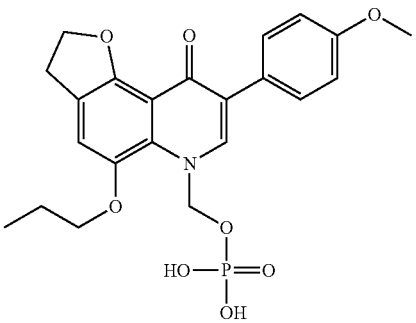

Production of [8-(4-methoxyphenyl)-9-oxo-5-propoxy-2,3-dihydro-9H-flo[2,3-f]quinolin-6-ylmethyl] monophosphate The above compound was prepared in the same manner as in Example 24 using appropriate starting material.

$^1$H-NMR (DMSO-d$_6$) δ ppm: 1.00-1.05 (3H, t, J=7.4 Hz), 1.79-1.90 (2H, m), 3.15-3.22 (2H, m), 4.00-4.06 (2H, t, J=6.7 Hz), 4.53-4.62 (2H, m), 6.21-6.25 (2H, d, J=10.6 Hz), 6.92-6.97 (2H, m), 7.36 (1H, s), 7.56-7.59 (2H, m), 7.90 (1H, s).

Example 55

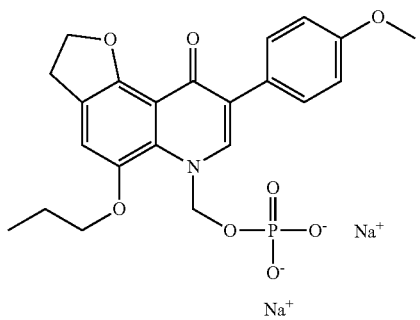

Production of [8-(4-methoxyphenyl)-9-oxo-5-propoxy-2,3-dihydro-9H-flo[2,3-f]quinolin-6-ylmethyl] monophosphate disodium salt The above compound was prepared in the same manner as in Example 25 using appropriate starting material.
$^1$H-NMR (D$_2$O) δ ppm: 0.92-0.97 (3H, t, J=7.4 Hz), 1.76-1.84 (2H, m), 3.12-3.19 (2H, t, J=8.9 Hz), 3.75 (3H, s), 3.93-3.99 (2H, t, J=6.8 Hz), 4.56-4.59 (2H, m), 5.95-5.99 (2H, d, J=8.9 Hz), 6.90-6.94 (2H, d, J=8.8 Hz), 7.27 (1H, s), 7.39-7.43 (2H, d, J=8.8 Hz), 8.01 (1H, s).

Example 56

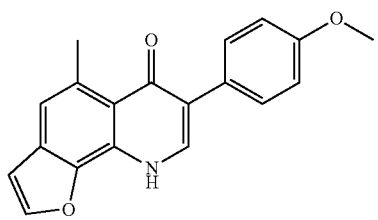

Production of 7-(4-methoxyphenyl)-5-methyl-9H-flo[3,2-h]quinolin-6-one

The above compound was prepared in the same manner as in Example 1 using appropriate starting material.
White Powder (Ethyl Acetate)
$^1$H-NMR (DMSO-d$_6$) δ ppm: 2.84 (3H, s), 3.76 (3H, s), 6.89-7.02 (3H, m), 7.22 (1H, s), 7.52-7.58 (2H, d, J=8.8 Hz), 7.77 (1H, s), 8.21 (1H, s), 12.06 (1H, brs).

Example 57

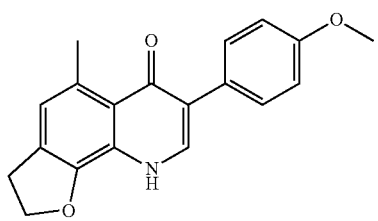

Production of 7-(4-methoxyphenyl)-5-methyl-2,3-dihydro-9H-flo[3,2-h]quinolin-6-one The above compound was prepared in the same manner as in Example 1 using appropriate starting material.
White Powder
$^1$H-NMR (DMSO-d$_6$) δ ppm: 2.73 (3H, s), 3.26-3.33 (2H, t, J=8.8 Hz), 3.75 (3H, s), 4.69-4.76 (2H, t, J=8.8 Hz), 6.87-6.93 (3H, m), 7.50-7.53 (2H, d, J=8.9 Hz), 7.64 (1H, s), 11.30 (1H, brs).

Example 58

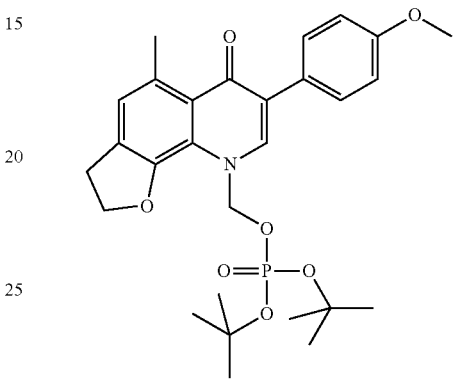

Production of di-tert-butyl 7-(4-methoxyphenyl)-5-methyl-6-oxo-3,6-dihydro-2H-flo[3,2-h]quinolin-9-ylmethyl phosphate The above compound was prepared in the same manner as in Example 23 using appropriate starting material.
$^1$H-NMR (CDCl$_3$) δ ppm: 1.39 (18H, s), 2.86 (3H, s), 3.26-3.33 (2H, t, J=8.8 Hz), 3.83 (3H, s), 4.66-4.73 (2H, t, J=8.9 Hz), 6.21-6.26 (2H, d, J=11.3 Hz), 6.92-6.99 (3H, m), 7.52-7.56 (2H, d, J=8.9 Hz), 7.66 (1H, s).

Example 59

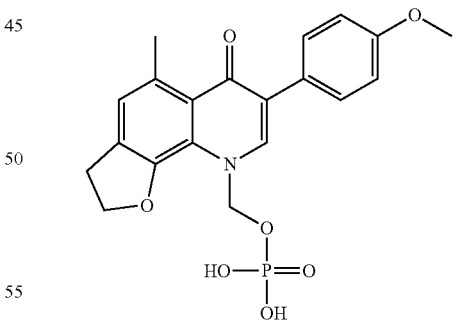

Production of [7-(4-methoxyphenyl)-5-methyl-6-oxo-3,6-dihydro-2H-flo[3,2-h]quinolin-9-ylmethyl] monophosphate The above compound was prepared in the same manner as in Example 24 using appropriate starting material.
$^1$H-NMR (DMSO-d$_6$) δ ppm: 2.75 (3H, s), 3.26-3.33 (2H, t, J=8.8 Hz), 3.75 (3H, s), 4.69-4.76 (2H, t, J=8.8 Hz), 6.15-6.19 (2H, d, J=10.8 Hz), 6.90-6.97 (3H, m), 7.52-7.58 (2H, d, J=8.9 Hz), 7.64 (1H, s).

Example 60

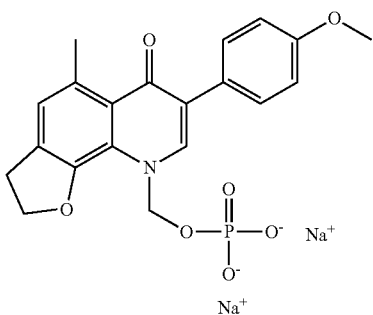

Production of [7-(4-methoxyphenyl)-5-methyl-6-oxo-3,6-dihydro-2H-flo[3,2-h]quinolin-9-ylmethyl] monophosphate disodium salt The above compound was prepared in the same manner as in Example 25 using appropriate starting material.
$^1$H-NMR (D$_2$O) δ ppm: 2.57 (3H, s), 3.06-3.13 (2H, t, J=8.8 Hz), 3.72 (3H, s), 4.50-4.58 (2H, m), 5.84-5.88 (2H, d, J=8.8 Hz), 6.84-6.87 (2H, d, J=8.8 Hz), 6.93 (1H, s), 7.27-7.31 (2H, d, J=8.8 Hz), 7.75 (1H, s).

Example 61

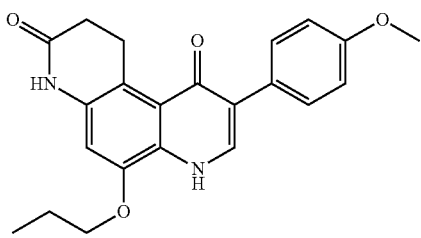

Production of 2-(4-methoxyphenyl)-5-propoxy-4,7,9,10-tetrahydro-[4,7]phenanthroline-1,8-dione The above compound was prepared in the same manner as in Example 1 using appropriate starting material.
Yellow Powder (Ethyl Acetate-Methanol)
Melting point: 132-133° C.
$^1$H-NMR (DMSO-d$_6$) δ ppm: 1.03-1.10 (3H, t, J=7.4 Hz), 1.80-2.00 (2H, m), 2.33-2.39 (2H, t, J=7.4 Hz), 3.70-3.80 (5H, m), 4.04-4.09 (2H, t, J=6.5 Hz), 6.85 (1H, s), 6.91-6.95 (2H, d, J=8.8 Hz), 7.53-7.56 (2H, d, J=8.8 Hz), 7.72-7.75 (1H, d, J=6.4 Hz), 9.94 (1H, s), 11.02-11.25 (1H, m).

Example 62

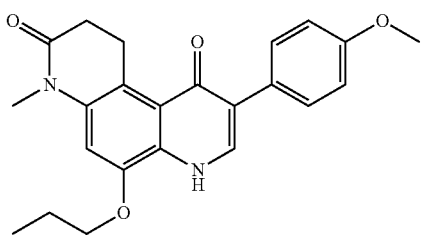

Production of 2-(4-methoxyphenyl)-7-methyl-5-propoxy-4,7,9,10-tetrahydro-[4,7]phenanthroline-1,8-dione The above compound was prepared in the same manner as in Example 1 using appropriate starting material.
Yellow Powder
Melting point: 89-91° C.
$^1$H-NMR (DMSO-d$_6$) δ ppm: 1.03-1.10 (3H, t, J=7.4 Hz), 1.82-2.00 (2H, m), 2.37-2.43 (2H, t, J=7.4 Hz), 3.32 (3H, s), 3.65-3.95 (5H, m), 4.17-4.22 (2H, t, J=6.5 Hz), 6.90-6.95 (2H, d, J=8.8 Hz), 7.05 (1H, s), 7.50-7.55 (2H, d, J=8.8 Hz), 7.76 (1H, s), 11.14 (1H, brs).

Example 63

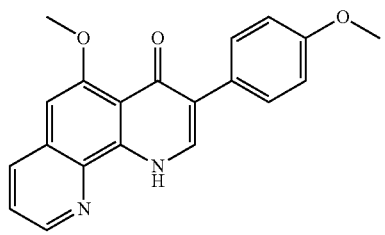

Production of 5-methoxy-3-(4-methoxyphenyl)-1H-[1,10]phenanthrolin-4-one

The above compound was prepared in the same manner as in Example 1 using appropriate starting material.
Yellow Powder (Ethanol)
Melting point: 118-120° C.
$^1$H-NMR (DMSO-d$_6$) δ ppm: 3.75 (3H, s), 3.89 (3H, s), 6.93 (2H, d, J=8.6 Hz), 7.00 (1H, s), 7.57 (2H, d, J=8.6 Hz), 7.63-7.68 (1H, m), 7.91 (1H, s), 8.26 (1H, d, J=8.2 Hz), 8.78 (1H, d, J=4.2 Hz), 12.23 (1H, brs).

Example 64

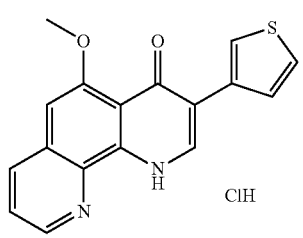

Production of 5-methoxy-3-thiophen-3-yl-1H-[1,10]phenanthrolin-4-one hydrochloride The above compound was prepared in the same manner as in Example 1 using appropriate starting materials.
Pale Brown Powder (Ethanol)
Melting point: 143-145° C.
$^1$H-NMR (DMSO-d$_6$) δ ppm: 3.98 (3H, s), 7.17 (1H, s), 7.59 (1H, s), 7.60 (1H, s), 7.70-7.75 (1H, m), 8.20 (1H, brs), 8.33 (1H, d, J=8.3 Hz), 8.50 (1H, s), 8.81-8.83 (1H, m).

Example 65

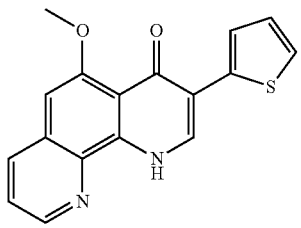

Production of 5-methoxy-3-thiophen-2-yl-1H-[1,10]phenanthrolin-4-one

The above compound was prepared in the same manner as in Example 1 using appropriate starting materials.
Pale Brown Powder (Ethanol)
Melting point: 265-267° C.
$^1$H-NMR (DMSO-d$_6$) δ ppm: 3.94 (3H, s), 7.07-7.10 (2H, m), 7.44 (1H, d, J=6.0 Hz), 7.60 (1H, d, J=3.7 Hz), 7.61-7.71 (1H, m), 8.29 (1H, d, J=8.3 Hz), 8.47 (1H, s), 8.80-8.83 (1H, m), 12.60 (1H, brs).

Example 66

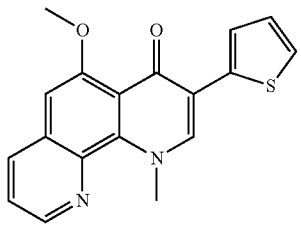

Production of 5-methoxy-1-methyl-3-thiophen-2-yl-1H-[1,10]phenanthrolin-4-one

The above compound was prepared in the same manner as in Example 3 using appropriate starting material.
Brown Powder (Ethyl Acetate-n-hexane)
Melting point: 216-218° C.
$^1$H-NMR (DMSO-d$_6$) δ ppm: 3.90 (3H, s), 4.54 (3H, s), 7.08-7.13 (2H, m), 7.44 (1H, d, J=5.1 Hz), 7.56-7.61 (1H, m), 7.65 (1H, d, J=3.7 Hz), 8.24 (1H, d, J=8.2 Hz), 8.64 (1H, s), 8.75-8.77 (1H, m).

Example 67

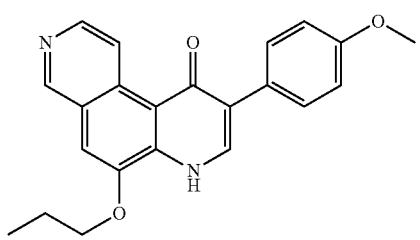

Production of 9-(4-methoxyphenyl)-6-propoxy-7H-[3,7]phenanthrolin-10-one

The above compound was prepared in the same manner as in Example 1 using appropriate starting material.
Melting point: 250-251° C.
$^1$H-NMR (CDCl$_3$) δ ppm: 1.14-1.19 (3H, t, J=7.4 Hz), 1.98-2.07 (2H, m), 3.87 (3H, s), 4.26-4.32 (2H, t, J=6.6 Hz), 6.98-7.02 (2H, d, J=8.7 Hz), 7.30 (1H, s), 7.61-7.64 (2H, d, J=6.6 Hz), 8.64-8.66 (1H, d, J=6.0 Hz), 9.10 (1H, s), 9.38-9.40 (1H, d, J=4.8 Hz), 9.97-9.99 (1H, d, J=5.9 Hz).

Example 68

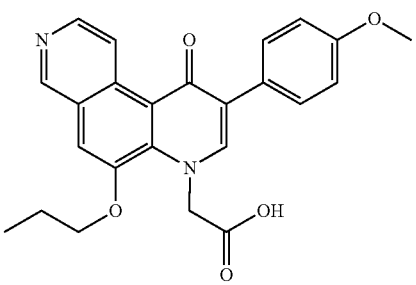

Production of [9-(4-methoxyphenyl)-10-oxo-6-propoxy-10H-[3,7]phenanthrolin-7-yl]acetic acid The above compound was prepared in the same manner as in Example 32 using appropriate starting material.
$^1$H-NMR (CDCl$_3$) δ ppm: 1.14-1.19 (3H, t, J=7.4 Hz), 1.98-2.07 (2H, m), 3.87 (3H, s), 4.26-4.32 (2H, t, J=6.6 Hz), 5.47 (2H, s), 6.98-7.02 (2H, d, J=8.7 Hz), 7.30 (1H, s), 7.61-7.64 (2H, d, J=6.6 Hz), 8.64-8.66 (1H, d, J=6.0 Hz), 9.10 (1H, s), 9.38-9.40 (1H, d, J=4.8 Hz).

Example 69

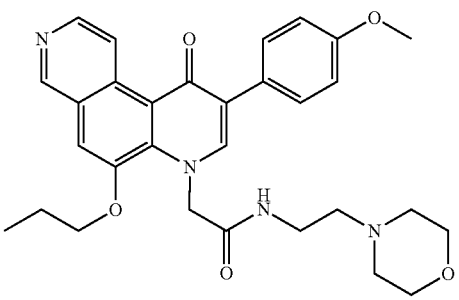

Production of 2-[9-(4-methoxyphenyl)-10-oxo-6-propoxy-10H-[3,7]phenanthrolin-7-yl]-N-(2-morpholin-4-ylethyl)acetamide The above compound was prepared in the same manner as in Example 33 using appropriate starting material.
Melting point: 189-192° C.
$^1$H-NMR (DMSO-d$_6$) δ ppm: 1.00-1.06 (3H, t, J=7.4 Hz), 1.82-1.91 (2H, m), 2.82-3.12 (8H, m), 3.60-3.80 (4H, m), 3.81 (3H, s), 4.14-4.20 (2H, t, J=6.8 Hz), 5.32 (2H, s), 7.00-7.03 (2H, d, J=7.8 Hz), 7.69-7.72 (2H, d, J=7.8 Hz), 7.78 (1H, s), 8.11 (1H, s), 8.20-8.30 (1H, m), 8.51-8.53 (1H, d, J=6.1 Hz) 9.19 (1H, s), 9.99-10.0 (1H, d, J=6.1 Hz).

Example 70

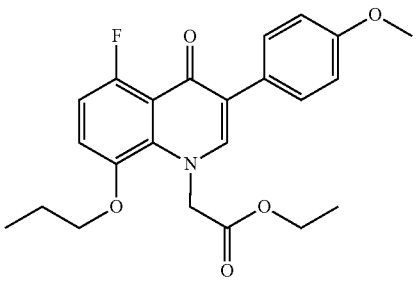

Production of ethyl[5-fluoro-3-(4-methoxyphenyl)-4-oxo-8-propoxy-4H-quinolin-1-yl]acetate The above compound was prepared in the same manner as in Example 31 using appropriate starting material.

$^1$H-NMR (DMSO-$d_6$) δ ppm: 0.96-1.02 (3H, t, J=7.4 Hz), 1.18-1.24 (3H, t, J=7.1 Hz), 1.69-1.80 (2H, m), 3.78 (3H, s), 3.94-4.00 (2H, t, J=6.7 Hz), 4.12-4.21 (2H, q, J=7.1 Hz), 5.32 (2H, s), 6.94-7.04 (3H, m), 7.21-7.26 (1H, m), 7.58-7.62 (2H, d, J=8.7 Hz), 8.02 (1H, s).

Example 71

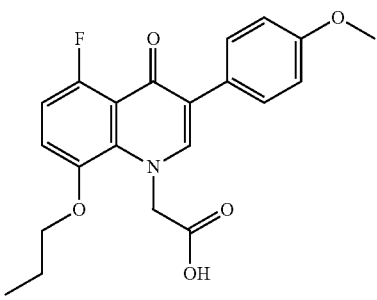

Production of [5-fluoro-3-(4-methoxyphenyl)-4-oxo-8-propoxy-4H-quinolin-1-yl]acetic acid The above compound was prepared in the same manner as in Example 32 using appropriate starting material.

$^1$H-NMR (DMSO-$d_6$) δ ppm: 0.97-1.03 (3H, t, J=7.4 Hz), 1.72-1.87 (2H, m), 3.82 (3H, s), 3.95-4.00 (2H, t, J=6.7 Hz), 5.24 (2H, s), 6.94-7.03 (3H, m), 7.20-7.26 (1H, m), 7.59-7.62 (2H, d, J=8.7 Hz), 8.02 (1H, s), 12.5-13.3 (1H, br).

Example 72

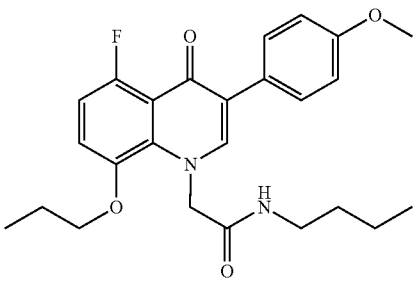

Production of N-butyl-2-[5-fluoro-3-(4-methoxyphenyl)-4-oxo-8-propoxy-4H-quinolin-1-yl]acetamide The above compound was prepared in the same manner as in Example 33 using appropriate starting materials.

White Powder $^1$H-NMR (DMSO-$d_6$) δ ppm: 0.81-0.87 (3H, t, J=7.1 Hz), 0.91-0.98 (3H, t, J=7.4 Hz), 1.19-1.45 (4H, m), 1.70-1.80 (2H, m), 3.02-3.09 (2H, q, 6.3 Hz), 3.76 (3H, s), 3.90-3.95 (2H, t, J=6.8 Hz), 5.13 (2H, s), 6.90-6.98 (3H, m), 7.15-7.20 (1H, m), 7.56-7.60 (2H, d, J=8.7 Hz), 7.90 (1H, s), 7.97-8.01 (1H, t, J=5.5 Hz).

Example 73

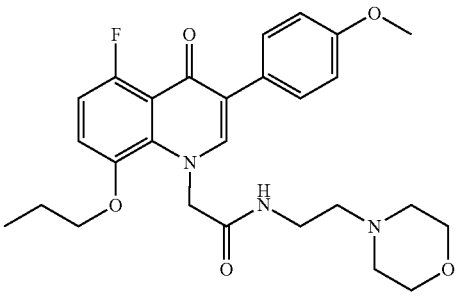

Production of 2-[5-fluoro-3-(4-methoxyphenyl)-4-oxo-8-propoxy-4H-quinolin-1-yl]-N-(2-morpholin-4-ylethyl)acetamide To a DMF solution (2 ml) of [5-fluoro-3-(4-methoxyphenyl)-4-oxo-8-propoxy-4H-quinolin-1-yl]acetic acid (800 mg, 2.07 mmol) were sequentially added a DMF solution (1 ml) of 4-(2-aminoethyl)morpholine (273 mg), triethylamine (506 mg, 5.0 mmol), diethylphosphorocyanidate (DEPC, 405 mg, 2.48 mmol) and DMF (1 ml) while ice-cooling, followed by stirring at room temperature for 23 hours. Water was added to the reaction mixture and then subjected to extraction using ethyl acetate. The thus-obtained organic layer was washed with an aqueous saturated sodium chloride solution twice, dried over anhydrous sodium sulfate and then concentrated under reduced pressure. The residue was purified using silica gel column chromatography (dichloromethane:methanol=30:1→15:1). The purified product was concentrated under reduced pressure, and the residue was recrystallized from ethyl acetate, giving a white powder of 2-[5-fluoro-3-(4-methoxyphenyl)-4-oxo-8-propoxy-4H-quinolin-1-yl]-N-(2-morpholin-4-ylethyl)acetamide (789 mg, yield: 77%).

Melting point: 139-141° C.

$^1$H-NMR (DMSO-$d_6$) δ ppm: 0.95 (3H, t, J=7.3 Hz), 1.71-1.80 (2H, m), 2.30-2.34 (6H, m), 3.18 (2H, q, J=6.5 Hz), 3.49-3.53 (4H, m), 3.76 (3H, s), 3.93 (2H, t, J=6.8 Hz), 5.14 (2H, s), 6.92-6.99 (3H, m), 7.18 (1H, dd, J=4.5 Hz, 9.0 Hz), 7.58 (2H, d, J=8.8 Hz), 7.90-7.95 (2H, m).

Example 74

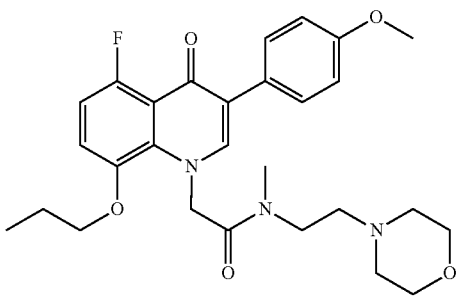

Production of 2-[5-fluoro-3-(4-methoxyphenyl)-4-oxo-8-propoxy-4H-quinolin-1-yl]-N-methyl-N-(2-morpholin-4-ylethyl)acetamide Sodium hydride (60% oil base, 61 mg, 1.4 mmol) was added to a DMF solution (2 ml) of 2-[5-fluoro-3-(4-methoxyphenyl)-4-oxo-8-propoxy-4H-quinolin-1-yl]-N-(2-morpholin-4-ylethyl)acetamide (580 mg, 1.16 mmol), and the resulting mixture was stirred at room temperature for 5 minutes. Methyl iodide (230 mg, 1.62 mmol) was added thereto, and the thus-obtained mixture was stirred at room temperature for 15 hours. Water and ethyl acetate were added to the reaction mixture, followed by separation. The thus-obtained organic layer was washed with an aqueous saturated sodium chloride solution and then concentrated under reduced pressure. The residue was purified using silica gel column chromatography (dichloromethane:methanol=30:1→15:1). The purified product was concentrated under reduced pressure, and the residue was recrystallized from ethyl acetate, giving a white powder of 2-[5-fluoro-3-(4-methoxyphenyl)-4-oxo-8-propoxy-4H-quinolin-1-yl]-N-methyl-N-(2-morpholin-4-ylethyl)acetamide (440 mg, yield: 74%).

Melting point: 218-220° C.

$^1$H-NMR (DMSO-d$_6$) δ ppm: 0.94 (3H, t, J=7.3 Hz), 1.64-1.72 (2H, m), 2.33-2.38 (4H, m), 2.43-2.50 (2H, m), 2.85 (1H, s), 2.99 (2H, s), 3.37 (2H, t, J=6.8 Hz), 3.44-3.48 (4H, m), 3.75 (3H, s), 3.89 (2H, t, J=6.7 Hz), 5.43 (2H, s), 6.89-6.97 (3H, m), 7.12-7.17 (1H, m), 7.53-7.57 (2H, m), 7.83 (1H, s).

Example 75

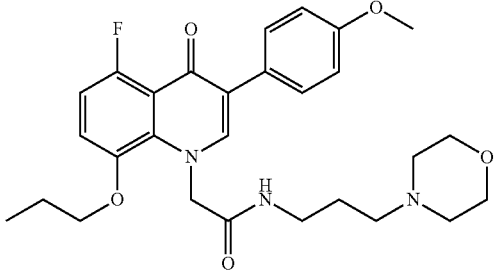

Production of 2-[5-fluoro-3-(4-methoxyphenyl)-4-oxo-8-propoxy-4H-quinolin-1-yl]-N-(3-morpholin-4-ylpropyl)acetamide The above compound was prepared in the same manner as in Example 73 using appropriate starting material.
White Powder (Ethyl Acetate-n-hexane)

Melting point: 117-119° C.

$^1$H-NMR (DMSO-d$_6$) δ ppm: 0.95 (3H, t, J=7.3 Hz), 1.52-1.57 (2H, m), 1.71-1.79 (2H, m), 2.21-2.29 (6H, m), 3.09 (2H, q, J=5.8 Hz), 3.49-3.54 (4H, m), 3.76 (3H, s), 3.93 (2H, t, J=6.8 Hz), 5.12 (2H, s), 6.92-6.99 (3H, m), 7.18 (1H, dd, J=4.5 Hz, 9.0 Hz), 7.58 (2H, d, J=8.8 Hz), 7.90 (1H, s), 8.00 (1H, t, J=5.4 Hz).

Example 76

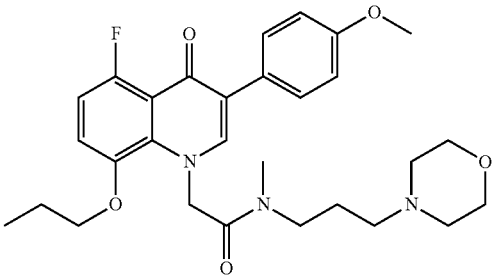

Production of 2-[5-fluoro-3-(4-methoxyphenyl)-4-oxo-8-propoxy-4H-quinolin-1-yl]-N-methyl-N-(3-morpholin-4-ylpropyl)acetamide The above compound was prepared in the same manner as in Example 74 using appropriate starting material.
White Powder (Ethyl Acetate-n-hexane)

Melting point: 166-168° C.

$^1$H-NMR (DMSO-d$_6$) δ ppm: 0.92-0.98 (3H, m), 1.65-1.71 (4H, m), 2.21-2.36 (6H, m), 2.82 (1H, s), 2.98 (2H, s), 3.20-3.30 (2H, m), 3.48-3.58 (4H, m), 3.76 (3H, s), 3.90 (2H, t, J=6.8 Hz), 5.43-5.45 (2H, m), 6.90-6.98 (3H, m), 7.13-7.18 (1H, m), 7.54-7.59 (2H, m), 7.86 (1H, s).

Example 77

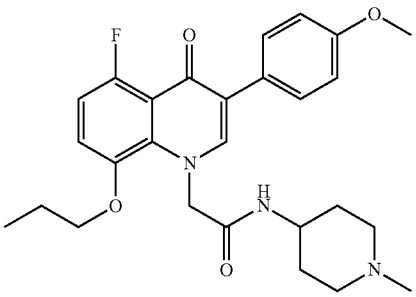

Production of 2-[5-fluoro-3-(4-methoxyphenyl)-4-oxo-8-propoxy-4H-quinolin-1-yl]-N-(1-methylpiperidin-4-yl)acetamide The above compound was prepared in the same manner as in Example 73 using appropriate starting material.
Pale Yellow Powder (Ethyl Acetate-n-hexane)

Melting point: 201-203° C.

$^1$H-NMR (DMSO-d$_6$) δ ppm: 0.95 (3H, t, J=7.3 Hz), 1.40-1.49 (2H, m), 1.67-1.84 (4H, m), 1.91-2.00 (2H, m), 2.14 (3H, s), 2.69-2.73 (2H, m), 3.55-3.75 (1H, m), 3.75 (3H, s), 3.93 (2H, t, J=6.7 Hz), 5.14 (2H, s), 6.90-6.98 (3H, m), 7.16 (1H, dd, J=4.4 Hz, 9.0 Hz), 7.58 (2H, d, J=8.6 Hz), 7.90 (1H, s), 8.03 (1H, d, J=7.3 Hz).

Example 78

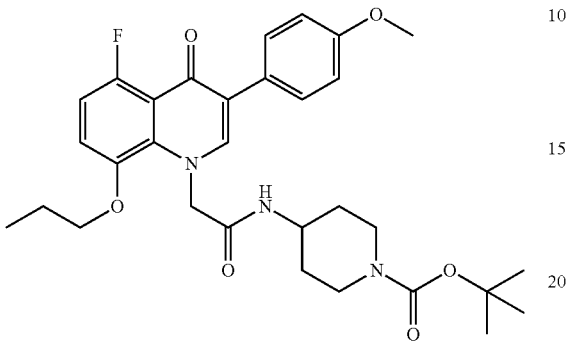

Production of tert-butyl 4-{2-[5-fluoro-3-(4-methoxyphenyl)-4-oxo-8-propoxy-4H-quinolin-1-yl]acetylamino}piperidine-1-carboxylate The above compound was prepared in the same manner as in Example 73 using appropriate starting material.

$^1$H-NMR (CDCl$_3$) δ ppm: 1.03 (3H, t, J=7.3 Hz), 1.31-1.38 (2H, m), 1.41 (9H, s), 1.80-1.86 (4H, m), 2.70-3.00 (2H, m), 3.79 (3H, s), 3.88-4.13 (5H, m), 4.94 (2H, s), 6.55 (1H, brs), 6.77-6.92 (4H, m), 7.31 (1H, s), 7.46 (2H, d, J=8.8 Hz).

Example 79

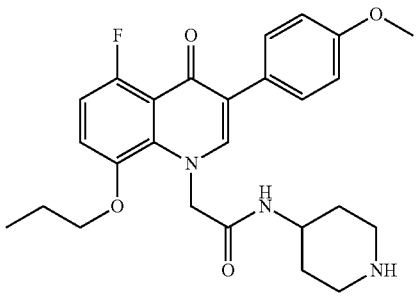

Production of 2-[5-fluoro-3-(4-methoxyphenyl)-4-oxo-8-propoxy-4H-quinolin-1-yl]-N-piperidin-4-ylacetamide A 4N hydrochloric acid ethyl acetate solution (25 ml) was added to an ethanol solution (12 ml) of tert-butyl 4-{2-[5-fluoro-3-(4-methoxyphenyl)-4-oxo-8-propoxy-4H-quinolin-1-yl]acetylamino}piperidine-1-carboxylate (820 mg, 1.44 mmol), followed by stirring at room temperature for 28 hours. The resulting mixture was concentrated under reduced pressure. After adding an aqueous sodium bicarbonate solution to the residue to adjust the pH to 8, the residue was washed with ethyl acetate. A 2N aqueous sodium hydroxide solution was added to the water layer to adjust its pH to 11, followed by extraction using dichloromethane. The thus-obtained organic layer was washed with an aqueous saturated sodium chloride solution and dried over anhydrous magnesium sulfate, and then concentrated under reduced pressure. The residue was recrystallized from ethanol-ethyl acetate, giving a white powder of 2-[5-fluoro-3-(4-methoxyphenyl)-4-oxo-8-propoxy-4H-quinolin-1-yl]-N-piperidin-4-ylacetamide (185 mg, yield: 27%).

Melting point: 226-228° C.

$^1$H-NMR (DMSO-d$_6$) δ ppm: 0.94 (3H, t, J=7.3 Hz), 1.22-1.33 (2H, m), 1.62-1.81 (4H, m), 2.36-2.45 (2H, m), 2.84-2.89 (2H, m), 3.55-3.75 (2H, m), 3.75 (3H, s), 3.92 (2H, t, J=6.7 Hz), 5.13 (2H, s), 6.90-6.98 (3H, m), 7.16 (1H, dd, J=4.5 Hz, 9.0 Hz), 7.56 (2H, d, J=8.6 Hz), 7.88 (1H, s), 8.01 (1H, d, J=7.5 Hz).

Example 80

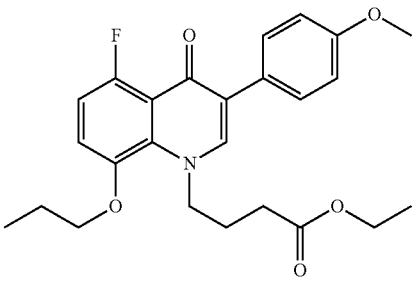

Production of ethyl 4-[5-fluoro-3-(4-methoxyphenyl)-4-oxo-8-propoxy-4H-quinolin-1-yl]butyrate The above compound was prepared in the same manner as in Example 31 using appropriate starting materials.

$^1$H-NMR (DMSO-d$_6$) δ ppm: 1.00-1.06 (3H, t, J=7.4 Hz), 1.06-1.12 (3H, t, J=7.13), 1.80-2.02 (4H, m), 2.24-2.30 (2H, t, J=7.4 Hz), 3.77 (3H, s), 3.92-4.00 (2H, q, J=7.1 Hz), 4.03-4.09 (2H, t, J=6.6 Hz), 4.54-4.60 (2H, t, J=6.87 Hz), 6.93-7.04 (3H, m), 7.24-7.29 (1H, m), 7.60-7.63 (2H, d, J=8.6 Hz), 7.97 (1H, s).

Example 81

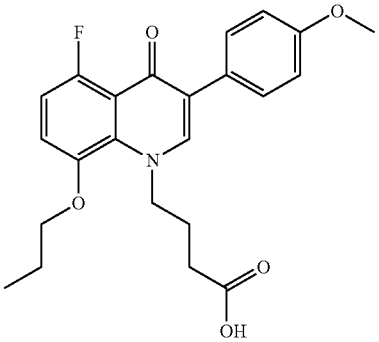

Production of 4-[5-fluoro-3-(4-methoxyphenyl)-4-oxo-8-propoxy-4H-quinolin-1-yl]butyric acid The above compound was prepared in the same manner as in Example 32 using appropriate starting material.

$^1$H-NMR (DMSO-d$_6$) δ ppm: 1.00-1.06 (3H, t, J=7.4 Hz), 1.78-2.00 (4H, m), 2.16-2.22 (2H, t, J=7.4 Hz), 3.78 (3H, s), 4.04-4.09 (2H, t, J=6.6 Hz), 4.54-4.60 (2H, t, J=7.0 Hz), 6.93-7.04 (3H, m), 7.24-7.30 (1H, m), 7.60-7.64 (2H, d, J=8.8 Hz), 7.97 (1H, s), 11.80-12.20 (1H, br).

Example 82

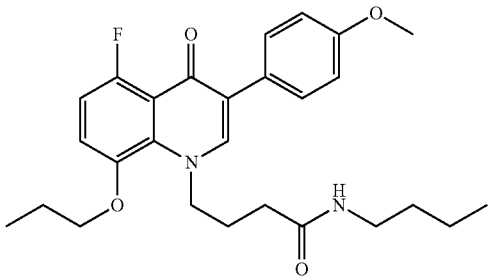

Production of N-butyl-4-[5-fluoro-3-(4-methoxyphenyl)-4-oxo-8-propoxy-4H-quinolin-1-yl]butylamide The above compound was prepared in the same manner as in Example 33 using appropriate starting materials.
Yellow Amorphous
$^1$H-NMR (DMSO-d$_6$) δ ppm: 0.78-0.84 (3H, t, J=7.1 Hz), 0.99-1.05 (3H, t, J=7.4 Hz), 1.10-1.42 (4H, m), 1.75-2.01 (6H, m), 2.92-2.97 (2H, m), 3.77 (3H, s), 4.03-4.08 (2H, t, J=6.6 Hz), 4.53-4.58 (2H, t, J=6.2 Hz), 6.92-7.03 (3H, m), 7.23-7.28 (1H, m), 7.60-7.63 (2H, t, J=8.6 Hz), 7.70-7.75 (1H, m), 7.93 (1H, s).

Example 83

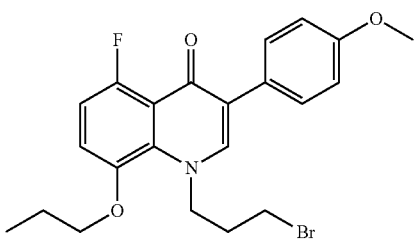

Production of 1-(3-bromopropyl)-5-fluoro-3-(4-methoxyphenyl)-8-propoxy-1H-quinolin-4-one The above compound was prepared in the same manner as in Example 17 using appropriate starting materials.
$^1$H-NMR (CDCl$_3$) δ ppm: 1.05-1.12 (3H, m), 1.85-1.96 (2H, m), 2.30-2.35 (2H, m), 3.33 (2H, t, J=6.1 Hz), 3.83 (3H, s), 3.96-4.05 (2H, m), 4.69 (2H, t, J=6.5 Hz), 6.85-7.03 (4H, m), 7.59-7.64 (3H, m).

Example 84

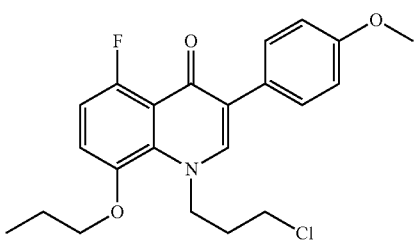

Production of 1-(3-chloropropyl)-5-fluoro-3-(4-methoxyphenyl)-8-propoxy-1H-quinolin-4-one The above compound was prepared in the same manner as in Example 17 using appropriate starting material.
$^1$H-NMR (CDCl$_3$) δ ppm: 1.05-1.13 (3H, m), 1.87-1.96 (2H, m), 2.22-2.27 (2H, m), 3.49 (2H, t, J=5.8 Hz), 3.83 (3H, s), 3.96-4.05 (2H, m), 4.70 (2H, t, J=6.5 Hz), 6.86-7.02 (4H, m), 7.59-7.64 (3H, m).

Example 85

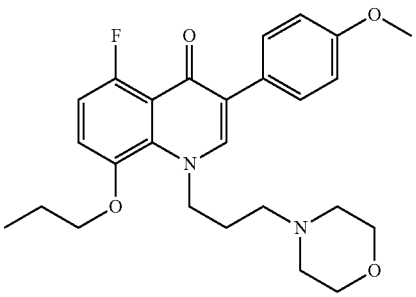

Production of 5-fluoro-3-(4-methoxyphenyl)-1-(3-morpholin-4-ylpropyl)-8-propoxy-1H-quinolin-4-one The above compound was prepared in the same manner as in Example 18 using appropriate starting material.
White Powder (Ethyl Acetate-n-hexane)
Melting point: 130-132° C.
$^1$H-NMR (DMSO-d$_6$) δ ppm: 0.99 (3H, t, J=7.3 Hz), 1.73-1.87 (4H, m), 2.07-2.20 (6H, m), 3.36-3.39 (4H, m), 3.74 (3H, s), 4.01 (2H, t, J=6.5 Hz), 4.56 (2H, t, J=6.3 Hz), 6.90-7.00 (3H, m), 7.21 (1H, dd, J=4.5 Hz, 9.0 Hz), 7.57 (2H, d, J=8.7 Hz), 7.98 (1H, s).

Example 86

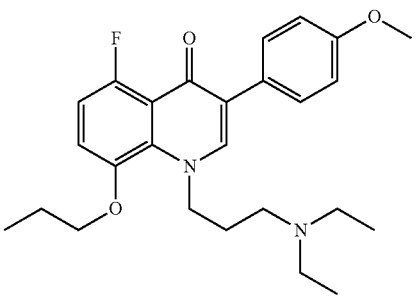

Production of 1-(3-diethylaminopropyl)-5-fluoro-3-(4-methoxyphenyl)-8-propoxy-1H-quinolin-4-one The above compound was prepared in the same manner as in Example 18 using appropriate starting materials.
White Powder (Diethyl Ether)
Melting point: 80-82° C.
$^1$H-NMR (DMSO-d$_6$) δ ppm: 0.81 (6H, t, J=7.0 Hz), 1.01 (3H, t, J=7.3 Hz), 1.75-1.87 (4H, m), 2.22-2.38 (6H, m), 3.75 (3H, s), 4.03 (2H, t, J=6.6 Hz), 4.54 (2H, t, J=6.7 Hz), 6.91-7.01 (3H, m), 7.23 (1H, dd, J=4.5 Hz, 9.0 Hz), 7.59 (2H, d, J=8.8 Hz), 7.96 (1H, s).

Example 87

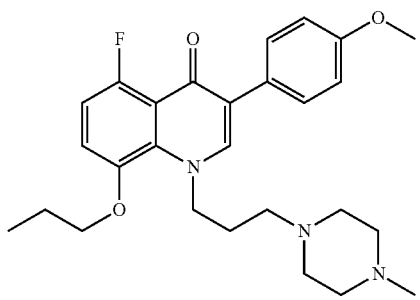

Production of 5-fluoro-3-(4-methoxyphenyl)-1-[3-(4-methylpiperazin-1-yl)propyl]-8-propoxy-1H-quinolin-4-one The above compound was prepared in the same manner as in Example 18 using appropriate starting materials.

White Powder (Ethyl Acetate-n-hexane)

Melting point: 152-154° C.

$^1$H-NMR (DMSO-d$_6$) δ ppm: 1.01 (3H, t, J=7.3 Hz), 1.78-1.86 (4H, m), 1.96 (3H, s), 2.04-2.14 (10H, m), 3.75 (3H, s), 4.02 (2H, t, J=6.5 Hz), 4.55 (2H, t, J=6.2 Hz), 6.90-7.01 (3H, m), 7.23 (1H, dd, J=4.5 Hz, 9.0 Hz), 7.58 (2H, d, J=8.8 Hz), 7.97 (1H, s).

Example 88

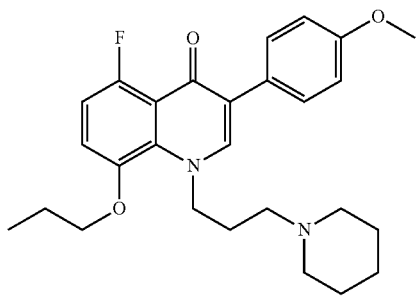

Production of 5-fluoro-3-(4-methoxyphenyl)-1-(3-piperidin-1-ylpropyl)-8-propoxy-1H-quinolin-4-one The above compound was prepared in the same manner as in Example 18 using appropriate starting materials.

White Powder (Ethyl Acetate-n-hexane)

Melting point: 132-134° C.

$^1$H-NMR (DMSO-d$_6$) δ ppm: 0.99 (3H, t, J=7.3 Hz), 1.20-1.40 (6H, m), 1.73-1.84 (4H, m), 2.02-2.10 (6H, m), 3.74 (3H, s), 4.00 (2H, t, J=6.4 Hz), 4.53 (2H, t, J=6.2 Hz), 6.89-7.00 (3H, m), 7.20 (1H, dd, J=4.5 Hz, 9.0 Hz), 7.57 (2H, d, J=8.6 Hz), 7.95 (1H, s).

Example 89

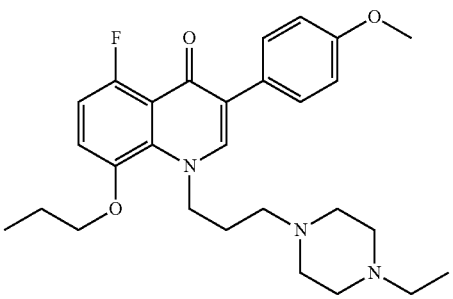

Production of 1-[3-(4-ethylpiperazin-1-yl)propyl]-5-fluoro-3-(4-methoxyphenyl)-8-propoxy-1H-quinolin-4-one The above compound was prepared in the same manner as in Example 18 using appropriate starting materials.

Pale Yellow Powder (Ethyl Acetate-n-hexane)

Melting point: 147-149° C.

$^1$H-NMR (DMSO-d$_6$) δ ppm: 0.80-1.00 (6H, m), 1.70-1.80 (4H, m), 2.00-2.20 (12H, m), 3.75 (3H, s), 4.00-4.06 (2H, m), 4.54-4.59 (2H, m), 6.90-7.00 (3H, m), 7.20-7.26 (1H, m), 7.55-7.60 (2H, m), 7.98 (1H, s).

Example 90

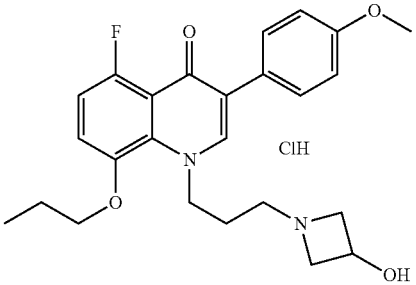

Production of 5-fluoro-1-[3-(3-hydroxy-azetidin-1-yl)propyl]-3-(4-methoxyphenyl)-8-propoxy-1H-quinolin-4-one hydrochloride The above compound was prepared in the same manner as in Example 18 using appropriate starting materials.

Pale Yellow Powder (Ethyl Acetate)

Melting point: 183-185° C.

$^1$H-NMR (DMSO-d$_6$) δ ppm: 1.00 (3H, t, J=7.3 Hz), 1.79-1.94 (4H, m), 3.08-3.14 (2H, m), 3.68-3.83 (5H, m), 4.05 (2H, t, J=6.7 Hz), 4.19-4.43 (3H, m), 4.54-4.60 (2H, m), 6.23 (1H, brs), 6.92-7.04 (3H, m), 7.27 (1H, dd, J=4.5 Hz, 9.0 Hz), 7.61 (2H, d, J=8.6 Hz), 8.00 (1H, s), 10.30 (1H, brs).

Example 91

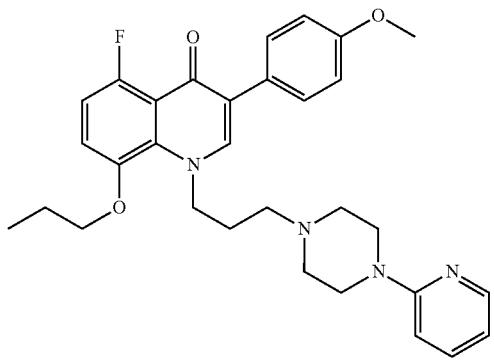

Production of 5-fluoro-3-(4-methoxyphenyl)-8-propoxy-1-[3-(4-pyridin-2-ylpiperazin-1-yl)propyl]-1H-quinolin-4-one The above compound was prepared in the same manner as in Example 18 using appropriate starting materials.
White Powder (Ethyl Acetate-n-hexane)
Melting point: 123-125° C.
$^1$H-NMR (DMSO-$d_6$) δ ppm: 1.01 (3H, t, J=7.3 Hz), 1.79-1.89 (4H, m), 2.14-2.27 (6H, m), 3.20-3.30 (4H, m), 3.74 (3H, s), 4.03 (2H, t, J=6.5 Hz), 4.60 (2H, t, J=6.0 Hz), 6.58 (1H, dd, J=5.0 Hz, 6.9 Hz), 6.69 (1H, d, J=8.6 Hz), 6.90-7.02 (3H, m), 7.23 (1H, dd, J=4.4 Hz, 9.0 Hz), 7.40-7.50 (1H, m), 7.58-7.61 (2H, m), 8.02-8.06 (2H, m).

Example 92

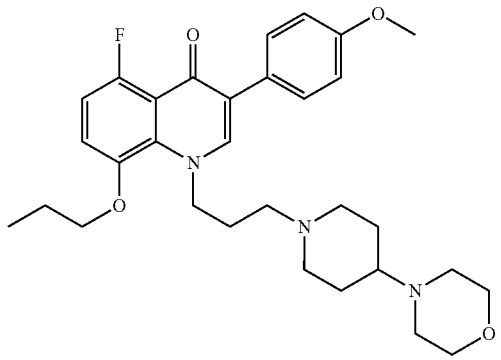

Production of 5-fluoro-3-(4-methoxyphenyl)-1-[3-(4-morpholin-4-ylpiperidin-1-yl)propyl]-8-propoxy-1H-quinolin-4-one The above compound was prepared in the same manner as in Example 18 using appropriate starting materials.
Pale Brown Powder (Ethyl Acetate)
Melting point: 168-170° C.
$^1$H-NMR (DMSO-$d_6$) δ ppm: 1.01 (3H, t, J=7.3 Hz), 1.12-1.20 (2H, m), 1.50-1.55 (2H, m), 1.68-1.86 (6H, m), 1.90-2.11 (3H, m), 2.30-2.33 (4H, m), 2.62-2.67 (2H, m), 3.48-3.51 (4H, m), 3.75 (3H, s), 4.03 (2H, t, J=6.5 Hz), 4.56 (2H, t, J=5.9 Hz), 6.90-7.01 (3H, m), 7.23 (1H, dd, J=4.5 Hz, 9.0 Hz), 7.60 (2H, d, J=8.8 Hz), 7.99 (1H, s).

Example 93

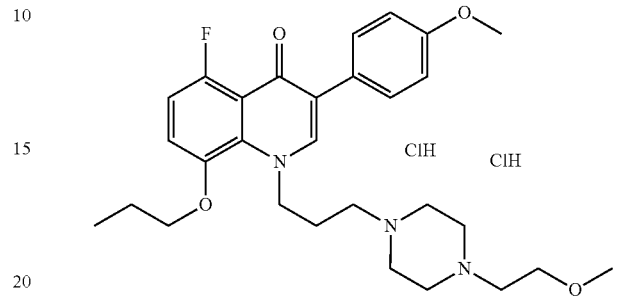

Production of 5-fluoro-1-{3-[4-(2-methoxyethyl)piperazin-1-yl]propyl}-3-(4-methoxyphenyl)-8-propoxy-1H-quinolin-4-one dihydrochloride The above compound was prepared in the same manner as in Example 18 using appropriate starting materials.
Pale Beige Color Powder (Ethyl Acetate)
Melting point: 184-186° C.
$^1$H-NMR (DMSO-$d_6$) δ ppm: 1.01 (3H, t, J=7.3 Hz), 1.81-1.89 (2H, m), 2.00-2.25 (2H, m), 2.80-2.97 (2H, m), 3.25 (3H, s), 3.20-3.40 (4H, m), 3.60-3.65 (8H, m), 3.75 (3H, s), 4.06 (2H, t, J=6.7 Hz), 4.60 (2H, t, J=6.3 Hz), 6.91-7.04 (3H, m), 7.26 (1H, dd, J=4.5 Hz, 9.0 Hz), 7.61 (2H, d, J=8.8 Hz), 8.03 (1H, s).

Example 94

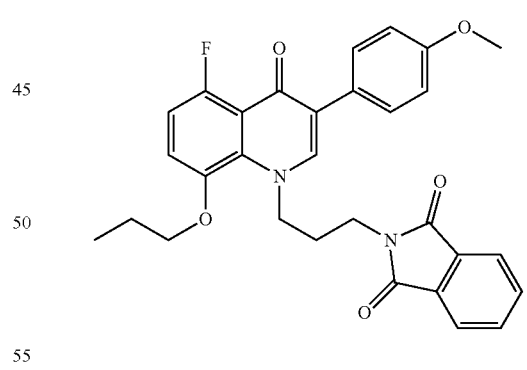

Production of 2-{3-[5-fluoro-3-(4-methoxyphenyl)-4-oxo-8-propoxy-4H-quinolin-1-yl]propyl}isoindole-1,3-dione Sodium hydride (60% oil base, 800 mg, 18.3 mmol) was added to a DMF solution (25 ml) of 5-fluoro-3-(4-methoxyphenyl)-8-propoxy-1H-quinolin-4-one (5.0 g, 15.2 mmol). The mixture was stirred for 30 minutes at room temperature. N-Bromopropyl phthalimide (4.48 g, 16.7 mmol) was added to the mixture and stirred at room temperature for 30 minutes and at 50° C. for 5 hours. The reaction mixture was ice-cooled and water (20 ml) and ethyl acetate were added thereto, followed by stirring for 2 hours. The generated insoluble matter was separated, washed with water, and then dried, giving a pale yellow powder of 2-{3-[5-fluoro-3-(4-methoxyphenyl)-4-oxo-8-propoxy-4H-quinolin-1yl]propyl}isoindole-1,3-dione (4.63 g, yield: 59%).

$^1$H-NMR (DMSO-$d_6$) δ ppm: 0.94 (3H, t, J=7.3 Hz), 1.74-1.83 (2H, m), 2.03 (2H, t, J=7.4 Hz), 3.62 (2H, t, J=6.6 Hz), 3.76 (3H, s), 4.01 (2H, t, J=6.7 Hz), 4.61 (2H, t, J=7.5 Hz), 6.91-7.02 (3H, m), 7.25 (1H, dd, J=4.5 Hz, 9.0 Hz), 7.58 (2H, d, J=8.8 Hz), 7.78-7.86 (4H, m), 8.06 (1H, s).

Example 95

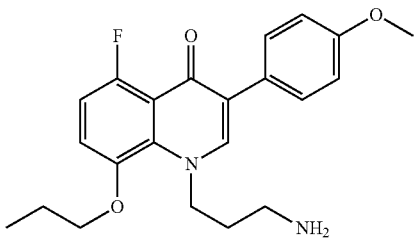

Production of 1-(3-aminopropyl)-5-fluoro-3-(4-methoxyphenyl)-8-propoxy-1H-quinolin-4-one Hydrazine hydrate (0.62 ml, 12.8 mmol) was added to an ethanol solution (60 ml) of 2-{3-[5-fluoro-3-(4-methoxyphenyl)-4-oxo-8-propoxy-4H-quinolin-1-yl]propyl}isoindole-1,3-dione (2.0 g, 3.88 mmol) and heated under reflux for 4 hours. The resulting mixture was concentrated under reduced pressure, a 5N aqueous sodium hydroxide solution was added to the thus-obtained residue, and then the resulting mixture was subjected to extraction using dichloromethane. The thus-obtained organic layer was sequentially washed with water and an aqueous saturated sodium chloride solution, dried over anhydrous magnesium sulfate, and then concentrated under reduced pressure, giving a yellow oily 1-(3-aminopropyl)-5-fluoro-3-(4-methoxyphenyl)-8-propoxy-1H-quinolin-4-one (1.4 g, yield: 94%).

$^1$H-NMR (CDCl$_3$) δ ppm: 1.09 (3H, t, J=7.3 Hz), 1.23 (2H, brs), 1.84-1.95 (4H, m), 2.69 (2H, t, J=6.8 Hz), 3.82 (3H, s), 4.01 (2H, t, J=6.7 Hz), 4.61 (2H, t, J=6.9 Hz), 6.83-7.02 (4H, m), 7.59-7.65 (3H, m).

Example 96

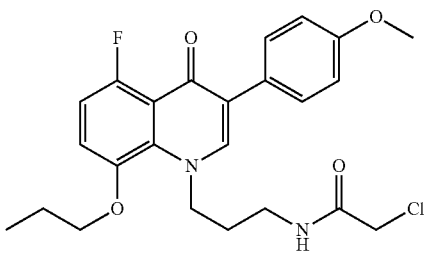

Production of 2-chloro-N-{3-[5-fluoro-3-(4-methoxyphenyl)-4-oxo-8-propoxy-4H-quinolin-1-yl]propyl}acetamide A dichloromethane solution (6 ml) of 1-(3-aminopropyl)-5-fluoro-3-(4-methoxyphenyl)-8-propoxy-1H-quinolin-4-one (645 mg, 1.67 mmol) was ice-cooled. Triethylamine (253 mg, 2.5 mmol) and chloroacetyl chloride (207 mg, 1.83 mmol) were added to the solution and stirred at room temperature for 2 hours. Water was added to the reaction mixture, followed by extraction using dichloromethane. The thus-obtained organic layer was condensed, and the residue was then purified using silica gel column chromatography (dichloromethane:ethyl acetate=4:1→2:1). The purified product was concentrated to dryness under reduced pressure, giving a white powder of 2-chloro-N-{3-[5-fluoro-3-(4-methoxyphenyl)-4-oxo-8-propoxy-4H-quinolin-1-yl]propyl}acetamide (372 mg, yield: 48%).

$^1$H-NMR (CDCl$_3$) δ ppm: 1.10 (3H, t, J=7.3 Hz), 1.86-2.09 (4H, m), 3.33 (2H, q, J=6.9 Hz), 3.83 (3H, s), 4.01 (2H, s), 4.04 (2H, t, J=6.8 Hz), 4.56 (2H, t, J=6.9 Hz), 6.66 (1H, brs), 6.86-6.96 (3H, m), 7.03 (1H, dd, J=4.5 Hz, 9.0 Hz), 7.52 (1H, s), 7.61 (2H, d, J=8.8 Hz).

Example 97

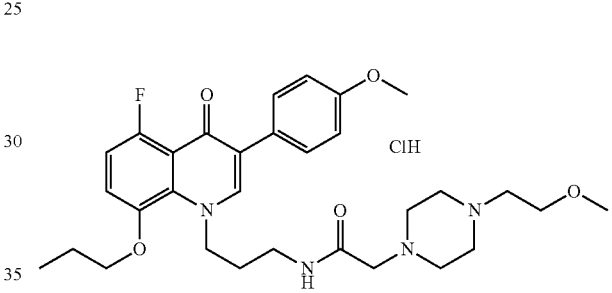

Production of N-{3-[5-fluoro-3-(4-methoxyphenyl)-4-oxo-8-propoxy-4H-quinolin-1-yl]propyl}-2-[4-(2-methoxyethyl)piperazin-1-yl]acetamide hydrochloride 2-Chloro-N-{3-[5-fluoro-3-(4-methoxyphenyl)-4-oxo-8-propoxy-4H-quinolin-1-yl]propyl}acetamide (370 mg, 0.8 mmol) was suspended in acetonitrile (12 ml). 1-(2-Methoxyethyl)piperazine (138 mg, 0.96 mmol), triethylamine (162 mg, 1.6 mmol) and acetonitrile (2 ml) were added to the suspension, and stirred at 70 to 80° C. for 6 hours. The resulting mixture was concentrated under reduced pressure, and the residue was subjected to extraction using ethyl acetate. The extract was then sequentially washed with water, an aqueous saturated sodium chloride solution, and an aqueous saturated sodium bicarbonate solution. The washed product was concentrated under reduced pressure, and the residue was purified using silica gel column chromatography (dichloromethane:methanol=30:1→10:1). The purified product was concentrated under reduced pressure, and the residue was then dissolved in ethyl acetate (5 ml). A 4N hydrogen chloride ethyl acetate solution (0.19 ml) was added thereto and stirred, and then the mixture was concentrated to dryness under reduced pressure, giving a pale yellow amorphous solid of N-{3-[5-fluoro-3-(4-methoxyphenyl)-4-oxo-8-propoxy-4H-quinolin-1-yl]propyl}-2-[4-(2-methoxyethyl)piperazin-1-yl]acetamide hydrochloride (200 mg).

$^1$H-NMR (DMSO-$d_6$) δ ppm: 1.00 (3H, t, J=7.3 Hz), 1.78-1.89 (4H, m), 2.50-3.00 (4H, m), 2.96-3.20 (8H, m), 3.25 (3H, s), 3.62-3.66 (4H, m), 3.75 (3H, s), 3.98-4.04 (2H, m), 4.56 (2H, t, J=6.4 Hz), 6.91-7.02 (3H, m), 7.24 (1H, dd, J=4.5 Hz, 9.1 Hz), 7.60 (2H, d, J=8.8 Hz), 8.00 (1H, s), 8.07 (1H, brs).

Example 98

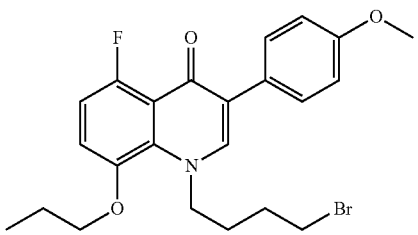

Production of 1-(4-bromobutyl)-5-fluoro-3-(4-methoxyphenyl)-8-propoxy-1H-quinolin-4-one The above compound was prepared in the same manner as in Example 17 using appropriate starting materials.
$^1$H-NMR (CDCl$_3$) δ ppm: 1.06-1.13 (3H, m), 1.70-2.00 (6H, m), 3.39 (2H, t, J=6.3 Hz), 3.83 (3H, s), 4.03 (2H, t, J=6.7 Hz), 4.53 (2H, t, J=6.8 Hz), 6.86-7.03 (4H, m), 7.49 (1H, s), 7.57-7.63 (2H, m).

Example 99

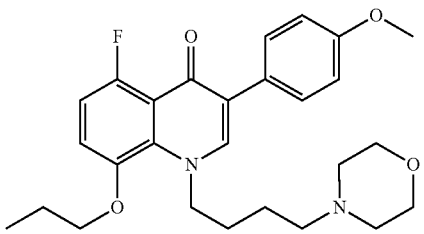

Production of 5-fluoro-3-(4-methoxyphenyl)-1-(4-morpholin-4-ylbutyl)-8-propoxy-1H-quinolin-4-one The above compound was prepared in the same manner as in Example 18 using appropriate starting material.
White Powder (Ethyl Acetate-n-hexane)
Melting point: 118-120° C.
$^1$H-NMR (DMSO-d$_6$) δ ppm: 0.98 (3H, t, J=7.3 Hz), 1.27-1.35 (2H, m), 1.62-1.82 (4H, m), 2.13-2.19 (6H, m), 3.44-3.47 (4H, m), 3.73 (3H, s), 3.98 (2H, t, J=6.5 Hz), 4.49 (2H, t, J=6.8 Hz), 6.89-6.99 (3H, m), 7.19 (1H, dd, J=4.5 Hz, 9.0 Hz), 7.57 (2H, d, J=8.6 Hz), 7.95 (1H, s).

Example 100

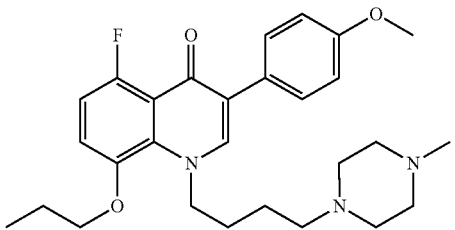

Production of 5-fluoro-3-(4-methoxyphenyl)-1-[4-(4-methyl piperazin-1-yl)butyl]-8-propoxy-1H-quinolin-4-one The above compound was prepared in the same manner as in Example 18 using appropriate starting materials.
Pale Yellow Amorphous
$^1$H-NMR (DMSO-d$_6$) δ ppm: 0.99 (3H, t, J=7.3 Hz), 1.27-1.32 (2H, m), 1.62-1.65 (2H, m), 1.79 (2H, q, J=6.9 Hz), 2.07 (3H, s), 2.11-2.21 (10H, m), 3.74 (3H, s), 4.00 (2H, t, J=6.5 Hz), 4.49 (2H, t, J=6.8 Hz), 6.90-7.00 (3H, m), 7.21 (1H, dd, J=4.5 Hz, 9.0 Hz), 7.58 (2H, d, J=8.6 Hz), 7.96 (1H, s).

Example 101

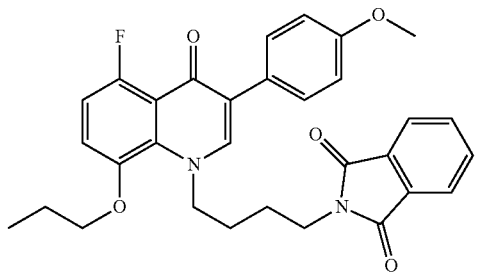

Production of 2-{4-[5-fluoro-3-(4-methoxyphenyl)-4-oxo-8-propoxy-4H-quinolin-1-yl]butyl}isoindole-1,3-dione The above compound was prepared in the same manner as in Example 94 using appropriate starting material.
$^1$H-NMR (DMSO-d$_6$) δ ppm: 0.96 (3H, t, J=7.3 Hz), 1.50-1.80 (6H, m), 3.57 (2H, t, J=6.3 Hz), 3.76 (3H, s), 3.97 (2H, t, J=6.7 Hz), 4.49 (2H, t, J=6.8 Hz), 6.88-6.95 (3H, m), 7.18 (1H, dd, J=4.5 Hz, 9.1 Hz), 7.60 (2H, d, J=8.7 Hz), 7.80-7.90 (4H, m), 8.01 (1H, s).

Example 102

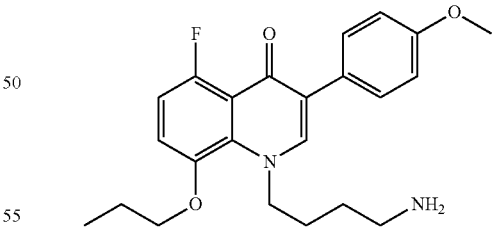

Production of 1-(4-aminobutyl)-5-fluoro-3-(4-methoxyphenyl)-8-propoxy-1H-quinolin-4-one The above compound was prepared in the same manner as in Example 95 using appropriate starting material.
$^1$H-NMR (CDCl$_3$) δ ppm: 1.10 (3H, t, J=7.3 Hz), 1.36-1.60 (4H, m), 1.75-1.95 (4H, m), 2.69 (2H, t, J=6.9 Hz), 3.82 (3H, s), 4.01 (2H, t, J=6.6 Hz), 4.50 (2H, t, J=7.3 Hz), 6.83-7.02 (4H, m), 7.50 (1H, s), 7.60 (2H, d, J=8.5 Hz).

Example 103

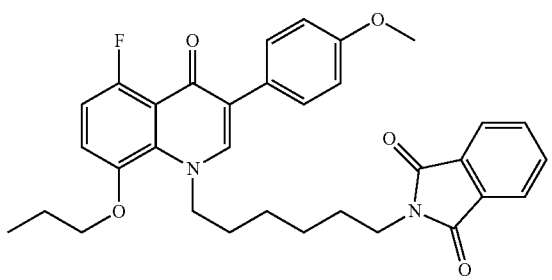

Production of 2-{6-[5-fluoro-3-(4-methoxyphenyl)-4-oxo-8-propoxy-4H-quinolin-1-yl]hexyl}isoindole-1,3-dione The above compound was prepared in the same manner as in Example 94 using appropriate starting material.

$^{1}$H-NMR (CDCl$_3$) δ ppm: 1.08 (3H, t, J=7.3 Hz), 1.20-1.77 (8H, m), 1.83-1.94 (2H, m), 3.65 (2H, t, J=6.9 Hz), 3.82 (3H, s), 4.01 (2H, t, J=6.5 Hz), 4.46 (2H, t, J=7.3 Hz), 6.83-7.04 (4H, m), 7.49 (1H, s), 7.61 (2H, d, J=8.7 Hz), 7.68-7.83 (4H, m).

Example 104

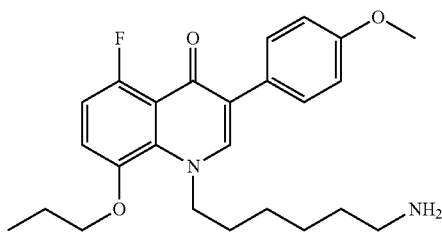

Production of 1-(6-aminohexyl)-5-fluoro-3-(4-methoxyphenyl)-8-propoxy-1H-quinolin-4-one The above compound was prepared in the same manner as in Example 95 using appropriate starting material.

$^{1}$H-NMR (CDCl$_3$) δ ppm: 1.10 (3H, t, J=7.3 Hz), 1.30-1.80 (10H, m), 1.87-1.95 (2H, m), 2.65 (2H, t, J=6.4 Hz), 3.83 (3H, s), 4.01 (2H, t, J=6.6 Hz), 4.47 (2H, t, J=7.5 Hz), 6.88-7.03 (4H, m), 7.50 (1H, s), 7.62 (2H, d, J=8.7 Hz).

Example 105

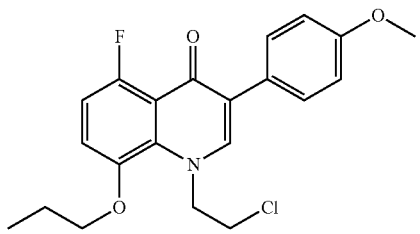

Production of 1-(2-chloroethyl)-5-fluoro-3-(4-methoxyphenyl)-8-propoxy-1H-quinolin-4-one The above compound was prepared in the same manner as in Example 17 using appropriate starting materials.

$^{1}$H-NMR (CDCl$_3$) δ ppm: 1.07-1.13 (3H, t, J=7.4 Hz), 1.81-2.01 (2H, m), 3.83 (3H, s), 3.84-3.89 (2H, t, J=6.3 Hz), 4.00-4.05 (2H, t, J=6.7 Hz), 4.74-4.79 (2H, t, J=6.3 Hz), 6.89-7.04 (4H, m), 7.54 (1H, s), 7.59-7.62 (2H, d, J=8.8 Hz).

Example 106

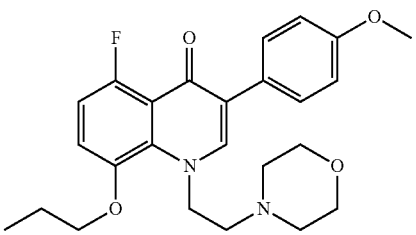

Production of 5-fluoro-3-(4-methoxyphenyl)-1-(2-morpholin-4-ylethyl)-8-propoxy-1H-quinolin-4-one Potassium carbonate (2.1 g, 15.2 mmol) and 4-(2-chloroethyl)morpholine hydrochloride (1.36 g, 7.31 mmol) were added to an N-methylpyrrolidone (NMP) solution (5 ml) of 5-fluoro-3-(4-methoxyphenyl)-8-propoxy-1H-quinolin-4-one (1.0 g, 3.05 mmol) and then stirred at 50 to 60° C. for 45 hours. Water and ethyl acetate were added to the reaction mixture, followed by separation. The thus-obtained organic layer was washed with an aqueous saturated sodium chloride solution twice, and then concentrated under reduced pressure. The residue was purified using silica gel column chromatography (dichloromethane:methanol=50:1→30:1). The purified product was concentrated under reduced pressure, and the residue was recrystallized from ethyl acetate, giving a white powder of 5-fluoro-3-(4-methoxyphenyl)-1-(2-morpholin-4-ylethyl)-8-propoxy-1H-quinolin-4-one (1.01 g, yield: 75%).

Melting point: 206-208° C.

$^{1}$H-NMR (DMSO-d$_6$) δ ppm: 1.02 (3H, t, J=7.3 Hz), 1.78-1.87 (2H, m), 2.33-2.36 (4H, m), 2.59 (2H, t, J=5.6 Hz), 3.43-3.47 (4H, m), 3.77 (3H, s), 4.05 (2H, t, J=6.5 Hz), 4.66 (2H, t, J=5.7 Hz), 6.94-7.02 (3H, m), 7.25 (1H, dd, J=4.5 Hz, 9.0 Hz), 7.60 (2H, d, J=8.8 Hz), 7.95 (1H, s).

Example 107

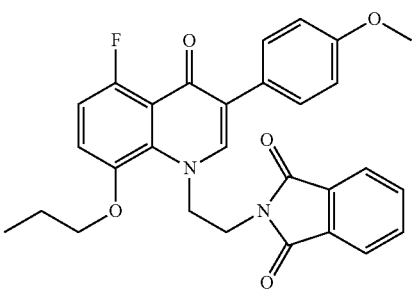

Production of 2-{2-[5-fluoro-3-(4-methoxyphenyl)-4-oxo-8-propoxy-4H-quinolin-1-yl]ethyl}isoindole-1,3-dione The above compound was prepared in the same manner as in Example 94 using appropriate starting material.
¹H-NMR (CDCl₃) δ ppm: 1.11 (3H, t, J=7.3 Hz), 1.85-2.01 (2H, m), 3.76 (3H, s), 4.03-4.12 (4H, m), 4.84 (2H, t, J=5.6 Hz), 6.84-6.89 (3H, m), 6.92-7.00 (1H, m), 7.56 (2H, d, J=8.6 Hz), 7.68-7.79 (5H, m).

Example 108

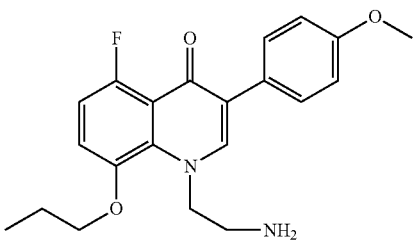

Production of 1-(2-aminoethyl)-5-fluoro-3-(4-methoxyphenyl)-8-propoxy-1H-quinolin-4-one The above compound was prepared in the same manner as in Example 95 using appropriate starting material.
¹H-NMR (CDCl₃) δ ppm: 1.10 (3H, t, J=7.3 Hz), 1.36 (2H, brs), 1.84-1.95 (2H, m), 3.10 (2H, t, J=6.0 Hz), 3.82 (3H, s), 4.01 (2H, t, J=6.7 Hz), 4.54 (2H, t, J=6.1 Hz), 6.84-7.02 (4H, m), 7.60-7.64 (3H, m).

Example 109

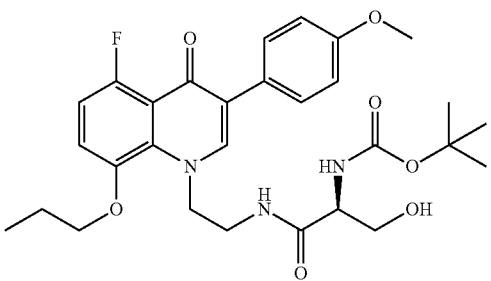

Production of tert-butyl((S)-1-{2-[5-fluoro-3-(4-methoxyphenyl)-4-oxo-8-propoxy-4H-quinolin-1-yl]ethylcarbamoyl}-2-hydroxyethyl)carbamate A DMF solution (0.5 ml) of N-(tert-butoxycarbonyl)-L-serine (174 mg, 0.85 mmol), triethylamine (198 mg, 1.96 mmol), diethyl phosphorocyanidate (DEPC, 176 mg, 0.97 mmol) and DMF (0.5 ml) were sequentially added to a DMF solution (1 ml) of 1-(2-aminoethyl)-5-fluoro-3-(4-methoxyphenyl)-8-propoxy-1H-quinolin-4-one (300 mg, 0.81 mmol) while ice-cooling, and stirred at room temperature for 20 hours. Water was added to the reaction mixture and then subjected to extraction using ethyl acetate. The thus-obtained organic layer was washed with an aqueous saturated sodium chloride solution twice. The washed product was dried over anhydrous sodium sulfate and then concentrated under reduced pressure. The residue was purified using silica gel column chromatography (dichloromethane:methanol=40:1→30:1). The purified product was concentrated to dryness under reduced pressure, giving a white amorphous solid of tert-butyl((S)-1-{2-[5-fluoro-3-(4-methoxyphenyl)-4-oxo-8-propoxy-4H-quinolin-1-yl]ethylcarbamoyl}-2-hydroxyethyl)carbamate (338 mg, yield: 75%).
¹H-NMR (CDCl₃) δ ppm: 1.09 (3H, t, J=7.3 Hz), 1.38 (9H, s), 1.87-1.95 (2H, m), 3.08 (1H, brs), 3.45-3.60 (3H, m), 3.69-3.79 (1H, m), 3.76 (3H, s), 3.99 (2H, t, J=6.8 Hz), 4.34 (1H, brs), 4.64 (2H, brs), 5.87 (1H, d, J=7.9 Hz), 6.56 (1H, dd, J=8.9 Hz, 11.7 Hz), 6.73 (2H, d, J=8.7 Hz), 6.91 (1H, dd, J=4.5 Hz, 9.0 Hz), 7.36 (2H, d, J=8.7 Hz), 7.46 (1H, s), 8.26 (1H, brs).

Example 110

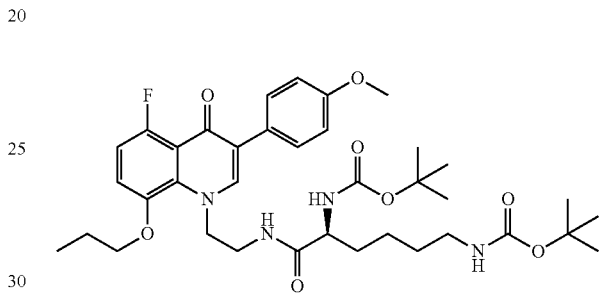

Production of tert-butyl((S)-5-tert-butoxycarbonylamino-5-{2-[5-fluoro-3-(4-methoxyphenyl)-4-oxo-8-propoxy-4H-quinolin-1-yl]ethylcarbamoyl}pentyl)carbamate The above compound was prepared in the same manner as in Example 109 using appropriate starting material.
¹H-NMR (CDCl₃) δ ppm: 0.90-1.05 (4H, m), 1.12 (3H, t, J=7.3 Hz), 1.37 (9H, s), 1.41 (9H, s), 1.48-1.60 (2H, m), 1.87-1.99 (2H, m), 2.80-2.90 (2H, m), 3.40-3.50 (1H, m), 3.80 (3H, s), 3.91-4.24 (5H, m), 4.53 (1H, brs), 5.27-5.33 (1H, m), 5.75-5.78 (1H, m), 6.43-6.52 (1H, m), 6.84-6.90 (3H, m), 7.39-7.48 (3H, m), 8.09 (1H, brs).

Example 111

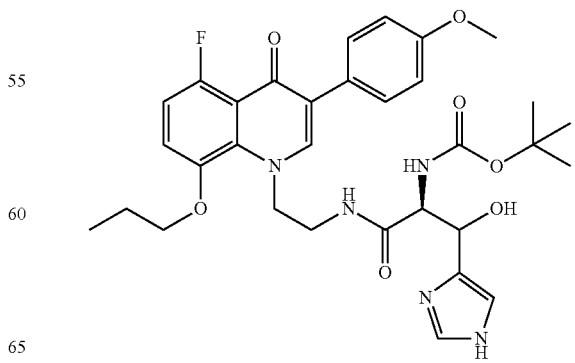

Production of tert-butyl[(S)-1-{2-[5-fluoro-3-(4-methoxyphenyl)-4-oxo-8-propoxy-4H-quinolin-1-yl]ethylcarbamoyl}-2-(1H-imidazol-4-yl)ethyl]carbamate The above compound was prepared in the same manner as in Example 109 using appropriate starting material.

$^1$H-NMR (CDCl$_3$) δ ppm: 1.10 (3H, t, J=7.3 Hz), 1.39 (9H, s), 1.85-2.01 (2H, m), 2.72-2.90 (2H, m), 3.50-3.60 (1H, m), 3.76 (3H, s), 3.77-3.86 (1H, m), 4.02 (2H, t, J=6.7 Hz), 4.30-4.43 (2H, m), 4.82-4.88 (1H, m), 5.82 (1H, brs), 6.57 (1H, s), 6.72-6.84 (3H, m), 6.94-6.99 (1H, m), 7.08 (1H, s), 7.37-7.45 (3H, m), 8.05 (1H, brs).

Example 112

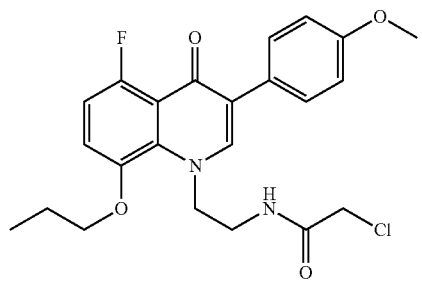

Production of 2-chloro-N-{2-[5-fluoro-3-(4-methoxyphenyl)-4-oxo-8-propoxy-4H-quinolin-1-yl]ethyl}acetamide The above compound was prepared in the same manner as in Example 96 using appropriate starting material.

$^1$H-NMR (CDCl$_3$) δ ppm: 1.12 (3H, t, J=7.3 Hz), 1.90-1.98 (2H, m), 3.64-3.70 (2H, m), 3.83 (3H, s), 3.98 (2H, s), 4.03 (2H, t, J=6.6 Hz), 4.72-4.76 (2H, m), 6.51 (1H, dd, J=9.0 Hz, 11.7 Hz), 6.78 (2H, d, J=8.8 Hz), 6.89 (1H, dd, J=4.5 Hz, 9.0 Hz), 7.25-7.32 (3H, m), 8.54 (1H, brs).

Example 113

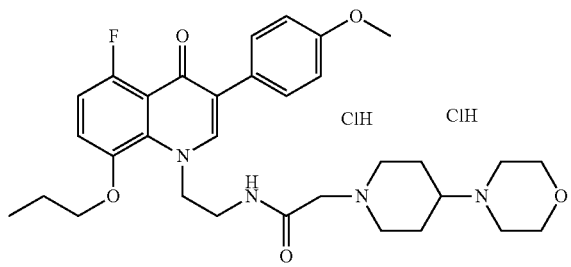

Production of N-{2-[5-fluoro-3-(4-methoxyphenyl)-4-oxo-8-propoxy-4H-quinolin-1-yl]ethyl}-2-(4-morpholin-4-ylpiperidin-1-yl)acetamide dihydrochloride The above compound was prepared in the same manner as in Example 97 using appropriate starting materials.

$^1$H-NMR (DMSO-d$_6$) δ ppm: 1.00 (3H, t, J=7.3 Hz), 1.75-1.96 (7H, m), 2.50-2.80 (2H, m), 2.85-3.25 (10H, m), 3.76 (3H, s), 3.80-3.95 (4H, m), 4.04 (2H, t, J=6.5 Hz), 4.69 (2H, brs), 6.93-7.02 (3H, m), 7.25 (1H, dd, J=4.5 Hz, 9.1 Hz), 7.64 (2H, d, J=8.8 Hz), 7.87 (1H, s), 8.69 (1H, brs).

Example 114

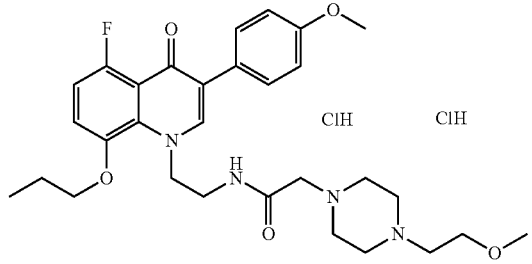

Production of N-{2-[5-fluoro-3-(4-methoxyphenyl)-4-oxo-8-propoxy-4H-quinolin-1-yl]ethyl}-2-[4-(2-methoxyethyl)piperazin-1-yl]acetamide dihydrochloride The above compound was prepared in the same manner as in Example 97 using appropriate starting materials.

$^1$H-NMR (DMSO-d$_6$) δ ppm: 0.98 (3H, t, J=7.3 Hz), 1.76-1.85 (2H, m), 2.95-3.05 (4H, m), 3.25 (3H, s), 3.10-3.30 (2H, m), 3.39-3.64 (10H, m), 3.75 (3H, s), 4.02 (2H, t, J=6.5 Hz), 4.68 (2H, brs), 6.91-7.01 (3H, m), 7.23 (1H, dd, J=4.5 Hz, 9.1 Hz), 7.59 (2H, d, J=8.7 Hz), 7.86 (1H, s), 8.57 (1H, t, J=5.4 Hz).

Example 115

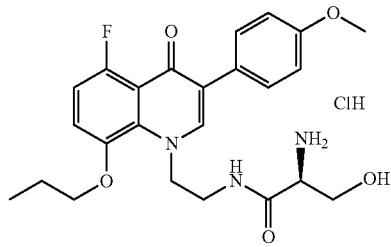

Production of (S)-2-amino-N-{2-[5-fluoro-3-(4-methoxyphenyl)-4-oxo-8-propoxy-4H-quinolin-1-yl]ethyl}-3-hydroxypropionamide hydrochloride A 4N hydrogen chloride ethyl acetate solution (5 ml) was added to an ethanol solution (5 ml) of tert-butyl((S)-1-{2-[5-fluoro-3-(4-methoxyphenyl)-4-oxo-8-propoxy-4H-quinolin-1-yl]ethylcarbamoyl}-2-hydroxyethyl)carbamate (330 mg, 0.6 mmol) and stirred at room temperature for 14 hours. The resulting mixture was concentrated under reduced pressure. Water was added to the residue, which was then washed with ethyl acetate. A 2N aqueous sodium hydroxide solution (6 ml) was added to the water layer to adjust its pH to 11, followed by extraction with dichloromethane. The thus-obtained organic layer was washed with an aqueous saturated sodium chloride solution, dried over anhydrous magnesium sulfate, and then concentrated under reduced pressure. The residue was purified using silica gel column chromatography (dichloromethane:methanol=20:1→15:1). The purified product was concentrated under reduced pressure, the residue was dissolved in ethanol (3 ml) and ethyl acetate (3 ml), and a 4N hydrogen chloride ethylacetate solution (0.1 ml) was then added thereto. The mixture was stirred and concentrated to dryness under reduced pressure, and recrystallized from ethyl acetate, giving a white powder of (S)-2-amino-N-{2-[5-fluoro-3-(4-methoxyphenyl)-4-oxo-8-propoxy-4H-quinolin-1-yl]ethyl}-3-hydroxypropionamide hydrochloride (145 mg, yield: 50%).

$^1$H-NMR (DMSO-$d_6$) δ ppm: 1.00 (3H, t, J=7.3 Hz), 1.76-1.88 (2H, m), 3.23-3.50 (5H, m), 3.75 (3H, s), 4.05 (2H, t, J=6.5 Hz), 4.53-4.73 (2H, m), 5.40-5.42 (1H, m), 6.91-7.03 (3H, m), 7.26 (1H, dd, J=4.5 Hz, 9.0 Hz), 7.58 (2H, d, J=8.7 Hz), 7.80 (1H, s), 8.00 (2H, brs), 8.58 (1H, t, J=5.2 Hz).

Example 116

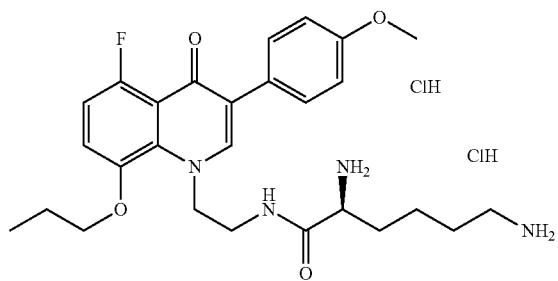

Production of (S)-2,6-diaminohexanoic {2-[5-fluoro-3-(4-methoxyphenyl)-4-oxo-8-propoxy-4H-quinolin-1-yl]ethyl}amide dihydrochloride The above compound was prepared in the same manner as in Example 115 using appropriate starting material.

$^1$H-NMR (DMSO-$d_6$) δ ppm: 0.99 (3H, t, J=7.3 Hz), 1.00-1.50 (6H, m), 1.77-1.86 (2H, m), 2.57 (2H, t, J=7.2 Hz), 3.32-3.44 (3H, m), 3.50-3.70 (4H, m), 3.74 (3H, s), 4.00-4.05 (2H, m), 4.53-4.82 (2H, m), 6.91-7.03 (3H, m), 7.24 (1H, dd, J=4.5 Hz, 9.1 Hz), 7.60 (2H, d, J=8.7 Hz), 7.86 (1H, s), 8.61 (1H, brs).

Example 117

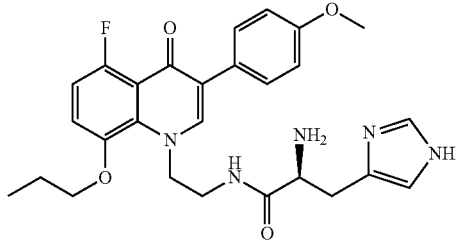

Production of (S)-2-amino-N-{2-[5-fluoro-3-(4-methoxyphenyl)-4-oxo-8-propoxy-4H-quinolin-1-yl]ethyl}-3-(1H-imidazol-4-yl)propionamide The above compound was prepared in the same manner as in Example 115 using appropriate starting material.

$^1$H-NMR (DMSO-$d_6$) δ ppm: 1.00 (3H, t, J=7.3 Hz), 1.78-1.86 (2H, m), 2.26 (1H, dd, J=9.3 Hz, 14.5 Hz), 2.65 (1H, dd, J=3.8 Hz, 14.5 Hz), 3.26 (1H, dd, J=3.8 Hz, 9.3 Hz), 3.30-3.55 (4H, m), 3.73 (3H, s), 3.98-4.05 (2H, m), 4.64 (2H, brs), 6.61 (1H, s), 6.87-7.01 (3H, m), 7.22 (1H, dd, J=4.5 Hz, 9.0 Hz), 7.48 (1H, s), 7.57 (2H, d, J=8.7 Hz), 7.79 (1H, s), 8.13 (1H, brs).

Example 118

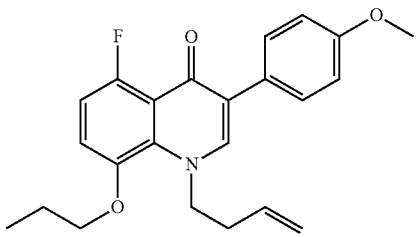

Production of 1-but-3-enyl-5-fluoro-3-(4-methoxyphenyl)-8-propoxy-1H-quinolin-4-one The above compound was prepared in the same manner as in Example 3 using appropriate starting materials.

$^1$H-NMR (CDCl$_3$) δ ppm: 1.09-1.15 (3H, t, J=7.4 Hz), 1.82-2.03 (2H, m), 2.38-2.64 (2H, m), 3.85 (3H, s), 4.02-4.07 (2H, t, J=6.7 Hz), 4.55-4.61 (2H, t, J=7.2 Hz), 4.96-5.15 (2H, m), 5.60-5.89 (1H, m), 6.79-7.08 (4H, m), 7.49 (1H, s), 7.61-7.64 (2H, d, J=8.8 Hz).

Example 119

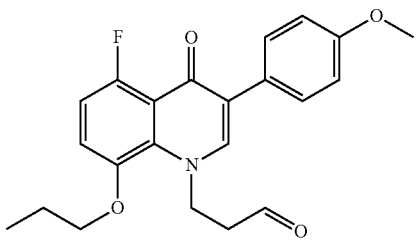

Production of 3-[5-fluoro-3-(4-methoxyphenyl)-4-oxo-8-propoxy-4H-quinolin-1-yl]propionaldehyde A dioxane (30 ml)-water (10 ml) solution of 1-but-3-enyl-5-fluoro-3-(4-methoxyphenyl)-8-propoxy-1H-quinolin-4-one (1.2 g, 3.15 mmol) was prepared. A 2.6-Lutidine (0.674 g, 6.29 mmol), 4% osmic acid solution (1 ml) and sodium periodate (2.69 g, 12.6 mmol) were added to the solution, and stirred at room temperature for 30 minutes. Water was added to the reaction mixture, then the mixture was extracted with dichloromethane, washed with water, and then dried over anhydrous sodium sulfate. The dried product was concentrated under reduced pressure, and the residue was then purified using silica gel column chromatography (n-hexane:ethyl acetate=100:0→0:100). The purified product was concentrated to dryness under reduced pressure, giving a pale yellow powder of 3-[5-fluoro-3-(4-methoxyphenyl)-4-oxo-8-propoxy-4H-quinolin-1-yl]propionaldehyde (1.0 g, yield: 83%).

¹H-NMR (CDCl₃) δ ppm: 1.05-1.10 (3H, t, J=7.4 Hz), 1.75-1.94 (2H, m), 3.04-3.92 (2H, t, J=6.6 Hz), 3.83 (3H, s), 3.99-4.04 (2H, t, J=6.8 Hz), 4.76-4.81 (2H, t, J=6.6 Hz), 6.82-7.06 (4H, m), 7.49-7.68 (3H, m), 9.81 (1H, s).

Example 120

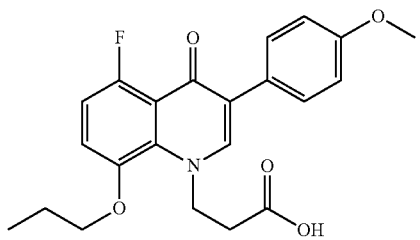

Production of 3-[5-fluoro-3-(4-methoxyphenyl)-4-oxo-8-propoxy-4H-quinolin-1-yl]propionic acid 3-[5-Fluoro-3-(4-methoxyphenyl)-4-oxo-8-propoxy-4H-quinolin-1-yl]propionaldehyde (1.0 g, 2.61 mmol) was dissolved in water (10 ml), tert-butyl alcohol (20 ml) and dichloromethane (20 ml). Sodium chlorite (3.2 g, 35.4 mmol), 2-methyl-2-butene (19.86 gm, 283 mmol) and sodium-dihydrogenphosphate dihydrate (2 g, 2.61 mmol) were added to the resulting solution, and the solution was stirred at room temperature for 1 hour. Water was added to the reaction mixture, the mixture was extracted with dichloromethane, and then washed with water and dried over anhydrous sodium sulfate. The dried product was concentrated under reduced pressure. The residue was purified using silica gel column chromatography (dichloromethane:ethyl acetate=50:50→0: 100). The purified product was concentrated to dryness under reduced pressure, giving a pale yellow powder of 3-[5-fluoro-3-(4-methoxyphenyl)-4-oxo-8-propoxy-4H-quinolin-1-yl]propionic acid (710 mg, yield: 68%).

¹H-NMR (DMSO-d₆) δ ppm: 0.96-1.02 (3H, t, J=7.4 Hz), 1.62-1.91 (2H, m), 2.75-2.80 (2H, t, J=6.9 Hz), 3.76 (3H, s), 4.01-4.07 (2H, t, J=6.6 Hz), 4.69-4.75 (2H, t, J=7.0 Hz), 6.90-7.03 (3H, m), 7.22-7.29 (1H, m), 7.59-7.63 (2H, d, J=8.8 Hz), 8.03 (1H, s).

Example 121

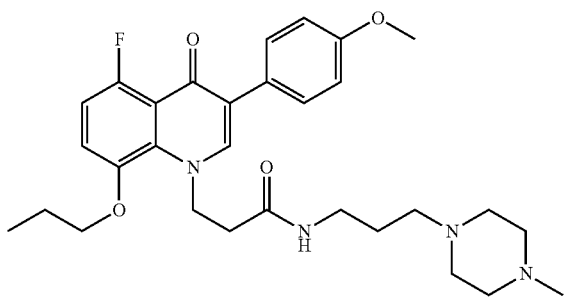

Production of 3-[5-fluoro-3-(4-methoxyphenyl)-4-oxo-8-propoxy-4H-quinolin-1-yl]-N-[3-(4-methylpiperazin-1-yl)propyl]propionamide The above compound was prepared in the same manner as in Example 33 using appropriate starting materials.

Melting point: 191-192° C.
¹H-NMR (DMSO-d₆) δ ppm: 0.99-1.05 (3H, t, J=7.4 Hz), 1.25-1.50 (2H, m), 1.75-1.90 (2H, m), 2.20-2.45 (2H, m), 2.50-3.00 (15H, m), 3.78 (3H, s), 3.98-4.05 (2H, m), 4.75-5.00 (2H, m), 6.94-7.05 (3H, m), 7.26-7.40 (1H, m), 7.58-7.62 (2H, d, J=8.7 Hz), 7.88-7.92 (2H, m).

Example 122

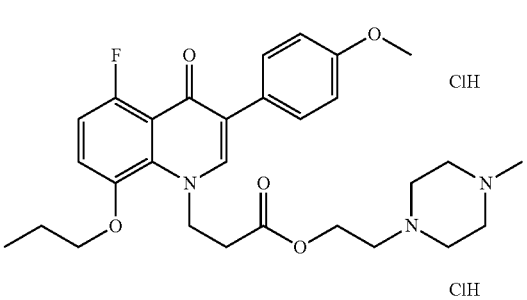

Production of 2-(4-methylpiperazin-1-yl)ethyl 3-[5-fluoro-3-(4-methoxyphenyl)-4-oxo-8-propoxy-4H-quinolin-1-yl]propionate dihydrochloride 1-(2-Hydroxyethyl)-4-methylpiperazine (199 mg, 1.38 mmol), dicyclohexylcarbodiimide (310 mg, 1.50 mmol) and 4-dimethylaminopyridine (168 mg, 1.38 mmol) were added to a DMF solution (10 ml) of 3-[5-fluoro-3-(4-methoxyphenyl)-4-oxo-8-propoxy-4H-quinolin-1-yl]propionic acid (500 mg, 1.25 mmol) and stirred overnight at room temperature. Water was added to the reaction mixture, the mixture was extracted with dichloromethane and washed with water and then dried over anhydrous sodium sulfate. The dried product was concentrated under reduced pressure, and the resulting residue was purified using silica gel column chromatography (ethyl acetate→dichloromethane:methanol=10:1). The residue was dissolved in ethyl acetate and a 4N hydrogen chloride ethylacetate solution was added thereto and stirred. The mixture was concentrated to dryness under reduced pressure, giving a pale yellow powder of 2-(4-methyl piperazin-1-yl) ethyl 3-[5-fluoro-3-(4-methoxyphenyl)-4-oxo-8-propoxy-4H-quinolin-1-yl]propionate dihydrochloride (110 mg, yield: 17%).

Melting point: 150-152° C.
¹H-NMR (DMSO-d₆) δ ppm: 0.99-1.05 (3H, t, J=7.4 Hz), 1.69-1.88 (2H, m), 2.78 (3H, s), 2.87-3.04 (2H, m), 3.10-3.60 (10H, m), 3.77 (3H, s), 4.01-4.11 (2H, t, J=6.8 Hz), 4.27-4.44 (2H, m), 4.67-4.94 (2H, m), 6.76-7.09 (3H, m), 7.16-7.33 (1H, m), 7.58-7.63 (2H, d, J=8.8 Hz), 8.07 (1H, s).

Example 123

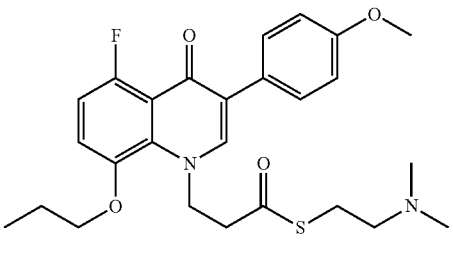

Production of S-(2-dimethylaminoethyl)3-[5-fluoro-3-(4-methoxyphenyl)-4-oxo-8-propoxy-4H-quinolin-1-yl]thiopropionate hydrochloride The above compound was prepared in the same manner as in Example 122 using appropriate starting material.
Melting point: 50-52° C.
$^1$H-NMR (DMSO-$d_6$) δ ppm: 0.97-1.03 (3H, t, J=7.4 Hz), 1.65-1.88 (2H, m), 2.68 (3H, s), 2.70 (3H, s), 2.93-3.10 (2H, m), 3.11-3.29 (4H, m), 3.76 (3H, s), 4.04-4.09 (2H, t, J=6.6 Hz), 4.68-4.94 (2H, m), 6.90-7.06 (3H, m), 7.26-7.31 (1H, m), 7.61-7.64 (2H, d, J=8.7 Hz), 8.00 (1H, s), 10.41-10.92 (1H, br).

Example 124

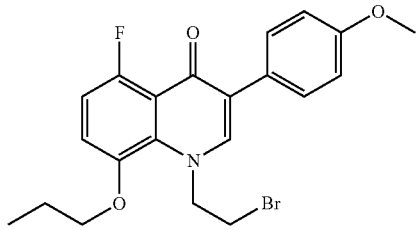

Production of 1-(2-bromoethyl)-5-fluoro-3-(4-methoxyphenyl)-8-propoxy-1H-quinolin-4-one The above compound was prepared in the same manner as in Example 17 using appropriate starting materials.
$^1$H-NMR (CDCl$_3$) δ ppm: 1.09-1.15 (3H, t, J=7.4 Hz), 1.82-2.03 (2H, m), 3.67-3.72 (2H, t, J=6.8 Hz), 3.84 (3H, s), 4.01-4.07 (2H, t, J=6.8 Hz), 4.79-4.85 (2H, t, J=6.8 Hz), 6.88-7.06 (4H, m), 7.53 (1H, s), 7.58-7.63 (2H, m).

Example 125

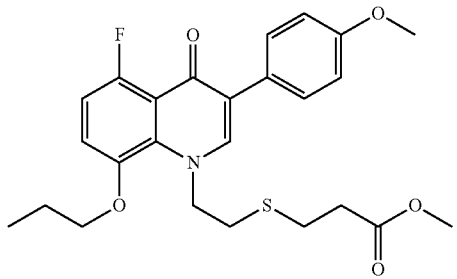

Production of methyl 3-{2-[5-fluoro-3-(4-methoxyphenyl)-4-oxo-8-propoxy-4H-quinolin-1-yl]ethylsulfanyl}propionate 1-(2-Chloroethyl)-5-fluoro-3-(4-methoxyphenyl)-8-propoxy-1H-quinolin-4-one (3.5 g, 8.98 mmol), methyl 3-mercaptopropionate (1.19 g, 9.88 mmol), and sodium iodide (1.48 g, 9.88 mmol) were added to DMF (30 ml) and stirred at 80° C. for 5 hours. Water and ethyl acetate were added to the reaction mixture, followed by separation. The thus-obtained organic layer was washed with water, dried over anhydrous magnesium sulfate, and then concentrated under reduced pressure. The residue was purified using silica gel column chromatography (dichloromethane). The purified product was concentrated to dryness under reduced pressure, giving a pale yellow powder of methyl 3-{2-[5-fluoro-3-(4-methoxyphenyl)-4-oxo-8-propoxy-4H-quinolin-1-yl]ethylsulfanyl}propionate (3.2 g, yield: 75%).
$^1$H-NMR (DMSO-$d_6$) δ ppm: 0.99-1.05 (3H, t, J=7.4 Hz), 2.65-2.80 (2H, m), 2.54-2.60 (2H, t, J=7.2 Hz), 2.70-2.76 (2H, t, J=7.2 Hz), 2.88-2.93 (2H, t, J=6.9 Hz), 3.56 (3H, s), 3.78 (3H, s), 4.03-4.09 (2H, t, J=6.6 Hz), 4.68-4.74 (2H, t, J=6.9 Hz), 6.85-7.08 (3H, m), 7.25-7.30 (1H, m), 7.52-7.67 (2H, m), 8.06 (1H, s).

Example 126

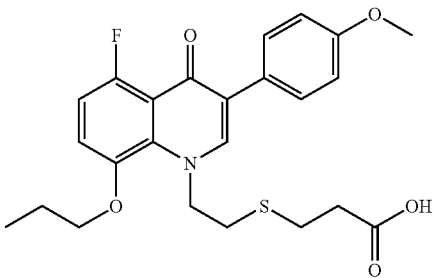

Production of 3-{2-[5-fluoro-3-(4-methoxyphenyl)-4-oxo-8-propoxy-4H-quinolin-1-yl]ethylsulfanyl}propionic acid Lithium hydroxide mono-hydrate (31 mg, 0.74 mmol) and water (5 ml) were added to an acetonitrile solution (10 ml) of methyl 3-{2-[5-fluoro-3-(4-methoxyphenyl)-4-oxo-8-propoxy-4H-quinolin-1-yl]ethylsulfanyl}propionate (175 mg, 0.37 mmol), and the mixture was stirred at room temperature for 2 hours. The reaction mixture was washed with ethyl acetate, and then 2N hydrochloric acid was added to the water layer to make the mixture acidic. The generated insoluble matter was separated, washed with water and then dried, giving a white powder of 3-{2-[5-fluoro-3-(4-methoxyphenyl)-4-oxo-8-propoxy-4H-quinolin-1-yl]ethylsulfanyl}propionic acid (140 mg, yield: 82%).
$^1$H-NMR (DMSO-$d_6$) δ ppm: 0.96-1.02 (3H, t, J=7.4 Hz), 1.70-1.90 (2H, m), 2.42-2.47 (2H, t, J=7.0 Hz), 2.64-2.70 (2H, t, J=7.0 Hz), 2.85-2.90 (2H, t, J=6.8 Hz), 3.74 (3H, s), 3.99-4.04 (2H, t, J=6.6 Hz), 4.65-4.70 (2H, t, J=6.8 Hz), 6.91-7.02 (3H, m), 7.20-7.26 (1H, m), 7.55-7.60 (2H, m), 8.01 (1H, s), 11.35-12.84 (1H, br).

Example 127

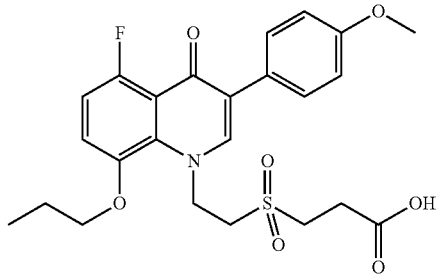

Production of 3-{2-[5-fluoro-3-(4-methoxyphenyl)-4-oxo-8-propoxy-4H-quinolin-1-yl]ethanesulfonyl}propionic acid 3-{2-[5-Fluoro-3-(4-methoxyphenyl)-4-oxo-8-propoxy-4H-quinolin-1-yl]ethylsulfanyl}propionic acid (2.26 g, 4.92 mmol) was dissolved in a mixed solvent of dichloromethane (100 ml) and methanol (20 ml), m-chloroperbenzoic acid (mCPBA, purity: 70%, 2.55 g, 10.33 mmol) was added thereto, and the mixture was then stirred at room temperature for 1 hour. The resulting reaction mixture was ice-cooled. An aqueous saturated sodium hydrogen sulfite solution (50 ml) was added to the reaction mixture, followed by extraction with dichloromethane. The thus-obtained organic layer was washed with water and then concentrated under reduced pressure. The residue was purified using silica gel column chromatography (dichloromethane:methanol=100:0→100:10). The purified product was concentrated under reduced pressure and subjected to recrystallization from ethyl acetate-n-hexane, giving a pale yellow powder of 3-{2-[5-fluoro-3-(4-methoxyphenyl)-4-oxo-8-propoxy-4H-quinolin-1-yl]ethanesulfonyl}propionic acid (2.2 g, yield: 91%).

$^1$H-NMR (DMSO-$d_6$) δ ppm: 0.97-1.03 (3H, t, J=7.4 Hz), 1.73-1.96 (2H, m), 2.64-2.70 (2H, t, J=7.7 Hz), 3.37-3.43 (2H, t, J=7.7 Hz), 3.66-3.72 (2H, t, J=6.7 Hz), 3.77 (3H, s), 4.05-4.11 (2H, t, J=6.8 Hz), 4.94-4.99 (2H, t, J=6.7 Hz), 6.93-7.06 (3H, m), 7.27-7.30 (1H, m), 7.59-7.63 (2H, m), 8.02 (1H, s).

Example 128

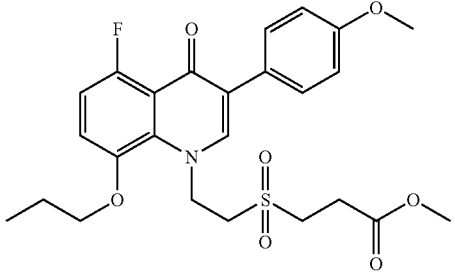

Production of methyl 3-{2-[5-fluoro-3-(4-methoxyphenyl)-4-oxo-8-propoxy-4H-quinolin-1-yl]ethanesulfonyl}propionate The above compound was prepared in the same manner as in Example 127 using appropriate starting material.

$^1$H-NMR (CDCl$_3$) δ ppm: 1.07-1.13 (3H, t, J=7.4 Hz), 1.84-2.03 (2H, m), 2.84-2.89 (2H, t, J=7.0 Hz), 3.27-3.33 (2H, t, J=7.0 Hz), 3.51-3.57 (2H, t, J=6.9 Hz), 3.70 (3H, s), 3.83 (3H, s), 4.05-4.09 (2H, t, J=6.8 Hz), 4.95-5.00 (2H, t, J=6.9 Hz), 6.86-6.94 (3H, m), 7.01-7.08 (1H, m), 7.58-7.64 (2H, m), 7.66 (1H, s).

Example 129

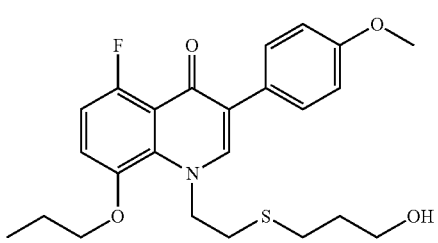

Production of 5-fluoro-1-[2-(3-hydroxypropylsulfanyl)ethyl]-3-(4-methoxyphenyl)-8-propoxy-1H-quinolin-4-one The above compound was prepared in the same manner as in Example 125 using appropriate starting material.

$^1$H-NMR (CDCl$_3$) δ ppm: 1.07-1.13 (3H, t, J=7.4 Hz), 1.60-1.75 (2H, m), 1.84-2.03 (2H, m), 2.40-2.60 (2H, m), 2.84-2.89 (2H, m), 3.60-3.75 (2H, m), 3.70 (3H, s), 4.05-4.09 (2H, t, J=6.8 Hz), 4.62-4.80 (2H, m), 6.86-6.94 (3H, m), 7.01-7.08 (1H, m), 7.58-7.64 (2H, m), 7.66 (1H, s).

Example 130

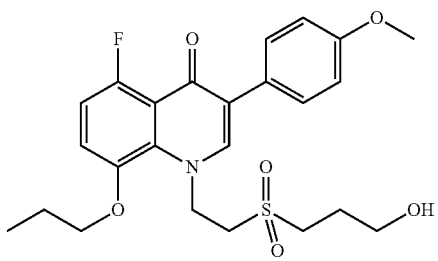

Production of 5-fluoro-1-[2-(3-hydroxypropane-1-sulfonyl)ethyl]-3-(4-methoxyphenyl)-8-propoxy-1H-quinolin-4-one The above compound was prepared in the same manner as in Example 127 using appropriate starting material.

$^1$H-NMR (DMSO-$d_6$) δ ppm: 0.97-1.03 (3H, t, J=7.4 Hz), 1.66-1.94 (4H, m), 3.38-3.53 (2H, m), 3.56-3.71 (2H, m), 3.77 (3H, s), 4.03-4.14 (4H, m), 4.67-4.70 (1H, t, J=5.1 Hz), 4.93-4.99 (2H, t, J=6.7 Hz), 6.93-7.06 (3H, m), 7.26-7.33 (1H, m), 7.59-7.62 (2H, m), 8.01 (1H, s).

Example 131

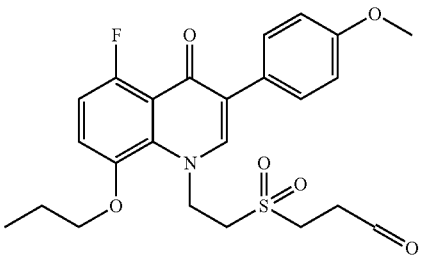

Production of 3-{2-[5-fluoro-3-(4-methoxyphenyl)-4-oxo-8-propoxy-4H-quinolin-1-yl]ethanesulfonyl}propionaldehyde O-iodoxybenzoic acid (IBX, 1.9 g, 6.78 mmol) was added to a dimethyl sulfoxide (DMSO) solution (3 ml) of 5-fluoro-1-[2-(3-hydroxypropane-1-sulfonyl)ethyl]-3-(4-methoxyphenyl)-8-propoxy-1H-quinolin-4-one (2.7 g, 5.65 mmol) and stirred overnight at room temperature. Water and ethyl acetate were added to the reaction mixture. Subsequently, insoluble matter was filtered off, and the filtrate was then separated. The thus-obtained organic layer was washed with water and concentrated under reduced pressure. The residue was purified using silica gel column chromatography (n-hexane:ethyl acetate=2:1→0:1). The purified material was concentrated to dryness under reduced pressure, giving a white powder of 3-{2-[5-fluoro-3-(4-methoxyphenyl)-4-oxo-8-propoxy-4H-quinolin-1-yl]ethanesulfonyl}propionaldehyde (1.8 g, yield: 67%).

$^1$H-NMR (DMSO-d$_6$) δ ppm: 0.97-1.03 (3H, t, J=7.4 Hz), 1.82-2.03 (2H, m), 2.80-3.01 (2H, m), 3.45-3.50 (2H, m), 3.60-3.70 (2H, m), 3.78 (3H, s), 4.03-4.09 (2H, t, J=6.8 Hz), 4.90-5.10 (2H, m), 6.93-7.06 (3H, m), 7.26-7.33 (1H, m), 7.59-7.62 (2H, m), 8.01 (1H, s), 9.67 (1H, s).

Example 132

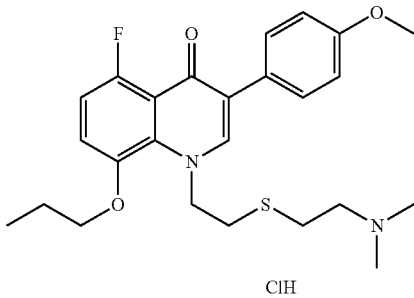

Production of 1-[2-(2-dimethylaminoethylsulfanyl)ethyl]-5-fluoro-3-(4-methoxyphenyl)-8-propoxy-1H-quinolin-4-one hydrochloride The above compound was prepared in the same manner as in Example 125 using appropriate starting material.

Melting point: 93-95° C.

$^1$H-NMR (DMSO-d$_6$) δ ppm: 0.99-1.05 (3H, t, J=7.4 Hz), 1.69-1.94 (2H, m), 2.69 (3H, s), 2.71 (3H, s), 2.85-3.04 (4H, m), 3.11-3.28 (2H, m), 3.76 (3H, s), 4.03-4.08 (2H, t, J=6.8 Hz), 4.64-4.87 (2H, m), 6.73-7.09 (3H, m), 7.12-7.34 (1H, m), 7.63-7.67 (2H, d, J=8.8 Hz), 8.14 (1H, s), 10.62-11.04 (1H, br).

Example 133

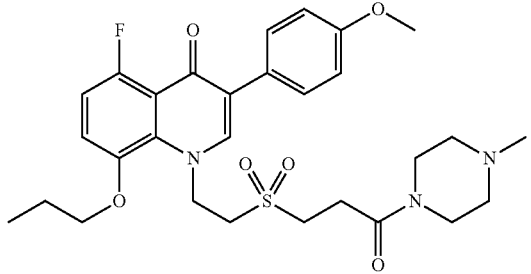

Production of 5-fluoro-3-(4-methoxyphenyl)-1-{2-[3-(4-methyl piperazin-1-yl)-3-oxo-propane-1-sulfonyl]ethyl}-8-propoxy-1H-quinolin-4-one The above compound was prepared in the same manner as in Example 33 using appropriate starting materials.

Melting point: 85-88° C.

$^1$H-NMR (DMSO-d$_6$) δ ppm: 0.97-1.03 (3H, t, J=7.4 Hz), 1.78-1.96 (2H, m), 2.25 (3H, s), 2.29-2.45 (4H, m), 2.75-2.80 (2H, t, J=7.4 Hz), 3.30-3.50 (6H, m), 3.65-3.70 (2H, t, J=6.7 Hz), 4.05-4.11 (2H, t, J=6.7 Hz), 4.95-5.00 (2H, t, J=6.7 Hz), 6.91-7.06 (3H, m), 7.27-7.32 (1H, m), 7.60-7.64 (2H, d, J=8.8 Hz), 8.03 (1H, s).

Example 134

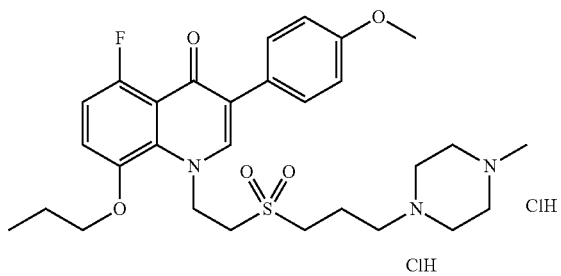

Production of 5-fluoro-3-(4-methoxyphenyl)-1-{2-[3-(4-methylpiperazin-1-yl)propane-1-sulfonyl]ethyl}-8-propoxy-1H-quinolin-4-one dihydrochloride N-methylpiperazine (0.455 mg, 4.54 mmol) was added to a methanol solution (20 ml) of 3-{2-[5-fluoro-3-(4-methoxyphenyl)-4-oxo-8-propoxy-4H-quinolin-1-yl]ethanesulfonyl}propionaldehyde (1.8 g, 3.79 mmol) while ice-cooling, and then the resulting mixture was stirred at room temperature for 1 hour. Sodium cyanoborohydride (0.238 g, 3.79 mmol) and acetic acid (2 ml) were added to the resulting mixture and stirred at room temperature for 3 hours. Water was added to the reaction mixture, then the mixture was subjected to extraction using ethyl acetate. The extract was washed with an aqueous saturated sodium bicarbonate solution and concentrated under reduced pressure. The residue was purified using silica gel column chromatography (dichloromethane:methanol=100:0→10:1). The purified product was concentrated under reduced pressure, and a 4N hydrogen chloride ethylacetate solution was added to an ethyl acetate solution of the residue. The thus-generated insoluble matter was separated, giving a yellow powder of 5-fluoro-3-(4-methoxyphenyl)-1-{2-[3-(4-methylpiperazin-1-yl)propane-1-sulfonyl]ethyl}-8-propoxy-1H-quinolin-4-one dihydrochloride (360 mg, yield: 15%).

Melting point: 72-74° C.

$^1$H-NMR (DMSO-d$_6$) δ ppm: 0.98-1.04 (3H, t, J=7.4 Hz), 1.78-1.96 (2H, m), 2.12-2.34 (2H, m), 2.80 (3H, s), 3.00-3.75 (14H, m), 3.77 (3H, s), 4.06-4.12 (2H, t, J=6.7 Hz), 4.98-5.03 (2H, t, J=6.4 Hz), 6.94-7.07 (3H, m), 7.28-7.33 (1H, m), 7.61-7.64 (2H, d, J=8.8 Hz), 8.05 (1H, s).

Example 135

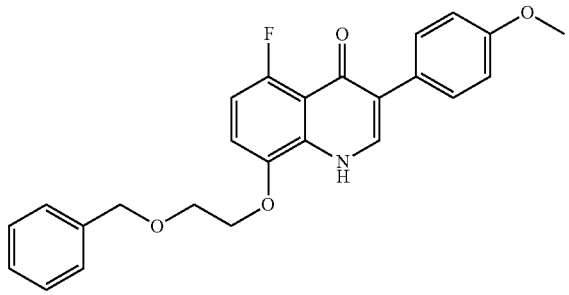

Production of 8-(2-benzyloxyethoxy)-5-fluoro-3-(4-methoxyphenyl)-1H-quinolin-4-one The above compound was prepared in the same manner as in Example 1 using appropriate starting material.
$^1$H-NMR (DMSO-d$_6$) δ ppm: 3.77 (3H, s), 3.87-3.90 (2H, t, J=4.3 Hz), 4.35-4.38 (2H, t, J=4.3 Hz), 4.58 (2H, s), 6.80-7.00 (3H, m), 7.10-7.32 (6H, m), 7.54-7.57 (2H, m), 7.79-7.82 (1H, d, J=6.2 Hz), 11.49 (1H, d, J=5.2 Hz).

Example 136

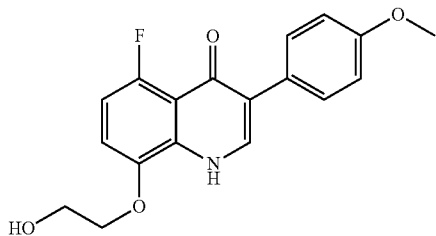

Production of 5-fluoro-8-(2-hydroxyethoxy)-3-(4-methoxyphenyl)-1H-quinolin-4-one 20% palladium hydroxide/carbon (5.0 g) was added to an ethanol solution (50 ml) of 8-(2-benzyloxyethoxy)-5-fluoro-3-(4-methoxyphenyl)-1H-quinolin-4-one (6.3 g, 15.0 mmol), followed by hydrogen substitution. The mixture was stirred at room temperature for 4 hours. After completion of the reaction, the catalyst was removed and the mixture was concentrated under reduced pressure. The residue was purified using silica gel column chromatography (dichloromethane:methanol=100:0→20:1). The purified material was concentrated to dryness under reduced pressure, giving a pale yellow powder of 5-fluoro-8-(2-hydroxyethoxy)-3-(4-methoxyphenyl)-1H-quinolin-4-one (5.2 g, yield: 99%).
$^1$H-NMR (DMSO-d$_6$) δ ppm: 3.77 (3H, s), 3.79-3.83 (2H, t, J=4.7 Hz), 4.12-4.16 (2H, t, J=4.7 Hz), 6.84-6.96 (3H, m), 7.12-7.17 (1H, m), 7.53-7.57 (2H, d, J=8.8 Hz), 7.85 (1H, s).

Example 137

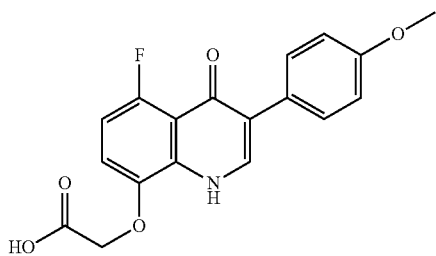

Production of [5-fluoro-3-(4-methoxyphenyl)-4-oxo-1,4-dihydro-quinolin-8-yloxy]acetic acid The above compound was prepared in the same manner as in Example 120 using appropriate starting material.
$^1$H-NMR (DMSO-d$_6$) δ ppm: 3.80 (3H, s), 4.92 (2H, s), 6.85-6.92 (3H, m), 7.11-7.16 (1H, m), 7.53-7.57 (2H, d, J=8.8 Hz), 7.80-7.82 (1H, d, J=6.2 Hz), 11.46-11.49 (1H, d, J=6.0 Hz), 13.10-13.30 (1H, br).

Example 138

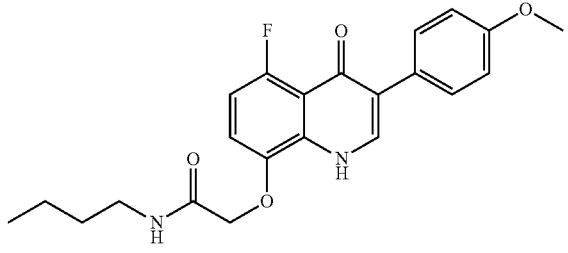

Production of N-butyl-2-[5-fluoro-3-(4-methoxyphenyl)-4-oxo-1,4-dihydroquinolin-8-yloxy]acetamide The above compound was prepared in the same manner as in Example 33 using appropriate starting materials.
Pale Brown Powder
$^1$H-NMR (DMSO-d$_6$) δ ppm: 0.84-0.90 (7.2 Hz), 1.10-1.60 (4H, m), 3.15-3.23 (2H, q, J=6.5 Hz), 3.76 (3H, s), 4.66 (2H, s), 6.87-6.96 (3H, m), 7.11-7.16 (1H, m), 7.55-7.59 (2H, d, J=8.5 Hz), 8.31-8.35 (1H, t, 5.8 Hz), 11.68 (1H, brs).

Example 139

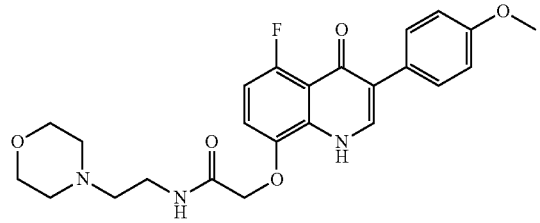

Production of 2-[5-fluoro-3-(4-methoxyphenyl)-4-oxo-1,4-dihydro-quinolin-8-yloxy]-N-(2-morpholin-4-ylethyl)acetamide The above compound was prepared in the same manner as in Example 33 using appropriate starting material.
Melting point: 180-182° C.
$^1$H-NMR (DMSO-d$_6$) δ ppm: 2.40-2.50 (2H, m), 3.10-3.14 (2H, m), 4.45 (2H, s), 3.28-3.54 (4H, m), 3.75 (3H, s), 3.80-4.21 (4H, m), 6.84-6.95 (3H, m), 7.10-7.15 (1H, m), 7.51-7.54 (2H, d, J=8.8 Hz), 8.20-8.50 (1H, m).

Example 140

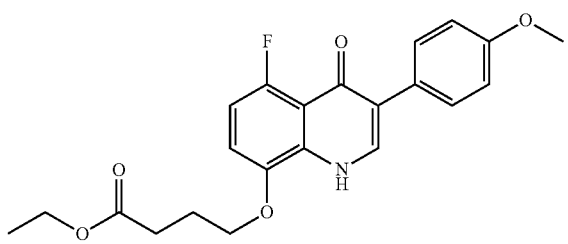

Production of ethyl 4-[5-fluoro-3-(4-methoxyphenyl)-4-oxo-1,4-dihydroquinolin-8-yloxy]butyrate The above compound was prepared in the same manner as in Example 1 using appropriate starting material.

$^1$H-NMR (CDCl$_3$) δ ppm: 1.22-1.27 (3H, t, J=7.1 Hz), 2.16-2.26 (2H, m), 2.54-2.59 (2H, t, J=6.6 Hz), 3.81 (3H, s), 4.10-4.20 (4H, m), 6.75-6.94 (4H, m), 7.55-7.72 (2H, m), 7.72-7.75 (1H, d, J=6.1 Hz), 9.49-9.51 (1H, d, J=5.2 Hz).

Example 141

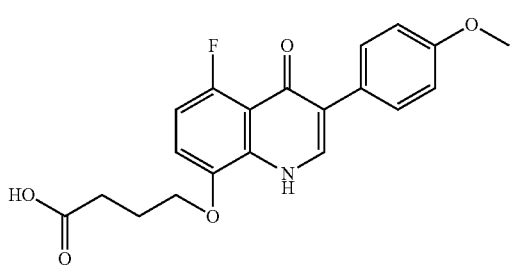

Production of 4-[5-fluoro-3-(4-methoxyphenyl)-4-oxo-1,4-dihydro-quinolin-8-yloxy]butyric acid The above compound was prepared in the same manner as in Example 32 using appropriate starting material.

$^1$H-NMR (DMSO-d$_6$) δ ppm: 1.89-2.01 (2H, m), 2.42-2.45 (2H, m), 3.69 (3H, s), 4.05-4.10 (2H, t, J=6.1 Hz), 6.76-6.89 (3H, m), 7.02-7.07 (1H, m), 7.45-7.49 (2H, d, J=8.5 Hz), 7.71-7.73 (1H, d, J=5.4 Hz), 11.21-11.23 (1H, d, J=4.9 Hz), 11.6-12.5 (1H, br).

Example 142

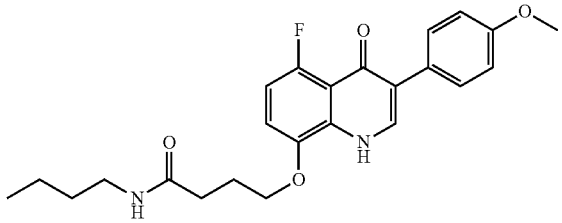

Production of N-butyl-4-[5-fluoro-3-(4-methoxyphenyl)-4-oxo-1,4-dihydroquinolin-8-yloxy]butylamide The above compound was prepared in the same manner as in Example 33 using appropriate starting materials.
White Amorphous $^1$H-NMR (DMSO-d$_6$) δ ppm: 0.79-0.86 (3H, t, J=7.1 Hz), 1.15-1.40 (4H, m), 2.00-2.10 (2H, m), 2.29-2.35 (2H, t, J=7.3 Hz), 2.99-3.10 (2H, m), 3.76 (3H, s), 4.10-4.15 (2H, t, J=6.2 Hz), 6.84-6.95 (3H, m), 7.10-7.16 (1H, m), 7.52-7.56 (2H, t, J=8.6 Hz), 7.70-7.85 (2H, m), 11.27 (1H, brs).

Example 143

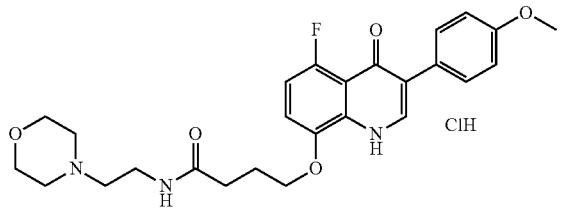

Production of 4-[5-fluoro-3-(4-methoxyphenyl)-4-oxo-1,4-dihydro-quinolin-8-yloxy]-N-(2-morpholin-4-ylethyl)butylamide hydrochloride The above compound was prepared in the same manner as in Example 33 using appropriate starting material.
Melting point: 180-182° C.

$^1$H-NMR (DMSO-d$_6$) δ ppm: 2.02-2.07 (2H, m), 2.40-2.43 (2H, m), 2.94-3.26 (6H, m), 3.28-3.54 (4H, m), 3.75 (3H, s), 3.80-4.21 (4H, m), 6.84-6.95 (3H, m), 7.10-7.15 (1H, m), 7.51-7.54 (2H, d, J=8.8 Hz), 8.20-8.50 (1H, m), 10.60-11.10 (1H, br).

Example 144

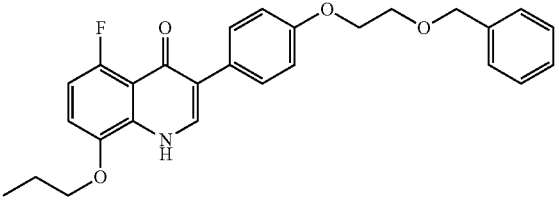

Production of 3-[4-(2-benzyloxyethoxy)phenyl]-5-fluoro-8-propoxy-1H-quinolin-4-one The above compound was prepared in the same manner as in Example 1 using appropriate starting materials.

$^1$H-NMR (CDCl$_3$) δ ppm: 1.03-1.09 (3H, t, J=7.4 Hz), 1.80-1.91 (2H, m), 3.81-3.85 (2H, m), 4.03-4.08 (2H, t, J=6.6 Hz), 4.63 (2H, s), 6.79-6.93 (4H, m), 7.30-7.37 (5H, m), 7.53-7.57 (2H, m), 7.69-7.72 (1H, d, J=6.1 Hz), 9.05-9.08 (1H, d, J=5.7 Hz).

Example 145

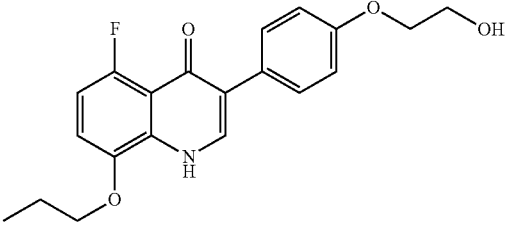

Production of 5-fluoro-3-[4-(2-hydroxyethoxy)phenyl]-8-propoxy-1H-quinolin-4-one The above compound was prepared in the same manner as in Example 136 using appropriate starting material.
$^1$H-NMR (DMSO-$d_6$) δ ppm: 1.06-1.09 (3H, t, J=7.4 Hz), 1.81-1.90 (2H, m), 3.70-3.75 (2H, m), 3.99-4.03 (2H, m), 4.09-4.14 (2H, t, J=6.4 Hz), 4.80-4.93 (1H, m), 6.86-6.97 (3H, m), 7.13-7.18 (1H, m), 7.53-7.57 (2H, d, J=8.7 Hz), 7.79-7.87 (1H, m), 11.0-11.5 (1H, m).

Example 146

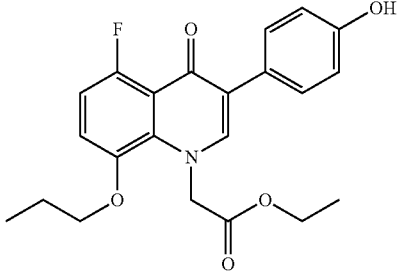

Production of ethyl[5-fluoro-3-(4-hydroxyphenyl)-4-oxo-8-propoxy-4H-quinolin-1-yl]acetate Ethyl[5-fluoro-3-(4-methoxyphenyl)-4-oxo-8-propoxy-4H-quinolin-1-yl]acetate (4.0 g, 9.6 mmol) was dissolved in dichloromethane (20 ml). A 1M-boron tribromide dichloromethane solution (35 ml, 35 mmol) was added dropwise to the dissolution at −10° C. After stirring at the same temperature for 2 hours, water was added to the reaction mixture, followed by extraction with dichloromethane. The thus-obtained organic layer was concentrated under reduced pressure. The residue was purified using silica gel column chromatography (dichloromethane:methanol=50:1→15:1). The purified product was concentrated to dryness under reduced pressure, giving a yellow powder of ethyl[5-fluoro-3-(4-hydroxyphenyl)-4-oxo-8-propoxy-4H-quinolin-1-yl]acetate (2.7 g, yield: 57%).
$^1$H-NMR (DMSO-$d_6$) δ ppm: 0.97 (3H, t, J=7.3 Hz), 1.19 (3H, t, J=7.1 Hz), 1.69-1.77 (2H, m), 3.95 (2H, t, J=6.6 Hz), 4.14 (2H, q, J=7.1 Hz), 5.29 (2H, s), 6.76 (2H, d, J=8.7 Hz), 6.97 (1H, dd, J=9.0 Hz, 11.7 Hz), 7.21 (1H, dd, J=4.5 Hz, 9.0 Hz), 7.45 (2H, d, J=8.7 Hz), 7.95 (1H, s), 9.41 (1H, s).

Example 147

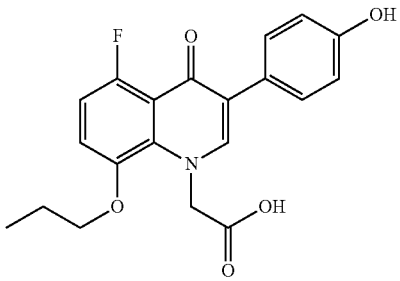

Production of [5-fluoro-3-(4-hydroxyphenyl)-4-oxo-8-propoxy-4H-quinolin-1-yl]acetic acid The above compound was prepared in the same manner as in Example 32 using appropriate starting material.
$^1$H-NMR (DMSO-$d_6$) δ ppm: 0.98 (3H, t, J=7.4 Hz), 1.73-1.82 (2H, m), 3.95 (2H, t, J=6.6 Hz), 5.21 (2H, s), 6.76 (2H, d, J=8.7 Hz), 6.96 (1H, dd, J=9.0 Hz, 11.6 Hz), 7.20 (1H, dd, J=4.5 Hz, 9.0 Hz), 7.45 (2H, d, J=8.7 Hz), 7.95 (1H, s), 9.40 (1H, s), 12.50 (1H, brs).

Example 148

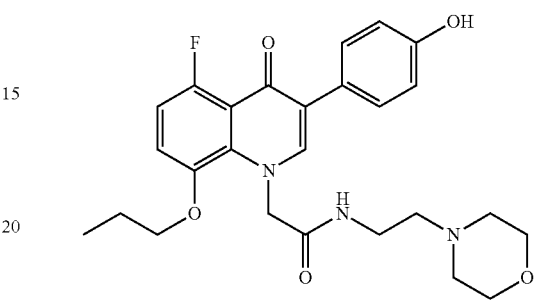

Production of 2-[5-fluoro-3-(4-hydroxyphenyl)-4-oxo-8-propoxy-4H-quinolin-1-yl]-N-(2-morpholin-4-ylethyl)acetamide 4-(2-Aminoethyl)morpholine (184 mg, 1.41 mmol), 1-(3-dimethylaminopropyl)-3-ethylcarbodiimide hydrochloride (WSC, 295 mg, 1.54 mmol) and 1-hydroxybenzotriazole (HOBT, 215 mg, 1.41 mmol) were added to a DMF solution (7 ml) of [5-fluoro-3-(4-hydroxyphenyl)-4-oxo-8-propoxy-4H-quinolin-1-yl]acetic acid (500 mg, 1.34 mmol) and then the mixture was stirred at room temperature for 23 hours. Water and triethylamine were added to the reaction mixture to make the reaction mixture basic, followed by extraction using ethyl acetate. The thus-obtained organic layer was washed with an aqueous saturated sodium chloride solution, and then concentrated under reduced pressure. The residue was purified using silica gel column chromatography (dichloromethane:methanol=30:1→10:1). The purified product was concentrated under reduced pressure, and the residue was recrystallized from ethyl acetate, giving a white powder of 2-[5-fluoro-3-(4-hydroxyphenyl)-4-oxo-8-propoxy-4H-quinolin-1-yl]-N-(2-morpholin-4-ylethyl)acetamide (157 mg, yield: 24%).
$^1$H-NMR (DMSO-$d_6$) δ ppm: 0.94 (3H, t, J=7.3 Hz), 1.70-1.78 (2H, m), 2.29-2.33 (6H, m), 3.17 (2H, q, J=6.3 Hz), 3.44-3.52 (4H, m), 3.92 (2H, t, J=6.8 Hz), 5.12 (2H, s), 6.75 (2H, d, J=8.7 Hz), 6.94 (1H, dd, J=8.9 Hz, 11.6 Hz), 7.16 (1H, dd, J=4.5 Hz, 9.0 Hz), 7.44 (2H, d, J=8.6 Hz), 7.83 (1H, s), 7.91 (1H, t, J=5.4 Hz), 9.50 (1H, s).

Example 149

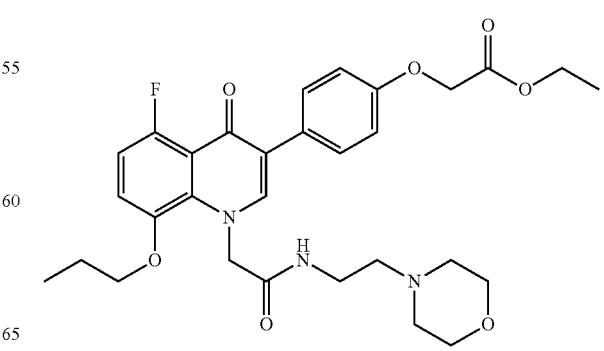

Production of ethyl(4-{5-fluoro-1-[(2-morpholin-4-ylethylcarbamoyl)methyl]-4-oxo-8-propoxy-1,4-dihydroquinolin-3-yl}phenoxy)acetate Potassium carbonate (129 mg, 0.93 mmol) and ethyl bromoacetate (114 mg, 0.68 mmol) were added to a DMF solution (4 ml) of 2-[5-fluoro-3-(4-hydroxyphenyl)-4-oxo-8-propoxy-4H-quinolin-1-yl]-N-(2-morpholin-4-ylethyl)acetamide (300 mg, 0.62 mmol), followed by stirring at room temperature for 87 hours. Water and ethyl acetate were added to the reaction mixture and the reaction mixture was then subjected to separation. The thus-obtained organic layer was washed with an aqueous saturated sodium chloride solution, and then concentrated under reduced pressure. The residue was purified using silica gel column chromatography (dichloromethane:methanol=50:1→20:1). The purified product was concentrated under reduced pressure, giving a pale yellow oily substance of ethyl [(4-{5-fluoro-1-[(2-morpholin-4-yl-ethylcarbamoyl)methyl]-4-oxo-8-propoxy-1,4-dihydroquinolin-3-yl}phenoxy)acetate (306 mg, yield: 87%).

$^1$H-NMR (CDCl$_3$) δ ppm: 1.02 (3H, t, J=7.3 Hz), 1.30 (3H, t, J=7.1 Hz), 1.79-1.88 (2H, m), 2.30-2.43 (6H, m), 3.35 (2H, q, J=6.0 Hz), 3.48-3.52 (4H, m), 3.91 (2H, t, J=6.9 Hz), 4.26 (2H, q, J=7.1 Hz), 4.59 (2H, s), 5.00 (2H, s), 6.76-6.96 (5H, m), 7.37 (1H, s), 7.51 (2H, d, J=8.8 Hz).

Example 150

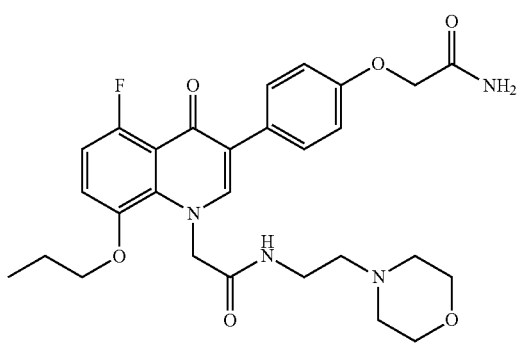

Production of 2-(4-{5-fluoro-1-[(2-morpholin-4-yl-ethylcarbamoyl)methyl]-4-oxo-8-propoxy-1,4-dihydroquinolin-3-yl}phenoxy)acetamide Ethyl (4-{5-fluoro-1-[(2-morpholin-4-yl-ethylcarbamoyl)methyl]-4-oxo-8-propoxy-1,4-dihydroquinolin-3-yl}phenoxy)acetate (300 mg) was added to a 7N ammonia-methanol solution (15 ml) and then stirred at 70° C. for 43 hours. The mixture was cooled to room temperature and concentrated under reduced pressure. The residue was purified using silica gel column chromatography (dichloromethane:methanol=50:1→9:1→ethyl acetate:methanol=10:1). The purified product was concentrated under reduced pressure, and the residue was recrystallized from ethyl acetate-n-hexane, giving a pale yellow powder of 2-(4-{5-fluoro-1-[(2-morpholin-4-yl-ethylcarbamoyl)methyl]-4-oxo-8-propoxy-1,4-dihydroquinolin-3-yl}phenoxy)acetamide (100 mg, yield: 35%).

$^1$H-NMR (DMSO-d$_6$) δ ppm: 0.95 (3H, t, J=7.3 Hz), 1.72-1.81 (2H, m), 2.32-2.34 (6H, m), 3.18 (2H, q, J=6.5 Hz), 3.50-3.54 (4H, m), 3.94 (2H, t, J=6.8 Hz), 4.43 (2H, s), 5.14 (2H, s), 6.92-7.00 (3H, m), 7.19 (1H, dd, J=4.5 Hz, 9.0 Hz), 7.39 (1H, s), 7.53 (1H, s), 7.59 (2H, d, J=8.8 Hz), 7.91-7.93 (2H, brs).

Example 151

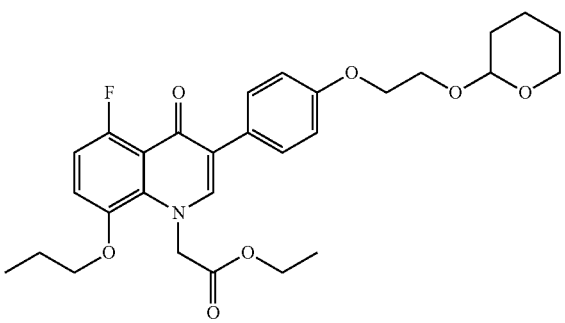

Production of ethyl(5-fluoro-4-oxo-8-propoxy-3-{4-[2-(tetrahydropyran-2-yloxy)ethoxy]phenyl}-4H-quinolin-1-yl)acetate The above compound was prepared in the same manner as in Example 149 using appropriate starting material.

$^1$H-NMR (CDCl$_3$) δ ppm: 1.05 (3H, t, J=7.3 Hz), 1.27 (3H, t, J=7.1 Hz), 1.53-1.74 (6H, m), 1.80-1.88 (2H, m), 3.50-3.60 (1H, m), 3.83-3.91 (2H, m), 3.95 (2H, t, J=6.8 Hz), 4.03-4.08 (1H, m), 4.16-4.28 (4H, m), 4.72 (1H, brs), 5.10 (2H, s), 6.84-7.00 (4H, m), 7.35 (1H, s), 7.58 (2H, d, J=8.8 Hz).

Example 152

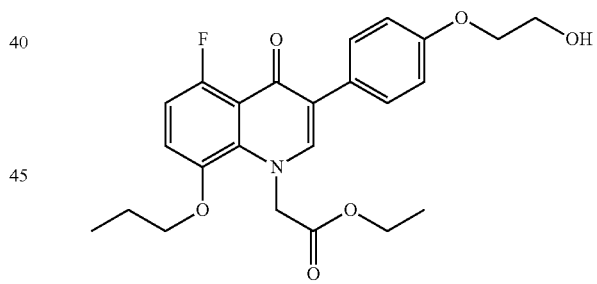

Production of ethyl{5-fluoro-3-[4-(2-hydroxyethoxy)phenyl]-4-oxo-8-propoxy-4H-quinolin-1-yl}acetate 2N hydrochloric acid (6.3 ml) was added to an ethanol solution (20 ml) of ethyl (5-fluoro-4-oxo-8-propoxy-3-{4-[2-(tetrahydropyran-2-yloxy)ethoxy]phenyl}-4H-quinolin-1-yl)acetate (840 mg, 1.59 mmol) and stirred at 50° C. for 2 hours. The resulting mixture was cooled to room temperature and then concentrated under reduced pressure. Ethyl acetate and water were added to the residue, followed by separation. The thus-obtained organic layer was washed with an aqueous saturated sodium chloride solution, and then concentrated under reduced pressure. The residue was purified using silica gel column chromatography (dichloromethane:methanol=30:1→15:1). The purified product was concentrated under reduced pressure, giving a pale yellow oily substance of ethyl{5-fluoro-3-[4-(2-hydroxyethoxy)phenyl]-4-oxo-8-propoxy-4H-quinolin-1-yl}acetate (627 mg, yield: 89%).

$^1$H-NMR (CDCl$_3$) δ ppm: 1.05 (3H, t, J=7.3 Hz), 1.27 (3H, t, J=7.1 Hz), 1.79-1.88 (3H, m), 3.92-3.98 (4H, m), 4.08-4.12 (2H, m), 4.24 (2H, q, J=7.1 Hz), 5.10 (2H, s), 6.84-7.00 (4H, m), 7.35 (1H, s), 7.58 (2H, d, J=8.8 Hz).

Example 153

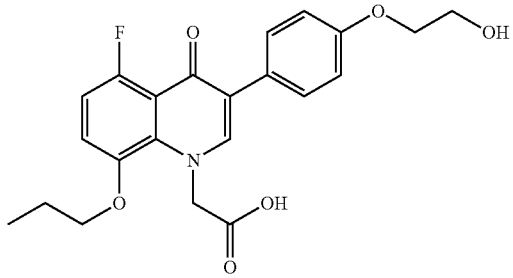

Production of {5-fluoro-3-[4-(2-hydroxyethoxy)phenyl]-4-oxo-8-propoxy-4H-quinolin-1-yl}acetic acid The above compound was prepared in the same manner as in Example 32 using appropriate starting material.

$^1$H-NMR (DMSO-d$_6$) δ ppm: 0.98 (3H, t, J=7.3 Hz), 1.71-1.85 (2H, m), 3.72 (2H, m), 3.93-4.02 (4H, m), 4.87 (1H, brs), 5.22 (2H, s), 6.93-7.02 (3H, m), 7.22 (1H, dd, J=4.5 Hz, 9.0 Hz), 7.57 (2H, d, J=8.8 Hz), 8.00 (1H, s), 12.50 (1H, brs).

Example 154

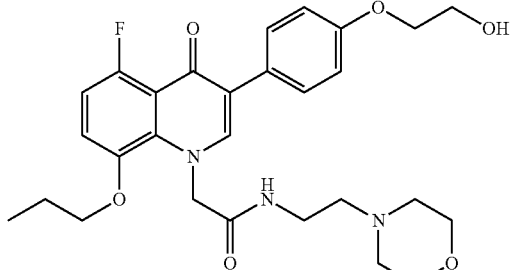

Production of 2-{5-fluoro-3-[4-(2-hydroxyethoxy)phenyl]-4-oxo-8-propoxy-4H-quinolin-1-yl}-N-(2-morpholin-4-ylethyl)acetamide The above compound was prepared in the same manner as in Example 148 using appropriate starting material.

$^1$H-NMR (DMSO-d$_6$) δ ppm: 0.95 (3H, t, J=7.3 Hz), 1.72-1.79 (2H, m), 2.30-2.40 (6H, m), 3.18 (2H, q, J=5.9 Hz), 3.50-3.53 (4H, m), 3.69-3.74 (2H, m), 3.91-4.00 (4H, m), 4.91 (1H, t, J=5.4 Hz), 5.14 (2H, s), 6.92-6.98 (3H, m), 7.18 (1H, dd, J=4.4 Hz, 9.0 Hz), 7.57 (2H, d, J=8.6 Hz), 7.90-7.93 (2H, brs).

Example 155

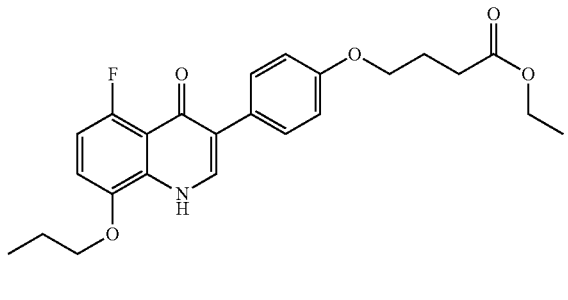

Production of ethyl 4-[4-(5-fluoro-4-oxo-8-propoxy-1,4-dihydro-quinolin-3-yl)phenoxy]butyrate The above compound was prepared in the same manner as in Example 1 using appropriate starting materials.

$^1$H-NMR (CDCl$_3$) δ ppm: 1.07-1.13 (3H, t, J=7.4 Hz), 1.25-1.31 (3H, t, J=7.1 Hz), 1.87-1.98 (2H, m), 2.10-2.17 (2H, m), 2.51-2.57 (2H, t, J=7.3 Hz), 4.00-4.21 (6H, m), 6.83-6.93 (4H, m), 7.55-7.59 (2H, d, J=8.4 Hz), 7.72-7.75 (1H, d, J=6.1 Hz), 8.93 (1H, brs).

Example 156

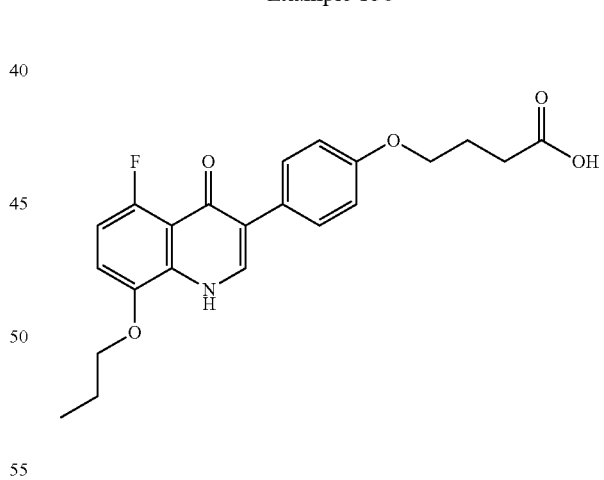

Production of 4-[4-(5-fluoro-4-oxo-8-propoxy-1,4-dihydro-quinolin-3-yl)phenoxy]butyric acid The above compound was prepared in the same manner as in Example 32 using appropriate starting material.

$^1$H-NMR (DMSO-d$_6$) δ ppm: 0.93-1.00 (3H, t, J=7.4 Hz), 1.69-1.91 (4H, m), 2.28-2.34 (2H, t, J=7.3 Hz), 3.89-3.94 (2H, t, J=6.4 Hz), 4.00-4.05 (2H, t, J=6.4 Hz), 6.67-6.87 (3H, m), 7.03-7.08 (1H, m), 7.43-7.47 (2H, d, J=8.7 Hz), 7.71-7.73 (1H, d, J=6.3 Hz), 11.18-11.20 (1H, d, J=6.0 Hz), 11.5-12.2 (1H, br).

Example 157

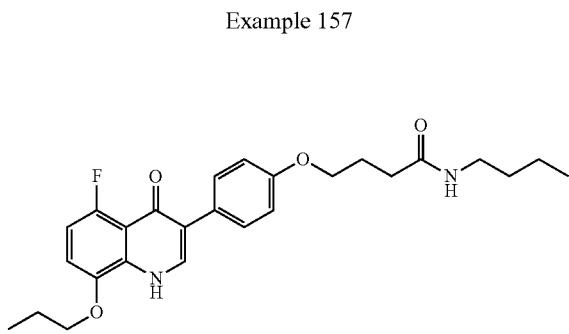

Production of N-butyl-4-[4-(5-fluoro-4-oxo-8-propoxy-1,4-dihydroquinolin-3-yl)phenoxy]butylamide The above compound was prepared in the same manner as in Example 33 using appropriate starting materials.
White Amorphous
$^1$H-NMR (DMSO-$d_6$) δ ppm: 0.81-0.87 (3H, t, J=7.3 Hz), 1.01-1.08 (3H, t, J=7.4 Hz), 1.20-1.40 (4H, m), 1.80-1.95 (4H, m), 2.19-2.25 (2H, t, J=7.4 Hz), 3.00-3.40 (2H, m), 3.93-3.99 (2H, t, J=6.3 Hz), 4.07-4.13 (2H, t, J=6.4 Hz), 6.84-6.93 (3H, m), 7.11-7.16 (1H, m), 7.51-7.54 (2H, d, J=8.5 Hz), 7.82 (2H, m), 11.24 (1H, brs).

Example 158

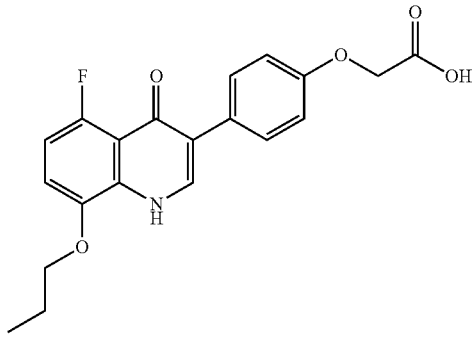

Production of [4-(5-fluoro-4-oxo-8-propoxy-1,4-dihydroquinolin-3-yl)phenoxy]acetic acid The above compound was prepared in the same manner as in Example 2 using appropriate starting materials.
$^1$H-NMR (DMSO-$d_6$) δ ppm: 1.03-1.09 (3H, t, J=7.4 Hz), 1.78-1.92 (2H, m), 4.09-4.14 (2H, t, J=6.4 Hz), 4.70 (2H, s), 6.86-6.97 (3H, m), 7.13-7.18 (1H, m), 7.51-7.56 (2H, m), 7.80-7.83 (1H, d, J=6.3 Hz), 11.27-11.29 (1H, d, J=6.0 Hz), 12.99 (1H, brs).

Example 159

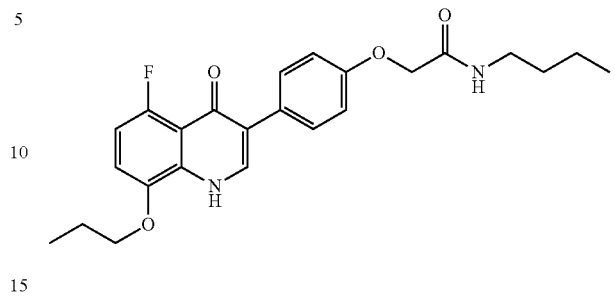

Production of N-butyl-2-[4-(5-fluoro-4-oxo-8-propoxy-1,4-dihydroquinolin-3-yl)phenoxy]acetamide The above compound was prepared in the same manner as in Example 33 using appropriate starting materials.
White Powder
$^1$H-NMR (DMSO-$d_6$) δ ppm: 0.83-0.88 (3H, t, J=7.2 Hz), 1.02-1.08 (3H, t, J=7.4 Hz), 1.23-1.50 (4H, m), 1.80-1.88 (2H, m), 3.08-3.16 (2H, m), 4.08-4.13 (2H, t, J=6.4 Hz), 4.47 (2H, s), 6.85-6.97 (3H, m), 7.12-7.17 (1H, m), 7.53-7.56 (2H, d, J=8.8 Hz), 7.80 (1H, s), 8.03-8.08 (1H, t, J=5.5 Hz), 11.24 (1H, brs).

Example 160

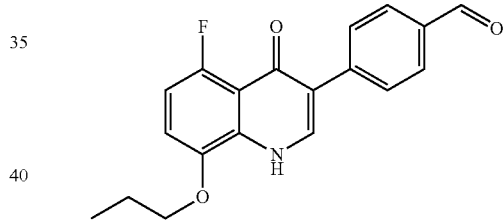

Production of 4-(5-fluoro-4-oxo-8-propoxy-1,4-dihydroquinolin-3-yl)benzaldehyde

The above compound was prepared in the same manner as in Example 2 using appropriate starting materials.
$^1$H-NMR (CDCl$_3$) δ ppm: 1.11 (3H, t, J=7.3 Hz), 1.86-2.00 (2H, m), 4.12 (2H, t, J=6.6 Hz), 6.85-6.98 (2H, m), 7.84-7.93 (5H, m), 8.90 (1H, brs), 10.02 (1H, s).

Example 161

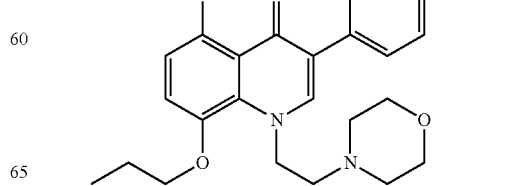

Production of 5-fluoro-3-[4-(4-morpholin-4-ylpiperidine-1-carbonyl)phenyl]-8-propoxy-1H-quinolin-4-one The above compound was prepared in the same manner as in Example 106 using appropriate starting material.

$^1$H-NMR (DMSO-$d_6$) δ ppm: 1.01 (3H, t, J=7.3 Hz), 1.74-1.86 (2H, m), 2.32-2.35 (4H, m), 2.59 (2H, t, J=5.4 Hz), 3.51-3.54 (4H, m), 4.04 (2H, t, J=6.5 Hz), 4.50 (2H, d, J=4.5 Hz), 4.66 (2H, d, J=5.4 Hz), 5.22 (1H, brs), 6.99 (1H, dd, J=8.9 Hz, 11.6 Hz), 7.22-7.33 (3H, m), 7.61 (2H, d, J=8.2 Hz), 7.97 (1H, s).

Example 162

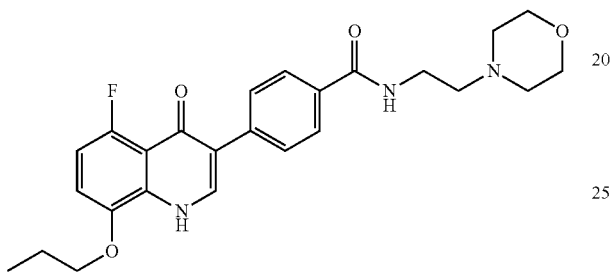

Production of 4-(5-fluoro-4-oxo-8-propoxy-1,4-dihydroquinolin-3-yl)-N-(2-morpholin-4-ylethyl)benzamide The above compound was prepared in the same manner as in Example 73 using appropriate starting material.

$^1$H-NMR (DMSO-$d_6$) δ ppm: 1.02 (3H, t, J=7.3 Hz), 1.75-1.89 (2H, m), 2.38-2.50 (6H, m), 3.38 (2H, q, J=6.3 Hz), 3.53-3.61 (4H, m), 4.08 (2H, t, J=6.4 Hz), 6.92 (1H, dd, J=8.7 Hz, 12.0 Hz), 7.15 (1H, dd, J=3.9 Hz, 8.8 Hz), 7.71 (2H, d, J=8.5 Hz), 7.89 (2H, d, J=8.5 Hz), 7.94 (1H, s), 8.41 (1H, t, J=5.5 Hz), 11.46 (1H, brs).

Example 163

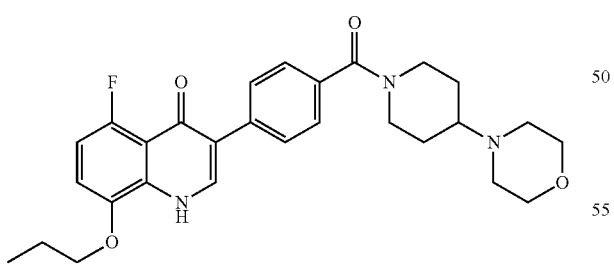

Production of 5-fluoro-3-[4-(4-morpholin-4-yl-piperidine-1-carbonyl)phenyl]-8-propoxy-1H-quinolin-4-one The above compound was prepared in the same manner as in Example 73 using appropriate starting materials.

$^1$H-NMR (DMSO-$d_6$) δ ppm: 1.02 (3H, t, J=7.3 Hz), 1.30-1.38 (2H, m), 1.75-1.89 (4H, m), 2.34-2.49 (4H, m), 2.79-3.02 (2H, m), 3.61-3.69 (6H, m), 4.08 (2H, t, J=6.4 Hz), 4.42 (1H, brs), 6.92 (1H, dd, J=8.8 Hz, 12.0 Hz), 7.15 (1H, dd, J=3.9 Hz, 8.8 Hz), 7.37 (2H, d, J=8.2 Hz), 7.67 (2H, d, J=8.2 Hz), 7.92 (1H, s), 11.45 (1H, brs).

Example 164

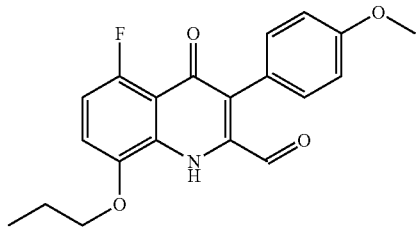

Production of 5-fluoro-3-(4-methoxyphenyl)-4-oxo-8-propoxy-1,4-dihydroquinoline-2-carbaldehyde The above compound was prepared in the same manner as in Example 2 using appropriate starting materials.

$^1$H-NMR (CDCl$_3$) δ ppm: 1.10-1.16 (3H, t, J=7.4 Hz), 1.86-2.00 (2H, m), 3.86 (3H, s), 4.02-4.07 (2H, t, J=6.5 Hz), 6.72-6.91 (1H, m), 6.92-7.05 (3H, m), 7.31-7.43 (2H, m), 9.25 (1H, brs), 9.77 (1H, s).

Example 165

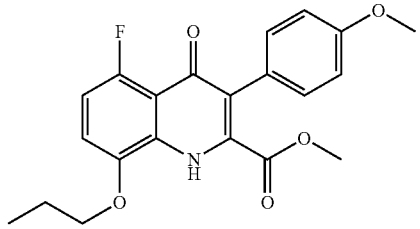

Production of methyl 5-fluoro-3-(4-methoxyphenyl)-4-oxo-8-propoxy-1,4-dihydroquinoline-2-carboxylic acid The above compound was prepared in the same manner as in Example 2 using appropriate starting materials.

$^1$H-NMR (CDCl$_3$) δ ppm: 1.10-1.16 (3H, t, J=7.4 Hz), 1.85-2.05 (2H, m), 3.70 (3H, s), 3.85 (3H, s), 4.10-4.15 (2H, t, J=6.5 Hz), 6.75-6.99 (4H, m), 7.12-7.22 (2H, m), 9.36 (1H, brs).

Example 166

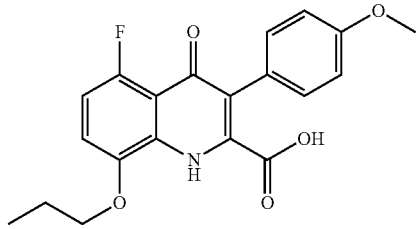

Production of 5-fluoro-3-(4-methoxyphenyl)-4-oxo-8-propoxy-1,4-dihydroquinoline-2-carboxylic acid The above compound was prepared in the same manner as in Example 32 using appropriate starting material.

$^1$H-NMR (DMSO-d$_6$) δ ppm: 1.00-1.06 (3H, t, J=7.4 Hz), 1.69-1.92 (2H, m), 3.76 (3H, s), 4.10-4.15 (2H, t, J=6.5 Hz), 6.88-6.97 (3H, m), 7.12-7.23 (3H, m), 10.78 (1H, brs), 13.00-15.00 (1H, br).

Example 167

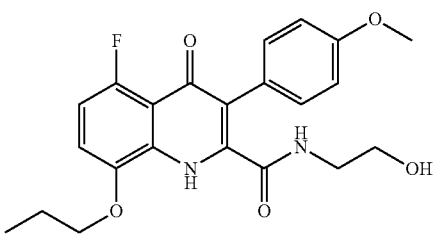

Production of 2-hydroxyethyl 5-fluoro-3-(4-methoxyphenyl)-4-oxo-8-propoxy-1,4-dihydroquinoline-2-carboamide Ethanolamine (10 ml) was added to methyl 5-fluoro-3-(4-methoxyphenyl)-4-oxo-8-propoxy-1,4-dihydroquinoline-2-carboxylic acid (3.2 g, 7.78 mmol) and stirred at 100° C. for 3 hours. The mixture was cooled to room temperature and purified using silica gel column chromatography (dichloromethane:methanol=100:0→20:1). The purified material was concentrated to dryness under reduced pressure, giving a pale yellow amorphous solid of 2-hydroxyethyl 5-fluoro-3-(4-methoxyphenyl)-4-oxo-8-propoxy-1,4-dihydroquinoline-2-carboamide (3.0 g, yield: 93%).

$^1$H-NMR (DMSO-d$_6$) δ ppm: 0.99-1.05 (3H, t, J=7.4 Hz), 1.69-1.95 (2H, m), 2.92-3.17 (4H, m), 3.76 (3H, s), 4.08-4.13 (2H, t, J=6.6 Hz), 4.32-4.57 (1H, m), 6.86-6.93 (3H, m), 7.15-7.21 (3H, m), 8.13-8.33 (1H, m), 11.09 (1H, brs).

Example 168

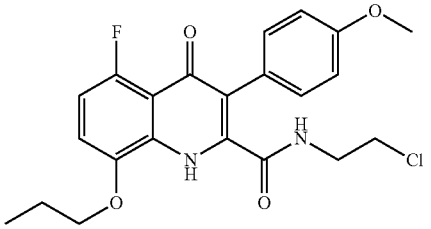

Production of 5-fluoro-3-(4-methoxyphenyl)-4-oxo-8-propoxy-1,4-dihydroquinoline-2-carboxy-(2-chloroethyl)amide Triphenyl phosphine (2.47 g, 9.8 mmol) and carbon tetrachloride (1.4 g, 9.1 mmol) were added to a THF solution (30 ml) of 5-fluoro-3-(4-methoxyphenyl)-4-oxo-8-propoxy-1,4-dihydro-quinoline-2-carboxy-(2-hydroxyethyl)amide (3.0 g, 7.24 mmol) and heated under reflux for 2 hours. The mixture was cooled to room temperature, and water was then added thereto, followed by extraction with dichloromethane. The thus-obtained organic layer was washed with water, dried over anhydrous sodium sulfate, and then concentrated under reduced pressure. The residue was purified using silica gel column chromatography (dichloromethane:methanol=100:0→20:1). The purified material was concentrated to dryness under reduced pressure, giving a white powder of 5-fluoro-3-(4-methoxyphenyl)-4-oxo-8-propoxy-1,4-dihydroquinoline-2-carboxy-(2-chloroethyl)amide (1.8 g, yield: 58%).

$^1$H-NMR (DMSO-d$_6$) δ ppm: 0.99-1.04 (3H, t, J=7.4 Hz), 1.75-1.89 (2H, m), 3.20-3.30 (4H, m), 3.75 (3H, s), 4.08-4.13 (2H, t, J=6.6 Hz), 6.86-6.95 (3H, m), 7.16-7.21 (3H, m), 8.64-8.69 (1H, t, J=5.4 Hz), 11.14 (1H, s).

Example 169

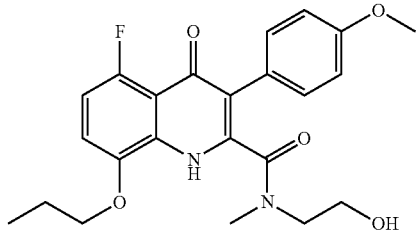

Production of 5-fluoro-3-(4-methoxyphenyl)-4-oxo-8-propoxy-1,4-dihydroquinoline-2-carboxy-(2-hydroxyethyl)methyl amide The above compound was prepared in the same manner as in Example 167 using appropriate starting material.

$^1$H-NMR (CDCl$_3$) δ ppm: 100-1.10 (3H, m), 1.83-1.95 (2H, m), 3.42-3.54 (5H, m), 3.60-3.65 (2H, m), 3.80 (1.2H, s), 3.82 (1.8H, s), 3.99-4.00 (0.8H, t, J=6.6 Hz), 4.06-4.12 (1.2H, t, J=6.6 Hz), 6.75-6.96 (4H, m), 7.32-7.45 (2H, m), 8.89 (0.6H, brs), 9.31 (0.4H, brs).

Example 170

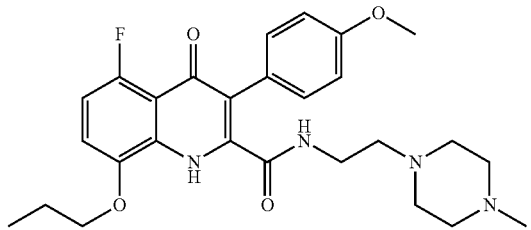

Production of 5-fluoro-3-(4-methoxyphenyl)-4-oxo-8-propoxy-1,4-dihydroquinoline-2-carboxy-[2-(4-methylpiperazin-1-yl)ethyl]amide N-methylpiperazine (276 mg, 2.76 mmol), sodium iodide (440 mg, 2.9 mmol) and potassium carbonate (572 mg, 4.14 mmol) were added to a DMF solution (8 ml) of 5-fluoro-3-(4-methoxyphenyl)-4-oxo-8-propoxy-1,4-dihydroquinoline-2-carboxy-(2-chloroethyl)amide (600 mg, 1.38 mmol) and stirred overnight at 80° C. The mixture was cooled to room temperature, and water was then added thereto, followed by extraction using chloroform. The thus-obtained organic layer was concentrated under reduced pressure, and the residue was then purified using medium pressure liquid chromatography (NH silica gel, dichloromethane:methanol=100:0→10:1). The purified product was concentrated under reduced pressure, giving a white powder of 5-fluoro-3-(4-methoxyphenyl)-4-oxo-8-propoxy-1,4-dihydro-quinoline-2-carboxy-[2-(4-methylpiperazin-1-yl)ethyl]amide (100 mg, yield: 14%).
Melting point: 106-107° C.
$^1$H-NMR (CDCl$_3$) δ ppm: 1.10-1.16 (3H, t, J=7.4 Hz), 1.90-1.99 (2H, m), 2.21-2.80 (13H, m), 3.28-3.35 (2H, m), 3.85 (3H, s), 4.08-4.14 (2H, t, J=6.5 Hz), 6.25-6.50 (1H, brs), 6.79-7.05 (4H, m), 7.28-7.32 (2H, m), 9.77-10.1 (1H, br).

Example 171

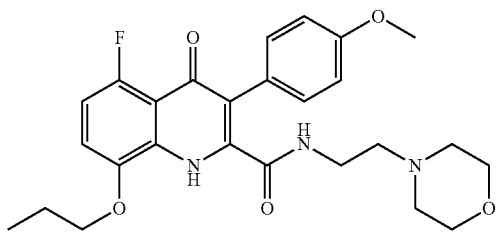

Production of 5-fluoro-3-(4-methoxyphenyl)-4-oxo-8-propoxy-1,4-dihydroquinoline-2-carboxy-[2-(morpholin-4-yl)ethyl]amide The above compound was prepared in the same manner as in Example 170 using appropriate starting material.
Melting point: 111-112° C.
$^1$H-NMR (CDCl$_3$) δ ppm: 1.10-1.16 (3H, t, J=7.4 Hz), 1.88-2.00 (2H, m), 2.17-2.25 (6H, m), 3.29-3.35 (2H, m), 3.54-3.58 (4H, m), 3.84 (3H, s), 4.08-4.14 (2H, t, J=6.4 Hz), 6.35-6.50 (1H, m), 6.79-7.05 (4H, m), 7.28-7.34 (2H, m), 9.96 (1H, s).

Example 172

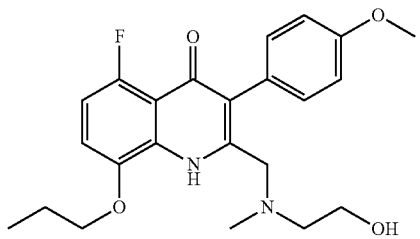

Production of 5-fluoro-2-{[(2-hydroxyethyl)methylamino]methyl}-3-(4-methoxyphenyl)-8-propoxy-1H-quinolin-4-one The above compound was prepared in the same manner as in Example 134 using appropriate starting materials.
$^1$H-NMR (CDCl$_3$) δ ppm: 1.07-1.13 (3H, t, J=7.4 Hz), 1.83-1.92 (2H, m), 2.32 (3H, s), 2.61-2.65 (2H, t, J=5.5 Hz), 3.75-3.80 (2H, m), 3.82 (3H, s), 4.04-4.12 (3H, m), 6.72-6.94 (4H, m), 7.13-7.17 (2H, m), 10.03 (1H, brs).

Example 173

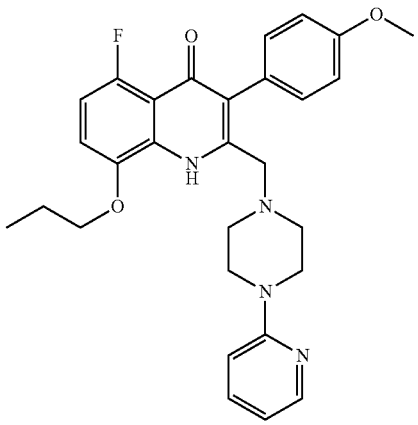

Production of 5-fluoro-3-(4-methoxyphenyl)-8-propoxy-2-(4-pyridin-2-yl-piperazin-1-ylmethyl)-1H-quinolin-4-one 1-(2-Pyridyl)piperazine (551 mg, 3.38 mmol) was added to a 1,2-dichloromethane solution (20 ml) of 5-fluoro-3-(4-methoxyphenyl)-4-oxo-8-propoxy-1,4-dihydroquinoline-2-carbaldehyde (800 mg, 2.25 mmol) and stirred at room temperature for 1 hour. Sodium triacetoxyborohydride (670 mg, 3.16 mmol) was added to the resulting mixture and stirred at room temperature for 4 hours. Dichloromethane was added to the resulting reaction mixture, washed with water, and then the mixture was dried over sodium sulfate. Thereafter, the solvent was removed under reduced pressure. The residue was then purified using NH silica gel column chromatography (dichloromethane:ethyl acetate=1:1). The solvent was removed under reduced pressure and the residue was recrystallized from ethyl acetate-n-hexane, giving a white powder of 5-fluoro-3-(4-methoxyphenyl)-8-propoxy-2-(4-pyridin-2-yl-piperazin-1-ylmethyl)-1H-quinolin-4-one (400 mg, yield: 35%).
Melting point: 211-212° C.
$^1$H-NMR (CDCl$_3$) δ ppm: 1.06-1.13 (3H, t, J=7.4 Hz), 1.84-1.93 (2H, m), 2.63-2.67 (4H, m), 3.50-3.65 (6H, m), 3.89 (3H, s), 4.06-4.11 (2H, t, J=6.3 Hz), 6.93-6.68 (2H, m), 6.76-6.98 (4H, m), 7.16-7.20 (2H, d, J=8.8 Hz), 7.45-7.56 (1H, m), 8.18-8.21 (1H, m), 10.0-10.2 (1H, brs).

Example 174

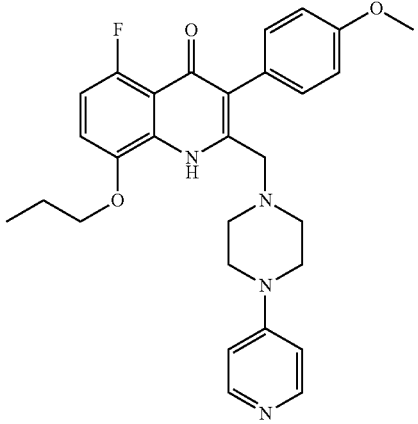

Production of 5-fluoro-3-(4-methoxyphenyl)-8-propoxy-2-(4-pyridin-4-yl-piperazin-1-ylmethyl)-1H-quinolin-4-one The above compound was prepared in the same manner as in Example 173 using appropriate starting material.
Melting point: 210-211° C.
$^1$H-NMR (CDCl$_3$) δ ppm: 1.05-1.11 (3H, t, J=7.4 Hz), 1.81-1.95 (2H, m), 2.66-2.70 (4H, m), 3.38-3.42 (4H, m), 3.56 (2H, s), 3.83 (3H, s), 4.06-4.11 (2H, t, J=6.3 Hz), 6.66-6.69 (2H, d, J=5.3 Hz), 6.76-6.97 (4H, m), 7.15-7.19 (2H, d, J=7.5 Hz), 8.28-8.30 (2H, d, J=5.3 Hz), 9.90-10.2 (1H, brs).

Example 175

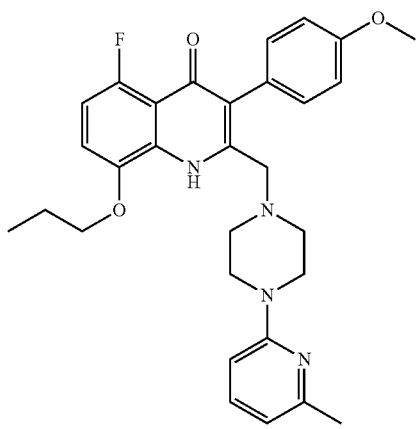

Production of 5-fluoro-3-(4-methoxyphenyl)-2-[4-(6-methylpyridin-2-yl)piperazin-1-ylmethyl]-8-propoxy-1H-quinolin-4-one The above compound was prepared in the same manner as in Example 173 using appropriate starting material.
Melting point: 205-206° C.
$^1$H-NMR (CDCl$_3$) δ ppm: 1.06-1.12 (3H, t, J=7.3 Hz), 1.85-1.93 (2H, m), 2.39 (3H, s), 2.62-2.64 (4H, m), 3.53 (2H, s), 3.55-3.70 (4H, m), 3.83 (3H, s), 4.05-4.10 (2H, t, J=6.4 Hz), 6.41-6.44 (1H, d, J=8.4 Hz), 6.50-6.53 (1H, d, J=7.3 Hz), 6.75-6.96 (4H, m), 7.16-7.20 (2H, d, J=8.8 Hz), 7.37-7.41 (1H, m), 10.2 (1H, s).

Example 176

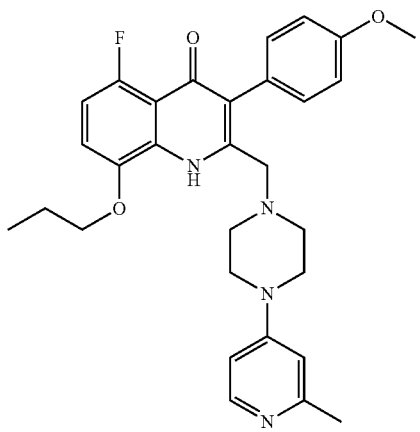

Production of 5-fluoro-3-(4-methoxyphenyl)-2-[4-(2-methylpyridin-4-yl)piperazin-1-ylmethyl]-8-propoxy-1H-quinolin-4-one The above compound was prepared in the same manner as in Example 173 using appropriate starting material.
Melting point: 205-207° C.
$^1$H-NMR (CDCl$_3$) δ ppm: 1.05-1.11 (3H, t, J=7.4 Hz), 1.81-1.95 (2H, m), 2.46 (3H, s), 2.60-2.70 (4H, m), 3.30-3.40 (4H, m), 3.54 (2H, s), 3.82 (3H, s), 4.05-4.10 (2H, t, J=6.3 Hz), 6.45-6.55 (2H, m), 6.74-6.95 (4H, m), 7.13-7.17 (2H, d, J=8.7 Hz), 8.17-8.19 (1H, d, J=5.9 Hz), 10.04 (1H, s).

Example 177

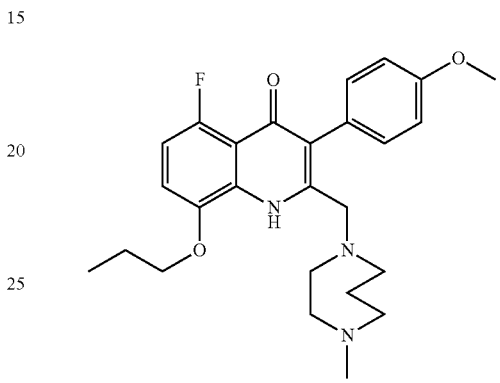

Production of 5-fluoro-3-(4-methoxyphenyl)-2-(4-methyl-[1,4]diazepam-1-ylmethyl)-8-propoxy-1H-quinolin-4-one The above compound was prepared in the same manner as in Example 173 using appropriate starting material.
Melting point: 243-244° C.
$^1$H-NMR (CDCl$_3$) δ ppm: 1.13-1.20 (3H, t, J=7.4 Hz), 1.50-1.70 (2H, m), 2.30-2.60 (3H, m), 2.70-2.90 (6H, m), 3.40-3.77 (4H, m), 3.83 (3H, s), 4.11-4.16 (2H, t, J=6.3 Hz), 6.76-6.96 (4H, m), 7.08-7.12 (2H, d, J=8.7 Hz), 9.60 (1H, s).

Example 178

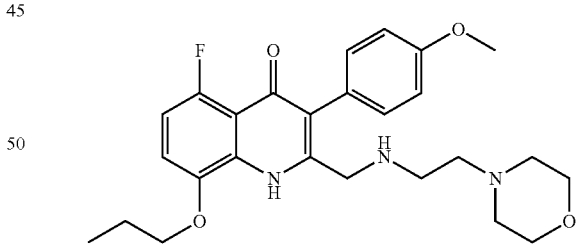

Production of 5-fluoro-3-(4-methoxyphenyl)-2-[(2-morpholin-4-ylethylamino)methyl]-8-propoxy-1H-quinolin-4-one The above compound was prepared in the same manner as in Example 173 using appropriate starting material.
Melting point: 135-137° C.
$^1$H-NMR (CDCl$_3$) δ ppm: 1.11-1.17 (3H, t, J=7.4 Hz), 1.87-2.15 (3H, m), 2.39-2.42 (4H, m), 2.46-2.51 (2H, t, J=5.7 Hz), 2.64-2.68 (2H, t, J=5.7 Hz), 3.65-3.68 (4H, t, J=4.6 Hz), 3.74 (2H, s), 3.83 (3H, s), 4.07-4.12 (2H, t, J=6.3 Hz), 6.74-6.96 (4H, m), 7.16-7.20 (2H, m), 10.35 (1H, s).

Example 179

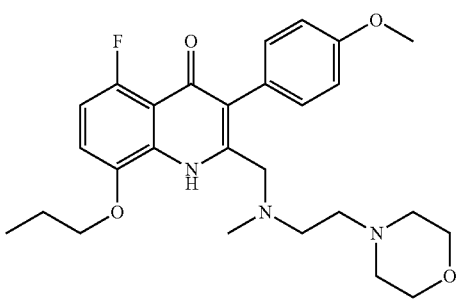

Production of 5-fluoro-3-(4-methoxyphenyl)-2-{[methyl-(2-morpholin-4-ylethyl)amino]methyl}-8-propoxy-1H-quinolin-4-one The above compound was prepared in the same manner as in Example 173 using appropriate starting material.
Melting point: 127-128° C.
$^1$H-NMR (CDCl$_3$) δ ppm: 1.10-1.17 (3H, t, J=7.4 Hz), 1.86-2.00 (2H, m), 2.30-2.42 (7H, m), 2.46-2.52 (2H, m), 2.58-2.64 (2H, m), 3.52 (2H, s), 3.52-3.63 (4H, t, J=4.6 Hz), 3.83 (3H, s), 4.08-4.13 (2H, t, J=6.3 Hz), 6.75-6.96 (4H, m), 7.13-7.18 (2H, d, J=8.7 Hz), 10.11 (1H, s).

Example 180

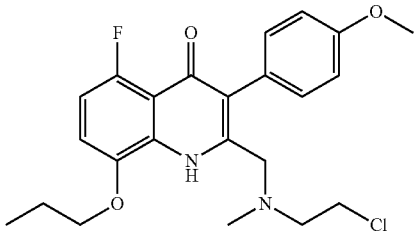

Production of 2-{[(2-chloroethyl)methylamino]methyl}-5-fluoro-3-(4-methoxyphenyl)-8-propoxy-1H-quinolin-4-one The above compound was prepared in the same manner as in Example 168 using appropriate starting material.
$^1$H-NMR (CDCl$_3$) δ ppm: 100-1.10 (3H, m), 1.83-1.95 (2H, m), 2.26 (3H, s), 2.64 (2H, m), 3.03 (2H, s), 3.48 2H, m), 3.82 (3H, s), 4.08-4.13 (2H, t, J=6.6 Hz), 6.75-6.96 (4H, m), 7.32-7.45 (2H, m), 8.89 (0.6H, brs), 9.31 (0.4H, brs).

Example 181

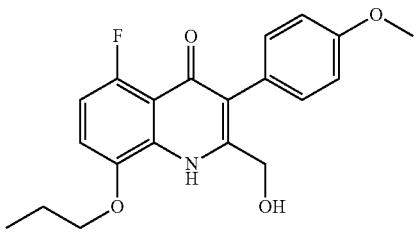

Production of 5-fluoro-2-hydroxymethyl-3-(4-methoxyphenyl)-8-propoxy-1H-quinolin-4-one A dichloromethane solution (30 ml) of methyl 5-fluoro-3-(4-methoxyphenyl)-4-oxo-8-propoxy-1,4-dihydroquinoline-2-carboxylate (5.0 g, 13 mmol) was cooled to −78° C., and hydrogenated diisobutylaluminium (DIBAL-H, 1M toluene solution, 30 ml) was added thereto dropwise under a nitrogen atmosphere. After completion of the addition, the mixture was stirred at the same temperature for 3 hours. The reaction mixture was heated to room temperature, and 5N sodium hydroxide was added thereto, followed by extraction with dichloromethane. The thus-obtained organic layer was washed with water, dried over sodium sulfate, and then concentrated under reduced pressure. The residue was purified using silica gel column chromatography (dichloromethane:methanol=10:1). The purified material was concentrated to dryness under reduced pressure, giving a yellow amorphous solid of 5-fluoro-2-hydroxymethyl-3-(4-methoxyphenyl)-8-propoxy-1H-quinolin-4-one (4.8 g, yield: 85%).
$^1$H-NMR (CDCl$_3$) δ ppm: 1.04-1.10 (3H, t, J=7.4 Hz), 1.83-1.92 (2H, m), 3.75 (3H, s), 4.02-4.07 (2H, t, J=6.5 Hz), 4.39 (2H, s), 4.67 (1H, brs), 6.71-6.83 (4H, m), 6.95-6.98 (2H, m), 9.82 (1H, s).

Example 182

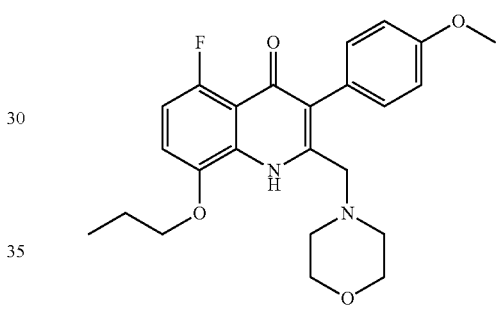

Production of 5-fluoro-3-(4-methoxyphenyl)-2-morpholin-4-ylmethyl-8-propoxy-1H-quinolin-4-one The above compound was prepared in the same manner as in Example 173 using appropriate starting material.
Melting point: 175-176° C.
$^1$H-NMR (DMSO-d$_6$) δ ppm: 1.09-1.14 (3H, t, J=7.4 Hz), 1.78-1.94 (2H, m), 2.32-2.47 (4H, m), 3.47 (2H, s), 3.55-3.68 (4H, m), 3.77 (3H, s), 4.12-4.16 (2H, t, J=6.2 Hz), 6.79-7.00 (3H, m), 7.06-7.14 (2H, m), 7.15-7.25 (1H, m), 10.21 (1H, brs).

Example 183

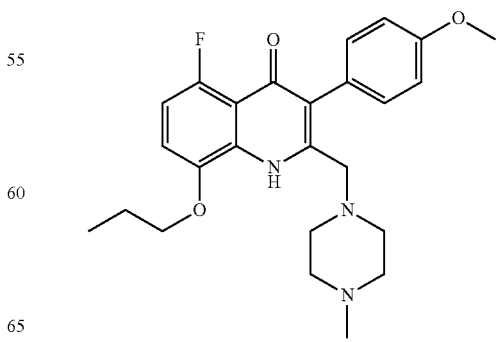

Production of 5-fluoro-3-(4-methoxyphenyl)-2-(4-methylpiperazin-1-ylmethyl)-8-propoxy-1H-quinolin-4-one The above compound was prepared in the same manner as in Example 173 using appropriate starting material.
Melting point: 204-205° C.
¹H-NMR (CDCl₃) δ ppm: 1.18-1.24 (3H, t, J=7.4 Hz), 1.86-2.08 (2H, m), 2.31 (3H, s), 2.36-2.79 (8H, m), 3.49 (2H, s), 3.84 (3H, s), 4.08-4.13 (2H, t, J=6.2 Hz), 6.68-7.00 (4H, m), 7.11-7.22 (2H, m), 10.21 (1H, brs).

Example 184

Production of 4-[5-fluoro-3-(4-methoxyphenyl)-4-oxo-8-propoxy-1,4-dihydroquinolin-2-yl]butyric acid The above compound was prepared in the same manner as in Example 32 using appropriate starting material.
Melting point: 154-156° C.
¹H-NMR (DMSO-d₆) δ ppm: 0.99 (3H, t, J=7.3 Hz), 1.65-1.71 (2H, m), 1.79-1.87 (2H, m), 2.09 (2H, t, J=7.4 Hz), 2.57 (2H, t, J=7.0 Hz), 3.76 (3H, s), 4.13 (2H, t, J=6.6 Hz), 6.81-6.94 (3H, m), 7.06 (2H, d, J=8.7 Hz), 7.14 (1H, dd, J=4.0 Hz, 8.8 Hz), 10.40 (1H, brs).

Example 185

Production of N-butyl-4-[5-fluoro-3-(4-methoxyphenyl)-4-oxo-8-propoxy-1,4-dihydroquinolin-2-yl]butylamide The above compound was prepared in the same manner as in Example 33 using appropriate starting materials.
Pale Yellow Powder (Diethyl Ether)
Melting point: 134-136° C.
¹H-NMR (DMSO-d₆) δ ppm: 0.82 (3H, t, J=6.9 Hz), 1.00 (3H, t, J=7.3 Hz), 1.19-1.30 (4H, m), 1.64-1.70 (2H, m), 1.84 (2H, q, J=6.9 Hz), 1.98-2.03 (2H, m), 2.48-2.56 (2H, m), 2.94-2.99 (2H, m), 3.75 (3H, s), 4.10 (2H, t, J=6.4 Hz), 6.81-6.93 (3H, m), 7.05-7.15 (3H, m), 7.82 (1H, t, J=5.0 Hz), 10.97 (1H, brs).

Example 186

Production of 5-fluoro-8-propoxy-3-pyrimidin-5-yl-1H-quinolin-4-one

The above compound was prepared in the same manner as in Example 2 using appropriate starting materials.
Melting point: >250° C.
¹H-NMR (DMSO-d₆) δ ppm: 1.06 (3H, t, J=7.4 Hz), 1.75-2.00 (2H, m), 4.14 (2H, t, J=6.4 Hz), 6.99 (1H, dd, J=8.8, 12.0 Hz), 7.23 (1H, dd, J=3.9, 8.8 Hz), 8.12 (1H, s), 9.08 (2H, s), 9.10 (1H, s), 11.68 (1H, s).

Example 187

Production of 5-fluoro-3-(1-methyl-1H-pyrazol-4-yl)-8-propoxy-1H-quinolin-4-one

The above compound was prepared in the same manner as in Example 2 using appropriate starting materials.
Melting point: 223-225° C.
¹H-NMR (DMSO-d₆) δ ppm: 1.06 (3H, t, J=7.4 Hz), 1.75-1.95 (2H, m), 3.87 (3H, s), 4.11 (2H, t, J=6.4 Hz), 6.90 (1H, dd, J=8.7, 12.0 Hz), 7.13 (1H, dd, J=3.9, 8.7 Hz), 7.95 (1H, s), 8.08 (1H, d, J=5.4 Hz), 8.37 (1H, s), 11.36 (1H, d, J=5.4 Hz).

Example 188

Production of di-tert-butyl 5-fluoro-3-(4-methoxyphenyl)-4-oxo-8-propoxy-4H-quinolin-1-ylmethyl phosphate The above compound was prepared in the same manner as in Example 23 using appropriate starting material.
$^1$H-NMR (CDCl$_3$) δ ppm: 1.11 (3H, t, J=7.4 Hz), 1.36 (18H, s), 1.85-2.05 (2H, m), 3.83 (3H, s), 4.07 (2H, t, J=6.6 Hz), 6.32 (2H, d, J=13.0 Hz), 6.90-7.00 (3H, m), 7.07 (1H, dd, J=4.5, 9.0 Hz), 7.63 (2H, d, J=8.9 Hz), 7.79 (1H, s).

Example 189

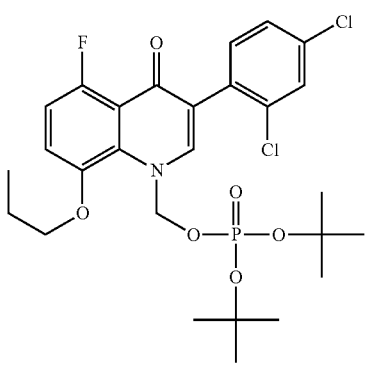

Production of di-tert-butyl 3-(2,4-dichlorophenyl)-5-fluoro-4-oxo-8-propoxy-4H-quinolin-1-ylmethyl phosphate The above compound was prepared in the same manner as in Example 23 using appropriate starting material.
$^1$H-NMR (CDCl$_3$) δ ppm: 1.11 (3H, t, J=7.4 Hz), 1.37 (18H, s), 1.85-2.05 (2H, m), 4.08 (2H, t, J=6.6 Hz), 6.30 (2H, d, J=12.6 Hz), 6.99 (1H, dd, J=9.0, 10.7 Hz), 7.13 (1H, dd, J=4.4, 9.0 Hz), 7.27 (1H, dd, J=2.1, 8.3 Hz), 7.37 (1H, d, J=8.3 Hz), 7.47 (1H, d, J=2.1 Hz), 7.75 (1H, s).

Example 190

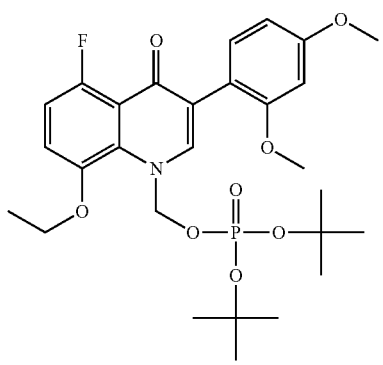

Production of di-tert-butyl 3-(2,4-dimethoxyphenyl)-8-ethoxy-5-fluoro-4-oxo-4H-quinolin-1-ylmethyl phosphate The above compound was prepared in the same manner as in Example 23 using appropriate starting material.
$^1$H-NMR (CDCl$_3$) δ ppm: 1.37 (18H, s), 1.54 (3H, t, J=7.0 Hz), 3.76 (3H, s), 3.83 (3H, s), 4.18 (2H, q, J=7.0 Hz), 6.28 (2H, d, J=11.9 Hz), 6.50-6.60 (2H, m), 6.93 (1H, dd, J=9.0, 10.9 Hz), 7.07 (1H, dd, J=4.5, 9.0 Hz), 7.34 (1H, d, J=9.0 Hz), 7.72 (1H, s).

Example 191

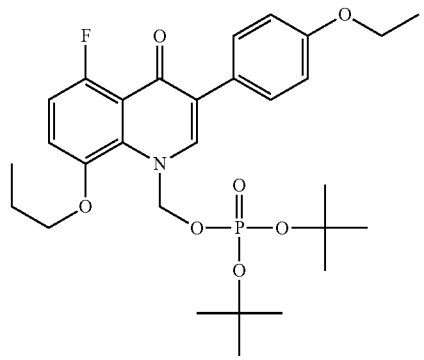

Production of di-tert-butyl 3-(4-ethoxyphenyl)-5-fluoro-4-oxo-8-propoxy-4H-quinolin-1-ylmethyl phosphate The above compound was prepared in the same manner as in Example 23 using appropriate starting material.
$^1$H-NMR (CDCl$_3$) δ ppm: 1.11 (3H, t, J=7.5 Hz), 1.36 (18H, s), 1.42 (3H, t, J=7.0 Hz), 1.85-2.05 (2H, m), 4.00-4.15 (4H, m), 6.32 (2H, d, J=13.0 Hz), 6.80-7.00 (3H, m), 7.08 (1H, dd, J=4.5, 9.0 Hz), 7.61 (2H, t, J=8.9 Hz), 7.78 (1H, s).

Example 192

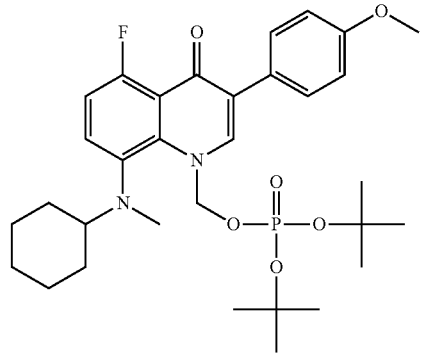

Production of di-tert-butyl 8-(cyclohexylmethylamino)-5-fluoro-3-(4-methoxyphenyl)-4-oxo-4H-quinolin-1-ylmethyl phosphate The above compound was prepared in the same manner as in Example 23 using appropriate starting material.
$^1$H-NMR (CDCl$_3$) δ ppm: 1.02-1.90 (28H, m), 2.50-2.75 (1H, m), 2.78 (3H, s), 3.84 (3H, s), 5.97 (1H, dd, J=9.4, 10.7

Hz), 6.80-7.05 (3H, m), 7.42 (1H, dd, J=5.1, 8.8 Hz), 7.51 (1H, dd, J=9.4, 12.1 Hz), 7.64 (2H, d, J=8.8 Hz), 7.71 (1H, s).

Example 193

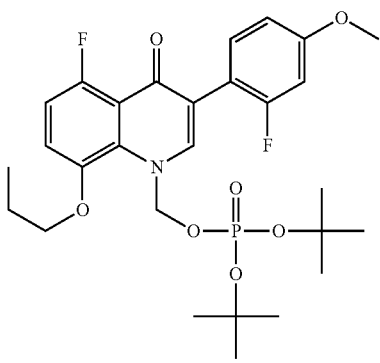

Production of di-tert-butyl 5-fluoro-3-(2-fluoro-4-methoxyphenyl)-4-oxo-8-propoxy-4H-quinolin-1-ylmethyl phosphate The above compound was prepared in the same manner as in Example 23 using appropriate starting material.

$^1$H-NMR (CDCl$_3$) δ ppm: 1.11 (3H, t, J=7.5 Hz), 1.36 (18H, s), 1.85-2.05 (2H, m), 3.82 (3H, s), 4.07 (2H, t, J=6.6 Hz), 6.30 (2H, d, J=12.6 Hz), 6.60-6.80 (2H, m), 6.96 (1H, dd, J=9.0, 10.8 Hz), 7.10 (1H, dd, J=4.5, 9.0 Hz), 7.51 (1H, t, J=8.4 Hz), 7.79 (1H, s).

Example 194

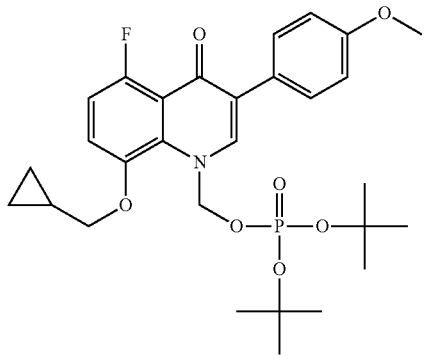

Production of di-tert-butyl 8-cyclopropylmethoxy-5-fluoro-3-(4-methoxyphenyl)-4-oxo-4H-quinolin-1-ylmethyl phosphate The above compound was prepared in the same manner as in Example 23 using appropriate starting material.

$^1$H-NMR (CDCl$_3$) δ ppm: 0.35-0.50 (2H, m), 0.60-0.75 (2H, m), 1.25-1.45 (19H, m), 3.83 (3H, s), 3.95 (2H, d, J=7.1

Hz), 6.40 (2H, d, J=13.1 Hz), 6.85-7.00 (3H, m), 7.04 (1H, dd, J=4.6, 9.0 Hz), 7.63 (2H, d, J=8.9 Hz), 7.79 (1H, s).

Example 195

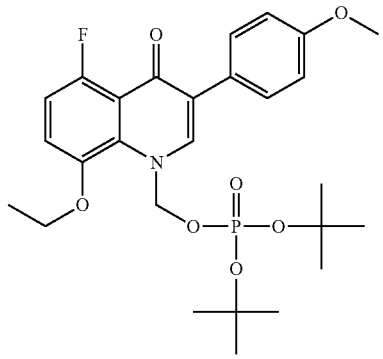

Production of di-tert-butyl 8-ethoxy-5-fluoro-3-(4-methoxyphenyl)-4-oxo-4H-quinolin-1-ylmethyl phosphate The above compound was prepared in the same manner as in Example 23 using appropriate starting material.

$^1$H-NMR (CDCl$_3$) δ ppm: 1.36 (18H, s), 1.55 (3H, t, J=7.0 Hz), 3.83 (3H, s), 4.19 (2H, q, J=7.0 Hz), 6.33 (2H, d, J=12.8 Hz), 6.90-7.00 (3H, m), 7.08 (1H, dd, J=4.5, 9.0 Hz), 7.63 (2H, d, J=8.8 Hz), 7.77 (1H, s).

Example 196

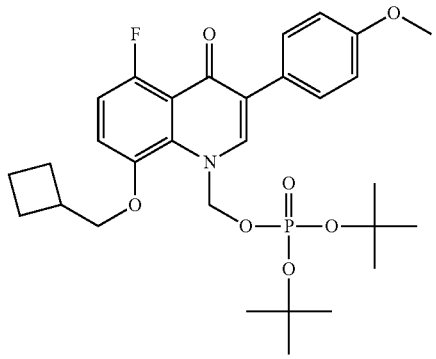

Production of di-tert-butyl 8-cyclobutylmethoxy-5-fluoro-3-(4-methoxyphenyl)-4-oxo-4H-quinolin-1-ylmethyl phosphate The above compound was prepared in the same manner as in Example 23 using appropriate starting material.

$^1$H-NMR (CDCl$_3$) δ ppm: 1.36 (18H, s), 1.85-2.10 (4H, m), 2.15-2.30 (2H, m), 2.85-3.00 (1H, m), 3.83 (3H, s), 4.07

(2H, d, J=7.0 Hz), 6.30 (2H, d, J=13.2 Hz), 6.90-7.00 (3H, m), 7.07 (1H, dd, J=4.5, 9.0 Hz), 7.63 (2H, d, J=8.9 Hz), 7.79 (1H, s).

Example 197

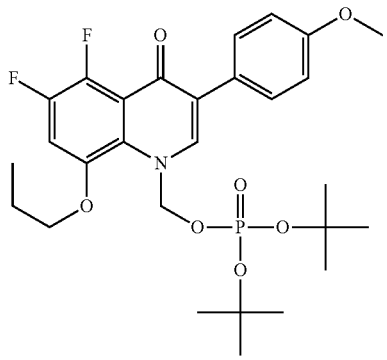

Production of di-tert-butyl 5,6-difluoro-3-(4-methoxyphenyl)-4-oxo-8-propoxy-4H-quinolin-1-ylmethyl phosphate The above compound was prepared in the same manner as in Example 23 using appropriate starting material.

$^1$H-NMR (CDCl$_3$) δ ppm: 1.12 (3H, t, J=7.4 Hz), 1.36 (18H, s), 1.90-2.05 (2H, m), 3.83 (3H, s), 4.06 (2H, t, J=6.6 Hz), 6.28 (2H, d, J=13.2 Hz), 6.94 (2H, d, J=8.9 Hz), 7.02 (1H, dd, J=6.8, 11.6 Hz), 7.62 (2H, d, J=8.9 Hz), 7.78 (1H, s).

Example 198

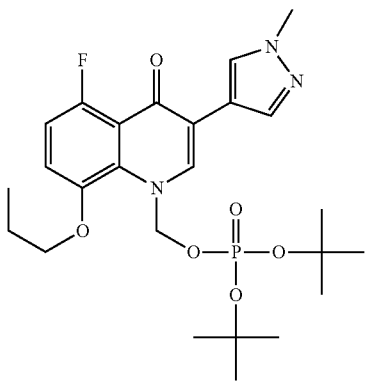

Production of di-tert-butyl 5-fluoro-3-(1-methyl-1H-pyrazol-4-yl)-4-oxo-8-propoxy-4H-quinolin-1-ylmethyl phosphate The above compound was prepared in the same manner as in Example 23 using appropriate starting material.

$^1$H-NMR (CDCl$_3$) δ ppm: 1.11 (3H, t, J=7.5 Hz), 1.37 (18H, s), 1.85-2.00 (2H, m), 3.93 (3H, s), 4.06 (2H, t, J=6.6 Hz), 6.34 (2H, d, J=13.1 Hz), 6.94 (1H, dd, J=9.0, 11.1 Hz), 7.06 (1H, dd, J=4.5, 9.0 Hz), 7.81 (1H, s), 8.01 (1H, s), 8.38 (1H, s).

Example 199

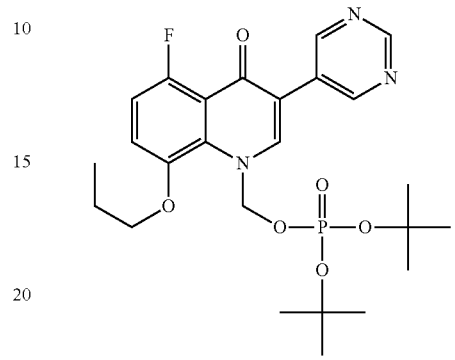

Production of di-tert-butyl 5-fluoro-4-oxo-8-propoxy-3-pyrimidin-5-yl-4H-quinolin-1-ylmethyl phosphate The above compound was prepared in the same manner as in Example 23 using appropriate starting material.

$^1$H-NMR (CDCl$_3$) δ ppm: 1.13 (3H, t, J=7.5 Hz), 1.36 (18H, s), 1.90-2.10 (2H, m), 4.10 (2H, t, J=6.6 Hz), 6.36 (2H, d, J=13.8 Hz), 7.01 (1H, dd, J=9.0, 10.9 Hz), 7.16 (1H, dd, J=4.5, 9.0 Hz), 7.96 (1H, s), 9.08 (2H, s), 9.15 (1H, s).

Example 200

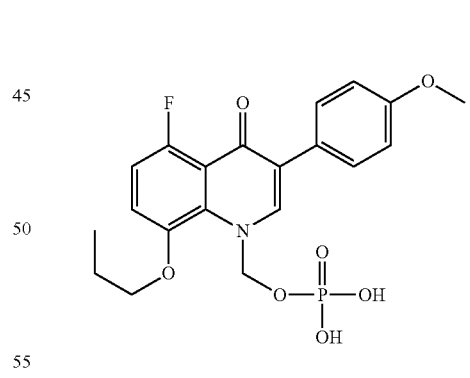

Production of [5-fluoro-3-(4-methoxyphenyl)-4-oxo-8-propoxy-4H-quinolin-1-ylmethyl]monophosphate The above compound was prepared in the same manner as in Example 24 using appropriate starting material.

$^1$H-NMR (DMSO-d$_6$) δ ppm: 1.02 (3H, t, J=7.4 Hz), 1.75-1.90 (2H, m), 3.77 (3H, s), 4.07 (2H, t, J=6.5 Hz), 6.26 (2H, d, J=11.2 Hz), 6.96 (2H, d, J=8.9 Hz), 7.06 (1H, dd, J=9.1, 11.6 Hz), 7.33 (1H, dd, J=4.5, 9.1 Hz), 7.58 (2H, d, J=8.9 Hz), 8.00 (1H, s).

Example 201

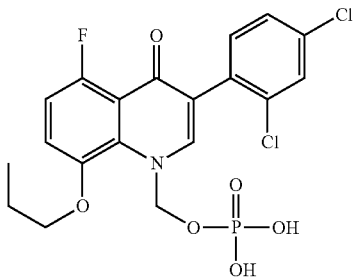

Production of [3-(2,4-dichloro-phenyl)-5-fluoro-4-oxo-8-propoxy-4H-quinolin-1-ylmethyl]monophosphate The above compound was prepared in the same manner as in Example 24 using appropriate starting material.

$^1$H-NMR (DMSO-$d_6$) δ ppm: 1.04 (3H, t, J=7.4 Hz), 1.80-1.95 (2H, m), 4.10 (2H, t, J=6.5 Hz), 6.24 (2H, d, J=11.2 Hz), 7.13 (1H, dd, J=9.0, 11.4 Hz), 7.40 (1H, dd, J=4.6, 9.0 Hz), 7.42 (1H, d, J=8.2 Hz), 7.52 (1H, dd, J=2.1, 8.2 Hz), 7.69 (1H, d, J=2.1 Hz), 7.97 (1H, s).

Example 202

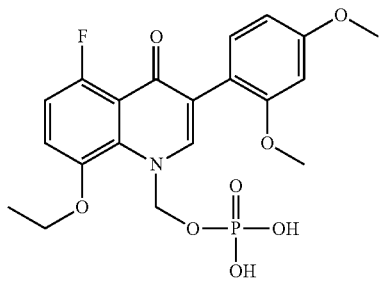

Production of [3-(2,4-dimethoxyphenyl)-8-ethoxy-5-fluoro-4-oxo-4H-quinolin-1-ylmethyl]monophosphate The above compound was prepared in the same manner as in Example 24 using appropriate starting material.

$^1$H-NMR (DMSO-$d_6$) δ ppm: 1.45 (3H, t, J=6.9 Hz), 3.69 (3H, s), 3.80 (3H, s), 4.19 (2H, q, J=6.9 Hz), 6.20 (2H, d, J=9.7 Hz), 6.56 (1H, dd, J=2.4, 8.2 Hz), 6.61 (1H, d, J=2.4 Hz), 7.07 (1H, dd, J=9.0, 11.5 Hz), 7.16 (1H, d, J=8.2 Hz), 7.35 (1H, dd, J=4.5, 9.0 Hz), 7.80 (1H, s).

Example 203

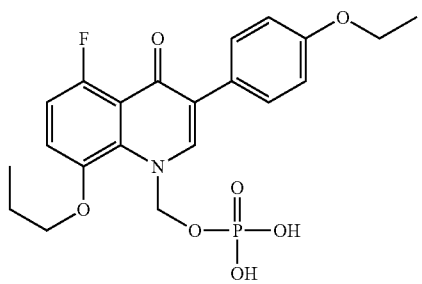

Production of [3-(4-ethoxyphenyl)-5-fluoro-4-oxo-8-propoxy-4H-quinolin-1-ylmethyl]monophosphate The above compound was prepared in the same manner as in Example 24 using appropriate starting material.

$^1$H-NMR (DMSO-$d_6$) δ ppm: 1.05 (3H, t, J=7.4 Hz), 1.35 (3H, t, J=7.0 Hz), 1.75-1.95 (2H, m), 4.00-4.15 (4H, m), 6.28 (2H, d, J=11.2 Hz), 6.96 (2H, d, J=8.8 Hz), 7.08 (1H, dd, J=9.0, 11.6 Hz), 7.35 (1H, dd, J=4.5, 9.0 Hz), 7.59 (2H, d, J=8.8 Hz), 8.03 (1H, s).

Example 204

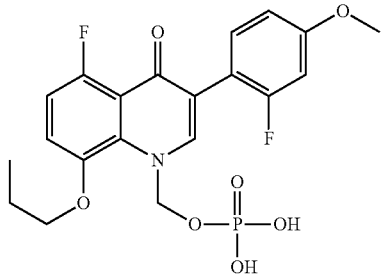

Production of [5-fluoro-3-(2-fluoro-4-methoxyphenyl)-4-oxo-8-propoxy-4H-quinolin-1-ylmethyl]monophosphate The above compound was prepared in the same manner as in Example 24 using appropriate starting material.

$^1$H-NMR (DMSO-$d_6$) δ ppm: 1.04 (3H, t, J=7.4 Hz), 1.75-1.95 (2H, m), 3.81 (3H, s), 4.09 (2H, d, J=6.9 Hz), 6.24 (2H, d, J=10.9 Hz), 6.75-7.00 (2H, m), 7.11 (1H, dd, J=9.0, 11.4 Hz), 7.24-7.50 (2H, m), 7.95 (1H, s).

Example 205

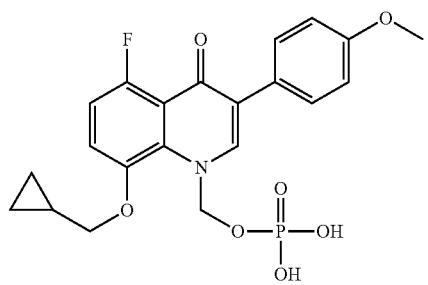

Production of [8-cyclopropylmethoxy-5-fluoro-3-(4-methoxyphenyl)-4-oxo-4H-quinolin-1-ylmethyl] monophosphate The above compound was prepared in the same manner as in Example 24 using appropriate starting material.

$^1$H-NMR (DMSO-$d_6$) δ ppm: 0.35-0.45 (2H, m), 0.55-0.70 (2H, m), 1.30-1.45 (1H, m), 3.79 (3H, s), 3.99 (2H, d, J=7.2 Hz), 6.36 (2H, d, J=11.2 Hz), 6.98 (2H, d, J=8.9 Hz), 7.07 (1H, dd, J=9.0, 11.6 Hz), 7.33 (1H, dd, J=4.5, 9.0 Hz), 7.60 (2H, d, J=8.9 Hz), 8.03 (1H, s).

Example 206

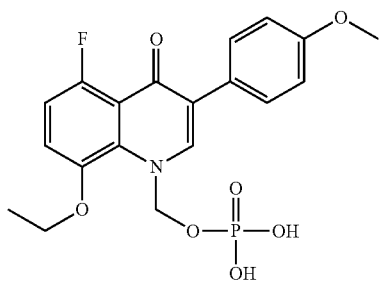

Production of [8-ethoxy-5-fluoro-3-(4-methoxyphenyl)-4-oxo-4H-quinolin-1-ylmethyl]monophosphate The above compound was prepared in the same manner as in Example 24 using appropriate starting material.

$^1$H-NMR (DMSO-$d_6$) δ ppm: 1.45 (3H, t, J=6.9 Hz), 3.79 (3H, s), 4.19 (2H, q, J=6.9 Hz), 6.28 (2H, d, J=10.8 Hz), 6.98 (2H, d, J=8.9 Hz), 7.08 (1H, dd, J=9.0, 11.6 Hz), 7.36 (1H, dd, J=4.5, 9.0 Hz), 7.60 (2H, d, J=8.9 Hz), 8.03 (1H, s).

Example 207

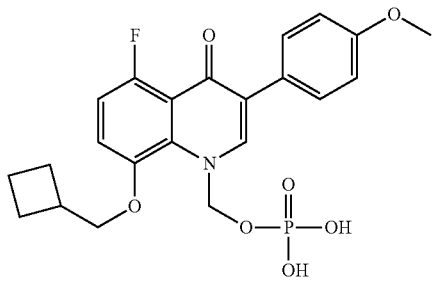

Production of [8-cyclobutylmethoxy-5-fluoro-3-(4-methoxyphenyl)-4-oxo-4H-quinolin-1-ylmethyl] monophosphate The above compound was prepared in the same manner as in Example 24 using appropriate starting material.

$^1$H-NMR (DMSO-$d_6$) δ ppm: 1.60-2.20 (6H, m), 2.70-2.95 (1H, m), 3.79 (3H, s), 4.11 (2H, d, J=6.9 Hz), 6.25 (2H, d, J=11.5 Hz), 6.97 (2H, d, J=8.9 Hz), 7.08 (1H, dd, J=9.0, 11.5 Hz), 7.35 (1H, dd, J=4.5, 9. Hz), 7.60 (2H, d, J=8.9 Hz), 8.02 (1H, s).

Example 208

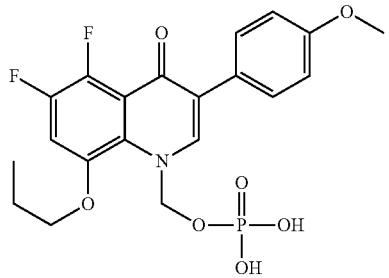

Production of [5,6-difluoro-3-(4-methoxyphenyl)-4-oxo-8-propoxy-4H-quinolin-1-ylmethyl]monophosphate The above compound was prepared in the same manner as in Example 24 using appropriate starting material.

$^1$H-NMR (DMSO-$d_6$) δ ppm: 1.04 (3H, t, J=7.4 Hz), 1.705-2.00 (2H, m), 3.78 (3H, s), 4.12 (2H, t, J=6.5 Hz), 6.25 (2H, d, J=11.5 Hz), 6.98 (2H, d, J=8.8 Hz), 7.50-7.70 (3H, m), 8.07 (1H, s).

Example 209

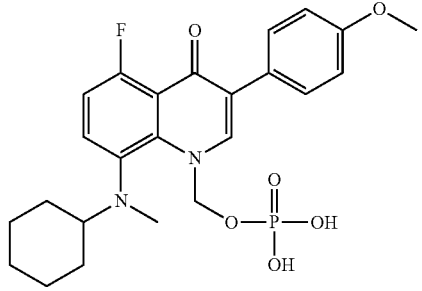

Production of [8-(cyclohexylmethylamino)-5-fluoro-3-(4-methoxyphenyl)-4-oxo-4H-quinolin-1-ylmethyl]monophosphate The above compound was prepared in the same manner as in Example 24 using appropriate starting material.

$^1$H-NMR (DMSO-$d_6$) δ ppm: 0.75-2.00 (10H, m), 3.79 (3H, s), 3.83 (3H, s), 3.90-4.60 (1H, m), 5.85 (1H, d, J=9.5 Hz), 6.48 (1H, d, J=9.5 Hz), 7.00 (2H, d, J=8.9 Hz), 7.33 (1H, dd, J=8.6, 11.6 Hz), 7.52 (2H, d, J=8.9 Hz), 8.16 (1H, dd, J=3.2, 8.6 Hz), 8.22 (1H, s).

Example 210

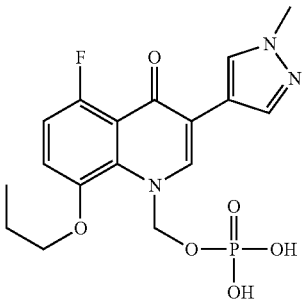

Production of [5-fluoro-3-(1-methyl-1H-pyrazol-4-yl)-4-oxo-8-propoxy-4H-quinolin-1-ylmethyl]monophosphate The above compound was prepared in the same manner as in Example 24 using appropriate starting material.

$^1$H-NMR (DMSO-$d_6$) δ ppm: 1.04 (3H, t, J=7.4 Hz), 1.75-1.95 (2H, m), 3.80-4.15 (5H, m), 6.29 (2H, d, J=10.5 Hz), 7.07 (1H, dd, J=9.0, 11.6 Hz), 7.32 (1H, dd, J=4.5, 9.0 Hz), 7.87 (1H, s), 8.31 (1H, s), 8.32 (1H, s).

Example 211

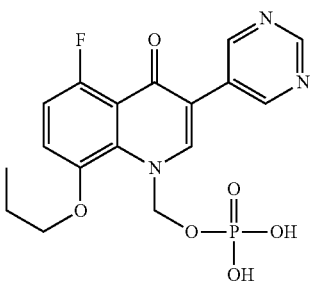

Production of (5-fluoro-4-oxo-8-propoxy-3-pyrimidin-5-yl-4H-quinolin-1-ylmethyl)monophosphate The above compound was prepared in the same manner as in Example 24 using appropriate starting material.

$^1$H-NMR (DMSO-$d_6$) δ ppm: 1.05 (3H, t, J=6.6 Hz), 1.75-1.95 (2H, m), 4.11 (2H, t, J=6.5 Hz), 6.32 (2H, d, J=12.0 Hz), 7.17 (1H, dd, J=9.1, 11.4 Hz), 7.43 (1H, dd, J=4.5, 9.1 Hz), 8.39 (1H, s), 9.10 (2H, s), 9.13 (1H, s).

Example 212

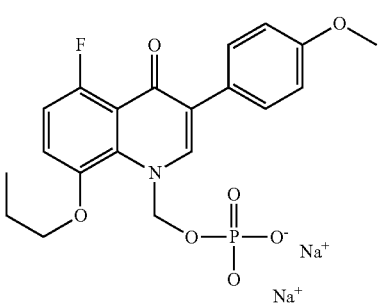

Production of [5-fluoro-3-(4-methoxyphenyl)-4-oxo-8-propoxy-4H-quinolin-1-ylmethyl]monophosphate disodium salt The above compound was prepared in the same manner as in Example 25 using appropriate starting material.

Melting point: 204-206° C.

$^1$H-NMR (D$_2$O) δ ppm: 0.97 (3H, t, J=7.4 Hz), 1.75-1.85 (2H, m), 3.76 (3H, s), 4.00 (2H, t, J=6.7 Hz), 6.04 (2H, d, J=9.1 Hz), 6.90-7.05 (3H, m), 7.18 (1H, dd, J=4.6, 9.1 Hz), 7.42 (2H, d, J=8.7 Hz), 8.14 (1H, s).

Example 213

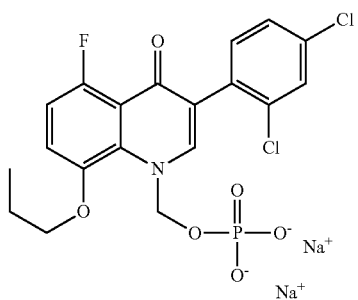

Production of [3-(2,4-dichlorophenyl)-5-fluoro-4-oxo-8-propoxy-4H-quinolin-1-ylmethyl]monophosphate disodium salt Melting point: 208-210° C.

The above compound was prepared in the same manner as in Example 25 using appropriate starting material.

$^1$H-NMR (D$_2$O) δ ppm: 0.96 (3H, t, J=7.5 Hz), 1.75-1.95 (2H, m), 4.07 (2H, t, J=6.7 Hz), 6.08 (2H, d, J=8.8 Hz), 7.05 (1H, dd, J=9.1, 12.2 Hz), 7.30 (1H, dd, J=4.7, 9.1 Hz), 7.32-7.40 (2H, m), 7.50-7.55 (1H, m), 8.21 (1H, s).

Example 214

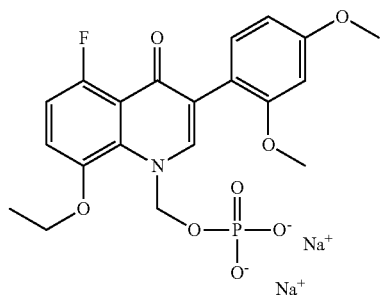

Production of [3-(2,4-dimethoxyphenyl)-8-ethoxy-5-fluoro-4-oxo-4H-quinolin-1-ylmethyl]monophosphate disodium salt The above compound was prepared in the same manner as in Example 25 using appropriate starting material.

Melting point: 205-207° C.

$^1$H-NMR (D$_2$O) δ ppm: 1.40 (3H, t, J=7.0 Hz), 3.66 (3H, s), 3.77 (3H, s), 4.16 (2H, q, J=7.0 Hz), 6.03 (2H, d, J=8.2 Hz), 6.55-6.65 (2H, m), 7.02 (1H, dd, J=9.0, 12.3 Hz), 7.17 (1H, d, J=9.0 Hz), 7.28 (1H, dd, J=4.7, 9.0 Hz), 8.09 (1H, s).

Example 215

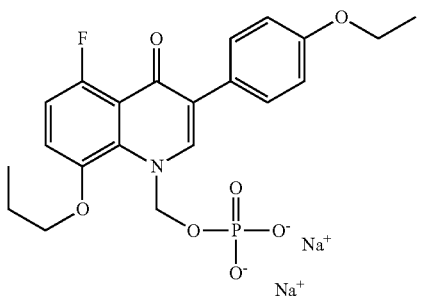

Production of [5-fluoro-3-(4-ethoxyphenyl)-4-oxo-8-propoxy-4H-quinolin-1-ylmethyl]monophosphate disodium salt The above compound was prepared in the same manner as in Example 25 using appropriate starting material.

Melting point: 200-202° C.

$^1$H-NMR (D$_2$O) δ ppm: 0.93 (3H, t, J=7.5 Hz), 1.27 (3H, t, J=7.0 Hz), 1.70-1.90 (2H, m), 3.95-4.10 (4H, m), 6.03 (2H, d, J=8.9 Hz), 6.90-7.05 (3H, m), 7.20 (1H, dd, J=4.6, 9.1 Hz), 7.40 (2H, d, J=8.7 Hz), 8.15 (1H, s).

Example 216

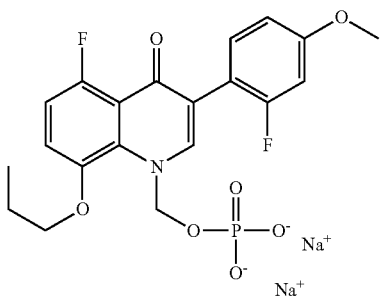

Production of [5-fluoro-3-(2-fluoro-4-methoxyphenyl)-4-oxo-8-propoxy-4H-quinolin-1-ylmethyl]monophosphate disodium salt The above compound was prepared in the same manner as in Example 25 using appropriate starting material.

Melting point: 208-210° C.

$^1$H-NMR (D$_2$O) δ ppm: 0.57 (3H, t, J=7.4 Hz), 1.70-1.85 (2H, m), 3.69 (3H, s), 3.96 (2H, d, J=6.7 Hz), 5.98 (2H, d, J=8.9 Hz), 6.65-6.75 (2H, m), 6.95 (1H, dd, J=8.4, 12.2 Hz), 7.15-7.30 (2H, m), 8.12 (1H, s).

Example 217

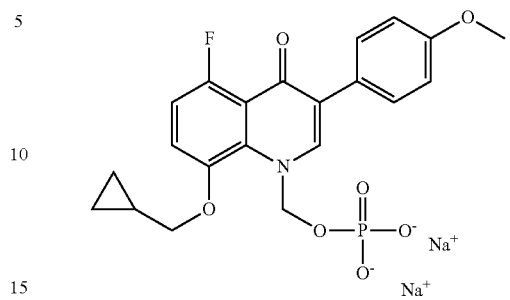

Production of [8-cyclopropylmethoxy-5-fluoro-3-(4-methoxyphenyl)-4-oxo-4H-quinolin-1-ylmethyl]monophosphate disodium salt The above compound was prepared in the same manner as in Example 25 using appropriate starting material.

Melting point: 202-204° C.

$^1$H-NMR (D$_2$O) δ ppm: 0.20-0.35 (2H, m), 0.40-0.60 (2H, m), 1.20-1.45 (1H, m), 3.73 (3H, s), 3.90 (2H, d, J=7.3 Hz), 6.09 (2H, d, J=9.2 Hz), 6.80-7.05 (3H, m), 7.21 (1H, dd, J=4.7, 9.0 Hz), 7.40 (2H, d, J=8.8 Hz), 8.15 (1H, s).

Example 218

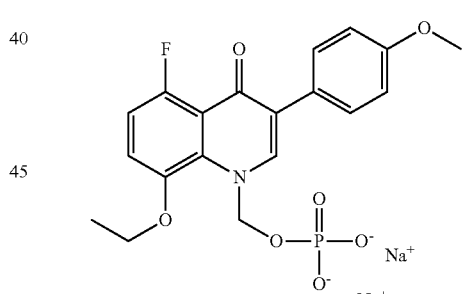

Production of [8-ethoxy-5-fluoro-3-(4-methoxyphenyl)-4-oxo-4H-quinolin-1-ylmethyl]monophosphate disodium salt The above compound was prepared in the same manner as in Example 25 using appropriate starting material.

Melting point: 206-208° C.

$^1$H-NMR (D$_2$O) δ ppm: 1.38 (3H, t, J=7.0 Hz), 3.73 (3H, s), 4.10 (2H, q, J=7.0 Hz), 6.01 (2H, d, J=8.4 Hz), 6.90-7.05 (3H, m), 7.19 (1H, dd, J=4.6, 8.9 Hz), 7.40 (2H, d, J=8.8 Hz), 8.13 (1H, s).

Example 219

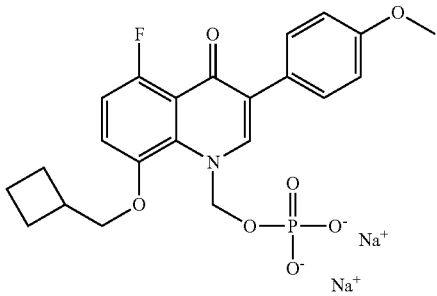

Production of [8-cyclobutylmethoxy-5-fluoro-3-(4-methoxyphenyl)-4-oxo-4H-quinolin-1-ylmethyl] monophosphate disodium salt The above compound was prepared in the same manner as in Example 25 using appropriate starting material.
Melting point: 205-207° C.
$^1$H-NMR (D$_2$O) δ ppm: 1.63-2.10 (6H, m), 2.75-3.00 (1H, m), 3.72 (3H, s), 4.00 (2H, d, J=7.2 Hz), 5.99 (2H, d, J=9.8 Hz), 6.90-7.05 (3H, m), 7.17 (1H, dd, J=4.7, 9.1 Hz), 7.40 (2H, d, J=8.7 Hz), 8.14 (1H, s).

Example 220

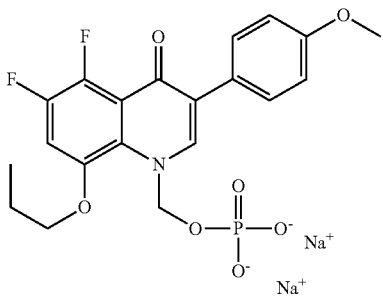

Production of [5,6-difluoro-3-(4-methoxyphenyl)-4-oxo-8-propoxy-4H-quinolin-1-ylmethyl]monophosphate disodium salt The above compound was prepared in the same manner as in Example 25 using appropriate starting material.
Melting point: 205-206° C.
$^1$H-NMR (D$_2$O) δ ppm: 0.94 (3H, d, J=7.5 Hz), 1.70-1.95 (2H, m), 3.73 (3H, s), 4.01 (2H, t, J=6.5 Hz), 6.02 (2H, d, J=9.1 Hz), 6.90-7.50 (5H, m), 8.16 (1H, s).

Example 221

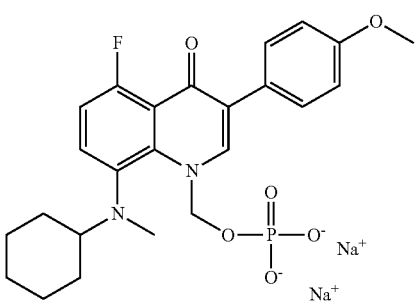

Production of [8-(cyclohexylmethylamino)-5-fluoro-3-(4-methoxyphenyl)-4-oxo-4H-quinolin-1-ylmethyl]monophosphate disodium salt The above compound was prepared in the same manner as in Example 25 using appropriate starting material.
Melting point: 196-198° C.
$^1$H-NMR (D$_2$O) δ ppm: 0.60-1.75 (10H, m), 2.40-2.60 (1H, m), 2.66 (3H, s), 3.73 (3H, s), 5.80 (1H, dd, J=7.7, 7.8 Hz), 6.80-7.05 (4H, m), 7.35-7.55 (3H, m), 8.18 (1H, s).

Example 222

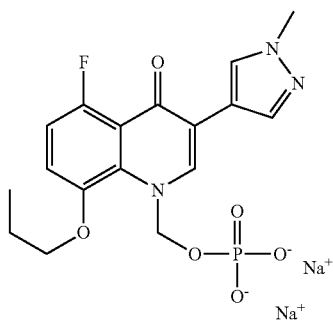

Production of [5-fluoro-3-(1-methyl-1H-pyrazol-4-yl)-4-oxo-8-propoxy-4H-quinolin-1-ylmethyl]monophosphate disodium salt The above compound was prepared in the same manner as in Example 25 using appropriate starting material.
Melting point: 212-214° C.
$^1$H-NMR (D$_2$O) δ ppm: 0.94 (3H, d, J=7.5 Hz), 1.70-1.90 (2H, m), 3.79 (3H, s), 3.93 (2H, t, J=6.7 Hz), 5.99 (2H, d, J=9.1 Hz), 6.92 (1H, dd, J=9.0, 12.3 Hz), 7.08 (1H, dd, J=4.7, 9.0 Hz), 7.86 (1H, s), 8.02 (1H, s), 8.30 (1H, s).

Example 223

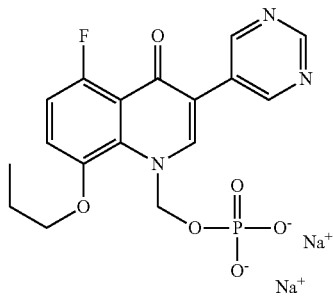

Production of (5-fluoro-4-oxo-8-propoxy-3-pyrimidin-5-yl-4H-quinolin-1-ylmethyl)monophosphate disodium salt The above compound was prepared in the same manner as in Example 25 using appropriate starting material.
Melting point: 205-207° C.
$^1$H-NMR (D$_2$O) δ ppm: 0.96 (3H, d, J=7.4 Hz), 1.70-1.95 (2H, m), 4.06 (2H, t, J=6.7 Hz), 6.10 (2H, d, J=9.6 Hz), 7.05 (1H, dd, J=8.9, 12.1 Hz), 7.29 (1H, dd, J=4.4, 8.9 Hz), 8.41 (1H, s), 8.94 (2H, s), 8.96 (1H, s).

Example 224

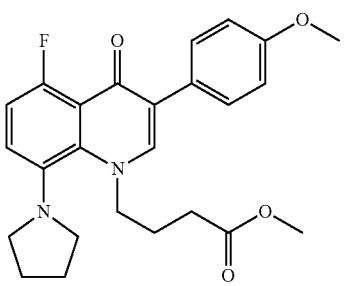

Production of ethyl 4-[5-fluoro-3-(4-methoxyphenyl)-4-oxo-8-pyrrolidin-1-yl-4H-quinolin-1-yl]butyrate The above compound was prepared in the same manner as in Example 31 using appropriate starting materials.

$^1$H-NMR (CDCl$_3$) δ ppm: 1.23-1.29 (3H, t, J=7.1 Hz), 1.70-1.78 (2H, m), 1.91-2.15 (6H, m), 2.52-2.87 (2H, m), 3.14-3.44 (2H, m), 4.00-4.08 (2H, q, J=6.1 Hz), 4.59-4.64 (2H, t, J=6.9 Hz), 6.87-7.03 (3H, m), 7.14-7.37 (1H, m), 7.51 (1H, s), 7.55-7.73 (2H, m).

Example 225

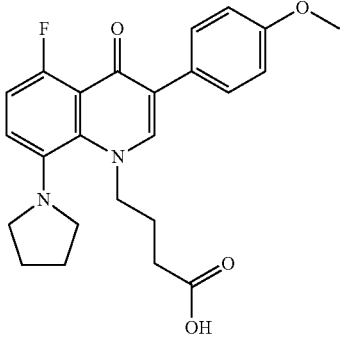

Production of 4-[5-fluoro-3-(4-methoxyphenyl)-4-oxo-8-pyrrolidin-1-yl-4H-quinolin-1-yl]butyric acid The above compound was prepared in the same manner as in Example 32 using appropriate starting material.

$^1$H-NMR (DMSO-d$_6$) δ ppm: 1.63-1.81 (2H, m), 1.87-2.14 (6H, m), 2.57-2.81 (2H, m), 3.14-3.39 (2H, m), 3.81 (3H, s), 4.61-4.66 (2H, t, J=6.8 Hz), 6.84-7.01 (3H, m), 7.25-7.30 (1H, m), 7.52-7.63 (3H, m).

Example 226

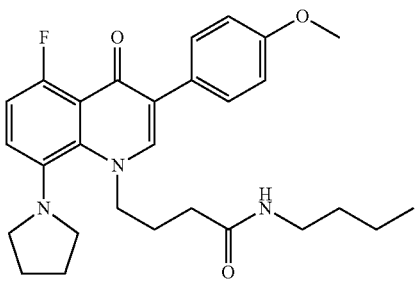

Production of N-butyl-4-[5-fluoro-3-(4-methoxyphenyl)-4-oxo-8-pyrrolidin-1-yl-4H-quinolin-1-yl]butylamide The above compound was prepared in the same manner as in Example 33 using appropriate starting materials.
Brown Amorphous $^1$H-NMR (CDCl$_3$) δ ppm: 0.82-0.88 (3H, t, J=7.1 Hz), 1.21-1.31 (4H, m), 1.74-1.77 (2H, m), 1.89-2.10 (2H, m), 2.60-2.80 (2H, m), 3.04-3.12 (2H, m), 3.20-3.45 (2H, m), 3.82 (3H, s), 4.58-4.63 (2H, m), 5.20-5.30 (1H, m), 6.88-6.94 (2H, m), 7.23-7.28 (1H, m), 7.52 (1H, s), 7.61-7.67 (2H, m).

Example 227

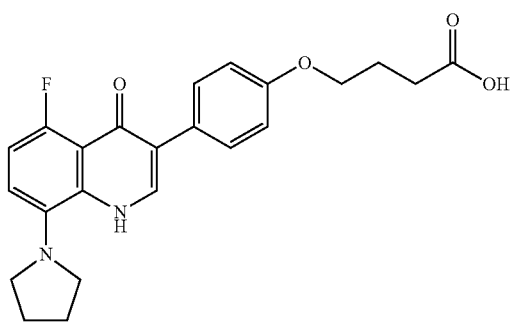

Production of 4-[4-(5-fluoro-4-oxo-8-pyrrolidin-1-yl-1,4-dihydroquinolin-3-yl)phenoxy]butyric acid The above compound was prepared in the same manner as in Example 32 using appropriate starting material.

$^1$H-NMR (DMSO-d$_6$) δ ppm: 1.80-2.00 (6H, m), 2.33-2.39 (2H, t, J=7.2 Hz), 3.00-3.05 (4H, m), 3.96-4.01 (2H, t, J=6.4 Hz), 6.84-6.93 (3H, m), 7.32-7.37 (1H, m), 7.50-7.53 (2H, d, J=8.7 Hz), 7.79 (1H, s), 10.95 (1H, s), 11.80-12.20 (1H, brs).

Example 228

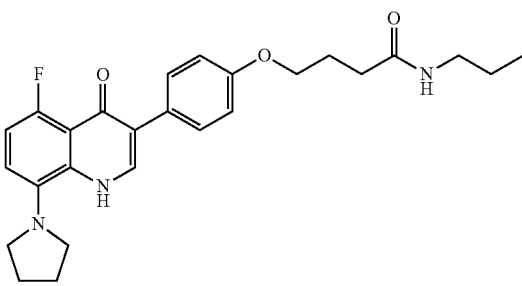

Production of N-butyl-4-[4-(5-fluoro-4-oxo-8-pyrrolidin-1-yl-1,4-dihydroquinolin-3-yl)phenoxy]butylamide The above compound was prepared in the same manner as in Example 33 using appropriate starting materials.
Pale Yellow Powder $^1$H-NMR (DMSO-d$_6$) δ ppm: 0.81-0.87 (3H, t, J=7.0 Hz), 1.19-1.40 (4H, m), 1.85-1.95 (6H, m), 2.19-2.25 (2H, t, J=7.2 Hz), 2.97-3.10 (6H, m), 3.93-3.98 (2H, t, J=6.3 Hz), 6.85-6.93 (3H, m), 7.34-7.39 (1H, m), 7.51-7.54 (2H, d, J=8.3 Hz), 7.75-7.83 (2H, m), 10.97 (1H, brs).

Example 229

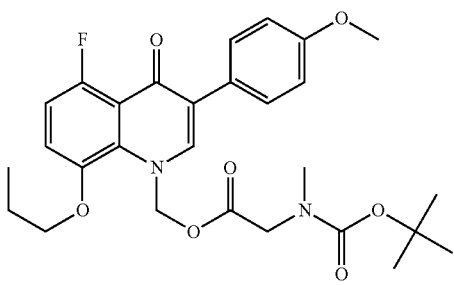

Production of 5-fluoro-3-(4-methoxyphenyl)-4-oxo-8-propoxy-4H-quinolin-1-ylmethyl(tert-butoxycarbonylmethylamino)acetate Sodium iodide (1.4 g, 0.9 mmol) and sodium hydride (60% oil base, 220 mg, 5.5 mmol) were added to a DMF solution (15 ml) of 5-fluoro-3-(4-methoxyphenyl)-8-propoxy-1H-quinolin-4-one (1.0 g, 3.0 mmol) and stirred at room temperature for 10 minutes. Chloromethyl(tert-butoxycarbonylmethylamino)acetate (2.52 g, 10.6 mmol) was added to the reaction mixture while ice-cooling, and then the mixture was stirred at room temperature for 3 hours. An aqueous sodium bicarbonate solution was added to the reaction mixture and then the mixture was subjected to extraction using ethyl acetate. The thus-obtained organic layer was dried over sodium sulfate, and then concentrated under reduced pressure. The residue was purified using silica gel column chromatography (n-hexane:ethyl acetate=2:1). The purified material was concentrated to dryness under reduced pressure, giving a pale yellow amorphous solid of 5-fluoro-3-(4-methoxyphenyl)-4-oxo-8-propoxy-4H-quinolin-1-ylmethyl(tert-butoxycarbonyl methylamino)acetate (290 mg, yield: 18%).

$^1$H-NMR (CDCl$_3$) δ ppm: 100-1.15 (3H, m), 1.29-1.44 (9H, s), 1.85-2.00 (2H, m), 2.88-2.90 (3H, s), 3.84 (3H, s), 3.90-4.15 (4H, m), 6.46-6.51 (2H, s), 6.90-7.15 (4H, m), 7.59 (2H, d, J=8.6 Hz), 7.74-7.79 (1H, s).

Example 230

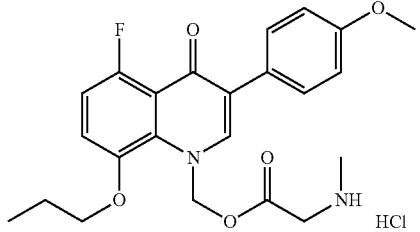

Production of 5-fluoro-3-(4-methoxyphenyl)-4-oxo-8-propoxy-4H-quinolin-1-ylmethyl methylaminoacetate hydrochloride A 4N hydrogen chloride ethylacetate solution (1 ml) was added to an ethyl acetate solution (2 ml) of 5-fluoro-3-(4-methoxyphenyl)-4-oxo-8-propoxy-4H-quinolin-1-ylmethyl(tert-butoxycarbonylmethylamino)acetate (100 mg, 0.19 mmol) and stirred at room temperature for 3 hours. The deposited insoluble matter was collected by filtration, washed with acetone, and then dried, giving a white powder of 5-fluoro-3-(4-methoxyphenyl)-4-oxo-8-propoxy-4H-quinolin-1-ylmethyl methylaminoacetate hydrochloride (78.3 mg, yield: 88%).

$^1$H-NMR (DMSO-d$_6$) δ ppm: 1.03 (3H, t, J=7.4 Hz), 1.80-1.90 (2H, m), 2.45-2.60 (3H, m), 3.79 (3H, s), 4.07 (2H, s), 4.10 (2H, t, J=6.6 Hz), 6.61 (2H, s), 6.99 (2H, d, J=8.9 Hz), 7.11 (1H, dd, J=9.1, 11.5 Hz), 7.39 (1H, dd, J=4.5, 9.1 Hz), 7.60 (2H, d, J=8.9 Hz), 8.17 (1H, s), 9.14 (2H, br).

Example 231

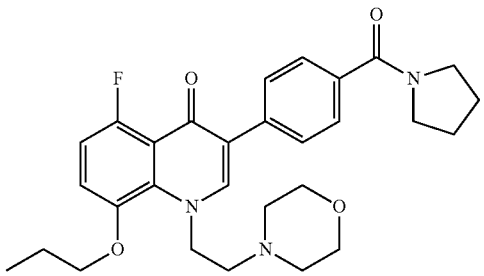

Production of 5-fluoro-1-(2-morpholin-4-ylethyl)-8-propoxy-3-[4-(pyrrolidine-1-carbonyl)phenyl]-1H-quinolin-4-one The above compound was prepared in the same manner as in Example 106 using appropriate starting material.

$^1$H-NMR (DMSO-d$_6$) δ ppm: 1.00 (3H, t, J=7.4 Hz), 1.77-1.88 (6H, m), 2.31-2.34 (4H, m), 2.58 (2H, t, J=5.4 Hz), 3.37-3.44 (8H, m), 4.04 (2H, t, J=6.5 Hz), 4.67 (2H, d, J=5.4 Hz), 7.01 (1H, dd, J=9.0 Hz, 11.6 Hz), 7.27 (1H, dd, J=4.5 Hz, 9.0 Hz), 7.52 (2H, d, J=8.3 Hz), 7.72 (2H, d, J=8.3 Hz), 8.05 (1H, s).

Example 232

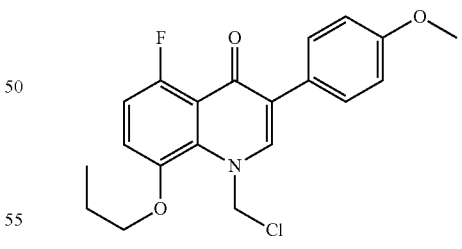

Production of 1-chloromethyl-5-fluoro-3-(4-methoxyphenyl)-8-propoxy-1H-quinolin-4-one A 4N hydrogen chloride ethylacetate solution (2 ml) was added to an ethyl acetate solution (3 ml) of di-tert-butyl 5-fluoro-3-(4-methoxyphenyl)-4-oxo-8-propoxy-4H-quinolin-1-ylmethyl phosphate (300 mg, 0.55 mmol) while ice-cooling and the mixture was stirred at room temperature for 2 hours. The deposited insoluble matter was collected by filtration and dried, giving a white powder of 1-chloromethyl-5-fluoro-3-(4-methoxyphenyl)-8-propoxy-1H-quinolin-4-one (18 mg, yield: 92%).

$^1$H-NMR (CDCl$_3$) δ ppm: 1.13 (3H, t, J=7.5 Hz), 1.70-2.10 (2H, m), 3.84 (3H, s), 4.11 (2H, t, J=6.6 Hz), 6.40 (2H, s), 6.90-7.05 (3H, m), 7.12 (1H, dd, J=4.5, 9.0 Hz), 7.51 (1H, s), 8.59 (2H, d, J=8.8 Hz).

Example 233

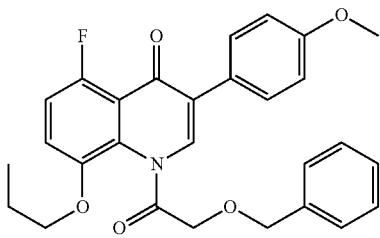

Production of 1-(2-benzyloxyacetyl)-5-fluoro-3-(4-methoxyphenyl)-8-propoxy-1H-quinolin-4-one Benzyloxyacetyl chloride (1.9 ml, 3 equivalent weight) was added to a dichloromethane solution (50 ml) of 4-(tert-butyldimethylsilyloxy)-5-fluoro-3-(4-methoxyphenyl)-8-propoxy-quinolin (1.5 g, 3.4 mmol) while ice-cooling and the mixture was stirred overnight at room temperature. An aqueous sodium bicarbonate solution was added to the reaction mixture, followed by extraction using ethyl acetate. The thus-obtained organic layer was dried over sodium sulfate, and then concentrated under reduced pressure. The residue was purified using silica gel column chromatography (n-hexane: ethyl acetate=2:1). The purified product was concentrated under reduced pressure, giving a colorless oily substance of 1-(2-benzyloxyacetyl)-5-fluoro-3-(4-methoxyphenyl)-8-propoxy-1H-quinolin-4-one (250 mg, yield: 15%).

$^1$H-NMR (CDCl$_3$) δ ppm: 1.00 (3H, t, J=7.4 Hz), 1.70-1.90 (2H, m), 3.84 (3H, s), 3.95 (2H, t, J=6.4 Hz), 4.38 (2H, s), 4.52 (2H, s), 6.94 (2H, d, J=8.8 Hz), 6.95-7.40 (7H, m), 7.57 (2H, d, J=8.8 Hz), 7.92 (1H, s).

Example 234

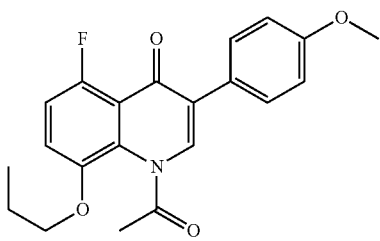

Production of 1-acetyl-5-fluoro-3-(4-methoxyphenyl)-8-propoxy-1H-quinolin-4-one

The above compound was prepared in the same manner as in Example 233 using appropriate starting material.

$^1$H-NMR (CDCl$_3$) δ ppm: 1.05 (3H, t, J=7.5 Hz), 1.80-2.00 (2H, m), 2.41 (3H, s), 3.83 (3H, s), 4.02 (2H, t, J=5.7 Hz), 6.95 (2H, d, J=8.9 Hz), 7.00-7.15 (2H, m), 7.59 (2H, d, J=8.9 Hz), 8.02 (1H, s).

Example 235

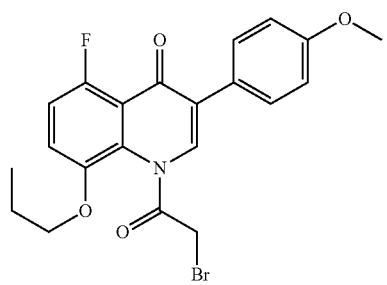

Production of 1-(2-bromoacetyl)-5-fluoro-3-(4-methoxyphenyl)-8-propoxy-1H-quinolin-4-one The above compound was prepared in the same manner as in Example 233 using appropriate starting material.

$^1$H-NMR (CDCl$_3$) δ ppm: 0.95-1.15 (3H, m), 1.70-2.05 (2H, m), 3.80-4.20 (7H, m), 6.50-8.00 (7H, m).

Example 236

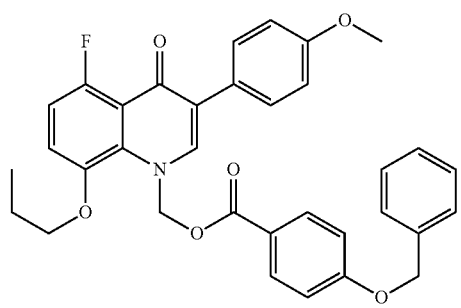

Production of 5-fluoro-3-(4-methoxyphenyl)-4-oxo-8-propoxy-4H-quinolin-1-ylmethyl 4-benzyloxybenzoate The above compound was prepared in the same manner as in Example 229 using appropriate starting material.

$^1$H-NMR (CDCl$_3$) δ ppm: 1.06 (3H, t, J=7.4 Hz), 1.80-2.00 (2H, m), 3.84 (3H, s), 4.08 (2H, t, J=6.7 Hz), 5.11 (2H, s), 6.62 (2H, s), 6.90-7.15 (6H, m), 7.30-7.45 (5H, m), 7.62 (2H, d, J=8.9 Hz), 7.84 (1H, s), 7.94 (2H, d, J=8.9 Hz).

Example 237

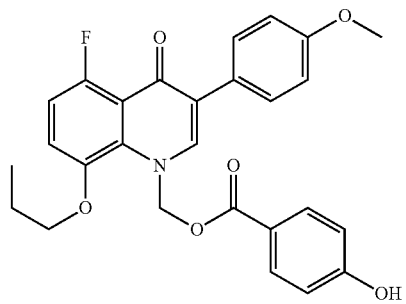

Production of 5-fluoro-3-(4-methoxyphenyl)-4-oxo-8-propoxy-4H-quinolin-1-ylmethyl 4-hydroxybenzoate 10% palladium/carbon (260 mg) was added to a THF (30 ml) and ethanol (15 ml) solution of 5-fluoro-3-(4-methoxyphenyl)-4-oxo-8-propoxy-4H-quinolin-1-ylmethyl 4-benzyloxybenzoate (2.6 g, 4.6 mmol). The mixture was subjected to hydrogen substitution and stirred at room temperature for 3 hours. After completion of the reaction, the catalyst was removed by conducting filtration using Celite, and the mixture was concentrated to dryness under reduced pressure, giving a pale yellow powder of 5-fluoro-3-(4-methoxyphenyl)-4-oxo-8-propoxy-4H-quinolin-1-ylmethyl 4-hydroxybenzoate (2.22 g, yield: quantitative).

$^1$H-NMR (CDCl$_3$) δ ppm: 1.06 (3H, t, J=7.4 Hz), 1.80-2.00 (2H, m), 3.81 (3H, s), 4.08 (2H, t, J=6.7 Hz), 6.63 (2H, s), 6.42 (2H, d, J=8.8 Hz), 6.90-7.00 (3H, m), 7.10 (1H, dd, J=4.4, 9.0 Hz), 7.22 (1H, br), 7.58 (2H, d, J=8.8 Hz), 7.83 (2H, d, J=8.8 Hz), 7.88 (1H, s).

Example 238

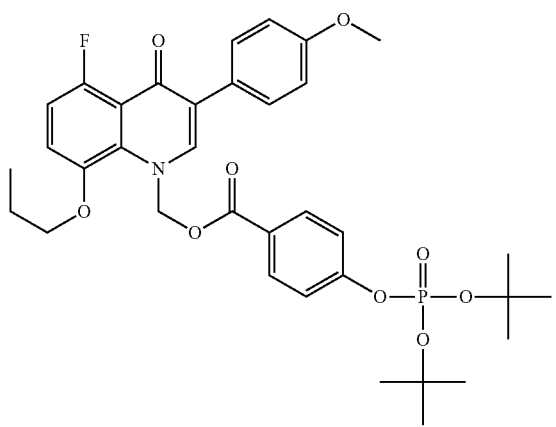

Production of 5-fluoro-3-(4-methoxyphenyl)-4-oxo-8-propoxy-4H-quinolin-1-ylmethyl 4-(di-tert-butylphosphonooxy)benzoate 5-Fluoro-3-(4-methoxyphenyl)-4-oxo-8-propoxy-4H-quinolin-1-ylmethyl 4-hydroxybenzoate (2.2 g, 4.6 mmol) was suspended in acetone (50 ml). Tetrasol (420 mg) and di-tert-butyl diisopropyl phosphoramidite (1.9 ml) were added thereto and the resulting suspension was stirred at room temperature for 2 hours. The reaction mixture was ice-cooled, and an aqueous 30% hydrogen peroxide solution (2.9 ml) was added thereto, followed by stirring at the same temperature for 2 hours. An aqueous sodium thiosulphate solution and an aqueous sodium bicarbonate solution were added to the reaction mixture. The resulting mixture was stirred and then concentrated under reduced pressure. Water was added to the residue, followed by extraction using ethyl acetate. The thus-obtained organic layer was washed with an aqueous saturated sodium chloride solution, dried over sodium sulfate, and then concentrated under reduced pressure. The residue was purified using silica gel column chromatography (n-hexane:ethyl acetate=100:1→2:1). The purified material was concentrated to dryness under reduced pressure, giving a white amorphous solid of 5-fluoro-3-(4-methoxyphenyl)-4-oxo-8-propoxy-4H-quinolin-1-ylmethyl 4-(di-tert-butylphosphonooxy)benzoate (2.51 g, yield: 81%).

$^1$H-NMR (CDCl$_3$) δ ppm: 1.06 (3H, t, J=7.4 Hz), 1.50 (18H, s), 1.80-2.00 (2H, m), 3.84 (3H, s), 4.08 (2H, t, J=6.7 Hz), 6.63 (2H, s), 6.90-7.00 (3H, m), 7.10 (1H, dd, J=4.4, 9.0 Hz), 7.26 (2H, d, J=8.5 Hz), 7.62 (2H, d, J=8.7 Hz), 7.83 (1H, s), 7.97 (2H, d, J=8.5 Hz).

Example 239

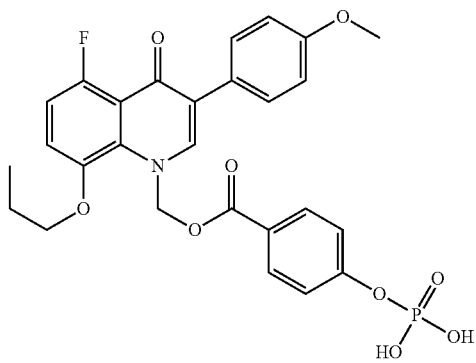

Production of 5-fluoro-3-(4-methoxyphenyl)-4-oxo-8-propoxy-4H-quinolin-1-ylmethyl 4-phosphonoxybenzoate Trifluoro-acetic acid (2 ml) was added to a dichloromethane solution (10 ml) of 5-fluoro-3-(4-methoxyphenyl)-4-oxo-8-propoxy-4H-quinolin-1-ylmethyl 4-(di-tert-butylphosphonooxy)benzoate (500 mg) while ice-cooling, and then the mixture was stirred at the same temperature for 1 hour. The resulting mixture was concentrated under reduced pressure at a bath temperature of not higher than 30° C. The residue was recrystallized from ethyl acetate-n-hexane, giving a pale yellow powder of 5-fluoro-3-(4-methoxyphenyl)-4-oxo-8-propoxy-4H-quinolin-1-ylmethyl 4-phosphonoxybenzoate (406.7 mg, yield: 98%).

$^1$H-NMR (DMSO-d$_6$) δ ppm: 0.93 (3H, t, J=7.4 Hz), 1.60-1.85 (2H, m), 3.79 (3H, s), 4.06 (2H, t, J=6.5 Hz), 6.64 (2H, s), 6.98 (2H, d, J=8.8 Hz), 7.09 (1H, dd, J=9.1, 11.5 Hz), 7.27 (2H, d, J=8.7 Hz), 7.37 (1H, dd, J=4.4, 9.1 Hz), 7.62 (2H, d, J=8.8 Hz), 7.92 (2H, d, J=8.7 Hz), 8.38 (1H, s).

Example 240

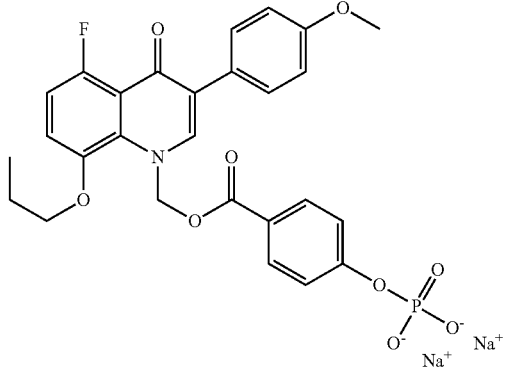

Production of 5-fluoro-3-(4-methoxyphenyl)-4-oxo-8-propoxy-4H-quinolin-1-ylmethyl 4-phosphonoxybenzoate disodium salt 5-Fluoro-3-(4-methoxyphenyl)-4-oxo-8-propoxy-4H-quinolin-1-ylmethyl 4-phosphonoxybenzoate (397 mg) was suspended in isopropyl alcohol (10 ml) while ice-cooling. A 1N aqueous sodium hydroxide solution (1.5 ml) was added thereto and the suspension was stirred at the same temperature for 1 hour. The deposited insoluble matter was collected by filtration and recrystallized from acetone-water, giving a white powder of 5-fluoro-3-(4-methoxyphenyl)-4-oxo-8-propoxy-4H-quinolin-1-ylmethyl 4-phosphonoxybenzoate disodium salt (338.6 mg).

Melting point: 205-207° C.
$^1$H-NMR (D$_2$O) δ ppm: 0.81 (3H, t, J=7.4 Hz), 1.50-2.00 (2H, m), 3.60 (3H, s), 3.89 (2H, t, J=6.7 Hz), 6.30 (2H, s), 6.68 (2H, d, J=8.7 Hz), 6.92 (1H, dd, J=9.1, 12.1 Hz), 7.05-7.20 (5H, m), 7.75 (2H, d, J=8.9 Hz), 7.79 (1H, s).

Example 241

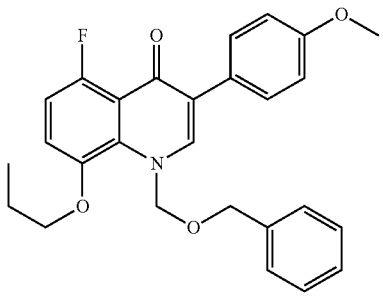

Production of 1-benzyloxymethyl-5-fluoro-3-(4-methoxyphenyl)-8-propoxy-1H-quinolin-4-one The above compound was prepared in the same manner as in Example 229 using appropriate starting material.
$^1$H-NMR (CDCl$_3$) δ ppm: 1.06 (3H, t, J=7.5 Hz), 1.75-2.00 (2H, m), 3.84 (3H, s), 4.00 (2H, t, J=6.6 Hz), 4.44 (2H, s), 5.92 (2H, s), 6.90-7.40 (9H, m), 7.59 (2H, d, J=8.8 Hz), 7.76 (1H, s).

Example 242

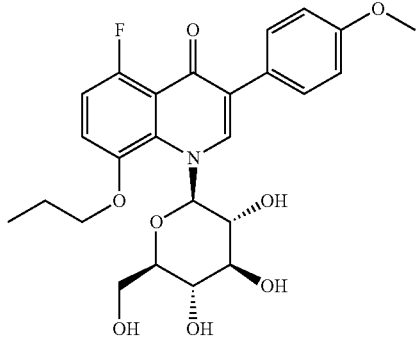

Production of 5-fluoro-3-(4-methoxyphenyl)-8-propoxy-1-((2R,3R,4S,5S,6R)-3,4,5-trihydroxy-6-hydroxymethyltetrahydro-pyran-2-yl)-1H-quinolin-4-one 1-Bromo-2,3,4,6-tetra-O-acetyl-α-D-glucopyranosyl (17.0 g, 41.3 mmol), benzyltri-n-butylammonium bromide (1.3 g, 4.16 mmol), potassium carbonate (14.37 g, 104 mmol) and water (0.45 ml) were sequentially added in this order to a chloroform solution (90 ml) of 5-fluoro-3-(4-methoxyphenyl)-8-propoxy-1H-quinolin-4-one (6.75 g, 20.6 mmol). Chloroform (27 ml) was added to the resulting reaction mixture and the mixture was then stirred at room temperature for 39 hours. 2N hydrochloric acid (80 ml) was added to the thus-obtained mixture while ice-cooling, followed by extraction with dichloromethan. The thus-obtained organic layer was washed with an aqueous saturated sodium chloride solution and then concentrated under reduced pressure. The residue was purified using silica gel column chromatography (dichloromethane:ethyl acetate=30:1→4:1). The purified product was concentrated under reduced pressure. The residue was dissolved in ethanol (100 ml), and an aqueous solution (8.16 ml) of potassium hydroxide (5.44 g) was added thereto, followed by stirring at room temperature for 3 hours. The resulting reaction mixture was concentrated under reduced pressure. 2N hydrochloric acid (20.4 ml) was added to the residue, and extraction was conducted using ethyl acetate. The thus-obtained organic layer was washed with an aqueous saturated sodium chloride solution and then concentrated under reduced pressure. The residue was purified using silica gel column chromatography (dichloromethane:methanol=50:1→20:1→ethyl acetate:methanol=30:1). The purified product was concentrated under reduced pressure, and the residue was then recrystallized from ethyl acetate, giving a white powder of 5-fluoro-3-(4-methoxyphenyl)-8-propoxy-1-((2R,3R,4S,5S,6R)-3,4,5-trihydroxy-6-hydroxymethyltetrahydropyran-2-yl)-1H-quinolin-4-one (0.38 g).
$^1$H-NMR (DMSO-d$_6$) δ ppm: 1.03 (3H, t, J=7.3 Hz), 1.79-1.88 (2H, m), 3.24-3.41 (3H, m), 3.54-3.70 (3H, m), 3.76 (3H, s), 3.96-4.11 (2H, m), 4.69 (1H, t, J=5.5 Hz), 5.14-5.16 (2H, m), 5.33 (1H, d, J=5.4 Hz), 6.51 (1H, d, J=8.9 Hz), 6.94-7.05 (3H, m), 7.29 (1H, dd, J=4.5 Hz, 9.1 Hz), 7.54 (2H, d, J=8.8 Hz), 7.99 (1H, s).

Example 243

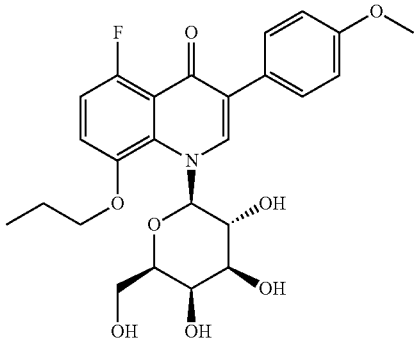

Production of 5-fluoro-3-(4-methoxyphenyl)-8-propoxy-1-((2R,3R,4S,5R,6R)-3,4,5-trihydroxy-6-hydroxymethyl tetrahydropyran-2-yl)-1H-quinolin-4-one The above compound was prepared in the same manner as in Example 242 using appropriate starting material.
$^1$H-NMR (DMSO-d$_6$) δ ppm: 1.03 (3H, t, J=7.3 Hz), 1.81-1.89 (2H, m), 3.30-3.40 (1H, m), 3.57-3.58 (3H, m), 3.71-3.75 (2H, m), 3.77 (3H, s), 3.96-4.12 (2H, m), 4.67-4.76 (2H, m), 4.91 (1H, d, J=5.7 Hz), 5.17 (1H, d, J=5.4 Hz), 6.43 (1H, d, J=8.8 Hz), 6.96-7.05 (3H, m), 7.28 (1H, dd, J=4.5 Hz, 9.1 Hz), 7.52 (2H, d, J=8.8 Hz), 8.05 (1H, s).

Example 244

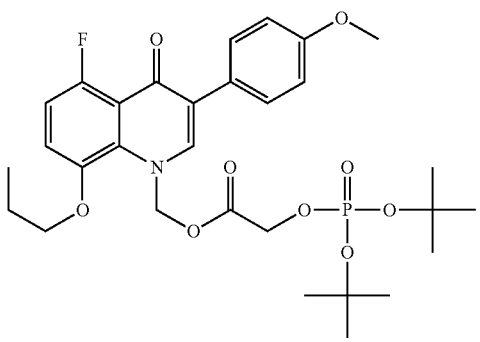

Production of 5-fluoro-3-(4-methoxyphenyl)-4-oxo-8-propoxy-4H-quinolin-1-ylmethyl (di-tert-butylphosphonooxy)acetate The above compound was prepared in the same manner as in Example 23 using appropriate starting materials.

¹H-NMR (CDCl₃) δ ppm: 1.09 (3H, t, J=7.4 Hz), 1.44 (18H, s), 1.80-2.00 (2H, m), 3.84 (3H, s), 4.06 (2H, t, J=6.7 Hz), 4.53 (2H, d, J=8.9 Hz), 6.51 (2H, s), 6.90-7.00 (3H, m), 7.08 (1H, dd, J=4.5, 9.0 Hz), 7.59 (2H, d, J=8.9 Hz), 7.73 (1H, s).

Example 245

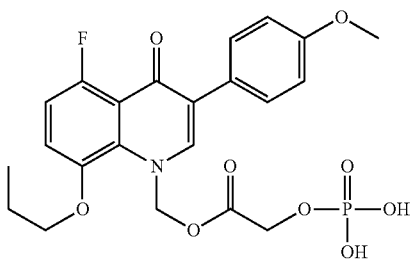

Production of 5-fluoro-3-(4-methoxyphenyl)-4-oxo-8-propoxy-4H-quinolin-1-ylmethyl phosphonoxyacetate The above compound was prepared in the same manner as in Example 239 using appropriate starting material.

¹H-NMR (DMSO-d₆) δ ppm: 1.00 (3H, d, J=7.4 Hz), 1.65-1.90 (2H, m), 3.79 (3H, s), 4.07 (2H, t, J=6.6 Hz), 4.45 (2H, d, J=9.0 Hz), 6.49 (2H, s), 6.98 (2H, d, J=8.9 Hz), 7.09 (1H, dd, J=9.1, 11.5 Hz), 7.36 (1H, dd, J=4.4, 9.1 Hz), 7.59 (2H, d, J=8.9 Hz), 8.16 (1H, s).

Example 246

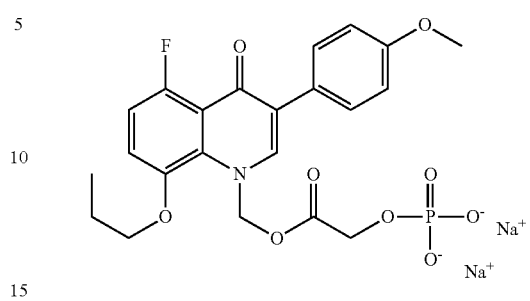

Production of 5-fluoro-3-(4-methoxyphenyl)-4-oxo-8-propoxy-4H-quinolin-1-ylmethyl phosphonoxyacetate disodium salt The above compound was prepared in the same manner as in Example 25 using appropriate starting material.

Melting point: 160-162° C.

¹H-NMR (D₂O) δ ppm: 0.84 (3H, d, J=7.4 Hz), 1.55-1.70 (2H, m), 3.61 (3H, s), 3.86 (2H, t, J=6.6 Hz), 4.25 (2H, d, J=6.9 Hz), 6.26 (2H, s), 6.73 (2H, d, J=8.7 Hz), 6.88 (1H, dd, J=9.2, 12.1 Hz), 7.08 (1H, dd, J=4.5, 9.2 Hz), 7.18 (2H, d, J=8.7 Hz), 7.78 (1H, s).

Example 247

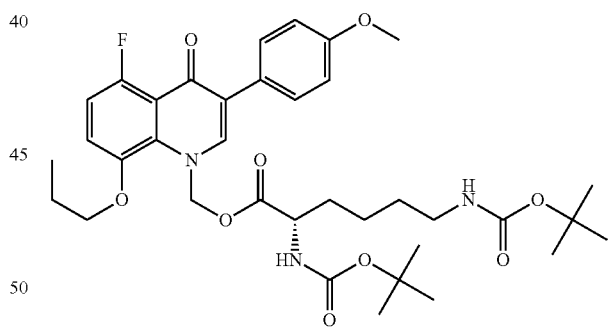

Production of 5-fluoro-3-(4-methoxyphenyl)-4-oxo-8-propoxy-4H-quinolin-1-ylmethyl(S)-2,6-bis-tert-butoxycarbonylaminohexanate The above compound was prepared in the same manner as in Example 229 using appropriate starting material.

¹H-NMR (CDCl₃) δ ppm: 1.10 (3H, t, J=7.4 Hz), 1.20-1.75 (24H, m), 1.80-2.00 (2H, m), 2.85-3.10 (2H, m), 3.84 (3H, s), 4.07 (2H, t, J=6.6 Hz), 4.15-4.30 (1H, m), 4.45-4.65 (1H, m), 5.00-5.25 (1H, m), 6.48 (2H, s), 6.90-7.05 (3H, m), 7.10 (1H, dd, J=4.5, 9.0 Hz), 7.59 (2H, d, J=8.8 Hz), 7.74 (1H, s).

Example 248

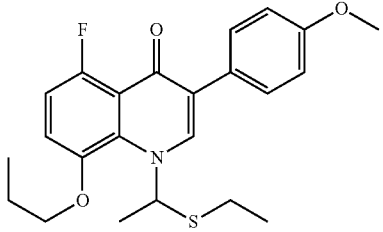

Production of 1-(1-ethylsulfanylethyl)-5-fluoro-3-(4-methoxyphenyl)-8-propoxy-1H-quinolin-4-one The above compound was prepared in the same manner as in Example 229 using appropriate starting materials.

$^1$H-NMR (CDCl$_3$) δ ppm: 1.08 (3H, t, J=7.3 Hz), 1.12 (3H, t, J=7.3 Hz), 1.79 (3H, d, J=6.7 Hz), 1.90-2.00 (2H, m), 2.30 (1H, q, J=7.3 Hz), 2.33 (1H, q, J=7.3 Hz), 3.85 (3H, s), 4.00 (1H, td, J=6.7, 8.9 Hz), 4.12 (1H, td, J=6.7, 8.9 Hz), 6.80-7.10 (5H, m), 7.66 (2H, d, J=8.8 Hz), 8.29 (1H, s).

Example 249

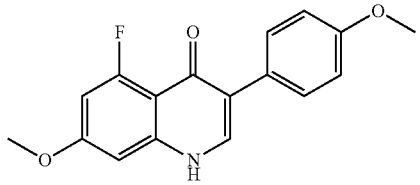

Production of 5-fluoro-7-methoxy-3-(4-methoxyphenyl)-1H-quinolin-4-one

The above compound was prepared in the same manner as in Example 1 using appropriate starting material.

$^1$H-NMR (DMSO-d$_6$) δ ppm: 3.76 (3H, s), 3.83 (3H, s), 6.65 (1H, d, J=13.6 Hz), 6.76 (1H, s), 6.92 (2H, d, J=8.8 Hz), 7.54 (2H, d, J=8.8 Hz), 7.90 (1H, d, J=5.8 Hz), 11.75 (1H, brs).

Example 250

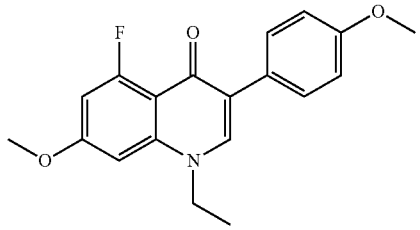

Production of 1-ethyl-5-fluoro-7-methoxy-3-(4-methoxyphenyl)-1H-quinolin-4-one

The above compound was prepared in the same manner as in Example 3 using appropriate starting materials.

$^1$H-NMR (DMSO-d$_6$) δ ppm: 1.33 (3H, t, J=6.9 Hz), 3.75 (3H, s), 3.89 (3H, s), 4.27 (2H, q, J=7.0 Hz), 6.74 (1H, d, J=13.7 Hz), 6.82 (1H, s), 6.92 (2H, d, J=8.7 Hz), 7.55 (2H, d, J=8.7 Hz), 8.04 (1H, s).

Example 251

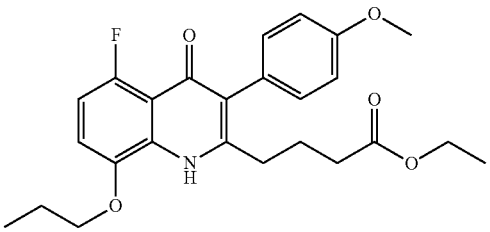

Production of ethyl 4-[5-fluoro-3-(4-methoxyphenyl)-4-oxo-8-propoxy-1,4-dihydroquinolin-2-yl]butyrate The above compound was prepared in the same manner as in Example 2 using appropriate starting materials.
White Powder (Ethyl Acetate)
Melting point: 177-179° C.

$^1$H-NMR (DMSO-d$_6$) δ ppm: 1.00 (3H, t, J=7.4 Hz), 1.06 (3H, t, J=7.1 Hz), 1.67-1.88 (4H, m), 2.16 (2H, t, J=7.4 Hz), 2.58 (2H, t, J=7.0 Hz), 3.76 (3H, s), 3.90 (2H, q, J=7.1 Hz), 4.14 (2H, t, J=6.6 Hz), 6.81-6.94 (3H, m), 7.06 (2H, d, J=8.6 Hz), 7.15 (1H, dd, J=4.0 Hz, 8.8 Hz), 10.40 (1H, brs).

Example 252

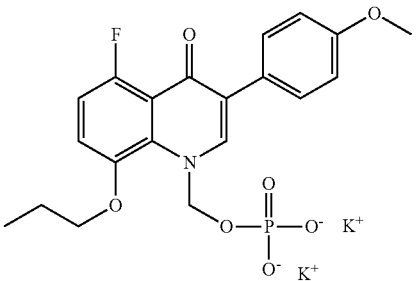

Production of [5-fluoro-3-(4-methoxyphenyl)-4-oxo-8-propoxy-4H-quinolin-1-ylmethyl]monophosphate dipotassium salt

[5-Fluoro-3-(4-methoxyphenyl)-4-oxo-8-propoxy-4H-quinolin-1-ylmethyl]monophosphate (800 mg, 1.83 mmol) was suspended in isopropyl alcohol (30 ml). A 1N-potassium hydroxide aqueous solution (3.66 ml, 3.66 mmol) was added thereto at 0° C. The resulting mixture was stirred at 0° C. for 1.5 hours. The generated insoluble matter was collected by filtration, recrystallized from acetone-water and then dried, giving a white powder of [5-fluoro-3-(4-methoxyphenyl)-4-oxo-8-propoxy-4H-quinolin-1-ylmethyl]monophosphate dipotassium salt (445 mg, yield: 47%).

Melting point: 184-186° C.

$^1$H-NMR (D$_2$O) δ ppm: 0.97 (3H, t, J=7.4 Hz), 1.79-1.88 (2H, m), 3.76 (3H, s), 4.01 (2H, t, J=6.7 Hz), 6.05 (2H, d, J=9.1 Hz), 6.93-7.01 (3H, m), 7.19 (1H, dd, J=4.6, 9.1 Hz), 7.43 (2H, d, J=8.8 Hz), 8.16 (1H, s).

Example 253

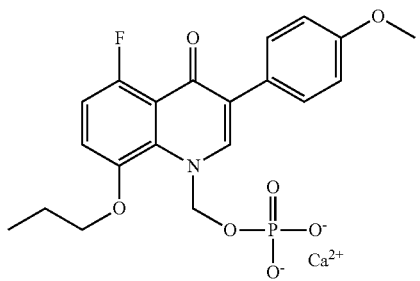

Production of [5-fluoro-3-(4-methoxyphenyl)-4-oxo-8-propoxy-4H-quinolin-1-ylmethyl]monophosphate calcium salt

[5-Fluoro-3-(4-methoxyphenyl)-4-oxo-8-propoxy-4H-quinolin-1-ylmethyl]monophosphate disodium salt (800 mg, 1.66 mmol) was dissolved in water (4 ml). A calcium chloride (202 mg, 1.82 mmol) aqueous solution (1 ml) was added thereto at room temperature. The deposited solid was collected by filtration, washed with water and acetone, and then dried, giving a white powder of [5-fluoro-3-(4-methoxyphenyl)-4-oxo-8-propoxy-4H-quinolin-1-ylmethyl]monophosphate calcium salt (690 mg, yield: 87%).

Melting point: 255-258° C. (Decomposed)

$^1$H-NMR (DMSO-d$_6$, 80° C.) δ ppm: 0.79-0.89 (3H, m), 1.68-1.76 (2H, m), 3.62 (3H, s), 3.91-4.01 (2H, m), 6.09-6.16 (2H, m), 6.74-6.90 (3H, m), 7.09-7.15 (1H, m), 7.40-7.70 (2H, m), 8.32 (1H, s).

Example 254

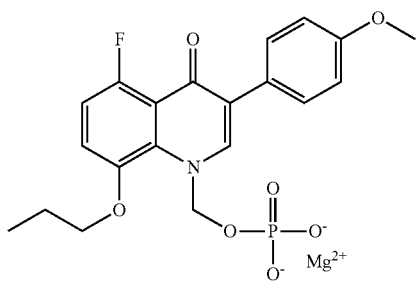

Production of [5-fluoro-3-(4-methoxyphenyl)-4-oxo-8-propoxy-4H-quinolin-1-ylmethyl]monophosphate magnesium salt

[5-Fluoro-3-(4-methoxyphenyl)-4-oxo-8-propoxy-4H-quinolin-1-ylmethyl]monophosphate disodium salt (1.0 g, 2.07 mmol) was suspended in methanol (10 ml). A methanol solution (4.3 ml) of magnesium chloride (198 mg, 2.08 mmol) was added thereto at room temperature. The resulting mixture was stirred at room temperature for 20 minutes. The solid deposited after condensation was collected by filtration, washed with water and acetone, and then dried, giving a white powder of [5-fluoro-3-(4-methoxyphenyl)-4-oxo-8-propoxy-4H-quinolin-1-ylmethyl]monophosphate magnesium salt (845 mg, yield: 88%).

Melting point: 265-269° C. (Decomposed)

$^1$H-NMR (DMSO-d$_6$, 80° C.) δ ppm: 0.99 (3H, t, J=7.4 Hz), 1.76-1.86 (2H, m), 3.64 (3H, s), 4.05 (2H, t, J=6.5 Hz), 6.09 (2H, d, J=10.4 Hz), 6.80-6.98 (3H, m), 7.24 (1H, dd, J=4.6, 8.6 Hz), 7.58 (2H, d, J=8.7 Hz), 8.00 (1H, s).

Pharmacological Test Example 1

Evaluation of the Improvement of Mitochondrial Dysfunction Using Human Neuroblastoma Cell Lines SH-SY5Y Treated with 1-methyl-4-phenylpyridinium (MPP$^+$)

In human neuroblastoma cell lines SH-SY5Y in which mitochondrial activity was injured by MPP$^+$ treatment (Bollimuntha S. et al., J Biol Chem, 280, 2132-2140 (2005) and Shang T. et al., J Biol Chem, 280, 34644-34653 (2005)), the improvement of mitochondrial dysfunction was evaluated on the basis of measurement values for mitochondrial oxidation reduction activity using Alamar Blue fluorescent dye after the compound addition (Nakai M. et al, Exp Neurol, 179, 103-110 (2003)).

The human neuroblastoma cell lines SH-SY5Y were cultured in Dulbecco's Modified Eagle's Medium containing 10% fetal bovine serum (DMEM containing 50 units/ml penicillin and 50 μg/ml streptomycin as antibiotics) at 37° C. in the presence of 5% carbon dioxide. Cells were scattered on a poly-D-lysine-coated 96-well black plate at a concentration of 3-6×10$^4$ cells/cm$^2$ (medium amount: 100 μl/well), and cultured in the above medium for two days. Further, the medium was changed to DMEM containing a 1% N2 supplement (N2-DMEM) or to a medium (100 μl/well) in which 1.5 mM MPP$^+$ was dissolved. The cells were cultured therein for 39 to 48 hours, and then subjected to a mitochondrial oxidation reduction activity measurement system. A sample compound that had been previously dissolved in dimethyl sulfoxide (DMSO) was diluted with N2-DMEM, and added in a volume of 10 μl/well 24 hours before the activity measurement (final compound concentration: 0.01 to 1 μg/ml).

After removal of the medium by suction, a balanced salt solution containing 10% Alamar Blue (154 mM sodium chloride, 5.6 mM potassium chloride, 2.3 mM calcium chloride, 1.0 mM magnesium chloride, 3.6 mM sodium bicarbonate, 5 mM glucose, 5 mM HEPES, pH 7.2) was added in a volume of 100 μl/well, and reacted in an incubator at 37° C. for 1 hour. The fluorescent intensity was detected using a fluorescence detector (a product of Hamamatsu Photonics K.K., excitation wavelength 530 nm, measurement wavelength 580 nm) to thereby measure the mitochondrial oxidation reduction activity.

The fluorescent intensity of the well of the cells cultured in a medium containing MPP$^+$ and in each of the sample compounds was relatively evaluated based on the 100% fluorescent intensity of the well of the cells cultured in a medium containing DMSO alone (final concentration: 0.1%). When the MPP$^+$-induced cell groups exhibited higher florescent intensity than the cell groups cultured in DMSO alone, the test compound was judged to have improved the activity of the mitochondrial dysfunction.

TABLE 1

Evaluation of the improvement of mitochondrial dysfunction using human neuroblastoma cell lines SH-SY5Y treated with 1-methyl-4-phenylpyridinium (MPP$^+$)

| Test Compound | Fluorescence Intensity (%) | | | | | |
|---|---|---|---|---|---|---|
| Concentration (μg/ml) | 0 | 0.01 | 0.03 | 0.1 | 0.3 | 1 |
| Compound of Example 7 | 51 | 66 | 71 | 78 | 80 | 75 |
| Compound of Example 12 | 48 | 80 | 74 | 83 | 82 | 68 |
| Compound of Example 36 | 46 | 69 | 67 | 86 | 90 | 89 |
| Compound of Example 48 | 46 | 60 | 81 | 92 | 93 | 80 |
| Compound of Example 57 | 59 | 64 | 65 | 68 | 74 | 65 |
| Compound of Example 69 | 48 | 78 | 64 | 68 | 67 | 65 |
| Compound of Example 139 | 45 | 53 | 58 | 57 | 60 | 55 |
| Compound of Example 161 | 41 | 59 | 55 | 67 | 71 | 66 |
| Compound of Example 163 | 43 | 61 | 61 | 63 | 60 | 63 |
| Compound of Example 171 | 49 | 61 | 61 | 65 | 67 | 68 |
| Compound of Example 212 | 36 | 46 | 62 | 63 | 70 | 72 |
| Compound of Example 222 | 46 | 59 | 64 | 66 | 62 | 73 |

Pharmacological Test 2

Evaluation of Dopaminergic Neuronal Protective Activity Using C57BL/6 Mouse Treated with 1-methyl-4-phenyl 1,2,3,6-tetrahydro Pyridine (MPTP)

Using a mouse having MPTP-induced dopaminergic neurons (Chan P. et al., J Neurochem, 57, 348-351 (1991)), the dopamine neuroprotective activity was evaluated based on dopamine contents and protein levels of tyrosine hydroxylase (TH) and dopamine transporter (DAT) (i.e., dopaminergic neuronal marker proteins) in the brain corpus striatum region after the compound administration (Mori A. et al., Neurosci Res, 51, 265-274 (2005)). A male C57BL/6 mouse (provided by Japan Charles River Inc., 10 to 12 weeks) was used as a test animal. MPTP was dissolved in a physiological salt solution so that the concentration became 4 mg/ml, and then administered to the mouse subcutaneously in a volume of 10 ml/kg. The test compound was suspended in a 5% gum arabic/physiological salt solution (w/v) so that a compound having a concentration of 1 mg/ml could be obtained. Each of the test compounds or solvents thereof was orally administered to the mouse after 30 minutes, 24 hours, and 48 hours of the MPTP administration. The mouse was decapitated after 72 hours of the MPTP administration, the brain was removed, and each side of the striatum was dissected.

The left striatum was used as a sample to detect the protein levels by Western blot analysis. Each tissue was homogenized in a HEPES buffer sucrose solution (0.32 M sucrose, 4 μg/ml pepstatin, 5 μg/ml aprotinin, 20 μg/ml trypsin inhibitor, 4 μg/ml leupeptin, 0.2 mM phenylmethanesulfonyl fluoride, 2 mM ethylenediaminetetraacetic acid (EDTA), 2 mM ethylene glycol bis(β aminoethyl ether) tetraacetic acid, 20 mM HEPES, pH 7.2), and assayed for protein using a bicinchoninic acid kit for protein assay (provided by Pierce Corporation). Each homogenized sample, having an equal amount of protein that had been dissolved in a Laemmli sample buffer solution, was subjected to electrophoresis through sodium dodecyl sulfurate polyacrylamide gels. The protein separated by electrophoresis was electrically transferred to polyvinylidene fluoride membranes. The membranes were reacted with specific primary antibodies for TH, DAT, and housekeeping proteins, i.e., the αl subunit of Na$^+$/K$^+$-ATPase and actin (Na$^+$/K$^+$-ATPase, a product of UpState Biotechnology Inc.; others are products of Chemi-Con Corporation). Subsequently, a horseradish peroxidase-labeled secondary antibody (a product of Amersham K.K.) for each primary antibody was fixed, and the chemiluminescence associated with enzyme activity of peroxidase was detected using X-ray film. The density of the protein band on the film was analyzed using a densitometer (a product of Bio-rad Laboratories Inc.) to obtain the TH value relative to Na$^+$/K$^+$-ATPase and the DAT value relative to actin.

The right striatum, the tissue weight of which was measured immediately after dissection, was used as an analysis sample for determining the dopamine content. Each tissue was homogenized in a 0.1 N perchloric acid solution containing isoproterenol as an internal standard substance of the measurement, using an ultrasonic homogenizer while being cooled with ice. The supernatant obtained from 20,000 g of homogenate that had been centrifuged at 4° C. for 15 minutes was subjected to a high performance liquid chromatography with a reversed phase column (a product of Eicom Corporation). A mobile phase 15% methanol 0.1 M citric acid/0.1 M sodium acetate buffer solution (containing 190 mg/L 1-sodium octane sulfonate, 5 mg/L EDTA, pH 3.5) was flowed at a rate of 0.5 ml/min, and the dopamine peak of each sample was detected using an electrochemical detector (applied voltage+750 mV vs. Ag/AgCl, a product of Eicom Corporation). With reference to the identified dopamine peak, the dopamine content per tissue weight was calculated in each sample using analysis software (a product of Gilson Inc.). In both analyses, the value of the sample derived from the MPTP-induced mice in which only the test compound or the solvent was administered was expressed relative to the value of the sample derived from the mice without MPTP treatment (100%). Values were analyzed statistically using a nonclinical statistical analysis system. Values of significance probability<0.05 were defined as statistically significant. In the MPTP-induced mice, when the test drug group showed an increase in protein level compared to the solvent group, and a significant difference was observed between these groups in the t-assay, the test drug was judged to have dopamine neuroprotective activity.

Pharmacological Test Example 3

Evaluation of the Neuroprotective Action in Rat Middle Cerebral Artery Occlusion-Reperfusion Model The neuroprotective action of an experimental compound was evaluated in a middle cerebral artery (MCA) occlusion-reperfusion rat model of stroke [Koizumi J. et al., Jpn J Stroke, 8, 1-8 (1986)] using the cerebral infarct volume as an index [Kitagawa H. et al., Neurol Res, 24, 317-323 (2002)].

Male Wistar rats (12-16 weeks old, Japan SLC, Inc.) were used as the experimental animals. Each rat was kept at 37° C. under isoflurane anesthetization, and immobilized in the supine position while breathing voluntarily. Each rat was subjected to a median incision in the cervical region, and the right common carotid artery (CCA), the right external carotid artery (ECA) and the right internal carotid artery (ICA) were exposed without damaging the vagus nerve. Subsequently, the right CCA and the right ECA were ligated, the right ICA was controlled with a suture at its origin and a small incision was made in the right CCA. The occlusion of the right MCA at its origin was produced by insertion of a silicon coated No. 4-0 nylon filament having 0.30-0.35 mm in diameter and about 17 mm in length into the ICA. The right ICA was ligated together with the filament, the skin was temporarily sutured, and the rats were returned to their cages. After 1.5 hours of occlusion, the cervical wound was reopened under isoflurane anesthesia, and the filament was slightly withdrawn to allow reperfusion. The cervical wound was closed, and the rats were returned to their cages. The experimental compounds were dissolved in a Tris buffer solution or a physiological saline solution to produce a concentration of 1.5 to 15 mg/ml, and the prepared solutions or vehicle were intravenously administered in the quantity of 2 ml/kg immediately after the vascular occlusion and reperfusion.

Twenty-four hours after reperfusion, the rat whole brains were removed and the forebrain coronal sections were prepared in 2-mm thick from the boundary of the cerebrum and cerebellum. The slices were incubated in a 1% 2,3,5-triphenyltetrazolium chloride (TTC) solution at 37° C. for 30 minutes and fixed by immersion in 10% neutralized formalin. The images of the slices were scanned, and the area of the TTC achromatic region on the surface was measured using image-analysis software (Win ROOF Ver. 5.6, Mitani Corporation). The measured area value was multiplied by the thickness of 2 mm to determine the volume of each slice, and the sum of the thus-obtained volumes was defined as the total cerebral infarct volume.

The statistical difference in cerebral infarct volume between the vehicle administered group (control group) and the compound administered group was analyzed by a t-test (two-tailed) using a non-clinical statistical analysis system. A probability less than 0.05 was defined as a statistically significant difference. When a statistically significant decrease in the cerebral infarct volume was observed in the compound administered group compared to the control group, it was determined that the experimental compound had a neuroprotective effect.

The invention claimed is:

1. A quinolone compound represented by Formula (1):

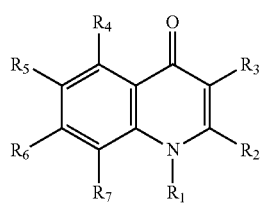

or a salt thereof,
wherein $R_1$ represents:
(1) hydrogen,
(2) $C_1$-$C_6$ alkyl,
(3) halogen-substituted $C_1$-$C_6$ alkyl,
(4) $C_2$-$C_6$ alkenyl,
(5) $C_1$-$C_6$ alkanoyl,
(6) halogen-substituted $C_1$-$C_6$ alkanoyl,
(7) hydroxy $C_1$-$C_6$ alkyl,
(8) protected hydroxy $C_1$-$C_6$ alkyl,
(9) hydroxy $C_1$-$C_6$ alkanoyl,
(10) protected hydroxy $C_1$-$C_6$ alkanoyl,
(11) $C_1$-$C_6$ alkylthio $C_1$-$C_6$ alkyl,
(12) amino $C_1$-$C_6$ alkylthio $C_1$-$C_6$ alkyl optionally having one or more $C_1$-$C_6$ alkyl groups,
(13) hydroxy $C_1$-$C_6$ alkylthio $C_1$-$C_6$ alkyl,
(14) carboxy $C_1$-$C_6$ alkylthio $C_1$-$C_6$ alkyl,
(15) $C_1$-$C_6$ alkoxycarbonyl $C_1$-$C_6$ alkylthio $C_1$-$C_6$ alkyl,
(16) amino $C_1$-$C_6$ alkylthiocarbonyl $C_1$-$C_6$ alkyl optionally having one or more $C_1$-$C_6$ alkyl groups,
(17) hydroxy $C_1$-$C_6$ alkylsulfonyl $C_1$-$C_6$ alkyl,
(18) carboxy $C_1$-$C_6$ alkylsulfonyl $C_1$-$C_6$ alkyl,
(19) $C_1$-$C_6$ alkoxycarbonyl $C_1$-$C_6$ alkylsulfonyl $C_1$-$C_6$ alkyl,
(20) $C_1$-$C_6$ alkanoyl $C_1$-$C_6$ alkylsulfonyl $C_1$-$C_6$ alkyl,
(21) piperazinyl $C_1$-$C_6$ alkylsulfonyl $C_1$-$C_6$ alkyl optionally having one or more $C_1$-$C_6$ alkyl groups on the piperazine ring,
(22) piperazinylcarbonyl $C_1$-$C_6$ alkylsulfonyl $C_1$-$C_6$ alkyl optionally having one or more $C_1$-$C_6$ alkyl groups on the piperazine ring,
(23) $C_1$-$C_6$ alkanoyl $C_1$-$C_6$ alkyl,
(24) carboxy $C_1$-$C_6$ alkyl,
(25) $C_1$-$C_6$ alkoxycarbonyl $C_1$-$C_6$ alkyl,
(26) piperazinyl $C_1$-$C_6$ alkoxycarbonyl $C_1$-$C_6$ alkyl optionally having one or more $C_1$-$C_6$ alkyl groups on the piperazine ring,
(27) morpholinyl $C_1$-$C_6$ alkyl,
(28) oxazepanyl $C_1$-$C_6$ alkyl,
(29) amino $C_1$-$C_6$ alkyl optionally having one or more $C_1$-$C_6$ alkyl groups,
(30) piperazyl $C_1$-$C_6$ alkyl optionally having, on the piperazine ring, one or more substituents selected from the group consisting of $C_1$-$C_6$ alkyl, $C_1$-$C_6$ alkoxy $C_1$-$C_6$ alkyl, and pyridyl,
(31) piperidyl $C_1$-$C_6$ alkyl optionally having one or more morpholinyl groups,
(32) azetidyl $C_1$-$C_6$ alkyl optionally having one or more hydroxy groups on the azetidine ring,
(33) isoindolinyl $C_1$-$C_6$ alkyl optionally having one or more oxo groups,
(34) amino $C_1$-$C_6$ alkanoyloxy $C_1$-$C_6$ alkyl optionally having one or more substituents selected from the group consisting of $C_1$-$C_6$ alkyl and $C_1$-$C_6$ alkoxycarbonyl,
(35) carbamoyl $C_1$-$C_6$ alkyl optionally having one or more substituents selected from $C_1$-$C_6$ alkyl; morpholinyl $C_1$-$C_6$ alkyl; piperidyl optionally having one or more substituents selected from the group consisting of $C_1$-$C_6$ alkyl and $C_1$-$C_6$ alkoxycarbonyl; and piperazinyl $C_1$-$C_6$ alkyl optionally having one or more $C_1$-$C_6$ alkyl groups,
(36) phosphonooxy $C_1$-$C_6$ alkyl optionally having one or more hydroxy-protecting groups,
(37) phosphonooxy $C_1$-$C_6$ alkanoyloxy $C_1$-$C_6$ alkyl optionally having one or more hydroxy-protecting groups,
(38) benzoyloxy $C_1$-$C_6$ alkyl optionally having, on the benzene ring, one or more substituents selected from the group consisting of hydroxy, protected hydroxy, and phosphonooxy optionally having one or more hydroxyl-protecting groups,
(39) tetrahydropyranyl optionally having one or more substituents selected from the group consisting of hydroxy, hydroxy $C_1$-$C_6$ alkyl and carboxyl, or
(40) $C_1$-$C_6$ alkanoylamino $C_1$-$C_6$ alkyl optionally having, on the $C_1$-$C_6$ alkanoyl group, one or more substituents selected from the group consisting of halogen; hydroxy; amino; $C_1$-$C_6$ alkoxycarbonylamino; piperazinyl optionally having one or more $C_1$-$C_6$ alkoxy $C_1$-$C_6$ alkyl groups; imidazolyl; and morpholinylpiperidyl;

$R_2$ represents:
(1) hydrogen,
(2) $C_1$-$C_6$ alkyl,
(3) $C_1$-$C_6$ alkanoyl,
(4) hydroxy $C_1$-$C_6$ alkyl,
(5) carboxy,
(6) $C_1$-$C_6$ alkoxycarbonyl,
(7) carbamoyl optionally having one or more substituents selected from the group consisting of $C_1$-$C_6$ alkyl; halogen-substituted $C_1$-$C_6$ alkyl; hydroxy $C_1$-$C_6$ alkyl; piperazinyl $C_1$-$C_6$ alkyl optionally having one or more $C_1$-$C_6$ alkyl groups; and morpholinyl $C_1$-$C_6$ alkyl,
(8) carbamoyl $C_1$-$C_6$ alkyl optionally having one or more $C_1$-$C_6$ alkyl groups,
(9) morpholinyl $C_1$-$C_6$ alkyl,
(10) piperazinyl $C_1$-$C_6$ alkyl optionally having one or more substituents selected from the group consisting of $C_1$-$C_6$ alkyl and pyridyl optionally having one or more $C_1$-$C_6$ alkyl groups,
(11) diazepanyl $C_1$-$C_6$ alkyl,
(12) amino $C_1$-$C_6$ alkyl optionally having one or more substituents selected from the group consisting of $C_1$-$C_6$ alkyl, halogen-substituted $C_1$-$C_6$ alkyl, hydroxy $C_1$-$C_6$ alkyl, and morpholinyl $C_1$-$C_6$ alkyl,
(13) $C_1$-$C_6$ alkoxycarbonyl $C_1$-$C_6$ alkyl, or
(14) carboxy $C_1$-$C_6$ alkyl;

$R_3$ represents phenyl, thienyl, furyl, pyrazolyl, or pyrimidinyl, wherein:
the aromatic or heterocyclic ring represented by $R_3$ may be substituted with one or more substituents selected from the group consisting of the following substituents (1) to (14):
(1) $C_1$-$C_6$ alkyl,
(2) $C_1$-$C_6$ alkoxy,
(3) $C_1$-$C_6$ alkanoyl,
(4) halogen,
(5) hydroxy,
(6) hydroxy $C_1$-$C_6$ alkyl,
(7) hydroxy $C_1$-$C_6$ alkoxy,
(8) protected hydroxy $C_1$-$C_6$ alkoxy,
(9) carboxy $C_1$-$C_6$ alkoxy,
(10) $C_1$-$C_6$ alkoxycarbonyl $C_1$-$C_6$ alkoxy,
(11) pyrrolidinylcarbonyl,
(12) carbamoyl $C_1$-$C_6$ alkoxy optionally having one or more $C_1$-$C_6$ alkyl groups,
(13) carbamoyl optionally having one or more morpholinyl $C_1$-$C_6$ alkyl groups, and
(14) morpholinylpiperidylcarbonyl;

$R_4$ and $R_5$ are linked to form a group represented by any of the following formulae:

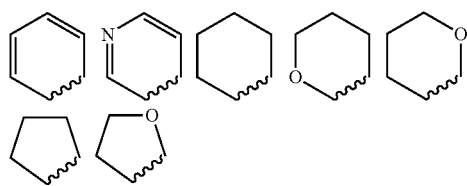

or a group represented by the following formula:

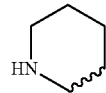

the group optionally having one or more substituents selected from the group consisting of $C_1$-$C_6$ alkyl and oxo groups;

$R_6$ represents hydrogen or $C_1$-$C_6$ alkoxy;
$R_7$ represents any of the following groups (1) to (11):
(1) hydrogen,
(2) $C_1$-$C_6$ alkoxy,
(3) hydroxy $C_1$-$C_6$ alkoxy,
(4) protected hydroxy $C_1$-$C_6$ alkoxy,
(5) $C_1$-$C_6$ alkoxy $C_1$-$C_6$ alkoxy,
(6) carbamoyl $C_1$-$C_6$ alkoxy optionally having one or more substituents selected from the group consisting of $C_1$-$C_6$ alkyl and morpholinyl $C_1$-$C_6$ alkyl,
(7) amino optionally having one or two substituents selected from the group consisting of $C_1$-$C_6$ alkyl and cyclo $C_3$-$C_8$ alkyl,
(8) cyclo $C_3$-$C_8$ alkyloxy,
(9) carboxy $C_1$-$C_6$ alkoxy,
(10) $C_1$-$C_6$ alkoxycarbonyl $C_1$-$C_6$ alkoxy, and
(11) pyrrolidinyl; and $R_6$ and $R_7$ may be linked to form a group represented by any of the following formulae:

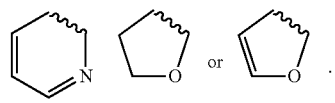

2. A quinolone compound of General Formula (1) or a salt thereof according to claim 1, wherein:

$R_1$ represents:
(1) hydrogen,
(2) $C_1$-$C_6$ alkyl,
(3) halogen-substituted $C_1$-$C_6$ alkyl,
(4) $C_2$-$C_6$ alkenyl,
(5) $C_1$-$C_6$ alkanoyl,
(6) halogen-substituted $C_1$-$C_6$ alkanoyl,
(7) hydroxy $C_1$-$C_6$ alkyl,
(8) phenyl $C_1$-$C_6$ alkoxy $C_1$-$C_6$ alkyl,
(9) hydroxy $C_1$-$C_6$ alkanoyl,
(10) phenyl $C_1$-$C_6$ alkoxy $C_1$-$C_6$ alkanoyl,
(11) $C_1$-$C_6$ alkylthio $C_1$-$C_6$ alkyl,
(12) amino $C_1$-$C_6$ alkylthio $C_1$-$C_6$ alkyl optionally having, on the amino group, two $C_1$-$C_6$ alkyl groups,
(13) hydroxy $C_1$-$C_6$ alkylthio $C_1$-$C_6$ alkyl,
(14) carboxy $C_1$-$C_6$ alkylthio $C_1$-$C_6$ alkyl,
(15) $C_1$-$C_6$ alkoxycarbonyl $C_1$-$C_6$ alkylthio $C_1$-$C_6$ alkyl,
(16) amino $C_1$-$C_6$ alkylthiocarbonyl $C_1$-$C_6$ alkyl optionally having, on the amino group, two $C_1$-$C_6$ alkyl groups,
(17) hydroxy $C_1$-$C_6$ alkylsulfonyl $C_1$-$C_6$ alkyl,
(18) carboxy $C_1$-$C_6$ alkylsulfonyl $C_1$-$C_6$ alkyl,
(19) $C_1$-$C_6$ alkoxycarbonyl $C_1$-$C_6$ alkylsulfonyl $C_1$-$C_6$ alkyl,
(20) $C_1$-$C_6$ alkanoyl $C_1$-$C_6$ alkylsulfonyl $C_1$-$C_6$ alkyl,
(21) piperazinyl $C_1$-$C_6$ alkylsulfonyl $C_1$-$C_6$ alkyl optionally having one $C_1$-$C_6$ alkyl group on the piperazine ring,
(22) piperazinylcarbonyl $C_1$-$C_6$ alkylsulfonyl $C_1$-$C_6$ alkyl optionally having one $C_1$-$C_6$ alkyl group on the piperazine ring,

(23) $C_1$-$C_6$ alkanoyl $C_1$-$C_6$ alkyl,
(24) carboxy $C_1$-$C_6$ alkyl,
(25) $C_1$-$C_6$ alkoxycarbonyl $C_1$-$C_6$ alkyl,
(26) piperazinyl $C_1$-$C_6$ alkoxycarbonyl $C_1$-$C_6$ alkyl optionally having one $C_1$-$C_6$ alkyl group on the piperazine ring,
(27) morpholinyl $C_1$-$C_6$ alkyl,
(28) oxazepanyl $C_1$-$C_6$ alkyl,
(29) amino $C_1$-$C_6$ alkyl optionally having one $C_1$-$C_6$ alkyl group on the amino group,
(30) piperazyl $C_1$-$C_6$ alkyl optionally having, on the piperazine ring, one substituent selected from the group consisting of $C_1$-$C_6$ alkyl, $C_1$-$C_6$ alkoxy $C_1$-$C_6$ alkyl, and pyridyl,
(31) piperidyl $C_1$-$C_6$ alkyl optionally having one morpholinyl group on the piperidine ring,
(32) azetidyl $C_1$-$C_6$ alkyl optionally having one hydroxy group on the azetidine ring,
(33) isoindolinyl $C_1$-$C_6$ alkyl optionally having two oxo groups on the isoindoline ring,
(34) amino $C_1$-$C_6$ alkanoyloxy $C_1$-$C_6$ alkyl optionally having, on the amino group, one or two substituents selected from the group consisting of $C_1$-$C_6$ alkyl and $C_1$-$C_6$ alkoxycarbonyl,
(35) carbamoyl $C_1$-$C_6$ alkyl optionally having, on the carbamoyl group, one substituent selected from $C_1$-$C_6$ alkyl; morpholinyl $C_1$-$C_6$ alkyl; piperidyl optionally having one substituent selected from the group consisting of $C_1$-$C_6$ alkyl and $C_1$-$C_6$ alkoxycarbonyl; and piperazinyl $C_1$-$C_6$ alkyl optionally having one $C_1$-$C_6$ alkyl group,
(36) phosphonooxy $C_1$-$C_6$ alkyl optionally having one or two $C_1$-$C_6$ alkyl groups on the phosphonooxy group,
(37) phosphonooxy $C_1$-$C_6$ alkanoyloxy $C_1$-$C_6$ alkyl optionally having one or two $C_1$-$C_6$ alkyl groups on the phosphonooxy group,
(38) benzoyloxy $C_1$-$C_6$ alkyl optionally having, on the benzene ring, one substituent selected from the group consisting of hydroxy, benzyloxy, and phosphonooxy optionally having one or two $C_1$-$C_6$ alkyl groups,
(39) tetrahydropyranyl optionally having three hydroxy groups and one hydroxy $C_1$-$C_6$ alkyl group, or
(40) $C_1$-$C_6$ alkanoylamino $C_1$-$C_6$ alkyl optionally having, on the $C_1$-$C_6$ alkanoyl group, one or two substituents selected from the group consisting of halogen; hydroxy; amino; $C_1$-$C_6$ alkoxycarbonylamino; piperazinyl optionally having one $C_1$-$C_6$ alkoxy $C_1$-$C_6$ alkyl group; imidazolyl; and morpholinylpiperidyl;
$R_2$ represents:
(1) hydrogen,
(2) $C_1$-$C_6$ alkyl,
(3) $C_1$-$C_6$ alkanoyl,
(4) hydroxy $C_1$-$C_6$ alkyl,
(5) carboxy,
(6) $C_1$-$C_6$ alkoxycarbonyl,
(7) carbamoyl optionally having one or two substituents selected from the group consisting of $C_1$-$C_6$ alkyl; halogen-substituted $C_1$-$C_6$ alkyl; hydroxy $C_1$-$C_6$ alkyl; piperazinyl $C_1$-$C_6$ alkyl optionally having one $C_1$-$C_6$ alkyl group on the piperazine ring; and morpholinyl $C_1$-$C_6$ alkyl,
(8) carbamoyl $C_1$-$C_6$ alkyl optionally having one $C_1$-$C_6$ alkyl group on the carbamoyl group,
(9) morpholinyl $C_1$-$C_6$ alkyl,
(10) piperazinyl $C_1$-$C_6$ alkyl optionally having, on the piperazine ring, one substituent selected from the group consisting of $C_1$-$C_6$ alkyl and pyridyl optionally having one $C_1$-$C_6$ alkyl group,
(11) diazepanyl $C_1$-$C_6$ alkyl, or
(12) amino $C_1$-$C_6$ alkyl optionally having, on the amino group, one or two substituents selected from the group consisting of $C_1$-$C_6$ alkyl, halogen-substituted $C_1$-$C_6$ alkyl, hydroxy $C_1$-$C_6$ alkyl, and morpholinyl $C_1$-$C_6$ alkyl;
$R_3$ represents phenyl, thienyl, furyl, pyrazolyl, or pyrimidinyl, wherein:
the aromatic or heterocyclic ring represented by $R_3$ may be substituted with one or two substituents selected from the group consisting of the following substituents (1) to (14):
(1) $C_1$-$C_6$ alkyl,
(2) $C_1$-$C_6$ alkoxy,
(3) $C_1$-$C_6$ alkanoyl,
(4) halogen,
(5) hydroxy,
(6) hydroxy $C_1$-$C_6$ alkyl,
(7) hydroxy $C_1$-$C_6$ alkoxy,
(8) tetrahydropyranyloxy $C_1$-$C_6$ alkoxy,
(9) carboxy $C_1$-$C_6$ alkoxy,
(10) $C_1$-$C_6$ alkoxycarbonyl $C_1$-$C_6$ alkoxy,
(11) pyrrolidinylcarbonyl,
(12) carbamoyl $C_1$-$C_6$ alkoxy optionally having one $C_1$-$C_6$ alkyl group on the carbamoyl group,
(13) carbamoyl optionally having one morpholinyl $C_1$-$C_6$ alkyl group, and
(14) morpholinylpiperidylcarbonyl;
$R_6$ represents hydrogen or $C_1$-$C_6$ alkoxy; and
$R_7$ represents any of the following groups (1) to (11):
(1) hydrogen,
(2) $C_1$-$C_6$ alkoxy,
(3) hydroxy $C_1$-$C_6$ alkoxy,
(4) benzyloxy $C_1$-$C_6$ alkoxy,
(5) $C_1$-$C_6$ alkoxy $C_1$-$C_6$ alkoxy,
(6) carbamoyl $C_1$-$C_6$ alkoxy optionally having, on the carbamoyl group, one substituent selected from the group consisting of $C_1$-$C_6$ alkyl and morpholinyl $C_1$-$C_6$ alkyl,
(7) amino optionally having two substituents selected from the group consisting of $C_1$-$C_6$ alkyl and cyclo $C_3$-$C_8$ alkyl,
(8) cyclo $C_3$-$C_8$ alkyloxy,
(9) carboxy $C_1$-$C_6$ alkoxy,
(10) $C_1$-$C_6$ alkoxycarbonyl $C_1$-$C_6$ alkoxy, and
(11) pyrrolidinyl.

3. A quinolone compound of General Formula (1) or a salt thereof according to claim 2, wherein
$R_1$ represents:
(1) hydrogen,
(2) $C_1$-$C_6$ alkyl,
(3) halogen-substituted $C_1$-$C_6$ alkyl,
(24) carboxy $C_1$-$C_6$ alkyl,
(25) $C_1$-$C_6$ alkoxycarbonyl $C_1$-$C_6$ alkyl,
(27) morpholinyl $C_1$-$C_6$ alkyl,
(28) oxazepanyl $C_1$-$C_6$ alkyl,
(30) piperazyl $C_1$-$C_6$ alkyl optionally having, on the piperazine ring, one $C_1$-$C_6$ alkoxy $C_1$-$C_6$ alkyl,
(31) piperidyl $C_1$-$C_6$ alkyl,
(35) carbamoyl $C_1$-$C_6$ alkyl optionally having one morpholinyl $C_1$-$C_6$ alkyl, or
(36) phosphonooxy $C_1$-$C_6$ alkyl optionally having one or two $C_1$-$C_6$ alkyl groups;
$R_2$ represents:
(1) hydrogen, or
(2) $C_1$-$C_6$ alkyl, R₃ represents phenyl, thienyl, or furyl, wherein:
the aromatic or heterocyclic ring represented by R₃ may be substituted with one $C_1$-$C_6$ alkoxy group,
R₆ represents hydrogen; and
R₇ represents $C_1$-$C_6$ alkoxy.

4. A quinolone compound represented by General Formula (1):

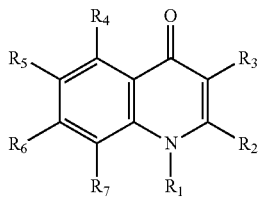

or a salt thereof,
wherein
R₁ represents:
(1) hydrogen,
(2) $C_1$-$C_6$ alkyl,
(3) halogen-substituted $C_1$-$C_6$ alkyl,
(4) $C_2$-$C_6$ alkenyl,
(5) $C_1$-$C_6$ alkanoyl,
(6) halogen-substituted $C_1$-$C_6$ alkanoyl,
(7) hydroxy $C_1$-$C_6$ alkyl,
(8) protected hydroxy $C_1$-$C_6$ alkyl,
(9) hydroxy $C_1$-$C_6$ alkanoyl,
(10) protected hydroxy $C_1$-$C_6$ alkanoyl,
(11) lower alkylthio $C_1$-$C_6$ alkyl,
(12) amino $C_1$-$C_6$ alkylthio $C_1$-$C_6$ alkyl optionally having one or more $C_1$-$C_6$ alkyl groups,
(13) hydroxy $C_1$-$C_6$ alkylthio $C_1$-$C_6$ alkyl,
(14) carboxy $C_1$-$C_6$ alkylthio $C_1$-$C_6$ alkyl,
(15) $C_1$-$C_6$ alkoxycarbonyl $C_1$-$C_6$ alkylthio $C_1$-$C_6$ alkyl,
(16) amino $C_1$-$C_6$ alkylthiocarbonyl $C_1$-$C_6$ alkyl optionally having one or more $C_1$-$C_6$ alkyl groups,
(17) hydroxy $C_1$-$C_6$ alkylsulfonyl $C_1$-$C_6$ alkyl,
(18) carboxy $C_1$-$C_6$ alkylsulfonyl $C_1$-$C_6$ alkyl,
(19) $C_1$-$C_6$ alkoxycarbonyl $C_1$-$C_6$ alkylsulfonyl $C_1$-$C_6$ alkyl,
(20) $C_1$-$C_6$ alkanoyl $C_1$-$C_6$ alkylsulfonyl $C_1$-$C_6$ alkyl,
(21) piperazinyl $C_1$-$C_6$ alkylsulfonyl $C_1$-$C_6$ alkyl optionally having one or more $C_1$-$C_6$ alkyl groups on the piperazine ring,
(22) piperazinylcarbonyl $C_1$-$C_6$ alkylsulfonyl $C_1$-$C_6$ alkyl optionally having one or more $C_1$-$C_6$ alkyl groups on the piperazine ring,
(23) $C_1$-$C_6$ alkanoyl $C_1$-$C_6$ alkyl,
(24) carboxy $C_1$-$C_6$ alkyl,
(25) $C_1$-$C_6$ alkoxycarbonyl $C_1$-$C_6$ alkyl,
(26) piperazinyl $C_1$-$C_6$ alkoxycarbonyl $C_1$-$C_6$ alkyl optionally having one or more $C_1$-$C_6$ alkyl groups on the piperazine ring,
(27) morpholinyl $C_1$-$C_6$ alkyl,
(28) oxazepanyl $C_1$-$C_6$ alkyl,
(29) amino $C_1$-$C_6$ alkyl optionally having one or more $C_1$-$C_6$ alkyl groups,
(30) piperazyl $C_1$-$C_6$ alkyl optionally having, on the piperazine ring, one or more substituents selected from the group consisting of $C_1$-$C_6$ alkyl, $C_1$-$C_6$ alkoxy $C_1$-$C_6$ alkyl, and pyridyl,
(31) piperidyl $C_1$-$C_6$ alkyl optionally having one or more morpholinyl groups,
(32) azetidyl $C_1$-$C_6$ alkyl optionally having one or more hydroxy groups on the azetidine ring,
(33) isoindolinyl $C_1$-$C_6$ alkyl optionally having one or more oxo groups,
(34) amino $C_1$-$C_6$ alkanoyloxy $C_1$-$C_6$ alkyl optionally having one or more substituents selected from the group consisting of $C_1$-$C_6$ alkyl and $C_1$-$C_6$ alkoxycarbonyl,
(35) carbamoyl $C_1$-$C_6$ alkyl optionally having one or more substituents selected from $C_1$-$C_6$ alkyl; morpholinyl $C_1$-$C_6$ alkyl; piperidyl optionally having one or more substituents selected from the group consisting of $C_1$-$C_6$ alkyl and $C_1$-$C_6$ alkoxycarbonyl; and piperazinyl $C_1$-$C_6$ alkyl optionally having one or more $C_1$-$C_6$ alkyl groups,
(36) phosphonooxy $C_1$-$C_6$ alkyl optionally having one or more hydroxy-protecting groups,
(37) phosphonooxy $C_1$-$C_6$ alkanoyloxy $C_1$-$C_6$ alkyl optionally having one or more hydroxy-protecting groups,
(38) benzoyloxy $C_1$-$C_6$ alkyl optionally having, on the benzene ring, one or more substituents selected from the group consisting of hydroxy, protected hydroxy, and phosphonooxy optionally having one or more hydroxyl-protecting groups,
(39) tetrahydropyranyl optionally having one or more substituents selected from the group consisting of hydroxy, hydroxy $C_1$-$C_6$ alkyl and carboxyl, or
(40) $C_1$-$C_6$ alkanoylamino $C_1$-$C_6$ alkyl optionally having, on the $C_1$-$C_6$ alkanoyl group, one or more substituents selected from the group consisting of halogen; hydroxy; amino; $C_1$-$C_6$ alkoxycarbonylamino; piperazinyl optionally having one or more $C_1$-$C_6$ alkoxy $C_1$-$C_6$ alkyl groups; imidazolyl; and morpholinylpiperidyl;
R₂ represents:
(1) hydrogen,
(2) $C_1$-$C_6$ alkyl,
(3) $C_1$-$C_6$ alkanoyl,
(4) hydroxy $C_1$-$C_6$ alkyl,
(5) carboxy,
(6) $C_1$-$C_6$ alkoxycarbonyl,
(7) carbamoyl optionally having one or more substituents selected from the group consisting of $C_1$-$C_6$ alkyl; halogen-substituted $C_1$-$C_6$ alkyl; hydroxy $C_1$-$C_6$ alkyl; piperazinyl $C_1$-$C_6$ alkyl optionally having one or more $C_1$-$C_6$ alkyl groups; and morpholinyl $C_1$-$C_6$ alkyl,
(8) carbamoyl $C_1$-$C_6$ alkyl optionally having one or more $C_1$-$C_6$ alkyl groups,
(9) morpholinyl $C_1$-$C_6$ alkyl,
(10) piperazinyl $C_1$-$C_6$ alkyl optionally having one or more substituents selected from the group consisting of $C_1$-$C_6$ alkyl and pyridyl optionally having one or more $C_1$-$C_6$ alkyl groups,
(11) diazepanyl $C_1$-$C_6$ alkyl,
(12) amino $C_1$-$C_6$ alkyl optionally having one or more substituents selected from the group consisting of $C_1$-$C_6$ alkyl, halogen-substituted $C_1$-$C_6$ alkyl, hydroxy $C_1$-$C_6$ alkyl, and morpholinyl $C_1$-$C_6$ alkyl,
(13) $C_1$-$C_6$ alkoxycarbonyl $C_1$-$C_6$ alkyl, or
(14) carboxy $C_1$-$C_6$ alkyl;
R₃ represents phenyl, thienyl, furyl, pyrazolyl, or pyrimidinyl, wherein:
the aromatic or heterocyclic ring represented by R₃ may be substituted with one or more substituents selected from the group consisting of the following substituents (1) to (14):
(1) $C_1$-$C_6$ alkyl,
(2) $C_1$-$C_6$ alkoxy,
(3) $C_1$-$C_6$ alkanoyl, (4) halogen,
(5) hydroxy,
(6) hydroxy $C_1$-$C_6$ alkyl,
(7) hydroxy $C_1$-$C_6$ alkoxy,
(8) protected hydroxy $C_1$-$C_6$ alkoxy,
(9) carboxy $C_1$-$C_6$ alkoxy,
(10) $C_1$-$C_6$ alkoxycarbonyl $C_1$-$C_6$ alkoxy,
(11) pyrrolidinylcarbonyl,
(12) carbamoyl $C_1$-$C_6$ alkoxy optionally having one or more $C_1$-$C_6$ alkyl groups,
(13) carbamoyl optionally having one or more morpholinyl $C_1$-$C_6$ alkyl groups, and
(14) morpholinylpiperidylcarbonyl;

$R_4$ represents halogen, $C_1$-$C_6$ alkyl, or $C_1$-$C_6$ alkoxy;

$R_5$ represents hydrogen or halogen; or $R_4$ and $R_5$ are linked to form a group represented by any of the following formulae:

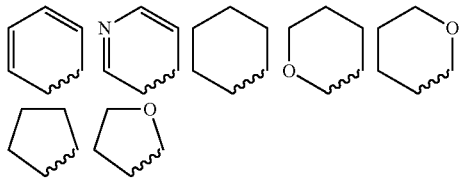

or a group represented by the following formula:

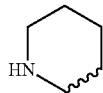

the group optionally having one or more substituents selected from the group consisting of $C_1$-$C_6$ alkyl and oxo groups; and $R_6$ and $R_7$ are linked to form a group represented by any of the following formulae:

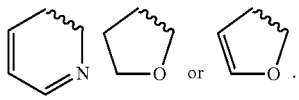

5. A quinolone compound of General Formula (1) or a salt thereof according to claim 4, wherein $R_1$ represents:
(1) hydrogen,
(2) $C_1$-$C_6$ alkyl, or
(36) phosphonooxy $C_1$-$C_6$ alkyl optionally having one or two $C_1$-$C_6$ alkyl groups;

$R_2$ represents hydrogen, $R_3$ represents phenyl wherein the aromatic or heterocyclic ring represented by $R_3$ may be substituted with one $C_1$-$C_6$ alkoxy group;

$R_4$ represents $C_1$-$C_6$ alkyl, or $C_1$-$C_6$ alkoxy; and $R_5$ represents hydrogen.

6. A quinolone compound represented by General Formula (1):

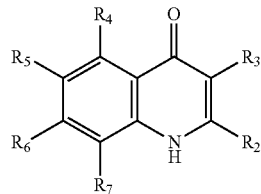

or a salt thereof, wherein
$R_1$ represents:
(3) halogen-substituted $C_1$-$C_6$ alkyl,
(4) $C_2$-$C_6$ alkenyl,
(5) $C_1$-$C_6$ alkanoyl,
(6) halogen-substituted $C_1$-$C_6$ alkanoyl,
(7) hydroxy $C_1$-$C_6$ alkyl,
(8) phenyl $C_1$-$C_6$ alkoxy $C_1$-$C_6$ alkyl,
(9) hydroxy $C_1$-$C_6$ alkanoyl,
(10) phenyl $C_1$-$C_6$ alkoxy $C_1$-$C_6$ alkanoyl,
(11) $C_1$-$C_6$ alkylthio $C_1$-$C_6$ alkyl,
(12) amino $C_1$-$C_6$ alkylthio $C_1$-$C_6$ alkyl optionally having one or two $C_1$-$C_6$ alkyl groups,
(13) hydroxy $C_1$-$C_6$ alkylthio $C_1$-$C_6$ alkyl,
(14) carboxy $C_1$-$C_6$ alkylthio $C_1$-$C_6$ alkyl,
(15) $C_1$-$C_6$ alkoxycarbonyl $C_1$-$C_6$ alkylthio $C_1$-$C_6$ alkyl,
(16) amino $C_1$-$C_6$ alkylthiocarbonyl $C_1$-$C_6$ alkyl optionally having one or two $C_1$-$C_6$ alkyl groups,
(17) hydroxy $C_1$-$C_6$ alkylsulfonyl $C_1$-$C_6$ alkyl,
(18) carboxy $C_1$-$C_6$ alkylsulfonyl $C_1$-$C_6$ alkyl,
(19) $C_1$-$C_6$ alkoxycarbonyl $C_1$-$C_6$ alkylsulfonyl $C_1$-$C_6$ alkyl,
(20) $C_1$-$C_6$ alkanoyl $C_1$-$C_6$ alkylsulfonyl $C_1$-$C_6$ alkyl,
(21) piperazinyl $C_1$-$C_6$ alkylsulfonyl $C_1$-$C_6$ alkyl optionally having one $C_1$-$C_6$ alkyl group on the piperazine ring,
(22) piperazinylcarbonyl $C_1$-$C_6$ alkylsulfonyl $C_1$-$C_6$ alkyl optionally having one $C_1$-$C_6$ alkyl group on the piperazine ring,
(23) $C_1$-$C_6$ alkanoyl $C_1$-$C_6$ alkyl,
(24) carboxy $C_1$-$C_6$ alkyl,
(25) $C_1$-$C_6$ alkoxycarbonyl $C_1$-$C_6$ alkyl,
(26) piperazinyl $C_1$-$C_6$ alkoxycarbonyl $C_1$-$C_6$ alkyl optionally having one $C_1$-$C_6$ alkyl group on the piperazine ring,
(27) morpholinyl $C_1$-$C_6$ alkyl,
(28) oxazepanyl $C_1$-$C_6$ alkyl,
(29) amino $C_1$-$C_6$ alkyl optionally having one or two $C_1$-$C_6$ alkyl groups,
(30) piperazyl $C_1$-$C_6$ alkyl optionally having, on the piperazine ring, one substituent selected from the group consisting of $C_1$-$C_6$ alkyl, $C_1$-$C_6$ alkoxy $C_1$-$C_6$ alkyl, and pyridyl,
(31) piperidyl $C_1$-$C_6$ alkyl optionally having one morpholinyl group,
(32) azetidyl $C_1$-$C_6$ alkyl optionally having one hydroxy group on the azetidine ring,
(33) isoindolinyl $C_1$-$C_6$ alkyl optionally having one or two oxo groups,
(34) amino $C_1$-$C_6$ alkanoyloxy $C_1$-$C_6$ alkyl optionally having one or two substituents selected from the group consisting of $C_1$-$C_6$ alkyl and $C_1$-$C_6$ alkoxycarbonyl,
(35) carbamoyl $C_1$-$C_6$ alkyl optionally having one or two substituents selected from $C_1$-$C_6$ alkyl; morpholinyl $C_1$-$C_6$ alkyl; piperidyl optionally having one substituent selected from the group consisting of $C_1$-$C_6$ alkyl and $C_1$-$C_6$ alkoxycarbonyl; and piperazinyl $C_1$-$C_6$ alkyl optionally having one $C_1$-$C_6$ alkyl group,

(36) phosphonooxy $C_1$-$C_6$ alkyl optionally having one or two $C_1$-$C_6$ alkyl groups on the phosphonooxy group,
(37) phosphonooxy $C_1$-$C_6$ alkanoyloxy $C_1$-$C_6$ alkyl optionally having one or two $C_1$-$C_6$ alkyl groups on the phosphonooxy group,
(38) benzoyloxy $C_1$-$C_6$ alkyl optionally having, on the benzene ring, one substituent selected from the group consisting of hydroxy, benzyloxy, and phosphonooxy optionally having one or two $C_1$-$C_6$ alkyl groups,
(39) tetrahydropyranyl optionally having one to four substituents selected from the group consisting of hydroxy, hydroxy $C_1$-$C_6$ alkyl and carboxyl, or
(40) $C_1$-$C_6$ alkanoylamino $C_1$-$C_6$ alkyl optionally having, on the $C_1$-$C_6$ alkanoyl group, one or two substituents selected from the group consisting of halogen; hydroxy; amino; $C_1$-$C_6$ alkoxycarbonylamino; piperazinyl optionally having one $C_1$-$C_6$ alkoxy $C_1$-$C_6$ alkyl group; imidazolyl; and morpholinylpiperidyl;

$R_2$ represents:
(1) hydrogen,
(2) $C_1$-$C_6$ alkyl,
(3) $C_1$-$C_6$ alkanoyl,
(4) hydroxy $C_1$-$C_6$ alkyl,
(5) carboxy,
(6) $C_1$-$C_6$ alkoxycarbonyl,
(7) carbamoyl optionally having one or two substituents selected from the group consisting of $C_1$-$C_6$ alkyl; halogen-substituted $C_1$-$C_6$ alkyl; hydroxy $C_1$-$C_6$ alkyl; piperazinyl $C_1$-$C_6$ alkyl optionally having one $C_1$-$C_6$ alkyl group on the piperazine ring; and morpholinyl $C_1$-$C_6$ alkyl,
(8) carbamoyl $C_1$-$C_6$ alkyl optionally having one $C_1$-$C_6$ alkyl group on the carbamoyl group,
(9) morpholinyl $C_1$-$C_6$ alkyl,
(10) piperazinyl $C_1$-$C_6$ alkyl optionally having, on the piperazine ring, one substituent selected from the group consisting of $C_1$-$C_6$ alkyl and pyridyl optionally having one $C_1$-$C_6$ alkyl group,
(11) diazepanyl $C_1$-$C_6$ alkyl, or
(12) amino $C_1$-$C_6$ alkyl optionally having, on the amino group, one or two substituents selected from the group consisting of $C_1$-$C_6$ alkyl, halogen-substituted $C_1$-$C_6$ alkyl, hydroxy $C_1$-$C_6$ alkyl, and morpholinyl $C_1$-$C_6$ alkyl;

$R_3$ represents phenyl, thienyl, furyl, pyrazolyl, or pyrimidinyl, wherein:
the aromatic or heterocyclic ring represented by $R_3$ may be substituted with one or two substituents selected from the group consisting of the following substituents (1) to (14):
(1) $C_1$-$C_6$ alkyl,
(2) $C_1$-$C_6$ alkoxy,
(3) $C_1$-$C_6$ alkanoyl,
(4) halogen,
(5) hydroxy,
(6) hydroxy $C_1$-$C_6$ alkyl,
(7) hydroxy $C_1$-$C_6$ alkoxy,
(8) tetrahydropyranyloxy $C_1$-$C_6$ alkoxy,
(9) carboxy $C_1$-$C_6$ alkoxy,
(10) $C_1$-$C_6$ alkoxycarbonyl $C_1$-$C_6$ alkoxy,
(11) pyrrolidinylcarbonyl,
(12) carbamoyl $C_1$-$C_6$ alkoxy optionally having one or two $C_1$-$C_6$ alkyl groups,
(13) carbamoyl optionally having one morpholinyl $C_1$-$C_6$ alkyl group, and
(14) morpholinylpiperidylcarbonyl;

$R_4$ represents halogen;
$R_5$ represents hydrogen or halogen;
$R_6$ represents hydrogen or $C_1$-$C_6$ alkoxy; and
$R_7$ represents any of the following groups (2) to (11):
(2) $C_1$-$C_6$ alkoxy,
(3) hydroxy $C_1$-$C_6$ alkoxy,
(4) benzyloxy $C_1$-$C_6$ alkoxy,
(5) $C_1$-$C_6$ alkoxy $C_1$-$C_6$ alkoxy,
(6) carbamoyl $C_1$-$C_6$ alkoxy optionally having one substituent selected from the group consisting of $C_1$-$C_6$ alkyl and morpholinyl $C_1$-$C_6$ alkyl,
(7) amino optionally having one or two substituents selected from the group consisting of $C_1$-$C_6$ alkyl and cyclo $C_3$-$C_8$ alkyl,
(8) cyclo $C_3$-$C_8$ alkyloxy,
(9) carboxy $C_1$-$C_6$ alkoxy,
(10) $C_1$-$C_6$ alkoxycarbonyl $C_1$-$C_6$ alkoxy, and
(11) pyrrolidinyl.

7. A quinolone compound of General Formula (1) or a salt thereof according to claim 6, wherein
$R_1$ represents:
(3) halogen-substituted $C_1$-$C_6$ alkyl,
(4) $C_2$-$C_6$ alkenyl,
(5) $C_1$-$C_6$ alkanoyl,
(6) halogen-substituted $C_1$-$C_6$ alkanoyl,
(8) benzyloxy $C_1$-$C_6$ alkyl,
(10) benzyloxy $C_1$-$C_6$ alkanoyl,
(11) $C_1$-$C_6$ alkylthio $C_1$-$C_6$ alkyl,
(12) amino $C_1$-$C_6$ alkylthio $C_1$-$C_6$ alkyl optionally having one or two $C_1$-$C_6$ alkyl groups,
(13) hydroxy $C_1$-$C_6$ alkylthio $C_1$-$C_6$ alkyl,
(14) carboxy $C_1$-$C_6$ alkylthio $C_1$-$C_6$ alkyl,
(15) $C_1$-$C_6$ alkoxycarbonyl $C_1$-$C_6$ alkylthio $C_1$-$C_6$ alkyl,
(16) amino $C_1$-$C_6$ alkylthiocarbonyl $C_1$-$C_6$ alkyl optionally having one or two $C_1$-$C_6$ alkyl groups,
(17) hydroxy $C_1$-$C_6$ alkylsulfonyl $C_1$-$C_6$ alkyl,
(18) carboxy $C_1$-$C_6$ alkylsulfonyl $C_1$-$C_6$ alkyl,
(19) $C_1$-$C_6$ alkoxycarbonyl $C_1$-$C_6$ alkylsulfonyl $C_1$-$C_6$ alkyl,
(20) $C_1$-$C_6$ alkanoyl $C_1$-$C_6$ alkylsulfonyl $C_1$-$C_6$ alkyl,
(21) piperazinyl $C_1$-$C_6$ alkylsulfonyl $C_1$-$C_6$ alkyl optionally having one $C_1$-$C_6$ alkyl group on the piperazine ring,
(22) piperazinylcarbonyl $C_1$-$C_6$ alkylsulfonyl $C_1$-$C_6$ alkyl optionally having one $C_1$-$C_6$ alkyl group on the piperazine ring,
(24) carboxy $C_1$-$C_6$ alkyl,
(25) $C_1$-$C_6$ alkoxycarbonyl $C_1$-$C_6$ alkyl,
(26) piperazinyl $C_1$-$C_6$ alkoxycarbonyl $C_1$-$C_6$ alkyl optionally having one $C_1$-$C_6$ alkyl group on the piperazine ring,
(27) morpholinyl $C_1$-$C_6$ alkyl,
(29) amino $C_1$-$C_6$ alkyl optionally having one or two $C_1$-$C_6$ alkyl groups,
(30) piperazyl $C_1$-$C_6$ alkyl optionally having, on the piperazine ring, one substituent selected from the group consisting of $C_1$-$C_6$ alkyl, $C_1$-$C_6$ alkoxy $C_1$-$C_6$ alkyl, and pyridyl,
(31) piperidyl $C_1$-$C_6$ alkyl optionally having one morpholinyl group,
(32) azetidyl $C_1$-$C_6$ alkyl optionally having one hydroxy group on the azetidine ring,
(33) isoindolinyl $C_1$-$C_6$ alkyl optionally having one or two oxo groups,
(34) amino $C_1$-$C_6$ alkanoyloxy $C_1$-$C_6$ alkyl optionally having one or two substituents selected from the group consisting of $C_1$-$C_6$ alkyl and $C_1$-$C_6$ alkoxycarbonyl,

(35) carbamoyl $C_1$-$C_6$ alkyl optionally having one or two substituents selected from $C_1$-$C_6$ alkyl; morpholinyl $C_1$-$C_6$ alkyl; piperidyl optionally having one substituent selected from the group consisting of $C_1$-$C_6$ alkyl and $C_1$-$C_6$ alkoxycarbonyl; and piperazinyl $C_1$-$C_6$ alkyl optionally having one $C_1$-$C_6$ alkyl group,
(36) phosphonooxy $C_1$-$C_6$ alkyl optionally having one or two $C_1$-$C_6$ alkyl groups on the phosphonooxy group,
(37) phosphonooxy $C_1$-$C_6$ alkanoyloxy $C_1$-$C_6$ alkyl optionally having one or two $C_1$-$C_6$ alkyl groups on the phosphonooxy group,
(38) benzoyloxy $C_1$-$C_6$ alkyl optionally having, on the benzene ring, one substituent selected from the group consisting of hydroxy, benzyloxy, and phosphonooxy optionally having one or two $C_1$-$C_6$ alkyl groups,
(39) tetrahydropyranyl optionally having one or four substituents selected from the group consisting of hydroxy, hydroxy $C_1$-$C_6$ alkyl and carboxyl, or
(40) $C_1$-$C_6$ alkanoylamino $C_1$-$C_6$ alkyl optionally having, on the $C_1$-$C_6$ alkanoyl group, one or two substituents selected from the group consisting of halogen; hydroxy; amino; $C_1$-$C_6$ alkoxycarbonylamino; piperazinyl optionally having one $C_1$-$C_6$ alkoxy $C_1$-$C_6$ alkyl group; imidazolyl; and morpholinylpiperidyl;
$R_2$ represents hydrogen;
$R_3$ represents phenyl, pyrazolyl, or pyrimidinyl, wherein:
the aromatic or heterocyclic ring represented by $R_3$ may be substituted with one or two substituents selected from the group consisting of the following substituents (1), (2), (4), (5), (7), (8), (10), (11), and (12):
(1) $C_1$-$C_6$ alkyl,
(2) $C_1$-$C_6$ alkoxy,
(4) halogen,
(5) hydroxy,
(7) hydroxy $C_1$-$C_6$ alkoxy,
(8) tetrahydropyranyloxy $C_1$-$C_6$ alkoxy,
(10) $C_1$-$C_6$ alkoxycarbonyl $C_1$-$C_6$ alkoxy,
(11) pyrrolidinylcarbonyl, and
(12) carbamoyl $C_1$-$C_6$ alkoxy;
$R_4$ represents halogen;
$R_5$ represents hydrogen or halogen;
$R_6$ represents hydrogen; and
$R_7$ represents any of the following groups (2), (7), (8) and (11):
(2) $C_1$-$C_6$ alkoxy,
(7) amino optionally having one or two substituents selected from the group consisting of $C_1$-$C_6$ alkyl and cyclo $C_3$-$C_8$ alkyl,
(8) cyclo $C_3$-$C_8$ alkyloxy, and
(11) pyrrolidinyl.

8. A quinolone compound represented by General Formula (1):

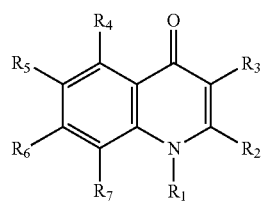

(1)

or a salt thereof, wherein
$R_1$ represents:
(1) hydrogen, or
(2) $C_1$-$C_6$ alkyl;
$R_2$ represents:
(3) $C_1$-$C_6$ alkanoyl,
(4) hydroxy $C_1$-$C_6$ alkyl,
(5) carboxy,
(6) $C_1$-$C_6$ alkoxycarbonyl,
(7) carbamoyl optionally having one or two substituents selected from the group consisting of $C_1$-$C_6$ alkyl; halogen-substituted $C_1$-$C_6$ alkyl; hydroxy $C_1$-$C_6$ alkyl; piperazinyl $C_1$-$C_6$ alkyl optionally having one $C_1$-$C_6$ alkyl group; and morpholinyl $C_1$-$C_6$ alkyl,
(8) carbamoyl $C_1$-$C_6$ alkyl optionally having one $C_1$-$C_6$ alkyl group,
(9) morpholinyl $C_1$-$C_6$ alkyl,
(10) piperazinyl $C_1$-$C_6$ alkyl optionally having one substituent selected from the group consisting of $C_1$-$C_6$ alkyl and pyridyl optionally having one $C_1$-$C_6$ alkyl group,
(11) diazepanyl $C_1$-$C_6$ alkyl,
(12) amino $C_1$-$C_6$ alkyl optionally having one or two substituents selected from the group consisting of $C_1$-$C_6$ alkyl, halogen-substituted $C_1$-$C_6$ alkyl, hydroxy $C_1$-$C_6$ alkyl, and morpholinyl $C_1$-$C_6$ alkyl,
(13) $C_1$-$C_6$ alkoxycarbonyl $C_1$-$C_6$ alkyl, or
(14) carboxy $C_1$-$C_6$ alkyl;
$R_3$ represents phenyl, thienyl, furyl, pyrazolyl, or pyrimidinyl, wherein:
the aromatic or heterocyclic ring represented by $R_3$ is substituted with one substituent selected from the group consisting of the following substituents (1) to (14):
(1) $C_1$-$C_6$ alkyl,
(2) $C_1$-$C_6$ alkoxy,
(3) $C_1$-$C_6$ alkanoyl,
(4) halogen,
(5) hydroxy,
(6) hydroxy $C_1$-$C_6$ alkyl,
(7) hydroxy $C_1$-$C_6$ alkoxy,
(8) protected hydroxy $C_1$-$C_6$ alkoxy,
(9) carboxy $C_1$-$C_6$ alkoxy,
(10) $C_1$-$C_6$ alkoxycarbonyl $C_1$-$C_6$ alkoxy,
(11) pyrrolidinylcarbonyl,
(12) carbamoyl $C_1$-$C_6$ alkoxy optionally having one $C_1$-$C_6$ alkyl group,
(13) carbamoyl optionally having one morpholinyl $C_1$-$C_6$ alkyl group, and
(14) morpholinylpiperidylcarbonyl;
$R_4$ represents halogen, $C_1$-$C_6$ alkyl, or $C_1$-$C_6$ alkoxy;
$R_5$ represents hydrogen or halogen;
$R_6$ represents hydrogen or $C_1$-$C_6$ alkoxy; and
$R_7$ represents any of the following groups (1) to (11):
(1) hydrogen,
(2) $C_1$-$C_6$ alkoxy,
(3) hydroxy $C_1$-$C_6$ alkoxy,
(4) benzyloxy $C_1$-$C_6$ alkoxy,
(5) $C_1$-$C_6$ alkoxy $C_1$-$C_6$ alkoxy,
(6) carbamoyl $C_1$-$C_6$ alkoxy optionally having one substituent selected from the group consisting of $C_1$-$C_6$ alkyl and morpholinyl $C_1$-$C_6$ alkyl,
(7) amino optionally having one or two substituents selected from the group consisting of $C_1$-$C_6$ alkyl and cyclo $C_3$-$C_8$ alkyl,
(8) cyclo $C_3$-$C_8$ alkyloxy,
(9) carboxy $C_1$-$C_6$ alkoxy,
(10) $C_1$-$C_6$ alkoxycarbonyl $C_1$-$C_6$ alkoxy, and
(11) pyrrolidinyl.

9. A quinolone compound of General Formula (1) or a salt thereof according to claim 8, wherein
R$_1$ represents hydrogen;
R$_2$ represents:
(3) C$_1$-C$_6$ alkanoyl,
(4) hydroxy C$_1$-C$_6$ alkyl,
(5) carboxy,
(6) C$_1$-C$_6$ alkoxycarbonyl,
(7) carbamoyl optionally having one or two substituents selected from the group consisting of C$_1$-C$_6$ alkyl; halogen-substituted C$_1$-C$_6$ alkyl; hydroxy C$_1$-C$_6$ alkyl; piperazinyl C$_1$-C$_6$ alkyl optionally having one C$_1$-C$_6$ alkyl group; and morpholinyl C$_1$-C$_6$ alkyl,
(8) carbamoyl C$_1$-C$_6$ alkyl optionally having one C$_1$-C$_6$ alkyl group,
(9) morpholinyl C$_1$-C$_6$ alkyl,
(10) piperazinyl C$_1$-C$_6$ alkyl optionally having one substituent selected from the group consisting of C$_1$-C$_6$ alkyl and pyridyl optionally having one C$_1$-C$_6$ alkyl group,
(11) diazepanyl C$_1$-C$_6$ alkyl,
(12) amino C$_1$-C$_6$ alkyl optionally having one or two substituents selected from the group consisting of C$_1$-C$_6$ alkyl, halogen-substituted C$_1$-C$_6$ alkyl, hydroxy C$_1$-C$_6$ alkyl, and morpholinyl C$_1$-C$_6$ alkyl, or
(14) carboxy C$_1$-C$_6$ alkyl;
R$_3$ represents phenyl, wherein:
the phenyl represented by R$_3$ is substituted with one C$_1$-C$_6$ alkoxy group,
R$_4$ represents halogen;
R$_5$ represents hydrogen;
R$_6$ represents hydrogen; and
R$_7$ represents C$_1$-C$_6$ alkoxy.

10. A quinolone compound represented by General Formula (1):

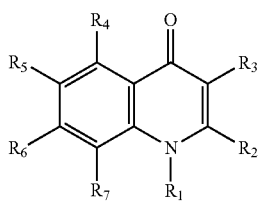

or a salt thereof, wherein
R$_1$ represents:
(1) hydrogen, or
(2) C$_1$-C$_6$ alkyl;
R$_2$ represents hydrogen;
R$_3$ represents phenyl, thienyl, furyl, pyrazolyl, or pyrimidinyl, wherein:
the aromatic or heterocyclic ring represented by R$_3$ is substituted with one substituent selected from the group consisting of the following substituents (7), (8), (9), (10), (11), (12), (13) and (14):
(7) hydroxy C$_1$-C$_6$ alkoxy,
(8) benzyloxy C$_1$-C$_6$ alkoxy,
(9) carboxy C$_1$-C$_6$ alkoxy,
(10) C$_1$-C$_6$ alkoxycarbonyl C$_1$-C$_6$ alkoxy,
(11) pyrrolidinylcarbonyl,
(12) carbamoyl C$_1$-C$_6$ alkoxy optionally having one C$_1$-C$_6$ alkyl group,
(13) carbamoyl optionally having one morpholinyl C$_1$-C$_6$ alkyl group, and
(14) morpholinylpiperidylcarbonyl;
R$_4$ represents halogen;
R$_5$ represents hydrogen or halogen;
R$_6$ represents hydrogen or C$_1$-C$_6$ alkoxy; and
R$_7$ represents any of the following groups (1) to (11):
(1) hydrogen,
(2) C$_1$-C$_6$ alkoxy,
(3) hydroxy C$_1$-C$_6$ alkoxy,
(4) benzyloxy C$_1$-C$_6$ alkoxy,
(5) C$_1$-C$_6$ alkoxy C$_1$-C$_6$ alkoxy,
(6) carbamoyl C$_1$-C$_6$ alkoxy optionally having one substituent selected from the group consisting of C$_1$-C$_6$ alkyl and morpholinyl C$_1$-C$_6$ alkyl,
(7) amino optionally having one or two substituents selected from the group consisting of C$_1$-C$_6$ alkyl and cyclo C$_3$-C$_8$ alkyl,
(8) cyclo C$_3$-C$_8$ alkyloxy,
(9) carboxy C$_1$-C$_6$ alkoxy,
(10) C$_1$-C$_6$ alkoxycarbonyl C$_1$-C$_6$ alkoxy, and
(11) pyrrolidinyl.

11. A quinolone compound of General Formula (1) or a salt thereof according to claim 10, wherein
R$_1$ represents hydrogen;
R$_3$ represents phenyl, wherein:
the phenyl represented by R$_3$ may be substituted with one substituent selected from the group consisting of the following substituents (7) to (14):
(7) hydroxy C$_1$-C$_6$ alkoxy,
(8) benzyloxy C$_1$-C$_6$ alkoxy,
(9) carboxy C$_1$-C$_6$ alkoxy,
(10) C$_1$-C$_6$ alkoxycarbonyl C$_1$-C$_6$ alkoxy,
(11) pyrrolidinylcarbonyl,
(12) carbamoyl C$_1$-C$_6$ alkoxy optionally having one C$_1$-C$_6$ alkyl group,
(13) carbamoyl optionally having one morpholinyl C$_1$-C$_6$ alkyl group, and
(14) morpholinylpiperidylcarbonyl;
R$_4$ represents halogen;
R$_5$ represents hydrogen;
R$_6$ represents hydrogen; and
R$_7$ represents any of the following groups (2) and (11):
(2) C$_1$-C$_6$ alkoxy; and
(11) pyrrolidinyl.

12. A quinolone compound represented by General Formula (1):

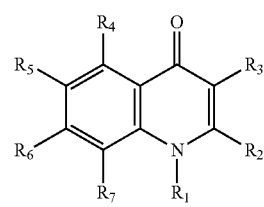

or a salt thereof, wherein
R$_1$ represents:
(1) hydrogen or
(2) C$_1$-C$_6$ alkyl;
R$_2$ represents hydrogen;
R$_3$ represents phenyl, wherein:
the phenyl represented by R$_3$ is substituted with one C$_1$-C$_6$ alkoxy,
R$_4$ represents halogen, C$_1$-C$_6$ alkyl, or C$_1$-C$_6$ alkoxy;
R$_5$ represents hydrogen or halogen;

$R_6$ represents hydrogen or $C_1$-$C_6$ alkoxy; and
$R_7$ represents any of the following groups (4), (6), (9), (10) and (11):
(4) benzyloxy $C_1$-$C_6$ alkoxy,
(6) carbamoyl $C_1$-$C_6$ alkoxy optionally having one substituent selected from the group consisting of $C_1$-$C_6$ alkyl and morpholinyl $C_1$-$C_6$ alkyl,
(9) carboxy $C_1$-$C_6$ alkoxy,
(10) $C_1$-$C_6$ alkoxycarbonyl $C_1$-$C_6$ alkoxy, and
(11) pyrrolidinyl.

13. A quinolone compound of General Formula (1) or a salt thereof according to claim 12, wherein
$R_1$ represents hydrogen;
$R_3$ represents phenyl, wherein:
the phenyl represented by $R_3$ may be substituted with one $C_1$-$C_6$ alkoxy,
$R_4$ represents halogen;
$R_5$ represents hydrogen;
$R_6$ represents hydrogen; and
$R_7$ represents any of the following groups (4), (6), (9), (10) and (11):
(4) benzyloxy $C_1$-$C_6$ alkoxy,
(6) carbamoyl $C_1$-$C_6$ alkoxy optionally having one substituent selected from the group consisting of $C_1$-$C_6$ alkyl and morpholinyl $C_1$-$C_6$ alkyl,
(9) carboxy $C_1$-$C_6$ alkoxy,
(10) $C_1$-$C_6$ alkoxycarbonyl $C_1$-$C_6$ alkoxy, and
(11) pyrrolidinyl.

14. A process for producing a quinolone compound represented by Formula (1b):

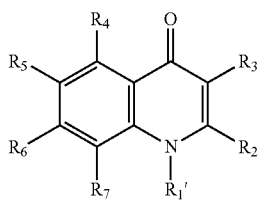

(1b)

wherein $R_2$, $R_3$, $R_4$, $R_5$, $R_6$, and $R_7$ are as defined in claim 1, 5, 7, 9, 11 or 13, and $R_1'$ is a group represented by $R_1$ as defined in claim 1, 5, 7, 9, 11 or 13 other than hydrogen, or a salt thereof;
the process comprising reacting a compound represented by the formula:

$R_1'$—$X_2$ wherein $X_2$ represents a group that undergoes the same substitution reaction as that of a halogen or a halogen atom, with a compound represented by the formula:

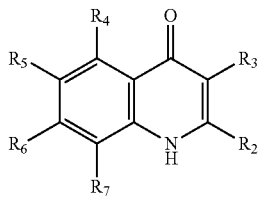

wherein $R_2$, $R_3$, $R_4$, $R_5$, $R_6$ and $R_7$ are as defined in claim 1, 5, 7, 9, 11 or 13.

15. A quinolone compound according to claim 1, selected from the group consisting of the following compounds:

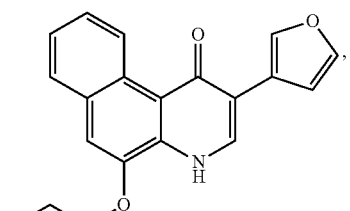

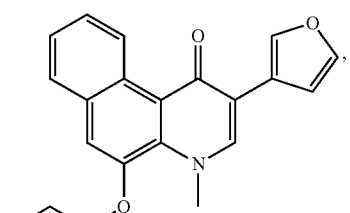

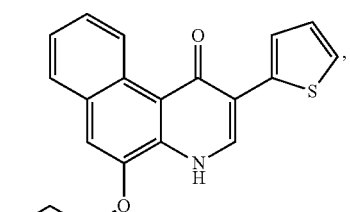

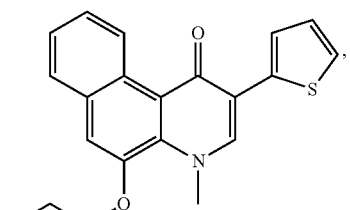

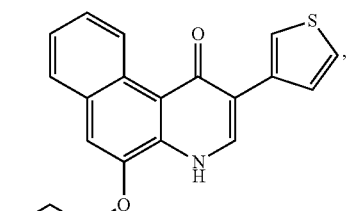

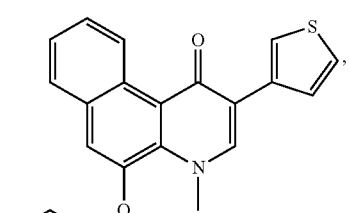

191
-continued
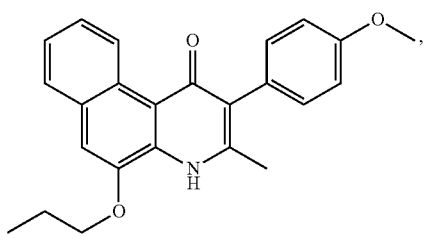
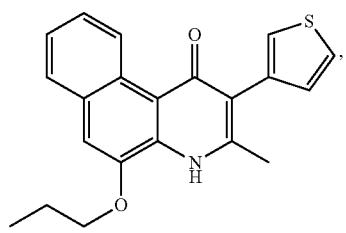
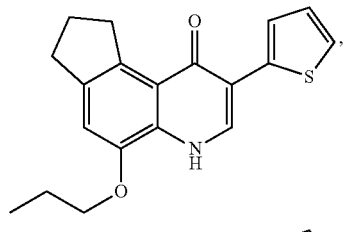
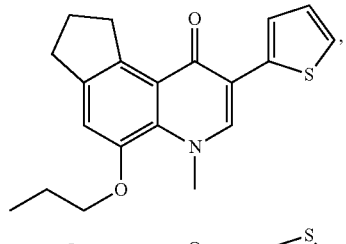
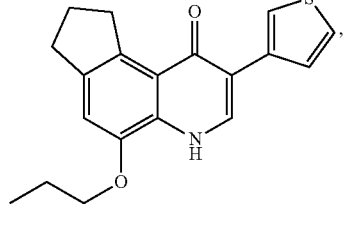
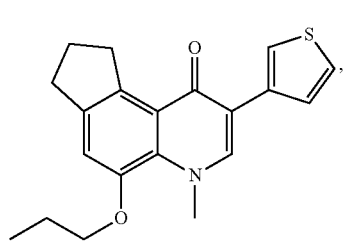
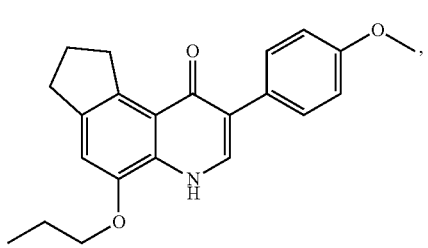
192
-continued
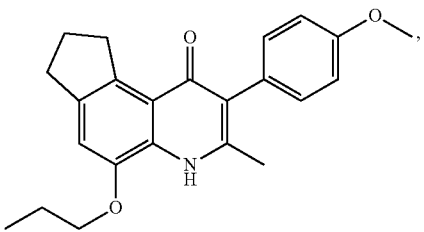
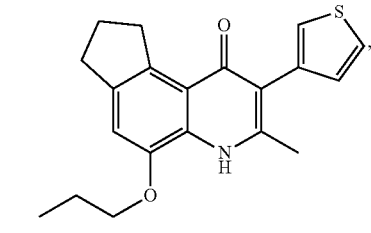
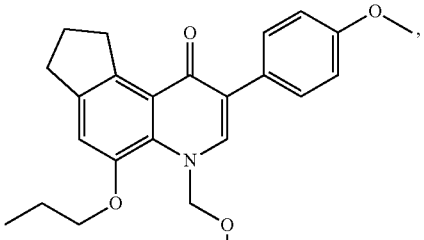
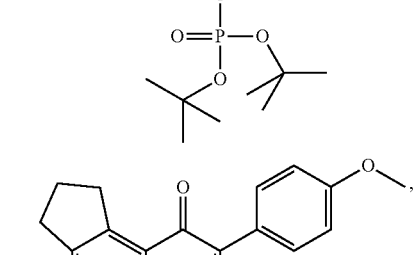
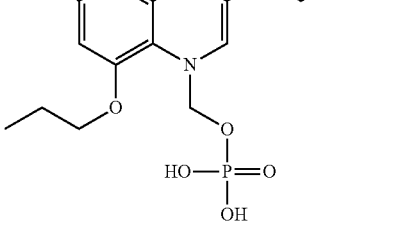
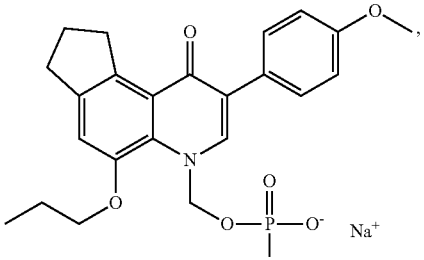
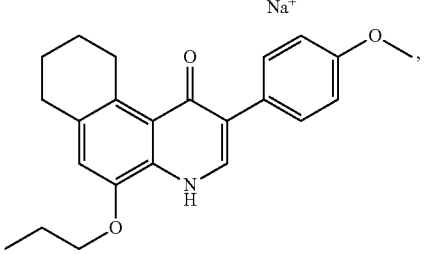

193
-continued
194
-continued
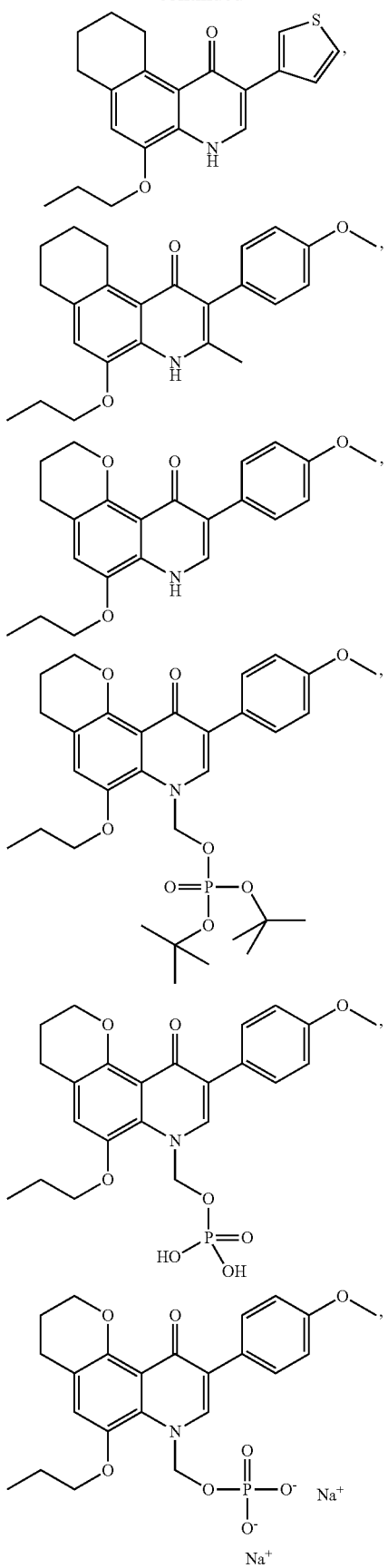
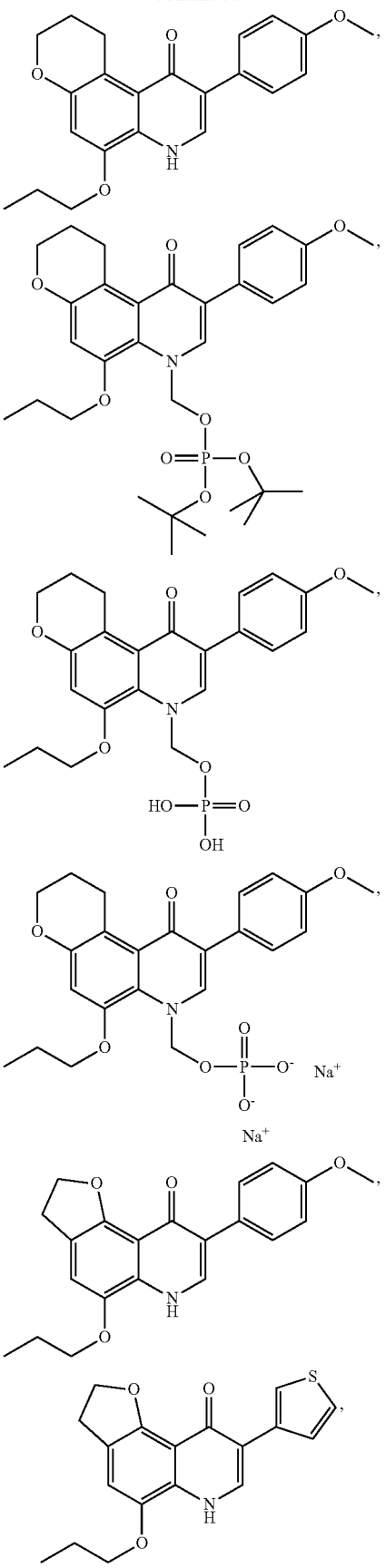

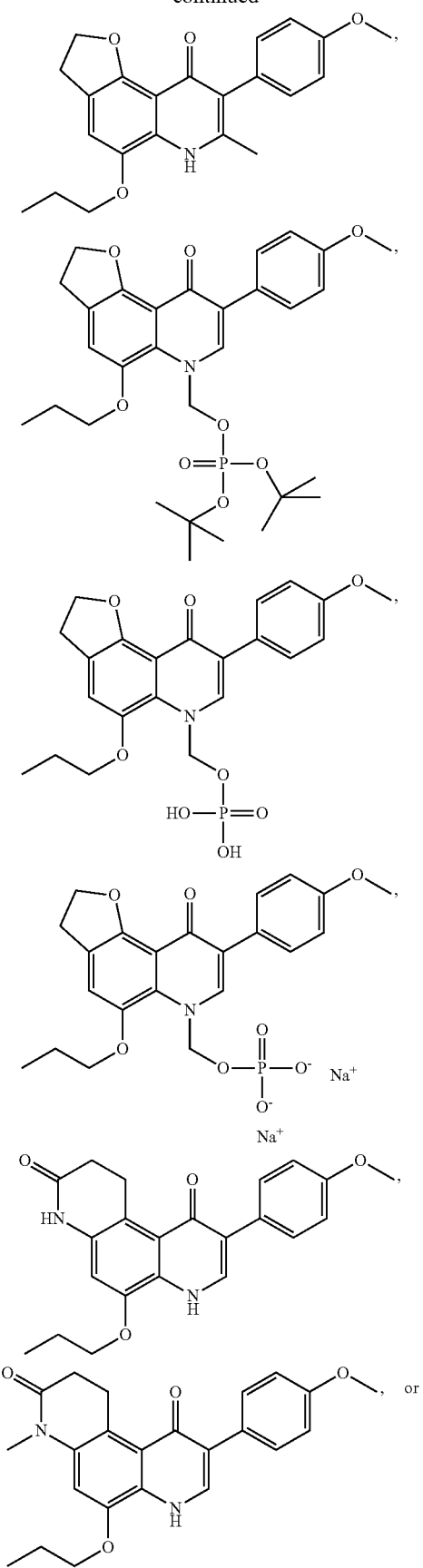
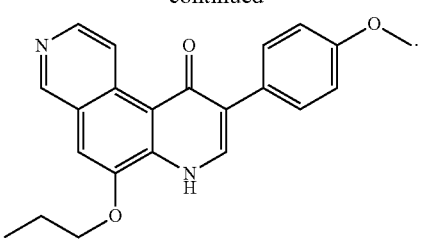
16. A quinolone compound according to claim 4, selected from the group consisting of the following compounds:
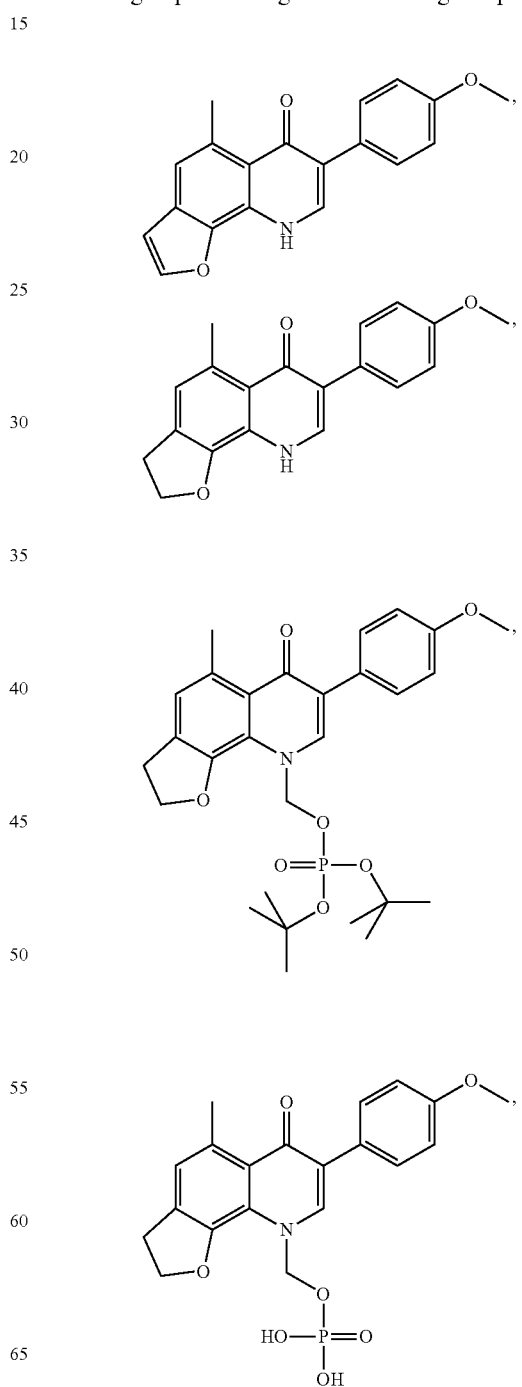

197
-continued
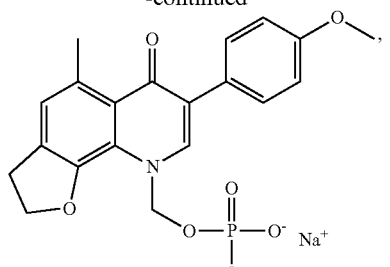
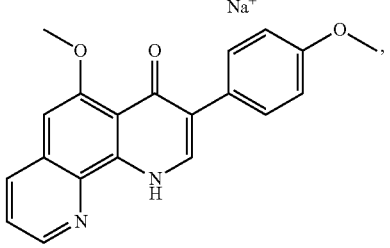
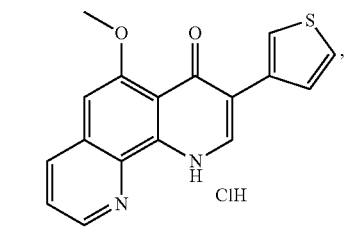
ClH
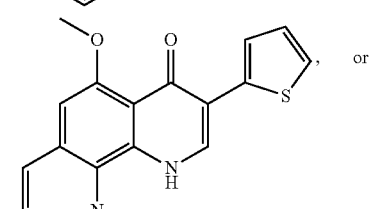 or
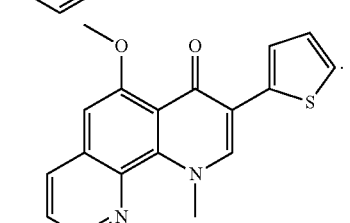
17. A quinolone compound according to claim 6, selected from the group consisting of the following compounds:
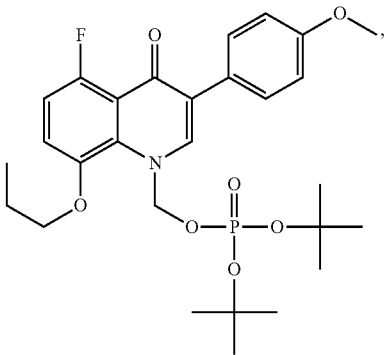
198
-continued
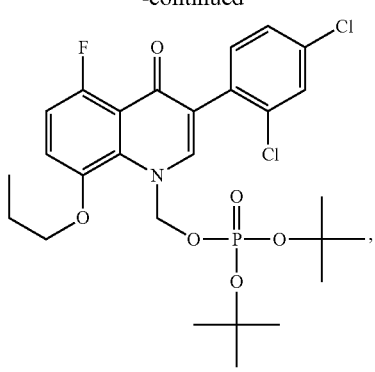
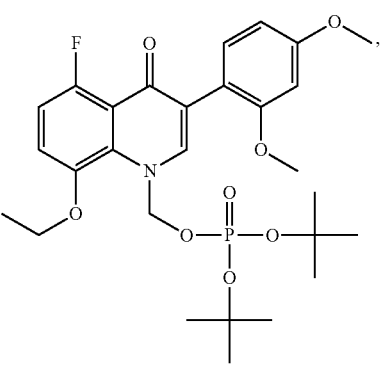
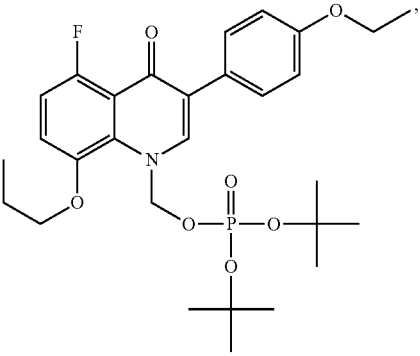
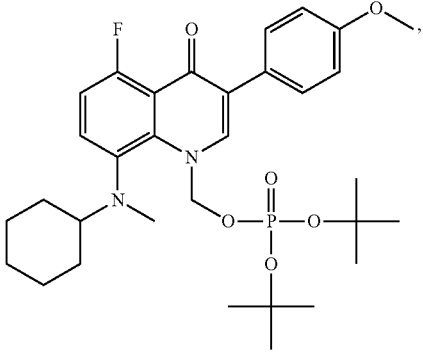

199
-continued
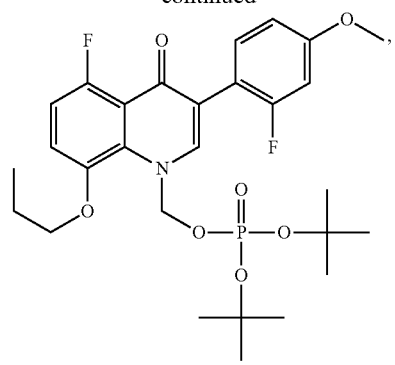
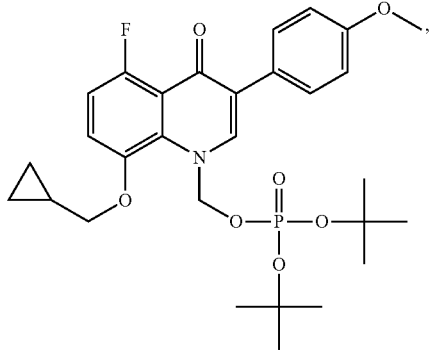
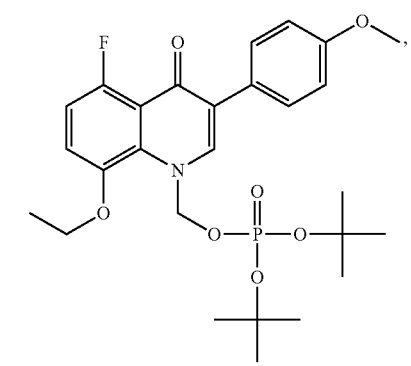
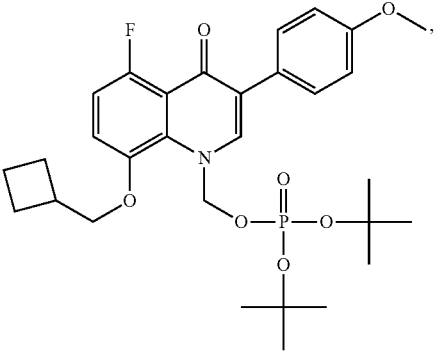
200
-continued
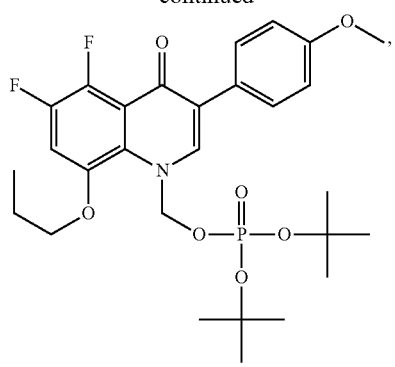
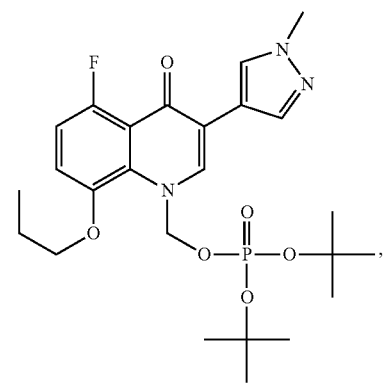
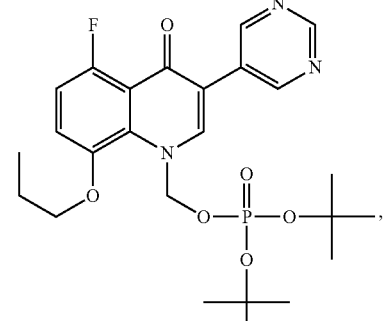
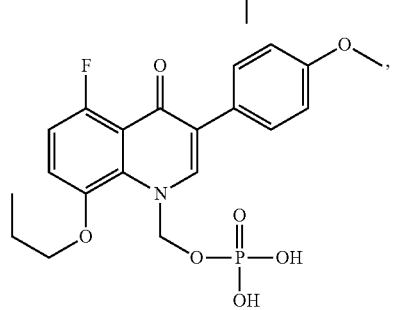
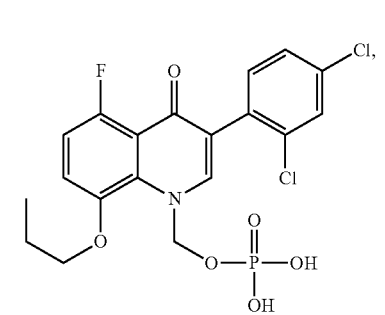

201
-continued
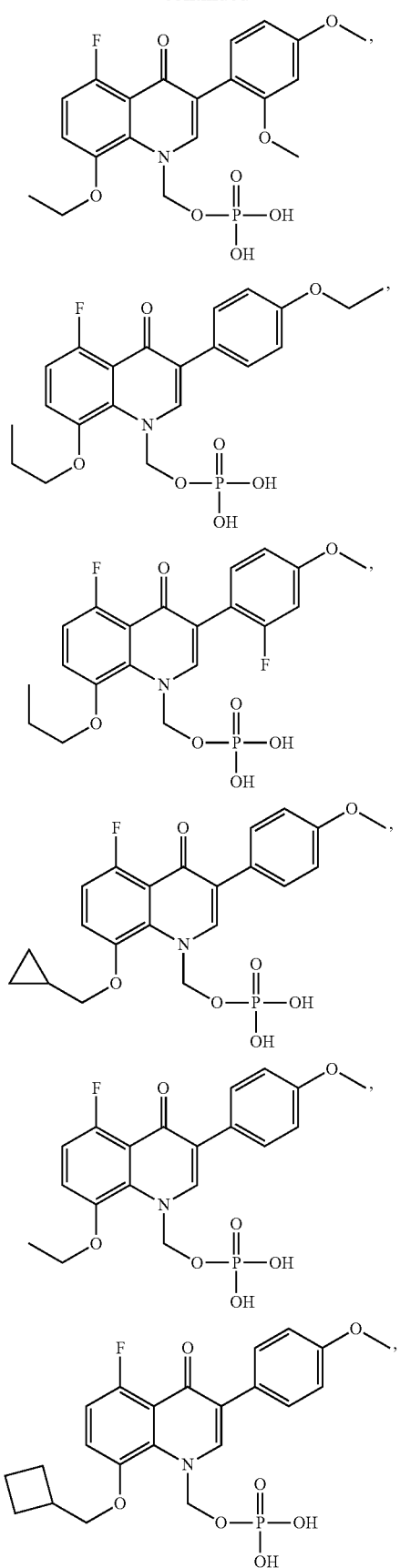
202
-continued
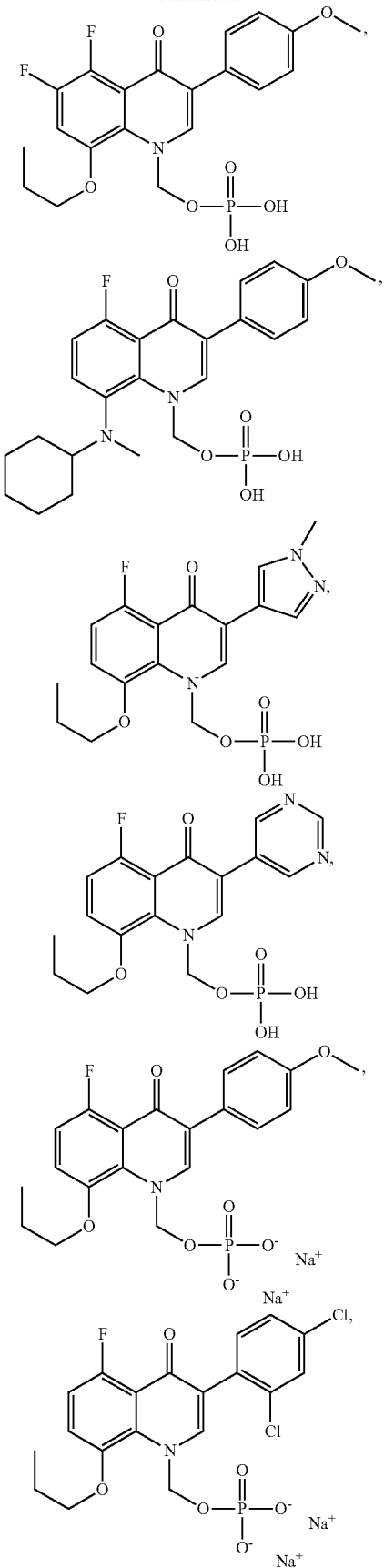

203
-continued
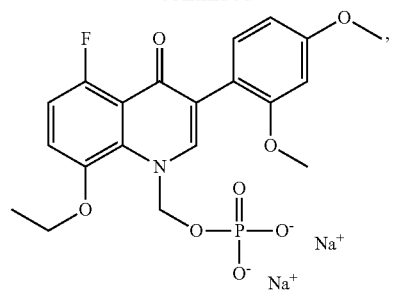
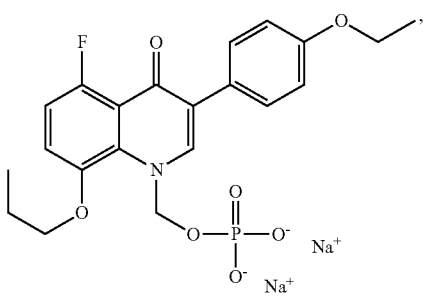
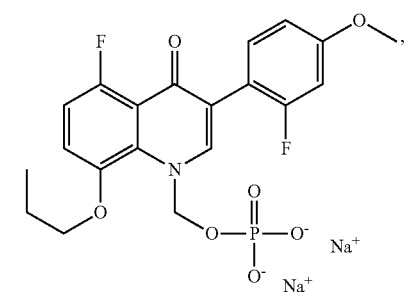
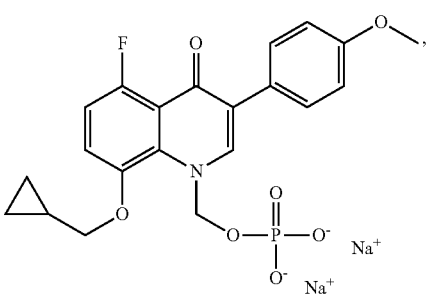
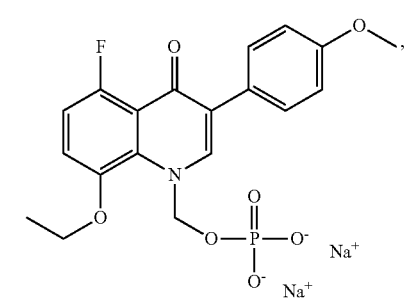
204
-continued
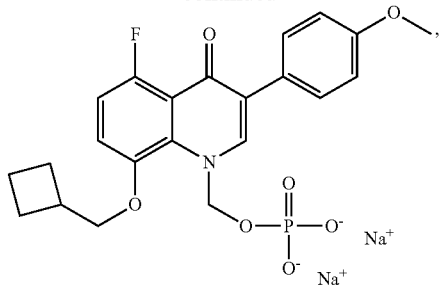
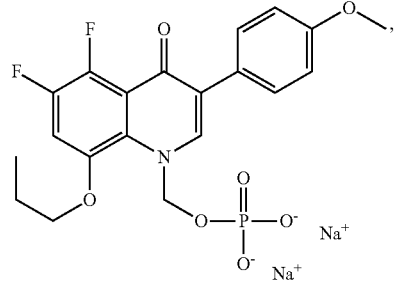
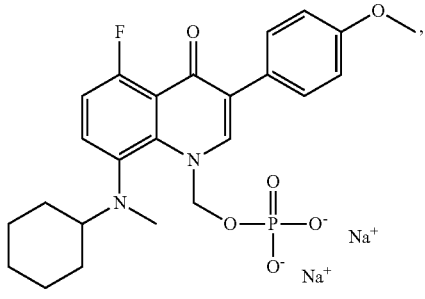
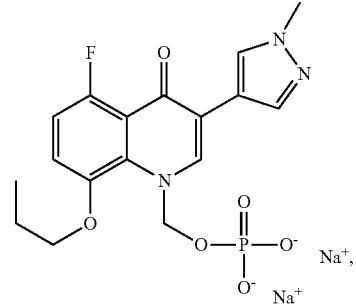
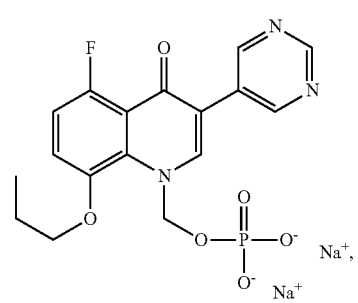

205
-continued
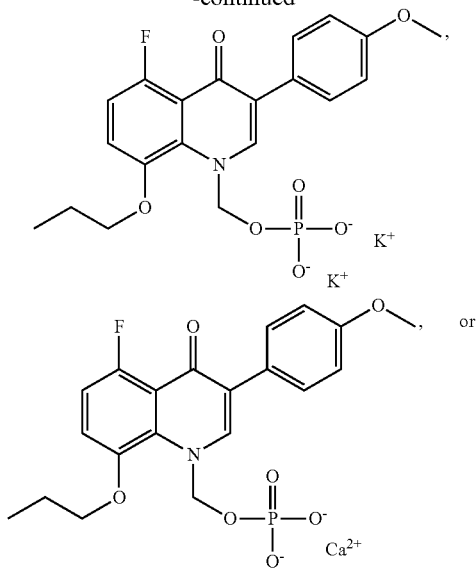
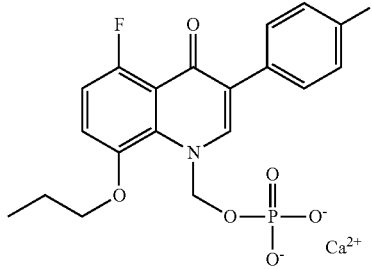
206
-continued
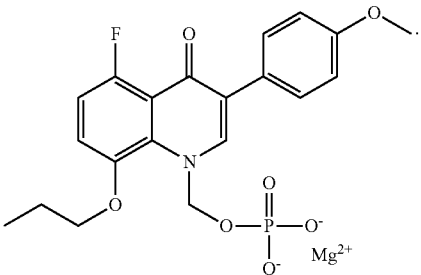
* * * * *